(12) United States Patent
Gordon et al.

(10) Patent No.: US 7,179,890 B2
(45) Date of Patent: Feb. 20, 2007

(54) VASCULAR ENDOTHELIAL GROWTH FACTOR-X

(75) Inventors: Robert D. Gordon, Beerse (BE); Jörg J. Sprengel, Beerse (BE); Jeffrey R. Yon, Beerse (BE); Josiena J. H. Dijkmans, Beerse (BE); Anna Gosiewska, Skillman, NJ (US); Sridevi N. Dhanaraj, Somerset, NJ (US); Jean Xu, Raritan, NJ (US)

(73) Assignee: Janssen Pharmaceutica.N.V., Beerse (BE)

( * ) Notice: Subject to any disclaimer, the term of this patent is extended or adjusted under 35 U.S.C. 154(b) by 0 days.

(21) Appl. No.: 10/924,025

(22) Filed: Aug. 23, 2004

(65) Prior Publication Data

US 2005/0153882 A1 Jul. 14, 2005

Related U.S. Application Data

(62) Division of application No. 09/468,647, filed on Dec. 21, 1999, now Pat. No. 6,783,953.

(60) Provisional application No. 60/164,131, filed on Nov. 8, 1999, provisional application No. 60/124,967, filed on Mar. 18, 1999.

(30) Foreign Application Priority Data

Dec. 22, 1998 (GB) ................................ 9828377.3

(51) Int. Cl.
  *C07K 1/00* (2006.01)
  *C07K 14/00* (2006.01)
  *A01N 37/18* (2006.01)
(52) U.S. Cl. .......................... 530/350; 530/399; 514/2
(58) Field of Classification Search ..................... None
  See application file for complete search history.

(56) References Cited

U.S. PATENT DOCUMENTS 6,391,311 B1 * 5/2002 Ferrara et al. ............ 424/198.1

FOREIGN PATENT DOCUMENTS

| EP | 0 550 296 A2 | 7/1993 |
|---|---|---|
| EP | 0 506 477 B1 | 6/1999 |
| EP | 0 984 063 A | 3/2000 |
| EP | 09 476 983 B1 | 3/2000 |
| WO | WO 90/11084 | 11/1990 |
| WO | WO 90/13649 | 11/1990 |
| WO | WO 91/02058 | 2/1991 |
| WO | WO 95/24473 | 9/1995 |
| WO | WO 96/26736 | 9/1996 |
| WO | WO 96/27007 | 9/1996 |
| WO | WO 96/39421 | 12/1996 |
| WO | WO 96/39515 | 12/1996 |
| WO | WO 97/05250 | 2/1997 |
| WO | WO 98/02543 | 1/1998 |
| WO | WO 98/07832 | 2/1998 |
| WO | WO 98/07832 A | 2/1998 |
| WO | WO 98/10071 | 3/1998 |
| WO | WO 98/16551 | 4/1998 |
| WO | WO 98/24811 | 6/1998 |
| WO | WO 98/24811 A | 6/1998 |
| WO | WO 98/2861 | 7/1998 |
| WO | WO 98/36075 | 8/1998 |
| WO | WO 98/49300 | 11/1998 |
| WO | WO 99/37671 A | 7/1999 |
| WO | WO 99/47667 A | 9/1999 |

OTHER PUBLICATIONS

Wells. 1990. Biochemistry 29:8509-8517.*
Ngo et al. 1994. The Protein Folding Problem and Tertiary Structure Prediction. pp. 492-495.*
Lockhart et al., *Nature Biotechnol.* 14:1675-1680 (1996).
von Heijne, *Nucleic Acids Res.* 14:4683-4690 (1986).
Muller et al., *Proc. Natl. Acad. Sci. USA* 94:7192-7197 (1997).
Korff and Augustin, *J of Cell Biol.* 143:1341-1352 (1998).
Christinger et al., *Proteins: Stucture, Function and Genetics* 26:353-357 (1996).
Achen et al., *Proc. Natl. Acad. Sci. USA* 95:548-553 (1998).
Siemeister et al., *Biochem. Biophys. Res. Commun.* 222:249-255 (1996).
Soker et al., *Cell* 92:735-745 (1998).
Neufeld et al., *FASEB J.* 13:9-22 (1999).
Oefner et al., *EMBO J.* 11:3921-3926 (1992).
Passanti et al., *Laboratory Investigation* 67:519-528 (1992).
Rocchigiani et al., *Genomics* 47:207-216 (1990).
Takahashi et al., *Cancer Res.* 55:3964-3968 (1995).
Tischer et al., *J. Biol. Chem.* 266:11947-11954 (1991).
Ferrara et al., *Regulation of Angiogenesis*, by Goldberg and Rosen (1997), Birkhauser Verlag.
Gajdusek and Carbon, *Cell Physiol.* 139:570-579 (1989).
McNeil et al., *J. Cell Biol.* 109:811-822 (1989).
Jakeman et al., *Clin. Invest.* 89:244-253 (1989).
Plate, *Nature* 359:845-848 (1992).
Kim, *Nature* 362:841-844 (1993).
Folkman, *Nature Med.* 1:27-31 (1995).

* cited by examiner

*Primary Examiner*—Lorraine Spector
*Assistant Examiner*—Shulamith H Shafer

(57) ABSTRACT

There is provided a novel vascular endothelial growth factor, herein designated VEGF-X, in addition to the nucleic acid molecule encoding it, a host cell transformed with said vector and compounds which inhibit or enhance angiogenesis. Also provided is the sequence of a CUB domain present in the sequence of VEGF-X which domain itself prevents angiogenesis and which is used to treat diseases associated with inappropriate vascularisation or angiogenesis.

2 Claims, 66 Drawing Sheets

Figure 22A:
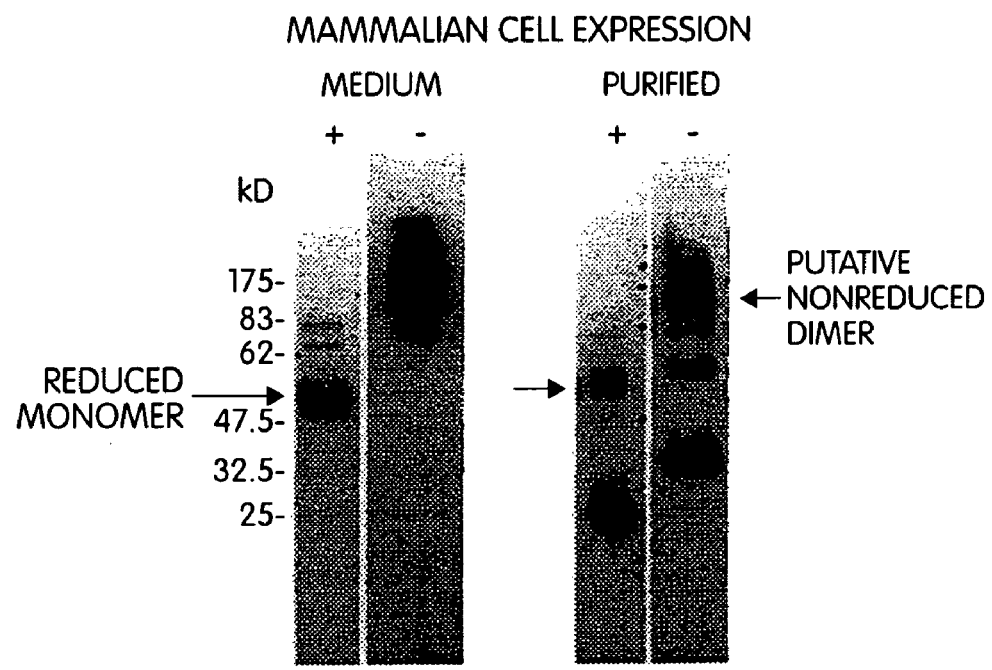

```
  1 AAAATGTATG GATACAACTT ACGTTTGATG AAAGATTTGG GCTTGAAGAC CCAGAAGATG
    TTTTACATAC CTATGTTGAA TGCAAACTAC TTTCTAAACC CGAACTTCTG GGTCTTCTAC

61 ACATATGCAA GTATGATTTT GTAGAAGTTG AGGAACCCAG TGATGGAACT ATATTAGGGC
    TGTATACGTT CATACTAAAA CATCTTCAAC TCCTTGGGTC ACTACCTTGA TATAATCCCG

121 GCTGGTGTGG TTCTGGTACT GTACCAGGAA AACAGATTTC TAAAGGAAAT CAAATTAGGA
    CGACCACACC AAGACCATGA CATGGTCCTT TTGTCTAAAG ATTTCCTTTA GTTTAATCCT

+1                   MetAsn IlePheLeu LeuAsnLeuLeu ThrGluGlu ValArgLeu
                  ]------------------------------------------------------
181 TAAGATTTGT ATCTGATGAA TATTTTCCTT CTGAACCTTC TAACAGAGGA GGTAAGATTA
    ATTCTAAACA TAGACTACTT ATAAAAGGAA GACTTGGAAG ATTGTCTCCT CCATTCTAAT

+1 TyrSerCysThr ProArgAsn PheSerVal SerIleArgGlu GluLeuLys ArgThrAsp
    ----------------------------------------------------------------
241 TACAGCTGCA CACCTCGTAA CTTCTCAGTG TCCATAAGGG AAGAACTAAA GAGAACCGAT
    ATGTCGACGT GTGGAGCATT GAAGAGTCAC AGGTATTCCC TTCTTGATTT CTCTTGGCTA

+1 ThrIlePheTrp ProGlyCys LeuLeuVal LysArgCysGly GlyAsnCys AlaCysCys
    ----------------------------------------------------------------
301 ACCATTTTCT GGCCAGGTTG TCTCCTGGTT AAACGCTGTG GTGGGAACTG TGCCTGTTGT
    TGGTAAAAGA CCGGTCCAAC AGAGGACCAA TTTGCGACAC CACCCTTGAC ACGGACAACA

+1 LeuHisAsnCys AsnGluCys GlnCysVal ProSerLysVal ThrLysLys TyrHisGlu
    ----------------------------------------------------------------
361 CTCCACAATT GCAATGAATG TCAATGTGTC CCAAGCAAAG TTACTAAAAA ATACCACGAG
    GAGGTGTTAA CGTTACTTAC AGTTACACAG GGTTCGTTTC AATGATTTT TATGGTGCTC

+1 ValLeuGlnLeu ArgProLys ThrGlyVal ArgGlyLeuHis LysSerLeu ThrAspVal
    ----------------------------------------------------------------
421 GTCCTTCAGT TGAGACCAAA GACCGGTGTC AGGGGATTGC ACAAATCACT CACCGACGTG
    CAGGAAGTCA ACTCTGGTTT CTGGCCACAG TCCCCTAACG TGTTTAGTGA GTGGCTGCAC

+1 AlaLeuGluHis HisGluGlu CysAspCys ValCysArgGly SerThrGly Gly
    ------------------------------------------------------------>
481 GCCCTGGAGC ACCATGAGGA GTGTGACTGT GTGTGCAGAG GGAGCACAGG AGGATAGCCG
    CGGGACCTCG TGGTACTCCT CACACTGACA CACACGTCTC CCTCGTGTCC TCCTATCGGC

541 CATCACCACC AGCAGCTCTT GCCCAGAGCT GTGCAGTGCA GTGGCTGATT CTATTAGAGA
    GTAGTGGTGG TCGTCGAGAA CGGGTCTCGA CACGTCACGT CACCGACTAA GATAATCTCT

601 ACGTATGCGT TATCTCCATC CTTAATCTCA GTTGTTTGCT TCAAGGACCT TTCATCTTCA
    TGCATACGCA ATAGAGGTAG GAATTAGAGT CAACAAACGA AGTTCCTGGA AAGTAGAAGT
```

Fig. 1-1

```
 661  GGATTTACAG TGCATTCTGA AAGAGGAGAC ATCAAACAGA ATTAGGAGTT GTGCAACAGC
      CCTAAATGTC ACGTAAGACT TTCTCCTCTG TAGTTTGTCT TAATCCTCAA CACGTTGTCG

721  TCTTTTGAGA GGAGGCCTAA AGGACAGGAG AAAAGGTCTT CAATCGTGGA AAGAAAATTA
      AGAAAACTCT CCTCCGGATT TCCTGTCCTC TTTTCCAGAA GTTAGCACCT TTCTTTTAAT

781  AATGTTGTAT TAAATAGATC ACCAGCTAGT TTCAGAGTTA CCATGTACGT ATTCCACTAG
      TTACAACATA ATTTATCTAG TGGTCGATCA AAGTCTCAAT GGTACATGCA TAAGGTGATC

841  CTGGGTTCTG TATTTCAGTT CTTTCGATAC GGCTTAGGGT AATGTCAGTA CAGGAAAAAA
      GACCCAAGAC ATAAAGTCAA GAAAGCTATG CCGAATCCCA TTACAGTCAT GTCCTTTTTT

901  ACTGTGCAAG TGAGCACCTG ATTCCGTTGC CTTGCTTAAC TCTAAAGCTC CATGTCCTGG
      TGACACGTTC ACTCGTGGAC TAAGGCAACG GAACGAATTG AGATTTCGAG GTACAGGACC

961  GCCTAAAATC GTATAAAATC TGGATTTTTT TTTTTTTTTT TGCTCATATT CACATATGTA
      CGGATTTTAG CATATTTTAG ACCTAAAAAA AAAAAAAAAA ACGAGTATAA GTGTATACAT

1021  AACCAGAACA TTCTATGTAC TACAAACCTG GTTTTTAAAA AGGAACTATG TTGCTATGAA
      TTGGTCTTGT AAGATACATG ATGTTTGGAC CAAAAATTTT TCCTTGATAC AACGATACTT

1081  TTAAACTTGT GTCGTGCTGA TAGGACAGAC TGGATTTTTC ATATTTCTTA TTAAAATTTC
      AATTTGAACA CAGCACGACT ATCCTGTCTG ACCTAAAAAG TATAAAGAAT AATTTTAAAG

1141  TGCCATTTAG AAGAAGAGAA CTACATTCAT GGTTTGGAAG AGATAAACCT GAAAAGAAGA
      ACGGTAAATC TTCTTCTCTT GATGTAAGTA CCAAACCTTC TCTATTTGGA CTTTTCTTCT

1201  GTGGCCTTAT CTTCACTTTA TCGATAAGTC AGTTTATTTG TTTCATTGTG TACATTTTTA
      CACCGGAATA GAAGTGAAAT AGCTATTCAG TCAAATAAAC AAAGTAACAC ATGTAAAAAT

1261  TATTCTCCTT TTGACATTAT AACTGTTGGC TTTTCTAATC TTGTTAAATA TATCTATTTT
      ATAAGAGGAA AACTGTAATA TTGACAACCG AAAAGATTAG AACAATTTAT ATAGATAAAA

1321  TACCAAAGGT ATTTAATATT CTTTTTTATG ACAACTTAGA TCAACTATTT TTAGCTTGGT
      ATGGTTTCCA TAAATTATAA GAAAAAATAC TGTTGAATCT AGTTGATAAA AATCGAACCA

1381  AAATTTTTCT AAACACAATT GTTATAGCCA GAGGAACAAA GATGATATAA AATATTGTTG
      TTTAAAAAGA TTTGTGTTAA CAATATCGGT CTCCTTGTTT CTACTATATT TTATAACAAC

1441  CTCTGACAAA AATACATGTA TTTCATTCTC GTATGGTGCT AGAGTTAGAT TAATCTGCAT
      GAGACTGTTT TTATGTACAT AAAGTAAGAG CATACCACGA TCTCAATCTA ATTAGACGTA

1501  TTTAAAAAAC TGAATTGGAA TAGAATTGGT AAGTTGCAAA GACTTTTTGA AAATAATTAA
      AAATTTTTTG ACTTAACCTT ATCTTAACCA TTCAACGTTT CTGAAAAACT TTTATTAATT
```

Fig. 1-2

```
1561  ATTATCATAT CTTCCATTCC TGTTATTGGA GATGAAAATA AAAAGCAACT TATGAAAGTA
      TAATAGTATA GAAGGTAAGG ACAATAACCT CTACTTTTAT TTTTCGTTGA ATACTTTCAT

1621  GACATTCAGA TCCAGCCATT ACTAACCTAT TCCTTTTTTG GGGAAATCTG AGCCTAGCTC
      CTGTAAGTCT AGGTCGGTAA TGATTGGATA AGGAAAAAAC CCCTTTAGAC TCGGATCGAG

1681  AGAAAAACAT AAAGCACCTT GAAAAGACT TGGCAGCTTC CTGATAAAGC GTGCTGTGCT
      TCTTTTTGTA TTTCGTGGAA CTTTTTCTGA ACCGTCGAAG GACTATTTCG CACGACACGA

1741  GTGCAGTAGG AACACATCCT ATTTATTGTG ATGTTGTGGT TTTATTATCT TAAACTCTGT
      CACGTCATCC TTGTGTAGGA TAAATAACAC TACAACACCA AAATAATAGA ATTTGAGACA

1801  TCCATACACT TGTATAAATA CATGGATATT TTTATGTACA GAAGTATGTC TCTTAACCAG
      AGGTATGTGA ACATATTTAT GTACCTATAA AAATACATGT CTTCATACAG AGAATTGGTC

1861  TTCACTTATT GTACCTGG
      AAGTGAATAA CATGGACC
```

Fig. 1-3

PREDICTED VEGF-LIKE PROTEIN ENCODED BY INCYTE CONTIG OF 8/12/98

```
  1  MNIFLLNLLT EEVRLYSCTP RNFSVSIREE LKRTDTIFWP GCLLVKRCGG
 51  NCACCLHNCN ECQCVPSKVT KKYHEVLQLR PKTGVRGLHK SLTDVALEHH
101  EECDCVCRGS TGG
```

Fig. 2

PCR PRIMERS FOR CLONING VEGF-X

```
vegfX1    AAAATGTATGGATACAACTTAC vegfX2    GTTTGATGAAGATTTGGGCTTG vegfX3    TTTCTAAAGGAAATCAAATTAG vegfX4    GATAAGATTTGTATCTGATG vegfX5    GATGTCTCCTCTTTCAG vegfX6    GCACAACTCCTAATTCTG vegfX7    AGCACCTGATTCCGTTGC vegfX8    TAGTACATAGAATGTTCTGG vegfX9    AAGAGACATACTTCTGTAC vegfX10   CCAGGTACAATAAGTGAACTG
```

Fig. 3

VARIANTS ISOLATED BY PCR

```
            a  b                    c  d              e  f
PCR primers- → →                    ← ←              ← ←
```

Incyte contig
(8/12/98)

clone 22, 29, 41 clone 52, 59 clone 15, 20 clones 57, 25,
      26, 27

2.1kb clones 1,
        2, 3 primers-      a-vegfX1        b-vegfX2        c-vegfX5
(see Fig. 3)  d-vegfX6        e-vegfX9        f-vegfX10

Fig. 4

VEGF-X 5' RACE PRIMERS vegfX11  CCTTTAGAAATCTGTTTTCCTGGTACAG vegfX12  GGAAAATATTCATCAGATACAAATCTTATCC vegfX13  GGTCCAGTGGCAAAGCTGAAGG vegfX14  CTGGTTCAAGATATCGAATAAGGTCTTCC

Fig. 5

DNA SEQUENCE ASSEMBLED FROM IN-HOUSE CLONES AND 5'RACE

```
  1 TGCCAGAGCA GGTGGGCGCT TCCACCCCAG TGCAGCCTTC CCCTGGCGGT GGTGAAAGAG
    ACGGTCTCGT CCACCCGCGA AGGTGGGGTC ACGTCGGAAG GGGACCGCCA CCACTTTCTC

61 ACTCGGGAGT CGCTGCTTCC AAAGTGCCCG CCGTGAGTGA GCTCTCACCC CAGTCAGCCA
    TGAGCCCTCA GCGACGAAGG TTTCACGGGC GGCACTCACT CGAGAGTGGG GTCAGTCGGT

+2   MetSerLeu PheGlyLeuLeu LeuLeuThr SerAlaLeu AlaGlyGlnArg GlnGlyTh
      ]----------------------------------------------------------------
121 AATGAGCCTC TTCGGGCTTC TCCTGCTGAC ATCTGCCCTG GCCGGCCAGA GACAGGGGAC
    TTACTCGGAG AAGCCCGAAG AGGACGACTG TAGACGGGAC CGGCCGGTCT CTGTCCCCTG

+2 rGlnAlaGlu SerAsnLeuSer SerLysPhe GlnPheSer SerAsnLysGlu GlnAsnGl
    ----------------------------------------------------------------
181 TCAGGCGGAA TCCAACCTGA GTAGTAAATT CCAGTTTTCC AGCAACAAGG AACAGAACGG
    AGTCCGCCTT AGGTTGGACT CATCATTTAA GGTCAAAAGG TCGTTGTTCC TTGTCTTGCC

+2 yValGlnAsp ProGlnHisGlu ArgIleIle ThrValSer ThrAsnGlySer IleHisSe
    ----------------------------------------------------------------
241 AGTACAAGAT CCTCAGCATG AGAGAATTAT TACTGTGTCT ACTAATGGAA GTATTCACAG
    TCATGTTCTA GGAGTCGTAC TCTCTTAATA ATGACACAGA TGATTACCTT CATAAGTGTC

+2 rProArgPhe ProHisThrTyr ProArgAsn ThrValLeu ValTrpArgLeu ValAlaVa
    ----------------------------------------------------------------
301 CCCAAGGTTT CCTCATACTT ATCCAAGAAA TACGGTCTTG GTATGGAGAT TAGTAGCAGT
    GGGTTCCAAA GGAGTATGAA TAGGTTCTTT ATGCCAGAAC CATACCTCTA ATCATCGTCA

+2 lGluGluAsn ValTrpIleGln LeuThrPhe AspGluArg PheGlyLeuGlu AspProGl
    ----------------------------------------------------------------
361 AGAGGAAAAT GTATGGATAC AACTTACGTT TGATGAAAGA TTTGGGCTTG AAGACCCAGA
    TCTCCTTTTA CATACCTATG TTGAATGCAA ACTACTTTCT AAACCCGAAC TTCTGGGTCT

+2 uAspAspIle CysLysTyrAsp PheValGlu ValGluGlu ProSerAspGly ThrIleLe
    ----------------------------------------------------------------
421 AGATGACATA TGCAAGTATG ATTTTGTAGA AGTTGAGGAA CCCAGTGATG GAACTATATT
    TCTACTGTAT ACGTTCATAC TAAAACATCT TCAACTCCTT GGGTCACTAC CTTGATATAA

+2 uGlyArgTrp CysGlySerGly ThrValPro GlyLysGln IleSerLysGly AsnGlnIl
    ----------------------------------------------------------------
481 AGGGCGCTGG TGTGGTTCTG GTACTGTACC AGGAAAACAG ATTTCTAAAG GAAATCAAAT
    TCCCGCGACC ACACCAAGAC CATGACATGG TCCTTTTGTC TAAAGATTTC CTTTAGTTTA

+2 eArgIleArg PheValSerAsp GluTyrPhe ProSerGlu ProGlyPheCys IleHisTy
    ----------------------------------------------------------------
541 TAGGATAAGA TTTGTATCTG ATGAATATTT TCCTTCTGAA CCAGGGTTCT GCATCCACTA
    ATCCTATTCT AAACATAGAC TACTTATAAA AGGAAGACTT GGTCCCAAGA CGTAGGTGAT
```

Fig. 6-1

```
      +2 rAsnIleVal MetProGlnPhe ThrGluAla ValSerPro SerValLeuPro ProSerAl
         ------------------------------------------------------------------
     601 CAACATTGTC ATGCCACAAT TCACAGAAGC TGTGAGTCCT TCAGTGCTAC CCCCTTCAGC
         GTTGTAACAG TACGGTGTTA AGTGTCTTCG ACACTCAGGA AGTCACGATG GGGGAAGTCG

+2 aLeuProLeu AspLeuLeuAsn AsnAlaIle ThrAlaPhe SerThrLeuGlu AspLeuIl
         ------------------------------------------------------------------
     661 TTTGCCACTG GACCTGCTTA ATAATGCTAT AACTGCCTTT AGTACCTTGG AAGACCTTAT
         AAACGGTGAC CTGGACGAAT TATTACGATA TTGACGGAAA TCATGGAACC TTCTGGAATA

+2 eArgTyrLeu GluProGluArg TrpGlnLeu AspLeuGlu AspLeuTyrArg ProThrTr
         ------------------------------------------------------------------
     721 TCGATATCTT GAACCAGAGA GATGGCAGTT GGACTTAGAA GATCTATATA GGCCAACTTG
         AGCTATAGAA CTTGGTCTCT CTACCGTCAA CCTGAATCTT CTAGATATAT CCGGTTGAAC

+2 pGlnLeuLeu GlyLysAlaPhe ValPheGly ArgLysSer ArgValValAsp LeuAsnLe
         ------------------------------------------------------------------
     781 GCAACTTCTT GGCAAGGCTT TTGTTTTTGG AAGAAAATCC AGAGTGGTGG ATCTGAACCT
         CGTTGAAGAA CCGTTCCGAA AACAAAAACC TTCTTTTAGG TCTCACCACC TAGACTTGGA

+2 uLeuThrGlu GluValArgLeu TyrSerCys ThrProArg AsnPheSerVal SerIleAr
         ------------------------------------------------------------------
     841 TCTAACAGAG GAGGTAAGAT TATACAGCTG CACACCTCGT AACTTCTCAG TGTCCATAAG
         AGATTGTCTC CTCCATTCTA ATATGTCGAC GTGTGGAGCA TTGAAGAGTC ACAGGTATTC

+2 gGluGluLeu LysArgThrAsp ThrIlePhe TrpProGly CysLeuLeuVal LysArgCy
         ------------------------------------------------------------------
     901 GGAAGAACTA AAGAGAACCG ATACCATTTT CTGGCCAGGT TGTCTCCTGG TTAAACGCTG
         CCTTCTTGAT TTCTCTTGGC TATGGTAAAA GACCGGTCCA ACAGAGGACC AATTTGCGAC

+2 sGlyGlyAsn CysAlaCysCys LeuHisAsn CysAsnGlu CysGlnCysVal ProSerLy
         ------------------------------------------------------------------
     961 TGGTGGGAAC TGTGCCTGTT GTCTCCACAA TTGCAATGAA TGTCAATGTG TCCCAAGCAA
         ACCACCCTTG ACACGGACAA CAGAGGTGTT AACGTTACTT ACAGTTACAC AGGGTTCGTT

+2 sValThrLys LysTyrHisGlu ValLeuGln LeuArgPro LysThrGlyVal ArgGlyLe
         ------------------------------------------------------------------
    1021 AGTTACTAAA AAATACCACG AGGTCCTTCA GTTGAGACCA AAGACCGGTG TCAGGGGATT
         TCAATGATTT TTTATGGTGC TCCAGGAAGT CAACTCTGGT TTCTGGCCAC AGTCCCCTAA

+2 uHisLysSer LeuThrAspVal AlaLeuGlu HisHisGlu GluCysAspCys ValCysAr
         ------------------------------------------------------------------
    1081 GCACAAATCA CTCACCGACG TGGCCCTGGA GCACCATGAG GAGTGTGACT GTGTGTGCAG
         CGTGTTTAGT GAGTGGCTGC ACCGGGACCT CGTGGTACTC CTCACACTGA CACACACGTC
```

Fig. 6-2

```
     +2 gGlySerThr GlyGly
        --------------->
1141 AGGGAGCACA GGAGGATAGC CGCATCACCA CCAGCAGCTC TTGCCCAGAG CTGTGCAGTG
     TCCCTCGTGT CCTCCTATCG GCGTAGTGGT GGTCGTCGAG AACGGGTCTC GACACGTCAC

1201 CAGTGGCTGA TTCTATTAGA GAACGTATGC GTTATCTCCA TCCTTAATCT CAGTTGTTTG
     GTCACCGACT AAGATAATCT CTTGCATACG CAATAGAGGT AGGAATTAGA GTCAACAAAC

1261 CTTCAAGGAC CTTTCATCTT CAGGATTTAC AGTGCATTCT GAAAGAGGAG ACATCAAACA
     GAAGTTCCTG GAAAGTAGAA GTCCTAAATG TCACGTAAGA CTTTCTCCTC TGTAGTTTGT

1321 GAATTAGGAG TTGTGCAACA GCTCTTTTGA GAGGAGGCCT AAAGGACAGG AGAAAAGGTC
     CTTAATCCTC AACACGTTGT CGAGAAAACT CTCCTCCGGA TTTCCTGTCC TCTTTTCCAG

1381 TTCAATCGTG GAAAGAAAAT TAAATGTTGT ATTAAATAGA TCACCAGCTA GTTTCAGAGT
     AAGTTAGCAC CTTTCTTTTA ATTTACAACA TAATTTATCT AGTGGTCGAT CAAAGTCTCA

1441 TACCATGTAC GTATTCCACT AGCTGGGTTC TGTATTTCAG TTCTTTCGAT ACGGCTTAGG
     ATGGTACATG CATAAGGTGA TCGACCCAAG ACATAAAGTC AAGAAAGCTA TGCCGAATCC

1501 GTAATGTCAG TACAGGAAAA AAACTGTGCA AGTGAGCACC TGATTCCGTT GCCTTGCTTA
     CATTACAGTC ATGTCCTTTT TTTGACACGT TCACTCGTGG ACTAAGGCAA CGGAACGAAT

1561 ACTCTAAAGC TCCATGTCCT GGGCCTAAAA TCGTATAAAA TCTGGATTTT TTTTTTTTTT
     TGAGATTTCG AGGTACAGGA CCCGGATTTT AGCATATTTT AGACCTAAAA AAAAAAAAAA

1621 TTTGCTCATA TTCACATATG TAAACCAGAA CATTCTATGT ACTACAAACC TGGTTTTTAA
     AAACGAGTAT AAGTGTATAC ATTTGGTCTT GTAAGATACA TGATGTTTGG ACCAAAAATT

1681 AAAGGAACTA TGTTGCTATG AATTAAACTT GTGTCGTGCT GATAGGACAG ACTGGATTTT
     TTTCCTTGAT ACAACGATAC TTAATTTGAA CACAGCACGA CTATCCTGTC TGACCTAAAA

1741 TCATATTTCT TATTAAAATT TCTGCCATTT AGAAGAAGAG AACTACATTC ATGGTTTGGA
     AGTATAAAGA ATAATTTTAA AGACGGTAAA TCTTCTTCTC TTGATGTAAG TACCAAACCT

1801 AGAGATAAAC CTGAAAAGAA GAGTGGCCTT ATCTTCACTT TATCGATAAG CCAGTTTATT
     TCTCTATTTG GACTTTTCTT CTCACCGGAA TAGAAGTGAA ATAGCTATTC GGTCAAATAA

1861 TGTTTCATTG TGTACATTTT TATATTCTCC TTTGACATT ATAACTGTTG GCTTTTCTAA
     ACAAAGTAAC ACATGTAAAA ATATAAGAGG AAAACTGTAA TATTGACAAC CGAAAAGATT

1921 TCTTGTTAAA TATATCTATT TTTACCAAAG GTATTTAATA TTCTTTTTTA TGACAACTTA
     AGAACAATTT ATATAGATAA AAATGGTTTC CATAAATTAT AAGAAAAAAT ACTGTTGAAT
```

Fig. 6-3

```
1981  GATCAACTAT TTTTAGCTTG GTAAATTTTT CTAAACACAA TTGTTATAGC CAGAGGAACA
      CTAGTTGATA AAAATCGAAC CATTTAAAAA GATTTGTGTT AACAATATCG GTCTCCTTGT

2041  AAGATGATAT AAAATATTGT TGCTCTGACA AAAATACATG TATTTCATTC TCGTATGGTG
      TTCTACTATA TTTTATAACA ACGAGACTGT TTTTATGTAC ATAAAGTAAG AGCATACCAC

2101  CTAGAGTTAG ATTAATCTGC ATTTTAAAAA ACTGAATTGG AATAGAATTG GTAAGTTGCA
      GATCTCAATC TAATTAGACG TAAAATTTTT TGACTTAACC TTATCTTAAC CATTCAACGT

2161  AAGACTTTTT GAAAATAATT AAATTATCAT ATCTTCCATT CCTGTTATTG GAGATGAAAA
      TTCTGAAAAA CTTTTATTAA TTTAATAGTA TAGAAGGTAA GGACAATAAC CTCTACTTTT

2221  TAAAAAGCAA CTTATGAAAG TAGACATTCA GATCCAGCCA TTACTAACCT ATTCCTTTTT
      ATTTTTCGTT GAATACTTTC ATCTGTAAGT CTAGGTCGGT AATGATTGGA TAAGGAAAAA

2281  TGGGGAAATC TGAGCCTAGC TCAGAAAAAC ATAAAGCACC TTGAAAAAGA CTTGGCAGCT
      ACCCCTTTAG ACTCGGATCG AGTCTTTTTG TATTTCGTGG AACTTTTTCT GAACCGTCGA

2341  TCCTGATAAA GCGTGCTGTG CTGTGCAGTA GGAACACATC CTATTTATTG TGATGTTGTG
      AGGACTATTT CGCACGACAC GACACGTCAT CCTTGTGTAG GATAAATAAC ACTACAACAC

2401  GTTTTATTAT CTTAAACTCT GTTCCATACA CTTGTATAAA TACATGGATA TTTTTATGTA
      CAAAATAATA GAATTTGAGA CAAGGTATGT GAACATATTT ATGTACCTAT AAAAATACAT

2461  CAGAAGTATG TCTCT
      GTCTTCATAC AGAGA
```

Fig. 6-4

NEW SEQUENCE + INCYTE ESTS

```
  1 ATTTGTTTAA ACCTTGGGAA ACTGGTTCAG GTCCAGGTTT TGCTTTGATC CTTTTCAAAA
    TAAACAAATT TGGAACCCTT TGACCAAGTC CAGGTCCAAA ACGAAACTAG GAAAAGTTTT

61 ACTGGAGACA CAGAAGAGGG CTTCTAGGAA AAAGTTTTGG GATGGGATTA TGTGGAAACT
    TGACCTCTGT GTCTTCTCCC GAAGATCCTT TTTCAAAACC CTACCCTAAT ACACCTTTGA

121 ACCCTGCGAT TCTCTGCTGC CAGAGCAGGC TCGGCGCTTC CACCCCAGTG CAGCCTTCCC
    TGGGACGCTA AGAGACGACG GTCTCGTCCG AGCCGCGAAG GTGGGGTCAC GTCGGAAGGG

181 CTGGCGGTGG TGAAAGAGAC TCGGGAGTCG CTGCTTCCAA AGTGCCCGCC GTGAGTGAGC
    GACCGCCACC ACTTTCTCTG AGCCCTCAGC GACGAAGGTT TCACGGGCGG CACTCACTCG

+2                      Met SerLeuPhe GlyLeuLeu LeuLeuThrSer AlaLeuAl
                         ]------------------------------------------
241 TCTCACCCCA GTCAGCCAAA TGAGCCTCTT CGGGCTTCTC CTGCTGACAT CTGCCCTGGC
    AGAGTGGGGT CAGTCGGTTT ACTCGGAGAA GCCCGAAGAG GACGACTGTA GACGGGACCG

+2 aGlyGlnArg GlnGlyThrGln AlaGluSer AsnLeuSer SerLysPheGln PheSerSe
    -----------------------------------------------------------------
301 CGGCCAGAGA CAGGGGACTC AGGCGGAATC CAACCTGAGT AGTAAATTCC AGTTTTCCAG
    GCCGGTCTCT GTCCCCTGAG TCCGCCTTAG GTTGGACTCA TCATTTAAGG TCAAAAGGTC

+2 rAsnLysGlu GlnTyrGlyVal GlnAspPro GlnHisGlu ArgIleIleThr ValSerTh
    -----------------------------------------------------------------
361 CAACAAGGAA CAGTACGGAG TACAAGATCC TCAGCATGAG AGAATTATTA CTGTGTCTAC
    GTTGTTCCTT GTCATGCCTC ATGTTCTAGG AGTCGTACTC TCTTAATAAT GACACAGATG

+2 rAsnGlySer IleHisSerPro ArgPhePro HisThrTyr ProArgAsnThr ValLeuVa
    -----------------------------------------------------------------
421 TAATGGAAGT ATTCACAGCC AAGGTTTCC TCATACTTAT CCAAGAAATA CGGTCTTGGT
    ATTACCTTCA TAAGTGTCGG GTTCCAAAGG AGTATGAATA GGTTCTTTAT GCCAGAACCA

+2 lTrpArgLeu ValAlaValGlu GluAsnVal TrpIleGln LeuThrPheAsp GluArgPh
    -----------------------------------------------------------------
481 ATGGAGATTA GTAGCAGTAG AGGAAAATGT ATGGATACAA CTTACGTTTG ATGAAAGATT
    TACCTCTAAT CATCGTCATC TCCTTTTACA TACCTATGTT GAATGCAAAC TACTTTCTAA
```

Fig. 7-1

```
    +2 eGlyLeuGlu AspProGluAsp AspIleCys LysTyrAsp PheValGluVal GluGluPr
       ------------------------------------------------------------------
541    TGGGCTTGAA GACCCAGAAG ATGACATATG CAAGTATGAT TTTGTAGAAG TTGAGGAACC
       ACCCGAACTT CTGGGTCTTC TACTGTATAC GTTCATACTA AAACATCTTC AACTCCTTGG

+2 oSerAspGly ThrIleLeuGly ArgTrpCys GlySerGly ThrValProGly LysGlnIl
       ------------------------------------------------------------------
601    CAGTGATGGA ACTATATTAG GGCGCTGGTG TGGTTCTGGT ACTGTACCAG GAAAACAGAT
       GTCACTACCT TGATATAATC CCGCGACCAC ACCAAGACCA TGACATGGTC CTTTTGTCTA

+2 eSerLysGly AsnGlnIleArg IleArgPhe ValSerAsp GluTyrPhePro SerGluPr
       ------------------------------------------------------------------
661    TTCTAAAGGA AATCAAATTA GGATAAGATT TGTATCTGAT GAATATTTTC CTTCTGAACC
       AAGATTTCCT TTAGTTTAAT CCTATTCTAA ACATAGACTA CTTATAAAAG GAAGACTTGG

+2 oGlyPheCys IleHisTyrAsn IleValMet ProGlnPhe ThrGluAlaVal SerProSe
       ------------------------------------------------------------------
721    AGGGTTCTGC ATCCACTACA ACATTGTCAT GCCACAATTC ACAGAAGCTG TGAGTCCTTC
       TCCCAAGACG TAGGTGATGT TGTAACAGTA CGGTGTTAAG TGTCTTCGAC ACTCAGGAAG

+2 rValLeuPro ProSerAlaLeu ProLeuAsp LeuLeuAsn AsnAlaIleThr AlaPheSe
       ------------------------------------------------------------------
781    AGTGCTACCC CCTTCAGCTT TGCCACTGGA CCTGCTTAAT AATGCTATAA CTGCCTTTAG
       TCACGATGGG GGAAGTCGAA ACGGTGACCT GGACGAATTA TTACGATATT GACGGAAATC

+2 rThrLeuGlu AspLeuIleArg TyrLeuGlu ProGluArg TrpGlnLeuAsp LeuGluAs
       ------------------------------------------------------------------
841    TACCTTGGAA GACCTTATTC GATATCTTGA ACCAGAGAGA TGGCAGTTGG ACTTAGAAGA
       ATGGAACCTT CTGGAATAAG CTATAGAACT TGGTCTCTCT ACCGTCAACC TGAATCTTCT

+2 pLeuTyrArg ProThrTrpGln LeuLeuGly LysAlaPhe ValPheGlyArg LysSerAr
       ------------------------------------------------------------------
901    TCTATATAGG CCAACTTGGC AACTTCTTGG CAAGGCTTTT GTTTTGGAA GAAAATCCAG
       AGATATATCC GGTTGAACCG TTGAAGAACC GTTCCGAAAA CAAAAACCTT CTTTTAGGTC

+2 gValValAsp LeuAsnLeuLeu ThrGluGlu ValArgLeu TyrSerCysThr ProArgAs
       ------------------------------------------------------------------
961    AGTGGTGGAT CTGAACCTTC TAACAGAGGA GGTAAGATTA TACAGCTGCA CACCTCGTAA
       TCACCACCTA GACTTGGAAG ATTGTCTCCT CCATTCTAAT ATGTCGACGT GTGGAGCATT

+2 nPheSerVal SerIleArgGlu GluLeuLys ArgThrAsp ThrIlePheTrp ProGlyCy
       ------------------------------------------------------------------
1021   CTTCTCAGTG TCCATAAGGG AAGAACTAAA GAGAACCGAT ACCATTTTCT GGCCAGGTTG
       GAAGAGTCAC AGGTATTCCC TTCTTGATTT CTCTTGGCTA TGGTAAAAGA CCGGTCCAAC
```

Fig. 7-2

```
      +2 sLeuLeuVal LysArgCysGly GlyAsnCys AlaCysCys LeuHisAsnCys AsnGluCy
         ----------------------------------------------------------------
    1081 TCTCCTGGTT AAACGCTGTG GTGGGAACTG TGCCTGTTGT CTCCACAATT GCAATGAATG
         AGAGGACCAA TTTGCGACAC CACCCTTGAC ACGGACAACA GAGGTGTTAA CGTTACTTAC

+2 sGlnCysVal ProSerLysVal ThrLysLys TyrHisGlu ValLeuGlnLeu ArgProLy
         ----------------------------------------------------------------
    1141 TCAATGTGTC CCAAGCAAAG TTACTAAAAA ATACCACGAG GTCCTTCAGT TGAGACCAAA
         AGTTACACAG GGTTCGTTTC AATGATTTTT TATGGTGCTC CAGGAAGTCA ACTCTGGTTT

+2 sThrGlyVal ArgGlyLeuHis LysSerLeu ThrAspVal AlaLeuGluHis HisGluGl
         ----------------------------------------------------------------
    1201 GACCGGTGTC AGGGGATTGC ACAAATCACT CACCGACGTG GCCCTGGAGC ACCATGAGGA
         CTGGCCACAG TCCCCTAACG TGTTTAGTGA GTGGCTGCAC CGGGACCTCG TGGTACTCCT

+2 uCysAspCys ValCysArgGly SerThrGly Gly
         ------------------------------------>
    1261 GTGTGACTGT GTGTGCAGAG GGAGCACAGG AGGATAGCCG CATCACCACC AGCAGCTCTT
         CACACTGACA CACACGTCTC CCTCGTGTCC TCCTATCGGC GTAGTGGTGG TCGTCGAGAA

1321 GCCCAGAGCT GTGCAGTGCA GTGGCTGATT CTATTAGAGA ACGTATGCGT TATCTCCATC
         CGGGTCTCGA CACGTCACGT CACCGACTAA GATAATCTCT TGCATACGCA ATAGAGGTAG

1381 CTTAATCTCA GTTGTTTGCT TCAAGGACCT TTCATCTTCA GGATTTACAG TGCATTCTGA
         GAATTAGAGT CAACAAACGA AGTTCCTGGA AAGTAGAAGT CCTAAATGTC ACGTAAGACT

1441 AAGAGGAGAC ATCAAACAGA ATTAGGAGTT GTGCAACAGC TCTTTTGAGA GGAGGCCTAA
         TTCTCCTCTG TAGTTTGTCT TAATCCTCAA CACGTTGTCG AGAAAACTCT CCTCCGGATT

1501 AGGACAGGAG AAAAGGTCTT CAATCGTGGA AAGAAAATTA AATGTTGTAT TAAATAGATC
         TCCTGTCCTC TTTTCCAGAA GTTAGCACCT TTCTTTTAAT TTACAACATA ATTTATCTAG

1561 ACCAGCTAGT TTCAGAGTTA CCATGTACGT ATTCCACTAG CTGGGTTCTG TATTTCAGTT
         TGGTCGATCA AAGTCTCAAT GGTACATGCA TAAGGTGATC GACCCAAGAC ATAAAGTCAA

1621 CTTTCGATAC GGCTTAGGGT AATGTCAGTA CAGGAAAAAA ACTGTGCAAG TGAGCACCTG
         GAAAGCTATG CCGAATCCCA TTACAGTCAT GTCCTTTTTT TGACACGTTC ACTCGTGGAC

1681 ATTCCGTTGC CTTGGCTTAA CTCTAAAGCT CCATGTCCTG GCCTAAAAT CGTATAAAAT
         TAAGGCAACG GAACCGAATT GAGATTTCGA GGTACAGGAC CCGGATTTTA GCATATTTTA

1741 CTGGATTTTT TTTTTTTTT TTGCGCATAT TCACATATGT AAACCAGAAC ATTCTATGTA
         GACCTAAAAA AAAAAAAAA AACGCGTATA AGTGTATACA TTTGGTCTTG TAAGATACAT

1801 CTACAAACCT GGTTTTAAA AAGGAACTAT GTTGCTATGA ATTAAACTTG TGTCATGCTG
         GATGTTTGGA CCAAAAATTT TTCCTTGATA CAACGATACT TAATTTGAAC ACAGTACGAC
```

Fig. 7-3

```
1861  ATAGGACAGA CTGGATTTTT CATATTTCTT ATTAAAATTT CTGCCATTTA GAAGAAGAGA
      TATCCTGTCT GACCTAAAAA GTATAAAGAA TAATTTTAAA GACGGTAAAT CTTCTTCTCT

1921  ACTACATTCA TGGTTTGGAA GAGATAAACC TGAAAAGAAG AGTGGCCTTA TCTTCACTTT
      TGATGTAAGT ACCAAACCTT CTCTATTTGG ACTTTTCTTC TCACCGGAAT AGAAGTGAAA

1981  ATCGATAAGT CAGTTTATTT GTTTCATTGT GTACATTTTT ATATTCTCCT TTTGACATTA
      TAGCTATTCA GTCAAATAAA CAAAGTAACA CATGTAAAAA TATAAGAGGA AAACTGTAAT

2041  TAACTGTTGG CTTTTCTAAT CTTGTTAAAT ATATCTATTT TTACCAAAGG TATTTAATAT
      ATTGACAACC GAAAAGATTA GAACAATTTA TATAGATAAA AATGGTTTCC ATAAATTATA

2101  TCTTTTTTAT GACAACTTAG ATCAACTATT TTTAGCTTGG TAAATTTTTC TAAACACAAT
      AGAAAAAATA CTGTTGAATC TAGTTGATAA AAATCGAACC ATTTAAAAAG ATTTGTGTTA

2161  TGTTATAGCC AGAGGAACAA AGATGATATA AAATATTGTT GCTCTGACAA AAATACATGT
      ACAATATCGG TCTCCTTGTT TCTACTATAT TTTATAACAA CGAGACTGTT TTTATGTACA

2221  ATTTCATTCT CGTATGGTGC TAGAGTTAGA TTAATCTGCA TTTTAAAAAA CTGAATTGGA
      TAAAGTAAGA GCATACCACG ATCTCAATCT AATTAGACGT AAAATTTTTT GACTTAACCT

2281  ATAGAATTGG TAAGTTGCAA AGACTTTTTG AAAATAATTA AATTATCATA TCTTCCATTC
      TATCTTAACC ATTCAACGTT TCTGAAAAAC TTTTATTAAT TTAATAGTAT AGAAGGTAAG

2341  CTGTTATTGG AGATGAAAAT AAAAAGCAAC TTATGAAAGT AGACATTCAG ATCCAGCCAT
      GACAATAACC TCTACTTTTA TTTTTCGTTG AATACTTTCA TCTGTAAGTC TAGGTCGGTA

2401  TACTAACCTA TTCCTTTTTT GGGGAAATCT GAGCCTAGCT CAGAAAAACA TAAAGCACCT
      ATGATTGGAT AAGGAAAAAA CCCCTTTAGA CTCGGATCGA GTCTTTTTGT ATTTCGTGGA

2461  TGAAAAAGAC TTGGCAGCTT CCTGATAAAG CGTGCTGTGC TGTGCAGTAG GAACACATCC
      ACTTTTTCTG AACCGTCGAA GGACTATTTC GCACGACACG ACACGTCATC CTTGTGTAGG

2521  TATTTATTGT GATGTTGTGG TTTTATTATC TTAAACTCTG TTCCATACAC TTGTATAAAT
      ATAAATAACA CTACAACACC AAAATAATAG AATTTGAGAC AAGGTATGTG AACATATTTA

2581  ACATGGATAT TTTTATGTAC AGAAGTATGT CTCTTAACCA GTTCACTTAT TGTACTCTGG
      TGTACCTATA AAAATACATG TCTTCATACA GAGAATTGGT CAAGTGAATA ACATGAGACC

2641  CAATTTAAAA GAAAATCAGT AAAATATTTT GCTTGTAAAA TGCTTAATAT CGTGCCTAGG
      GTTAAATTTT CTTTTAGTCA TTTTATAAAA CGAACATTTT ACGAATTATA GCACGGATCC

2701  TTATGTGGTG ACTATTTGAA TCAAAAATGT ATTGAATCAT CAAATAAAAG AATGTGGCTA
      AATACACCAC TGATAAACTT AGTTTTTACA TAACTTAGTA GTTTATTTTC TTACACCGAT

2761  TTTTGGGGAG AAAATT
      AAAACCCCTC TTTTAA
```

Fig. 7-4

ADDITIONAL OLIGONUCLEOTIDES USED FOR AMPLIFICATION
OF ENTIRE CODING REGION

5'-1   TTTGTTTAAACCTTGGGAAACTGG

5'-2   GTCCAGGTTTTGCTTTGATCC

Fig. 8

DNA SEQUENCE OF CLONES 4 & 7, IDENTICAL CLONES CONTAINING THE
ENTIRE OPEN READING FRAME

```
  1  TTTGTTTAAA CCTTGGGAAA CTGGTTCAGG TCCAGGTTTT GCTTTGATCC TTTTCAAAAA
     AAACAAATTT GGAACCCTTT GACCAAGTCC AGGTCCAAAA CGAAACTAGG AAAAGTTTTT

61  CTGGAGACAC AGAAGAGGGC TCTAGGAAAA AGTTTTGGAT GGGATTATGT GGAAACTACC
     GACCTCTGTG TCTTCTCCCG AGATCCTTTT TCAAAACCTA CCCTAATACA CCTTTGATGG

121  CTGCGATTCT CTGCTGCCAG AGCAGGCTCG GCGCTTCCAC CCCAGTGCAG CCTTCCCCTG
     GACGCTAAGA GACGACGGTC TCGTCCGAGC CGCGAAGGTG GGGTCACGTC GGAAGGGGAC

181  GCGGTGGTGA AAGAGACTCG GGAGTCGCTG CTTCCAAAGT GCCCGCCGTG AGTGAGCTCT
     CGCCACCACT TTCTCTGAGC CCTCAGCGAC GAAGGTTTCA CGGGCGGCAC TCACTCGAGA

+2                       MetSer LeuPheGly LeuLeuLeu LeuThrSerAla LeuAlaGl
                          ]------------------------------------------------
241  CACCCCAGTC AGCCAAATGA GCCTCTTCGG GCTTCTCCTG CTGACATCTG CCCTGGCCGG
     GTGGGGTCAG TCGGTTTACT CGGAGAAGCC CGAAGAGGAC GACTGTAGAC GGGACCGGCC

+2 yGlnArgGln GlyThrGlnAla GluSerAsn LeuSerSer LysPheGlnPhe SerSerAs
    ------------------------------------------------------------------
301  CCAGAGACAG GGGACTCAGG CGGAATCCAA CCTGAGTAGT AAATTCCAGT TTTCCAGCAA
     GGTCTCTGTC CCCTGAGTCC GCCTTAGGTT GGACTCATCA TTTAAGGTCA AAAGGTCGTT

+2 nLysGluGln AsnGlyValGln AspProGln HisGluArg IleIleThrVal SerThrAs
    ------------------------------------------------------------------
361  CAAGGAACAG AACGGAGTAC AAGATCCTCA GCATGAGAGA ATTATTACTG TGTCTACTAA
     GTTCCTTGTC TTGCCTCATG TTCTAGGAGT CGTACTCTCT TAATAATGAC ACAGATGATT

+2 nGlySerIle HisSerProArg PheProHis ThrTyrPro ArgAsnThrVal LeuValTr
    ------------------------------------------------------------------
421  TGGAAGTATT CACAGCCCAA GGTTTCCTCA TACTTATCCA AGAAATACGG TCTTGGTATG
     ACCTTCATAA GTGTCGGGTT CCAAAGGAGT ATGAATAGGT TCTTTATGCC AGAACCATAC

+2 pArgLeuVal AlaValGluGlu AsnValTrp IleGlnLeu ThrPheAspGlu ArgPheGl
    ------------------------------------------------------------------
481  GAGATTAGTA GCAGTAGAGG AAAATGTATG GATACAACTT ACGTTTGATG AAAGATTTGG
     CTCTAATCAT CGTCATCTCC TTTTACATAC CTATGTTGAA TGCAAACTAC TTTCTAAACC

+2 yLeuGluAsp ProGluAspAsp IleCysLys TyrAspPhe ValGluValGlu GluProSe
    -----------------------------------------------------------------
541  GCTTGAAGAC CCAGAAGATG ACATATGCAA GTATGATTTT GTAGAAGTTG AGGAACCCAG
     CGAACTTCTG GGTCTTCTAC TGTATACGTT CATACTAAAA CATCTTCAAC TCCTTGGGTC
```

Fig. 9-1

```
     +2 rAspGlyThr IleLeuGlyArg TrpCysGly SerGlyThr ValProGlyLys GlnIleSe
        ----------------------------------------------------------------
    601 TGATGGAACT ATATTAGGGC GCTGGTGTGG TTCTGGTACT GTACCAGGAA AACAGATTTC
        ACTACCTTGA TATAATCCCG CGACCACACC AAGACCATGA CATGGTCCTT TTGTCTAAAG

+2 rLysGlyAsn GlnIleArgIle ArgPheVal SerAspGlu TyrPheProSer GluProGl
        ----------------------------------------------------------------
    661 TAAAGGAAAT CAAATTAGGA TAAGATTTGT ATCTGATGAA TATTTTCCTT CTGAACCAGG
        ATTTCCTTTA GTTTAATCCT ATTCTAAACA TAGACTACTT ATAAAAGGAA GACTTGGTCC

+2 yPheCysIle HisTyrAsnIle ValMetPro GlnPheThr GluAlaValSer ProSerVa
        ----------------------------------------------------------------
    721 GTTCTGCATC CACTACAACA TTGTCATGCC ACAATTCACA GAAGCTGTGA GTCCTTCAGT
        CAAGACGTAG GTGATGTTGT AACAGTACGG TGTTAAGTGT CTTCGACACT CAGGAAGTCA

+2 lLeuProPro SerAlaLeuPro LeuAspLeu LeuAsnAsn AlaIleThrAla PheSerTh
        ----------------------------------------------------------------
    781 GCTACCCCCT TCAGCTTTGC CACTGGACCT GCTTAATAAT GCTATAACTG CCTTTAGTAC
        CGATGGGGGA AGTCGAAACG GTGACCTGGA CGAATTATTA CGATATTGAC GGAAATCATG

+2 rLeuGluAsp LeuIleArgTyr LeuGluPro GluArgTrp GlnLeuAspLeu GluAspLe
        ----------------------------------------------------------------
    841 CTTGGAAGAC CTTATTCGAT ATCTTGAACC AGAGAGATGG CAGTTGGACT TAGAAGATCT
        GAACCTTCTG GAATAAGCTA TAGAACTTGG TCTCTCTACC GTCAACCTGA ATCTTCTAGA

+2 uTyrArgPro ThrTrpGlnLeu LeuGlyLys AlaPheVal PheGlyArgLys SerArgVa
        ----------------------------------------------------------------
    901 ATATAGGCCA ACTTGGCAAC TTCTTGGCAA GGCTTTTGTT TTTGGAAGAA AATCCAGAGT
        TATATCCGGT TGAACCGTTG AAGAACCGTT CCGAAAACAA AAACCTTCTT TTAGGTCTCA

+2 lValAspLeu AsnLeuLeuThr GluGluVal ArgLeuTyr SerCysThrPro ArgAsnPh
        ----------------------------------------------------------------
    961 GGTGGATCTG AACCTTCTAA CAGAGGAGGT AAGATTATAC AGCTGCACAC CTCGTAACTT
        CCACCTAGAC TTGGAAGATT GTCTCCTCCA TTCTAATATG TCGACGTGTG GAGCATTGAA

+2 eSerValSer IleArgGluGlu LeuLysArg ThrAspThr IlePheTrpPro GlyCysLe
        ----------------------------------------------------------------
   1021 CTCAGTGTCC ATAAGGGAAG AACTAAAGAG AACCGATACC ATTTCTGGC CAGGTTGTCT
        GAGTCACAGG TATTCCCTTC TTGATTTCTC TTGGCTATGG TAAAGACCG GTCCAACAGA

+2 uLeuValLys ArgCysGlyGly AsnCysAla CysCysLeu HisAsnCysAsn GluCysGl
        ----------------------------------------------------------------
   1081 CCTGGTTAAA CGCTGTGGTG GGAACTGTGC CTGTTGTCTC CACAATTGCA ATGAATGTCA
        GGACCAATTT GCGACACCAC CCTTGACACG GACAACAGAG GTGTTAACGT TACTTACAGT
```

Fig. 9-2

```
     +2 nCysValPro SerLysValThr LysLysTyr HisGluVal LeuGlnLeuArg ProLysTh
        -----------------------------------------------------------------
   1141 ATGTGTCCCA AGCAAAGTTA CTAAAAAATA CCACGAGGTC CTTCAGTTGA GACCAAAGAC
        TACACAGGGT TCGTTTCAAT GATTTTTTAT GGTGCTCCAG GAAGTCAACT CTGGTTTCTG

+2 rGlyValArg GlyLeuHisLys SerLeuThr AspValAla LeuGluHisHis GluGluCy
        -----------------------------------------------------------------
   1201 CGGTGTCAGG GGATTGCACA AATCACTCAC CGACGTGGCC CTGGAGCACC ATGAGGAGTG
        GCCACAGTCC CCTAACGTGT TTAGTGAGTG GCTGCACCGG GACCTCGTGG TACTCCTCAC

+2 sAspCysVal CysArgGlySer ThrGlyGly
        ---------------------------------->
   1261 TGACTGTGTG TGCAGAGGGA GCACAGGAGG ATAGCCGCAT CACCACCAGC AGCTCTTGCC
        ACTGACACAC ACGTCTCCCT CGTGTCCTCC TATCGGCGTA GTGGTGGTCG TCGAGAACGG

1321 CAGAGCTGTG CAGTGCAGTG GCTGATTCTA TTAGAGAACG TATGCGTTAT CTCCATCCTT
        GTCTCGACAC GTCACGTCAC CGACTAAGAT AATCTCTTGC ATACGCAATA GAGGTAGGAA

1381 AATCTCAGTT GTTTGCTTCA AGGACCTTTC ATCTTCAGGA TTTACAGTGC ATTCTGAAAG
        TTAGAGTCAA CAAACGAAGT TCCTGGAAAG TAGAAGTCCT AAATGTCACG TAAGACTTTC

1441 AGGAGACATC AAACAGAATT AGGAGTTGTG CAA
        TCCTCTGTAG TTTGTCTTAA TCCTCAACAC GTT
```

Fig. 9-3

PREDICTED FULL-LENGTH POLYPEPTIDE SEQUENCE

```
  1  MSLFGLLLLT  SALAGQRQGT  QAESNLSSKF  QFSSNKEQYG  VQDPQHERII

51  TVSTNGSIHS  PRFPHTYPRN  TVLVWRLVAV  EENVWIQLTF  DERFGLEDPE

101  DDICKYDFVE  VEEPSDGTIL  GRWCGSGTVP  GKQISKGNQI  RIRFVSDEYF

151  PSEPGFCIHY  NIVMPQFTEA  VSPSVLPPSA  LPLDLLNNAI  TAFSTLEDLI

201  RYLEPERWQL  DLEDLYRPTW  QLLGKAFVFG  RKSRVVDLNL  LTEEVRLYSC

251  TPRNFSVSIR  EELKRTDTIF  WPGCLLVKRC  GGNCACCLHN  CNECQCVPSK

301  VTKKYHEVLQ  LRPKTGVRGL  HKSLTDVALE  HHEECDCVCR  GSTGG
```

Fig. 10

ALIGNMENT OF VEGF-X WITH OTHER VEGFs

```
                        *        20         *        40         *
VEGF_HUMAN  : -------------------------------------------------- :   -
PLGF_HUMAN  : -------------------------------------------------- :   -
VEGB_HUMAN  : -------------------------------------------------- :   -
VEGC_HUMAN  : -------------------------------------------------- :   -
VEGD_HUMAN  : -------------------------------------------------- :   -
990126vegx  : MSLFGLLLLTSALAGQRQGTQAESNLSSKFQFSSNKEQNGVQDPQHERII :  50

*        60         *        80         *       100
VEGF_HUMAN  : -------------------------------------------------- :   -
PLGF_HUMAN  : -------------------------------------------------- :   -
VEGB_HUMAN  : -------------------------------------------------- :   -
VEGC_HUMAN  : -------------------------------------------------- :   -
VEGD_HUMAN  : -------------------------------------------------- :   -
990126vegx  : TVSTNGSIHSPRFPHTYPRNTVLVWRLVAVEENVWIQLTFDERFGLEDPE : 100

*       120         *       140         *
VEGF_HUMAN  : -------------------------------------------------- :   -
PLGF_HUMAN  : -------------------------------------------------- :   -
VEGB_HUMAN  : -------------------------------------------------- :   -
VEGC_HUMAN  : -------------------MHLLGFFSVACSLLAAALLPGPREAPAAAA :  30
VEGD_HUMAN  : ----------------------------------------MYREWVVVNV :  10
990126vegx  : DDICKYDFVEV--EEPSDGTILGRWCGSGTVPGKQISKGNQIRIRFVSDE : 148

*       160         *       180         *       200
VEGF_HUMAN  : ----------------------------------------------MN :   2
PLGF_HUMAN  : ----------------------------------------------MP :   2
VEGB_HUMAN  : -------------------------------------------------- :   -
VEGC_HUMAN  : AFESGLDLSDAEPDAGEATAYASKDLEEQLRSVSSVDELMTVLYPEYWKM :  80
VEGD_HUMAN  : FMMLYVQLVQGSSNEHGPVKRSSQSTLERSEQQIRAASSLEELLRITHSE :  60
990126vegx  : YFPSEPGFCIHYNIVMPQFTEAVSPSVLPPSALPLDLLNNAITAFSTLED : 198

*       220         *       240         *
VEGF_HUMAN  : FLLSWVHWSLALLLYLHHAKWSQAAPMAEGGGQNHHEVVKFMD-VYQRSY :  51
PLGF_HUMAN  : VMRLFPCFLQLLAGLALPAVPPQQWALSAGNGSSEVEVVPFQE-VWGRSY :  51
VEGB_HUMAN  : ---MSPLLRRLLLAALLQLAPAQAPVSQPDAPGHQRKVVSWID-VYTRAT :  46
VEGC_HUMAN  : YKCQLRKGGWQHNREQANLNSRTEETIKFAAAHYNTEILKSIDNEWRKTQ : 130
VEGD_HUMAN  : DWKLWRCRLRLKSFTSMDSRSASHRSTRFAATFYDIETLKVIDEEWQRTQ : 110
990126vegx  : LIRYLEPERWQLDLEDLYRPTWQLLGKAFVFGRKSRVVDLNLLTEEVRLY : 248
```

Fig. 11-1

```
                         260         *         280    ⊛    *         300
VEGF_HUMAN   : CHPIETLVDIFQEYPDEIEYIFKPSCVPLMRCGG---CCND--EGLECVP :  96
PLGF_HUMAN   : CRALERLVDVVSEYPSEVEHMFSPSCVSLLRCTG---CCGD--ENLHCVP :  96
VEGB_HUMAN   : CQPREVVVPLTVELMGTVAKQLVPSCVTVQRCGG---CCPD--DGLECVP :  91
VEGC_HUMAN   : CMPREVCIDVGKEFGVATNTFFKPPCVSVYRCGG---CCNS--EGLQCMN : 175
VEGD_HUMAN   : CSPRETCVEVASELGKSTNTFFKPPCVNVFRCGG---CCNE--ESLICMN : 155
990126vegx   : SCTPRNFSVSIRDELKRTDTIFWPGCLLVKRCGSNCACCLHNCNECQCVP : 298

*         320         *         340         *
VEGF_HUMAN   : TEESNITMQIMRIKPHQG-----QHIGEMSFLQHNKCECRPKKDRARQEK : 141
PLGF_HUMAN   : VETANVTMQLLKIRSGDR-----PSYVELTFSQHVRCECRPLREKMKPER : 141
VEGB_HUMAN   : TGQHQVRMQILMIRYPS------SQLGEMSLEEHSQCECRPKKKDSAVKP : 135
VEGC_HUMAN   : TSTSYLSKTLFEITVPLSQG---PKPVTISFANHTSCRCMSKLDVYRQVH : 222
VEGD_HUMAN   : TSTSYISKQLFEISVPLTSV---PELVPVKVANHTGCKCLPTAPRHPYSI : 202
990126vegx   : SKVTKKYHEVLQLRPKTGVRGLHKSLTDVALEHHEECDCVCRGSTGG--- : 345

360         *         380         *         400
VEGF_HUMAN   : KSVRGKGKGQKRKRKKSRYKSWSVP------------------------- : 166
PLGF_HUMAN   : -------------------------------------------------- :   -
VEGB_HUMAN   : DSPR---------------------------------------------- : 139
VEGC_HUMAN   : SIIRRSLPATLPQCQAANKTCPTNYMWNNHICRCLAQEDFMFSSDAGDDS : 272
VEGD_HUMAN   : IRRSIQIPEEDRCSHSKKLCPIDMLWDSNKCKCVLQEENPLAGT------ : 246
990126vegx   : -------------------------------------------------- :   -

*         420         *         440         *
VEGF_HUMAN   : -------------------------------------------------- :   -
PLGF_HUMAN   : -------------------------------------------------- :   -
VEGB_HUMAN   : -------------------------------------------------- :   -
VEGC_HUMAN   : TDGFHDICGPNKELDEETCQCVCRAGLRPASCGPHKELDRNSCQCVCKNK : 322
VEGD_HUMAN   : -----------------------------------EDHSHLQEPALCGP : 260
990126vegx   : -------------------------------------------------- :   -

460         *         480         *         500
VEGF_HUMAN   : ---------CGPCSERRKHLFVQDPQTCKC-SCKNTDSRCKARQLELNER : 206
PLGF_HUMAN   : ---------CGDAVPRR--------------------------------- : 149
VEGB_HUMAN   : ---------PLCPRCTQHHQRPDPRTCRCRCRRRSFLRCQGRGLELNPD : 179
VEGC_HUMAN   : LFPSQCGANREFDENTCQCVCKRTCPRNQPLNPGKCACECTESPQKCLLK : 372
VEGD_HUMAN   : HMMFDEDRCECVCKTPCPKDLIQHPKNCSCFECKESLETCCQKHKLFHPD : 310
990126vegx   : -------------------------------------------------- :   -
```

Fig. 11-2

```
                    *         520         *         540         *
VEGF_HUMAN  : TCRCDKPRR---------------------------------------- : 215
PLGF_HUMAN  : ------------------------------------------------- :   -
VEGB_HUMAN  : TCRCRKLRR---------------------------------------- : 188
VEGC_HUMAN  : GKKFHHQTCSCYRRPCTNRQKACEPGFSYSEEVCRCVPSYWKRPQMS--- : 419
VEGD_HUMAN  : TCSCEDRCPFHTRPCASGKTACAKHCRFPKEKRAAQGPHSRKNP------ : 354
990126vegx  : ------------------------------------------------- :   -
```

Fig. 11-3

VARIANT POLYPEPTIDE SEQUENCES

```
                          *        20         *        40         *
FL_seq   : MSLFGLLLLTSALAGQRQGTQAESNLSSKFQFSSNKEQNGVQDPQHERII  :  50
clone41  : MSLFGLLLLTSALAGQRQGTQAESNLSSKFQFSSNKEQNGVQDPQHERII  :  50
clone20  : MSLFGLLLLTSALAGQRQGTQAESNLSSKFQFSSNKEQNGVQDPQHERII  :  50

60         *        80         *       100
FL_seq   : TVSTNGSIHSPRFPHTYPRNTVLVWRLVAVEENVWIQLTFDERFGLEDPE  : 100
clone41  : TVSTNGSIHSPRFPHTYPRNTVLVWRLVAVEENVWIQLTFDERFGLEDPE  : 100
clone20  : TVSTNGSIHSPRFPHTYPRNTVLVWRLVAVEENVWIQLTFDERFGLEDPE  : 100

*       120         *       140         *
FL_seq   : DDICKYDFVEVEEPSDGTILGRWCGSGTVPGKQISKGNQIRIRFVSDEYF  : 150
clone41  : DDICKYDFVEVEEPSDGTILGRWCGSGTVPGKQISKGNQIRIRFVSDEYF  : 150
clone20  : DDICKYDFVEVEEPSDGTILGRWCGSGTVPGKQISKGNQIRIRFVSDEYF  : 150

160         *       180         *       200
FL_seq   : PSEPGFCIHYNIVMPQFTEAVSPSVLPPSALPLDLLNNAITAFSTLEDLI  : 200
clone41  : PSEPSNRGGKIIQLHTS---------------------------------  : 167
clone20  : PSEPGFCIHYNIVMPQFTEAVSPSVLPPSALPLDLLNNAITAFSTLEDLI  : 200

*       220         *       240         *
FL_seq   : RYLEPERWQLDLEDLYRPTWQLLGKAFVFGRKSRVVDLNLLTEEVRLYSC  : 250
clone41  : --------------------------------------------------  :   -
clone20  : RYLEPERWQLDLEDLYRPTWQLLGKAFVFGRKSRVVDLNLLTE-------  : 243

260         *       280         *       300
FL_seq   : TPRNFSVSIREELKRTDTIFWPGCLLVKRCGGNCACCLHNCNECQCVPSK  : 300
clone41  : --------------------------------------------------  :   -
clone20  : --------------------------------------------------  :   -

*       320         *       340
FL_seq   : VTKKYHEVLQLRPKTGVRGLHKSLTDVALEHHEECDCVCRGSTGG     : 345
clone41  : ---------------------------------------------     :   -
clone20  : ------EVLQLRPKTGVRGLHKSLTDVALEHHEECDCVCRGSTGG     : 282
```

Fig. 12

PRIMERS FOR EXPRESSION OF VEGF-X

E. coli EXPRESSION OF DOMAINvegx-6   AATTGGATCCGAGAGTGGTGGATCTGAACC vegx-7   AATTGGATCCGGGAAGAAAATCCAGAGTGG vegx-8   GGTTGAATTCATTATTTTTAGTAACTTTGCTTGGGACAC vegx-9   AATTGAATTCATTATCCTCCTGTGCTCCCTC

BACULOVIRUS/INSECT CELL EXPRESSION OF FULL-LENGTH PROTEIN-vegbac1
AATTGGATCCGGAGTCTCACCATCACCACCATCATGAATCCAACCTGAGTAGTAAATTCC vegbac2
AATTGAATTCGCTATCCTCCTGTGCTCCCTCTGC

Fig. 13

```
 1  >3993180H1   LUNGNON03   INCYTE
 2  CACAAATCACTCACCGACGTGGCCCTGGAGCACCATGAGGNGTGTGACTGTGTGTGCAGAGG
 3  GAGCACAGGAGGATAGCCGCATCACCACCAGCAGCTCTTGCCCAGAGCTGTGCAGTGCAGTG
 4  GCTGATTCTATTAGAGAACGTATGCGTTATCTCCATCCTTAATCTCAGTTGTTTGCTTCAAG
 5  GACCTTTCATCTTCAGGATTTACAGTGCATTCTGAAAGAGGAGACATCAAACAGAATTAGGA
 6  GTTGTGCAACAGCTCTTTTGAGAGGAGGCTAAAGGACAGGAGAANAGGTCTT
 7  >3510192H1   CONCNOT01   INCYTE
 8  TGCAGTGCAGTGGCTGATTCTATTAGAGAACGTATGCGTTATCTCCATCCTTAATCTCAGTT
 9  GTTTGCTTCAAGGACCTTTCATCTTCAGGATTTACAGTGCATTCTGAAAGAGGAGACATCAA
10  ACAGAATTAGGAGTTGTGCAACAGCTCTTTTGAGAGGAGGCCTAAAGGACAGGAGAAAAGGT
11  CTTCAATCGTGGAAAGAAAATTAAATGTTGTATTAAATAGATCACCAGCTAGTTTCAGAGTT
12  ACCATGTACGTATTCCACTAGCTGGGTTCTGTATTT
13  >2559870H1   ADRETUT01   INCYTE
14  CACGAGGTCCTTCAGTTGAGACCAAAGACCGGTGTCAGGGGATTGCACAAATCACTCACCGA
15  CGTGGCCCTGGAGCACCATGAGGAGTGTGACTGTGTGTGCAGAGGGAGCACAGGGGATAGC
16  CGCATCACCACCAGCAGCTCTTGCCCAGAGCTGTGCAGTGCAGTGGCTGATTCTATTAGAGA
17  ACGTATGCGTTATCTCCATCCTTAATCTCAGTTGTTTGCTTCAAGGACCTTTCATCTTCAGG
18  ATTTACAGTGCATTCTGAAAGAGGAGA
19  >3979767H1   LUNGTUT08   INCYTE
20  GGAGGATAGCCGCATCACCACCAGCAGCTCTTGCCCAGAGCTGTGCAGTGCAGTGGCTGATT
21  CTATTAGAGAACGTATGCGTTATCTCCATCCTTAATCTCAGTTGTTTGCTTCAAGGACCTTT
22  CATCTTCAGGATTTACAGTGCATTCTGAAAGAGGAGACATCAAACAGAATTAGGAGTTGTGC
23  AACAGCTCTTTTGAGAGGAGGCCTAAAGGACAGGAGAAAAGGTCTTCAATCGTGGAAAGAAN
24  ATTAAATGTTGTATTAAATAGACACCAGCT
25  >3980011H1   LUNGTUT08   INCYTE
26  GGAGGATAGCCGCATCACCACCAGCAGCTCTTGCCCAGAGCTGTGCAGTGCAGTGGCTGATT
27  CTATTAGAGAACGTATGCGTTATCTCCATCCTTAATCTCAGTTGTTTGCTTCAAGGACCTTT
28  CATCTTCAGGATTTACATGCATTCTGAAAGAGGAGACATCAAACAGAATTAGGAGTTGTGCA
29  ACAGCTCTTTTGAGAGGAGGCCTAAAGGACAGGAGAAAAGGTCTTCAATCGTGGAAAGAAAA
30  TTAAATGTTGTATTAAATAGATCACCA
31  >4825396H1   BLADDIT01   INCYTE
32  GAGAACCGATACCATTTTCTGGCCAGGTTGTCTCCTGGTTAAACGCTGTGGTGGGAACTGTG
33  CCTGTTGTCTCCACAATTGCAATGAATGTCAATGTGTCCCAAGCAAAGTTACTAAAAAATAC
34  CACGAGGTCCTTCAGTTGAGACCAAAGACCGGTGTCAGGGGATTGCACAAATCACTCACCGA
35  CGTGGCCCTGGAGCACCATGAGGAGTGTGACTGTGTGTGCAGAGGGAGCACAGGAGGATAGC
36  CGCATCACCACCA
37  >3073703H1   BONEUNT01   INCYTE
38  AGAAAATCCAGAGTGGTGGATCTGAACCTTCTAACAGAGGAGGTAAGATTATACAGCTGCAC
39  ACCTCGTAACTTCTCAGTGTCCATAAGGGAAGAACTAAAGAGAACCGATACCATTTTCTGGC
40  CAGGTTGTCTCCTGGTTAAACGCTGTGGTGGGAACTGTGCCTGTTGTCTCCACAATTGCAAT
41  GAATGTCAATGTGTCCCAAGCAAAGTTACTAAAAAATACCACGAGGTCCTTCAGTTGAGACC
42  AAAGACCGGTGTCAGGGGATTGCACAAATCA
```

Fig. 14-1

```
 43 >1302516H1   PLACNOT02   INCYTE
 44 AGGAAATCAAATTAGGATAAGATTTGTATCTGATGAATATTTTCCTTCTGAACCTTCTAACA
 45 GAGGAGGTAAGATTATACAGCTGCACACCTCGTAACTTCTCAGTGTCCATAAGGGAAGAACT
 46 AAAGAGAACCGATACCATTTTCTGGCCAGGTTGTCTCCTGGTTAAACGCTGTGGTGGGAACT
 47 GTGCCTGTTGTCTCCCACAATTGCAATGAATGTCAATGTGTCCCAAGCAAAGTTACTAAAAA
 48 ATACCACGAGGTCC
 49 >3684109H1   HEAANOT01   INCYTE
 50 ATTTCATCTTCAGGATTTACAGTGCATTCTGAAANAGGAGAAATCAAACANAATTAGGAGTT
 51 GTGCAACAGCTCTTTTGAGAGGAGGCCTAAAGGACAGGAGAAAAGGTCTTCAATCGTGGAAA
 52 NAAAATTAAATGTTGTATTAAATAGATCACCAGCTAGTTTCAGAGTTACCATGTACGTATTC
 53 CACTAGCTGGGTTCTGTATTTCAGTTCTTTCGATACGGCTTAGGGTAATGTCAGTACAGGAA
 54 AAAAACTGTGCAAGTGAGCACCTGATTCCGTTGCCTTGCTT
 55 >4713188H1   BRAIHCT01   INCYTE
 56 CAAAGTTACTAAAAAATACCACGAGGTCCTTCAGTTGAGACCAAAGACCGGTGTCAGGGGAT
 57 TGCACAAATCACTCACCGACGTGGCCCTGGAGCACCATGAGGAGTGTGACTGTGTGTGCAGA
 58 GGGAGCACAGGAGGATAGCCGCATCACCACCAGCAGCTCTTGCCCAGAGCTGTGCAGTGCAG
 59 TGGCTGATTCTATTAGAGAACGTATGCGTTATCTCCATCCTTAATCTCAGTTGTTTGCT
 60 >458823H1   KERANOT01   INCYTE
 61 ANGAGTTGCCCAGAGCTGTGCAGTGCAGTGGCTGATTCTATTAGAGAACGTATGCGTTATCT
 62 CCATCCTTAATCTCAGTTGTTTGNTTCAAGGACCTTTCATCTTCAGGATTTACAGTGCATTC
 63 TGAAAGAGGAGACATCAAACAGAATTAGGAGTTGTGCAACAGCTCTTTTGAGAGGAGGCCTA
 64 AAGGNCAGGAGAAAAGGTCTTCAATCGTGGAAAGAAAATTAAATGTTGTATTAAATAGATC
 65 >1303909H1   PLACNOT02   INCYTE
 66 AGGAAATCAAATTAGGATAAGATTTGTATCTGATGAATATTTTCCTTCTGAACCTTCTAACA
 67 GAGGAGGTAAGATTATACAGCTGCACACCTCGTAACTTCTCAGTGTCCATAAGGGAAGAACT
 68 AAAGAGAACCGATACCATTTTCTGGCCAGGTTGTCTCCTGGTTAAACGCTGTGGTGGGAACT
 69 GTGCCTGTTGTCTCCCACAATTGCAATGAATGTCAATGTGTCCCAAG
 70 >2739211H1   OVARNOT09   INCYTE
 71 GTGCATTCTGAAAGAGGAGACATCAAACAGAATTAGGAGTTGTGCAACAGCTCTTTTGAGAG
 72 GAGGCCTAAAGGACAGGAGAAAAGGTCTTCAATCGTGGAAAGAAAATTAAATGTTGTATTAA
 73 ATAGATCACCAGCTAGTTTCAGAGTTACCATGTACGTATTCCACTAGCTGGGTTCTGTATTT
 74 CAGTTCTTTCGATACGGCTTAGGGTAATGTCAGTACAGGAAAAAAACTGTGCAAGTGAGCAC
 75 CTGAT
 76 >3325591H1   PTHYNOT03   INCYTE
 77 TGCAACAGCTCTTTTGAGAGGAGGCCTAAAGGACAGGAGAAAAGGTCTTCAATCGTGGAAAG
 78 AAAATTAAATGTTGTATTAAATAGATCACCAGCTAGTTTCAGAGTTACCATGTACGTATTCC
 79 ACTAGCTGGGTTCTGTATTTCAGTTCTTTCGATACGGCTTAGGGTAATGTCAGTACAGGAAA
 80 AAAACTGTGCAAGTGAGCACCTGATTCCGTTGCCTTGCTTAACCCTAAAGCNCCATGTCNNG
 81 GGCNAAAANCGAAAAT
```

Fig. 14-2

```
 82 >3733565H1   SMCCNOS01   INCYTE
 83 CCTTAATCTCAGTTGTTTGCTTCAAGGACCTTTCATCTTCAGGATTTACAGTGCATTCTGNA
 84 AGANGAGACATCAAACAGAATTAGGNGTTGTGCAAAAGCTCTTTTGAGAGGAGGCCTAAAGG
 85 ACAGGAGAAAAGGTCTNCAATCGTGGAAAGNAAATTAAATGTTGTATNAAATNGATCACCAG
 86 CTAGTTTCAGAGTTACCATGTACGTATTCCACTAGCTGGGNCNGTATTCAGTCTTTCGGAAC
 87 GGCTTAGGGTAATGTCAGTACAGGANAAAAACTGTGCAGTGAG
 88 >3554223H1   SYNONOT01   INCYTE
 89 ATTAAATAGATCACCAGCTAGTTTCAGAGTTACCATGTACGTATTCCACTAGCTGGGTTCTG
 90 TATTTCAGTTCTTTCGATACGGCTTAGGGTAATGTCAGTACAGGAAAAAACTGTGCAAGTG
 91 AGCACCTGATTCCGTTGCCTTGGCTTAACTCTAAAGCTCCATGTCCTGGGCCTAAAATCGTA
 92 TAAAATCTGGATTTTTTNTTTTTTTTGCGCATATTCACATATGTAAACCAGNACATTCTA
 93 TGTACNACAAACCTGGTTTTTAAAAAGGAAC
 94 >4507477H1   OVARTDT01   INCYTE
 95 GGCTAGTTTCAGAGTTACCATGTACGTATTCCACTAGCTGGGTTCTGTATTTCAGTTCTTTC
 96 GATACGGCTTAGGGTAATGTCAGTACAGGAAAAAACTGTGCAAGTGAGCACCTGATTCCGT
 97 TGCCTTGCTTAACTCTAAAGCTCCATGTCCTGGGCCTAAAATCGTATAAAATCTGGA
 98 >4163378H1   BRSTNOT32   INCYTE
 99 AATAGATCACCAGCTAGTTTCAGAGTTACCATGTACGTATTCCACTAGCTGGGNTCTGTATT
100 TCAGTTCCTTTCGATACGGCTTAGGGTAATGTCAGTACAGGAAAAAGCTGTGCAAGTGAGC
101 ACCTGATTCCGTTGCCTTGCTTAACTCTAAAGCTCCATGTCCTGGGCCTAAAATCGTATA
```

Fig. 14-3

```
 1 >2054675H1    BEPINOT01    INCYTE
 2 AAAGGAACTATGTTGCTATGAATTAAACTTGTGTCGTGCTGATAGGACAGACTGGATTTTTCA
 3 TATTTCTTATTAAAATTTCTGCCATTTAGAAGAAGAGAACTACATTCATGGTTTGGAAGAGAT
 4 AAACCTGAAAAGAAGAGTGGCCTTATCTTCACTTTATCGATAAGTCAGTTTATTTGTTTCATT
 5 GTGTACATTTTTATATTCTCCTTTTGACATTATAACTGTTGGCTTTTCTAATCTTGTTAAATA
 6 TATCTATTTTTACCAAAGGTATTTAATATTCTTTTTTA
 7 >3993180H1    LUNGNON03    INCYTE
 8 CACAAATCACTCACCGACGTGGCCCTGGAGCACCATGAGGNGTGTGACTGTGTGTGCAGAGGG
 9 AGCACAGGAGGATAGCCGCATCACCACCAGCAGCTCTTGCCCAGAGCTGTGCAGTGCAGTGGC
10 TGATTCTATTAGAGAACGTATGCGTTATCTCCATCCTTAATCTCAGTTGTTTGCTTCAAGGAC
11 CTTTCATCTTCAGGATTTACAGTGCATTCTGAAAGAGGAGACATCAAACAGAATTAGGAGTTG
12 TGCAACAGCTCTTTTGAGAGGAGGCTAAAGGACAGGAGAANAGGTCTT
13 >3510192H1    CONCNOT01    INCYTE
14 TGCAGTGCAGTGGCTGATTCTATTAGAGAACGTATGCGTTATCTCCATCCTTAATCTCAGTTG
15 TTTGCTTCAAGGACCTTTCATCTTCAGGATTTACAGTGCATTCTGAAAGAGGAGACATCAAAC
16 AGAATTAGGAGTTGTGCAACAGCTCTTTTGAGAGGAGGCCTAAAGGACAGGAGAAAAGGTCTT
17 CAATCGTGGAAGAAAATTAAATGTTGTATTAAATAGATCACCAGCTAGTTTCAGAGTTACCA
18 TGTACGTATTCCACTAGCTGGGTTCTGTATTT
19 >4164633H1    BRSTNOT32    INCYTE
20 CTTGTTAAATATATCTATTTTTACCAAAGGTATTTAATATTCTTTANTTATGACAACTTAGAT
21 CAACTATTTTTAGCTTGGTAAATTTTTCTAAACACAATTGTTATAGCCAGAGGAACAAAGATG
22 ATATAAAATATTGTTGCTCTGACAAAAATACATGTATTTCATTCTCGTATGGTGCTAGAGTTA
23 GATTAATCTGCATTTTAAAAAACTGAATTGGAATAGAATTGGTAAGTTGCAAAGACTTTTTGA
24 NAATAATTAAATTATCATATCTTCCATTCCTGTTATTGGGGGAGAAAAT
25 >2559870H1    ADRETUT01    INCYTE
26 CACGAGGTCCTTCAGTTGAGACCAAAGACCGGTGTCAGGGGATTGCACAAATCACTCACCGAC
27 GTGGCCCTGGAGCACCATGAGGAGTGTGACTGTGTGTGCAGAGGGAGCACAGGGGGATAGCCG
28 CATCACCACCAGCAGCTCTTGCCCAGAGCTGTGCAGTGCAGTGGCTGATTCTATTAGAGAACG
29 TATGCGTTATCTCCATCCTTAATCTCAGTTGTTTGCTTCAAGGACCTTTCATCTTCAGGATTT
30 ACAGTGCATTCTGAAAGAGGAGA
31 >3817470H1    BONSTUT01    INCYTE
32 TTAAAAGGAACTATGTTGCTATGAATTAAACTTGTGTCATGCTGATAGGACAGACTGGATTT
33 TTCATATTTCTTATTAAAATTTCTGCCATTTAGAAGAAGAGAACTACATTCATGGTTTGGAAG
34 AGATAAACCTGAAAAGAAGAGTGGCCTTATCTTCACTTTATCGATAAGTCAGTTTATTTGTTT
35 CATTGTGTACATTTTTATATTCTCCTTTTGACATTATAACTGTTGGCTTTCTAATCTGTTAAA
36 TATATCTATTTTTACCAAAGGTATTTAATATTCTTT
37 >3979767H1    LUNGTUT08    INCYTE
38 GGAGGATAGCCGCATCACCACCAGCAGCTCTTGCCCAGAGCTGTGCAGTGCAGTGGCTGATTC
39 TATTAGAGAACGTATGCGTTATCTCCATCCTTAATCTCAGTTGTTTGCTTCAAGGACCTTTCA
40 TCTTCAGGATTTACAGTGCATTCTGAAAGAGGAGACATCAAACAGAATTAGGAGTTGTGCAAC
41 AGCTCTTTTGAGAGGAGGCCTAAAGGACAGGAGAAAAGGTCTTCAATCGTGGAAGAANATTA
42 AATGTTGTATTAAATAGACACCAGCT
```

Fig. 15-1

```
43 >3980011H1    LUNGTUT08    INCYTE
44 GGAGGATAGCCGCATCACCACCAGCAGCTCTTGCCCAGAGCTGTGCAGTGCAGTGGCTGATTC
45 TATTAGAGAACGTATGCGTTATCTCCATCCTTAATCTCAGTTGTTTGCTTCAAGGACCTTTCA
46 TCTTCAGGATTTACATGCATTCTGAAAGAGGAGACATCAAACAGAATTAGGAGTTGTGCAACA
47 GCTCTTTTGAGAGGAGGCCTAAAGGACAGGAGAAAAGGTCTTCAATCGTGGAAAGAAAATTAA
48 ATGTTGTATTAAATAGATCACCA
49 >4825396H1    BLADDIT01    INCYTE
50 GAGAACCGATACCATTTTCTGGCCAGGTTGTCTCCTGGTTAAACGCTGTGGTGGGAACTGTGC
51 CTGTTGTCTCCACAATTGCAATGAATGTCAATGTGTCCCAAGCAAAGTTACTAAAAAATACCA
52 CGAGGTCCTTCAGTTGAGACCAAAGACCGGTGTCAGGGGATTGCACAAATCACTCACCGACGT
53 GGCCCTGGAGCACCATGAGGAGTGTGACTGTGTGTGCAGAGGGAGCACAGGAGGATAGCCGCA
54 TCACCACCA
55 >30737003H1    BONEUNT01    INCYTE
56 AGAAAATCCAGAGTGGTGGATCTGAACCTTCTAACAGAGGAGGTAAGATTATACAGCTGCACA
57 CCTCGTAACTTCTCAGTGTCCATAAGGGAAGAACTAAAGAGAACCGATACCATTTTCTGGCCA
58 GGTTGTCTCCTGGTTAAACGCTGTGGTGGGAACTGTGCCTGTTGTCTCCACAATTGCAATGAA
59 TGTCAATGTGTCCCAAGCAAAGTTACTAAAAAATACCACGAGGTCCTTCAGTTGAGACCAAAG
60 ACCGGTGTCAGGGGATTGCACAAATCA
61 >862169H1    BRAITUT03    INCYTE
62 AGATGATATAAAATATTGTTGCTCTGACAAAAATACATGTATTTCATTCTCGTATGGTGCTAG
63 AGTTAGATTAATCTGCATTTTAAAAAACTGAATTGGAATAGAATTGGTAAGTTGCAAAGACTT
64 TTTGAAAATAATTAAATTATCATATCTTCCATTCCTGTTATTGGAGATGAAAATAAAAAGCAA
65 CTTATGAAAGTAGACATTCAGATCCAGCCATTACTAACCTATTCCTTTTTGGGGAAATCTGA
66 GCCTAGC
67 >4201385H1    BRAITUT29    INCYTE
68 TTTTTAAAAAGGAACTATGTTGCTATGAATTAAACTTGTGTCGTGCTGATAGGACAGACTGGA
69 TTTTTCATATTTCTTATTAAAATTTCTGCCATTTAGAAGAAGAGAACTACATTCATGGTTTGG
70 AAGAGATAAACCTGAAAAGAAGAGTGGCCTATCTTCACTTTATCGATAAGTCAGTTTATTTGT
71 TTCATTGTGTACATTTTTATATTCTCCTTTGACATATAACTGTTGGCTTTTCTAATCTGTTAA
72 ATATATCTATTTTTACCAAAGGTATTTAATAT
73 >1302516H1    PLACNOT02    INCYTE
74 AGGAAATCAAATTAGGATAAGATTTGTATCTGATGAATATTTTCCTTCTGAACCTTCTAACAG
75 AGGAGGTAAGATTATACAGCTGCACACCTCGTAACTTCTCAGTGTCCATAAGGGAAGAACTAA
76 AGAGAACCGATACCATTTTCTGGCCAGGTTGTCTCCTGGTTAAACGCTGTGGTGGGAACTGTG
77 CCTGTTGTCTCCCACAATTGCAATGAATGTCAATGTGTCCCAAGCAAAGTTACTAAAAAATAC
78 CACGAGGTCC
79 >3684109H1    HEAANOT01    INCYTE
80 ATTTCATCTTCAGGATTTACAGTGCATTCTGAAANAGGAGAAATCAAACANAATTAGGAGTTG
81 TGCAACAGCTCTTTTGAGAGGAGGCCTAAAGGACAGGAGAAAAGGTCTTCAATCGTGGAAANA
82 AAATTAAATGTTGTATTAAATAGATCACCAGCTAGTTTCAGAGTTACCATGTACGTATTCCAC
83 TAGCTGGGTTCTGTATTTCAGTTCTTTCGATACGGCTTAGGGTAATGTCAGTACAGGAAAAAA
84 ACTGTGCAAGTGAGCACCTGATTCCGTTGCCTTGCTT
```

Fig. 15-2

```
 85 >2549720H1    LUNGTUT06   INCYTE
 86 TTAGCTTGGNAAATTTTTCTAAACACAATTGTTATAGCCAGAGGAACAAAGATGATATAAAAT
 87 ATTGTTGCTCTGACAAAAATACATGTATTTCATTCTCGTATGGTGCTAGAGTTAGATTAATCT
 88 GCATTTTAAAAAACTGAATTGGAATAGAATTGGTAAGTTGCAAAGACTTTTTGAAAATAATTA
 89 AATTATCATATCTTCCATTCCTGTTATTGGAGATGAAAATAAAAAGCAACTTATGANAGTAG
 90 >877279H1     LUNGAST01   INCYTE
 91 CTTTTTTATGACAACTTAGATCAACTATTTTTAGCTTGGTAAATTTTTCTAAACACAATTGTT
 92 ATAGCCAGAGGAACAAAGATGATATAAAATATTGTTGCTCTGACAAAAATACATGTATTTCAT
 93 TCTCGTATGGTGCTAGAGTTAGATTAATCTGCATTTTAAAAAACTGAATTGGAATAGAATTGG
 94 TAAGTTGCAAAGGCTTTTTGAAAATAATTAAATTATCATATCTTCCATTCCTGTTATTGGNGG
 95 >4713188H1    BRAIHCT01   INCYTE
 96 CAAAGTTACTAAAAAATACCACGAGGTCCTTCAGTTGAGACCAAAGACCGGTGTCAGGGGATT
 97 GCACAAATCACTCACCGACGTGGCCCTGGAGCACCATGAGGAGTGTGACTGTGTGTGCAGAGG
 98 GAGCACAGGAGGATAGCCGCATCACCACCAGCAGCTCTTGCCCAGAGCTGTGCAGTGCAGTGG
 99 CTGATTCTATTAGAGAACGTATGCGTTATCTCCATCCTTAATCTCAGTTGTTTGCT
100 >2171082H1    ENDCNOT03   INCYTE
101 AGATAAACCTGAAAAGAAGAGTGGCCTTATCTTCACTTTATCGATAAGTCAGTTTATTTGTTT
102 CATTGTGTACATTTTATATTCTCCTTTTGACATTATAACTGTTGGCTTTTCTAATCTTGTTA
103 AATATATCTATTTTTACCAAAGGTATTTAATATTCTTTTTTATGACAACTTAGATCAACTATT
104 TTTAGCTTGGTAAATTTTTCTAAACACAATTGTTATAGCCAGAGGAACAAAGATGA
105 >875860H1     LUNGAST01   INCYTE
106 CTGGATTTTTCATATTTCTTATTAAAATTTCTGCCATTTAGAAGAAGAGAACTACATTCATGG
107 TTTGGAAGAGATAAACCTGAAAAGAAGAGTGGCCTTATCTTCACTTTATCGATAAGTCAGTTT
108 ATTTGTTTCATTGTGTACATTTTATATTCTCCTTTTGACATTATAACTGTTGGCTTTTCTAAT
109 CTTGTTAAATATATCTATTTTTACCAAAGGTATTTAATATTCTTTTTTATGAC
110 >706168H1     SYNORAT04   INCYTE
111 GCTCATATTCACATATGTAAACCAGAACATTCTATGTACTACAAACCTGGTTTTTAAAAAGGA
112 NCTATGTTGCTATGAATTAAACTTGTGTCGTGCTGATAGGACAGACTGGATTTTTCATATTTC
113 TTATTAAAATTTCTGCCATTTAGAAGAAGAGAACTACATTCATGGTTTGGAAGAGATAAACCT
114 GAAAAGAAGAGTGGCCTTATCTTCANTTTATCGATAAGTCAGTTTATTTGTTTCA
115 >458823H1     KERANOT01   INCYTE
116 ANGAGTTGCCCAGAGCTGTGCAGTGCAGTGGCTGATTCTATTAGAGAACGTATGCGTTATCTC
117 CATCCTTAATCTCAGTTGTTTGNTTCAAGGACCTTTCATCTTCAGGATTTACAGTGCATTCTG
118 AAAGAGGAGACATCAAACAGAATTAGGAGTTGTGCAACAGCTCTTTTGAGAGGAGGCCTAAAG
119 GNCAGGAGAAAAGGTCTTCAATCGTGGAAAGAAAATTAAATGTTGTATTAAATAGATC
120 >538436H1     LNODNOT02   INCYTE
121 AAAGATGATATAAAATATTGTTGCTCTGACAAAAATACATGTATTTCATTCTCGTATGGTGCT
122 AGAGTTAGATTAATCTGCATTTTAAAAAACTGAATTGGAATAGAATTGGTAAGTTGCAAAGAC
123 TTTTTGAAAATAATTAAATTATCATATCTTCCATTCCTGTTATTGGAGATGAAAATAAAAAGC
124 AACTTATGAAAGTAGACATTCAGATCCAGCCATTACTAACCTAT
```

Fig. 15-3

125 >1303909H1 PLACNOT02 INCYTE
126 AGGAAATCAAATTAGGATAAGATTTGTATCTGATGAATATTTTCCTTCTGAACCTTCTAACAG
127 AGGAGGTAAGATTATACAGCTGCACACCTCGTAACTTCTCAGTGTCCATAAGGGAAGAACTAA
128 AGAGAACCGATACCATTTTCTGGCCAGGTTGTCTCCTGGTTAAACGCTGTGGTGGGAACTGTG
129 CCTGTTGTCTCCACAATTGCAATGAATGTCAATGTGTCCCAAG
130 >2739211H1 OVARNOT09 INCYTE
131 GTGCATTCTGAAAGAGGAGACATCAAACAGAATTAGGAGTTGTGCAACAGCTCTTTTGAGAGG
132 AGGCCTAAAGGACAGGAGAAAAGGTCTTCAATCGTGGAAAGAAAATTAAATGTTGTATTAAAT
133 AGATCACCAGCTAGTTTCAGAGTTACCATGTACGTATTCCACTAGCTGGGTTCTGTATTTCAG
134 TTCTTTCGATACGGCTTAGGGTAATGTCAGTACAGGAAAAAAACTGTGCAAGTGAGCACCTGA
135 T
136 >2550343H1 LUNGTUT06 INCYTE
137 TGTACATTTTTATATTCTCCTTTTGACATTATAACTGTTGGCTTTTCNAATCTTGTTAAATAT
138 ATCTATTTTTACCAAAGGTATTTAATATTCTTTTTTATGACAACTTAGATCAACTATTTTTAG
139 CTTGGTAAATTTTTCTAAACACAATTGTTATAGCCAGAGGAACAAAGATGATATAAAATATTG
140 TTGCTCTGACAAAAATACATGTATTTCATTCTCGTATGGTGCTA
141 >5321148H1 FIBPFEN06 INCYTE
142 CACAATTGTTATAGCCAGAGGAACAAAGATGATATAAAATATTGTTGCTCTGNCAAAAATACA
143 TGTATTTCATTCTCGTATGGTGCTAGAGTTAGATTAATCTGCATTTTAAAAAACTGAATTGGA
144 ATAGAATTGGTAAGTTGCAAAGACTTTTTGAAAATAATTAAATTATCATATCTTCCATTCCTG
145 TTATTGGAGATGAAAATAAAAGCAACTTATGAAAGTAAATTCAGATCCACCATTACTAAC
146 >879495H1 THYRNOT02 INCYTE
147 ATTTCATTCTCGTATGGTGCTAGAGTTAGATTAATCTGCATTTTAAAAAACTGAATTGGAATA
148 GAATTGGTAAGTTGCAAAGACTTTTTGAAAATAATTAAATTATCATATCTTCCATTCCTGTTA
149 TTGGAGATGAAAATAAAAGCAACTTATGAAAGTAGACATTCAGATCCAGCCATTACTAACCT
150 ATTCCTTTTTGGGGAAATCTGAGCCTAGCTCAGAAAAACATAAAGCACCTTGAAAAA
151 >3325591H1 PTHYNOT03 INCYTE
152 TGCAACAGCTCTTTTGAGAGGAGGCCTAAAGGACAGGAGAAAAGGTCTTCAATCGTGGAAAGA
153 AAATTAAATGTTGTATTAAATAGATCACCAGCTAGTTTCAGAGTTACCATGTACGTATTCCAC
154 TAGCTGGGTTCTGTATTTCAGTTCTTTCGATACGGCTTAGGGTAATGTCAGTACAGGAAAAAA
155 ACTGTGCAAGTGAGCACCTGATTCCGTTGCCTTGCTTAACCCTAAAGCNCCATGTCNNGGGCN
156 AAAANCGAAAAAT
157 >543890H1 OVARNOT02 INCYTE
158 TTTCTAAACACAATTGTTATAGCCAGAGGAACAAAGATGATATAAAATATTGTTGCTCTGACA
159 AAAATACATGTATTTCATTCTCGTATGGTGCTAGAGTTAGATTAATCTGCATTTTAAAAAACT
160 GAATTGGNATAGAATTGGTAAGTTGCAAAGNCTTTTTGAAAATAATTAAATTATCATATCTTC
161 CATTCCTGTTATTGGAGGATGGAAAATAAAAGCAACTTATGGAAAGTAGGACATTCAGATC
162 >3733565H1 SMCCNOS01 INCYTE
163 CCTTAATCTCAGTTGTTTGCTTCAAGGACCTTTCATCTTCAGGATTTACAGTGCATTCTGNAA
164 GANGAGACATCAAACAGAATTAGGNGTTGTGCAAAAGCTCTTTTGAGAGGAGGCCTAAAGGAC
165 AGGAGAAAAGGTCTNCAATCGTGGAAAGNAAATTAAATGTTGTATNAAATNGATCACCAGCTA
166 GTTTCAGAGTTACCATGTACGTATTCCACTAGCTGGGNCNGTATTCAGTCTTTCGGAACGGCT
167 TAGGGTAATGTCAGTACAGGANAAAAACTGTGCAGTGAG

Fig. 15-4

```
168 >4641939H1    PROSTMT03    INCYTE
169 GTACTACAAACCTGGTTTTTAAAAAGGAACTATGTTGCTATGAATTAAACTTGTGTCCATGCT
170 GATAGGACAGACTGGATTTTNCATATTTCTTATTAAAATTTCTGCCATTTAGAAGAAGAGAAC
171 TACATTCATGGTTTGGNAGAGATAAACCTGAAAAGAAGAGTGGCCTTATCTTCACTTTATCGA
172 TAAGTCAGTTTATTTGTTTCATGTGTACATTTTTATATTCTCCTTTGACATATAACGTGGCTT
173 T
174 >2007780H1    TESTNOT03    INCYTE
175 TTATATTCTCCTTTTGACATTATAACTGTTGGCTTTTCTAATCTTGTTAAATATATCTATTTT
176 TACCAAAGGTATTTAATATTCTTTTTATGACAACTTAGATCAACTATTTTTAGCTTGGTAAA
177 TTTTTCTAAACACAATTGTTATAGCCAGAGGAACAAAGATGATATAAAATATTGTTGCTCTGA
178 NAAAAATACATGTAT
179 >3085331H1    HEAONOT03    INCYTE
180 GCTCATATTCACATATGTAAACCAGAACATTCTATGTACTACAAACCTGGTTTTTAAAAAGGA
181 ACTATTTGCTATGAATTAAACTTGTGTCGTGCTGATAGGACAGACTGGNTTTTTCATATTTCT
182 TATTANAATTTCTGCCATTAGAAGAAGAGAACTACATTCATGGTTTGGAAGAGATAAACCTGA
183 AAAGAAGAGTGGCCTATTTCACTTTATCGATAAGTCAGT
184 >3414043H1    PTHYNOT04    INCYTE
185 GCTCATATTCACATATGTAAACCAGAACATTCTATGTACTACAAACCTGGTTTTTAAAAAGGA
186 ACTATGTTGCTATGAATTAAACTTGTGTCGTGCTGATAGGACAGACTGGATTTTTCATATTTC
187 TTATTAAAATTTCTGCCATTTAGAAGAAGAGAACTACATTCATGGTTTGGAAGAGATAAACCT
188 GAAA
189 >3705963H1    PENCNOT07    INCYTE
190 ANACTGTGCAAGTGAGCACCTGATTCCGTTGCCTTGCTTAACTCTAAAGCTCCATGTCCTGGG
191 CCTAAAATCGTATAAAATCTGGAnnnnnnnnnnnnnnnnnnnnGCTCATATTCACATATGTAAAC
192 CAGAACATTCTATGTACTACAAACCTGGTTTTTAAAAAGGAACTATGTTGCTATGAATTAAAC
193 TTGTGTCGTGCTGATAGGACAGACTGGATTTTTCATATTTCTTATTAAAATTTCTGCCATTAG
194 AAGAAGAGAACTACNTTCANGGTTTGGAAGAGATAACCCTGAAAAGANGGG
195 >5137051H1    OVARDIT04    INCYTE
196 AAAAAACTGAATTGGAATAGAATTGGTAAGTTGCAAAGACTNTTTGAAAATAATTAAATTATC
197 ATATCTTCCATTCCTGTTATTGGAGATGAAANATAAAAAGCAACTTATGAAAGTAGACATTCAG
198 ATCCAGCCATTACTAACCTATTCCTTTTTTGGGGAAATCTGAGCCTAGCTCAGAAAAACATAA
199 AGCACCTTGAAAAAGACTTGGCAGCTTCCTGATAAAGCGTGCTGTNTGTCAGTAGGAACACAT
200 CCTATTTATTGTGATGNTGTGGTTTATTAT
201 >3554223H1    SYNONOT01    INCYTE
202 ATTAAATAGATCACCAGCTAGTTTCAGAGTTACCATGTACGTATTCCACTAGCTGGGTTCTGT
203 ATTTCAGTTCTTTCGATACGGCTTAGGGTAATGTCAGTACAGGAAAAAAACTGTGCAAGTGAG
204 CACCTGATTCCGTTGCCTTGGCTTAACTCTAAAGCTCCATGTCCTGGGCCTAAAATCGTATAA
205 AATCTGGATTTTTTTNTTTTTTTTTGCGCATATTCACATATGTAAACCAGNACATTCTATGTA
206 CNACAAACCTGGTTTTTAAAAAGGAAC
207 >4507477H1    OVARTDT01    INCYTE
208 GGCTAGTTTCAGAGTTACCATGTACGTATTCCACTAGCTGGGTTCTGTATTTCAGTTCTTTCG
209 ATACGGCTTAGGGTAATGTCAGTACAGGAAAAAAACTGTGCAAGTGAGCACCTGATTCCGTTG
210 CCTTGCTTAACTCTAAAGCTCCATGTCCTGGGCCTAAAATCGTATAAAATCTGGA
```

Fig. 15-5

```
211 >1955646H1   CONNNOT01   INCYTE
212 TGGTAAGTTGCAAAGACTTTTTGAAAATAATTAAATTATCATATCTTCCATTCCTGTTATTGG
213 AGATGAAAATAAAAAGCAACTTATGAAAGTAGACATTCAGATCCAGCCATTACTAACCTATTC
214 CTTTTTTGGGGAAATCTGAGCCTAGCTCAGAAAAACATAAAGCACCTTGAAAAAGACTTGGCA
215 GCTTCCTGATAAAGCGTGCTGTGCTGTGCAGTAGGGAACACATCCTATTTATTGTGATGTTGT
216 GGTTTATATCCTAAACC
217 >4163378H1   BRSTNOT32   INCYTE
218 AATAGATCACCAGCTAGTTTCAGAGTTACCATGTACGTATTCCACTAGCTGGGNTCTGTATTT
219 CAGTTCCTTTCGATACGGCTTAGGGTAATGTCAGTACAGGAAAAAAGCTGTGCAAGTGAGCAC
220 CTGATTCCGTTGCCTTGCTTAACTCTAAAGCTCCATGTCCTGGGCCTAAAATCGTATA
221 >5095141H1   EPIMNON05   INCYTE
222 AGATAAACCTGAAAAGAAGAGTGGCCTTATNTTCACTTTATCGATAAGTCAGNTTATTTGTTT
223 CATTGTGTACATTTNNATATTCTCCTTTTGACATTATAACTGNTGGCTTTTCTAANCNTGTTA
224 AATATATCTATTTTTACCAAAGGTATTTAATATTCTTT
225 >943826H1    ADRENOT03   INCYTE
226 TATGGTGCTAGAGTTAGATTAATCTGCATTTTAAAAAACTGAATTGGAATAGAATTGGTAAGT
227 TGCAAAGACTTTTTGAAAATAATTAAATTATCATATCTTCCATTCCTGTTATTGGAGATGAAA
228 ATAAAAAGCAACTTATG
229 >3451273H1   UTRSNON03   INCYTE
230 TTTTTTNTTTTGCTCATATTCACATATGTAAACCNGAACATTCTATGTACNACAAACCTGGTT
231 TTTAAAAAGGAACTATGTTGCTATGAATTAAACTTGTGTCGTGCTGATAGGACAGACTGGATT
232 TTTCANATTTCTTANTAANNTTTCTGCCATTTAGAAGA
233 >1402278H1   LATRTUT02   INCYTE
234 GTACAGGAAAAAAACTGTGCAAGTGAGCACCTGATTCCGTTGCCTTGCTTAACTCTAAAGCTC
235 CATGTCCTGGGCCTAAAATCGTATAAAATCTGGAnnnnnnnnnnnnnnnnnnnGCTCATATTCA
236 CATATGTAAACCAGAACATTCTATGTACTACAAACCTGGTTTTTAAAAAGGAACTATGTTGCT
237 ATGAATTAAACTTGTGTCGTGCTGATAGGACAGACTGGATTTTTCATATTCTTA
238 >4361191H1   SKIRNOT01   INCYTE
239 GCAAAGACTTTTTGANAATNATTAANTTATCATATCTTCCATTCCTGTTATNGGAGATGANAA
240 TAAAAAGCAACTTATGAAAGTAGACATTCAGATCCAGCCATTACTAACCTATTCCTTTTTGG
241 GGAAATCTGAGCCTAGCNCAGAAAAACATAAAGCACCTTGAAAAAGACTTGGCAGCTTCCTGA
242 TAAAGCGTGCTGTGCTGTGCAGTAGGAACACATCCNATTTATTGTGNTGTNGNGGTTTTATGA
243 TC
244 >1307017H1   PLACNOT02   INCYTE
245 TGTCAGTACAGGAAAAAAACTGTGCAAGTGAGCACCTGATTCCGTTGCCTTGCTTAACTCTAA
246 AGCTCCATGTCCTGGGCCTAAAATCGTATAAAATCTGGAnnnnnnnnnnnnnnnnnnnGCTCAT
247 ATTCACATATGTAAACCAGAACATTCTATGTACTACAAACCTGGTTTTTAAAAAGGAACTATG
248 TTGCTATGAATTAAACTTGTGTCATGCTGATAGGACAGACTGGATTTTTCATAT
249 >5032225H1   HEARFET03   INCYTE
250 AATTATCATATCTTCCATTCCTGTTATTGGAGATGNAAATAAAAAGCAACTTATGAAAGTAGA
251 CATTCAGATCCAGCCATTACTAACCTATTCCTTTTTGGGGAAATCTGAGCCTAGCTCAGAAA
252 AACATAAAGCACCTTGAAAAAGACTGTCAGCTTCCTGATAAAGCGTGCTGTGCTGTGCAGTAG
253 GAACACATCCTATTTATTGTGATGTTGTGGTTTTATTATCTTAAACTCGTTCCAT
```

Fig. 15-6

```
254 >3732621H1   SMCCNOS01   INCYTE
255 ANAGATGATATAAAANATTGTTGCTCTGACAANNATACATGTATTTCATTCTCGTATGGTGCT
256 AGAGTTAGATTAATCTGCNTTTTAAAAAACTGANTTGGAATAGANTTGGTAAGTTGCAAAGNC
257 NTTTGAAAATNATTAAGTTATCAGAT
258 >3530274H1   BLADNOT09   INCYTE
259 TTCCATTCCTGTTATTGGAGATGAAAATAAAAAGCAACTTATGAAAGTAGACATTCAGATCCA
260 GCCATTACTAACCTATTCCTTTTTTGGGGAAATCTGAGCCTAGCTCAGAAAAACATAAAGCAC
261 CTTGAAAAAGACTTGGCAGCTTCCTGATAAAGCGTGCTGTGCTGTGCAGTAGGAACACATCCT
262 ATTTATTGTGATGTTGTGGTTTTATTATCTAAACTCTGTTCCATACACTTGTATAAATACATG
263 GATATTTTTATGTACAGAAGTATGTCTCTTAACCAGTTCA
264 >3530249H1   BLADNOT09   INCYTE
265 CTTCCATTCCTGTTATTGGAGATGAAAATAAAAAGCAACTTATGANAGTAGACATTCAGATCC
266 AGCCATTACTAACCTATTCCTTTTTGGGGAAATCTGAGCCTAGCTCAGAAAAACATAAAGCA
267 CCTTGAAAAGACTTGGCAGCTTCCTGATAAAGCGTGCTGTGCTGTGCAGTAGGAACACATCC
268 TATTTATTGTGATGTTGTGGTTTTATTATCTTAAACTCTGTTCCATACACTTGTATAAATACA
269 TGGATATTTTTATGTACAGAAGTATGTCTCTTAACCAGTTCACTTATTGTACCTGG
```

Fig. 15-7

| | | |
|---|---|---|
| VEGFE1 | AAAATGTATGGATACAACTTAC | 22 |
| VEGFE2 | GTTTGATGAAAGATTTGGGCTTG | 23 |
| VEGFE3 | TTTCTAAAGGAAATCAAATTAG | 22 |
| VEGFE4 | GATAAGATTTGTATCTGATG | 20 |
| VEGFE5 | GATGTCCTCTTTCAG | 17 |
| VEGFE6 | GCACAACTCCTAATTCTG | 18 |
| VEGFE7 | AGCACCTGATTCCGTTGC | 19 |
| VEGFE8 | TAGTACATAGAATGTTCTGG | 20 |
| VEGFE9 | AAGAGACATACTTCTGTAC | 19 |
| VEGFE10 | CCAGGTACAATAAGTGAACTG | 21 |

Fig. 16

```
+3                                          M  N  I  F  L  L  N  L  L  T  E  E  V  R  L  Y
                                            ]--------------------------------------------
  1 AGGAAATCAA ATTAGGATAA GATTTGTATC TGATGAATAT TTTCCTTCTG AACCTTCTAA CAGAGGAGGT AAGATTATAC
    TCCTTTAGTT AATCCTATT CTAAACATAG ACTACTTATA AAAGGAAGAC TTGGAAGATT GTCTCCTCCA TTCTAATATG

+3  S  C  T  P  R  N  F  S  V  S  I  R  E  E  L  K  R  T  D  T  I  F  W  P  G  C  L
    ----------------------]-----------------------------------------------------------
 81 AGCTGCACAC CTCGTAACTT CTCAGTGTCC ATAAGGGAAG AACTAAAGAG AACCGATACC ATTTTCTGGC CAGGTTGTCT
    TCGACGTGTG GAGCATTGAA GAGTCACAGG TATTCCCTTC TTGATTTCTC TTGGCTATGG TAAAAGACCG GTCCAACAGA
-2                                                                <---------------------

+3  L  V  K  R  C  G  G  N  C  A  C  C  L  H  C  N  E  C  Q  C  V  P  S  K  V
    ----------------------------------------------------------------------------------
161 CCTGGTTAAA CGCTGTGGTG GGAACTGTGC CTGTTGTCTC CACAATTGCA ATGAATGTCA ATGTGTCCCA AGCAAAGTTA
    GGACCAATTT GCGACACCAC CCTTGACACG ACAACAGAG GTGTTAACGT TACTTACAGT TACACAGGGT TCGTTTCAAT
-2  ------------------------------------------------------------------------

+3 T  K  K  Y  H  E  V  L  Q  L  R  P  K  T  G  V  R  G  L  H  K  S  L  T  D  V  A
   ----------------------------------------------------------------------------------
+1                                          V  S  G  D  C  T  N  H  S  P  T  W  P
                                            ]--------------------------------------
241 CTAAAAAATA CCACGAGGTC CTTCAGTTGA GACCAAAGAC CGGTGTCAGG GGATTGCACA AATCACTCAC CGACGTGGCC
    GATTTTTAT GGTGCTCCAG GAAGTCAACT CTGGTTTCTG GCCACAGTCC CCTAACGTGT TTAGTGAGTG GCTGCACCGG
-2  ----------------------------------------------------------------------[

+3 L  E  H  H  E  E  C  D  C  V  C  R  G  S  T  G  G
   ----------------------------------------------->
+2                                          V  Q  R  E  H  R  R  I  A  A  S  P  P  A  A  L  A
                                            ]--------------------------------------------
+1 W  S  T  M  R  S  V  T  V  C  A  E  G  A  Q  E  D  S  R  I  T  T  S  S  S  C
   ----------------------------------------------------------------------------------
321 CTGGAGCACC ATGAGGAGTG TGACTGTGTG TGCAGAGGGA GCACAGGAGG ATAGCCGCAT CACCACCAGC AGCTCTTGCC
    GACCTCGTGG TACTCCTCAC ACTGACACAC ACGTCTCCCT CGTGTCCTCC TATCGGCGTA GTGGTGGTCG TCGAGAACGG

+2 Q  S  C  A  V  Q  W  L  I  L  E  N  V  C  V  I  S  I  L  N  L  S  C  L  L  Q
   ----------------------------------------------------------------------------------
+1 P  E  L  C  S  A  V  A  D  S  I  R  E  R  M  R  Y  L  H  P
   ----------------------------------------------------------------->
401 CAGAGCTGTG CAGTGCAGTG GCTGATTCTA TTAGAGAACG TATGCGTTAT CTCCATCCTT AATCTCAGTT GTTTGCTTCA
    GTCTCGACAC GTCACGTCAC CGACTAAGAT AATCTCTTGC ATACGCAATA GAGGTAGGAA TTAGAGTCAA CAAACGAAGT
```

Fig. 17-1

```
    +2   G   P   F   I   F   R   I   Y   S   A   F
         ---------------------------------------->
481 AGGACCTTTC ATCTTCAGGA TTTACAGTGC ATTCTGAAAG AGGAGACATC AAACAGAATT AGGAGTTGTG CAACAGCTCT
    TCCTGGAAAG TAGAAGTCCT AAATGTCACG TAAGACTTTC TCCTCTGTAG TTTGTCTTAA TCCTCAACAC GTTGTCGAGA

561 TTTGAGAGGA GGCCTAAAGG ACAGGAGAAA AGGTCTTCAA TCGTGGAAAG AAAATTAAAT GTTGTATTAA ATAGATCACC
    AAACTCTCCT CCGGATTTCC TGTCCTCTTT TCCAGAAGTT AGCACCTTTC TTTTAATTTA CAACATAATT TATCTAGTGG

641 AGCTAGTTTC AGAGTTACCA TGTACGTATT CCACTAGCTG GGTTCTGTAT TTCAGTTCTT TCGATACGGC TTAGGGTAAT
    TCGATCAAAG TCTCAATGGT ACATGCATAA GGTGATCGAC CCAAGACATA AAGTCAAGAA AGCTATGCCG AATCCCATTA

721 GTCAGTACAG GAAAAAAACT GTGCAAGTGA GCACCTGATT CCGTTGCCTT GGCTTAACTC TAAAGCTCCA TGTCCTGGGC
    CAGTCATGTC CTTTTTTTGA CACGTTCACT CGTGGACTAA GGCAACGGAA CCGAATTGAG ATTTCGAGGT ACAGGACCCG

801 CTAAAATCGT ATAAAATCTG GA
    GATTTTAGCA TATTTTAGAC CT
```

Fig. 17-2

```
+3                                          M  N  I  F  L  L  N  L  T  E  E  V  R  L  Y
                                            ]----------------------------------------
  1 AGGAAATCAA ATTAGGATAA GATTTGTATC TGATGAATAT TTTCCTTCTG AACCTTCTAA CAGAGGAGGT AAGATTATAC
    TCCTTTAGTT TAATCCTATT CTAAACATAG ACTACTTATA AAAGGAAGAC TTGGAAGATT GTCTCCTCCA TTCTAATATG

+3 S  C  T  P  R  N  F  S  V  S  I  R  E  E  L  K  R  T  D  T  I  F  W  P  G  C  L
    ----------------]------------------------------------------------------------------
 81 AGCTGCACAC CTCGTAACTT CTCAGTGTCC ATAAGGGAAG AACTAAAGAG AACCGATACC ATTTTCTGGC CAGGTTGTCT
    TCGACGTGTG GAGCATTGAA GAGTCACAGG TATTCCCTTC TTGATTTCTC TTGGCTATGG TAAAAGACCG GTCCAACAGA
 -2                                                       <----------------------------

+3 L  V  K  R  C  G  G  N  C  A  C  C  L  H  C  N  E  C  Q  C  V  P  S  K  V
    -------------------------------------------------------------------------------
161 CCTGGTTAAA CGCTGTGGTG GGAACTGTGC CTGTTGTCTC CACAATTGCA ATGAATGTCA ATGTGTCCCA AGCAAAGTTA
    GGACCAATTT GCGACACCAC CCTTGACACG GACAACAGAG GTGTTAACGT TACTTACAGT TACACAGGGT TCGTTTCAAT
 -2 -------------------------------------------------------------------------------

+3 T  K  K  Y  H  E  V  L  Q  L  R  P  K  T  G  V  R  G  L  H  K  S  L  T  D  V  A
    -------------------------------------------------------------------------------------
 +1                                           V  S  G  D  C  T  N  H  S  P  T  W  P
                                              ]----------------------------------------
241 CTAAAAAATA CCACGAGGTC CTTCAGTTGA GACCAAAGAC CGGTGTCAGG GGATTGCACA AATCACTCAC CGACGTGGCC
    GATTTTTTAT GGTGCTCCAG GAAGTCAACT CTGGTTTCTG GCCACAGTCC CCTAACGTGT TTAGTGAGTG GCTGCACCGG
 -2 ------------------------------------------------------------------------------[

+3 L  E  H  H  E  E  C  D  C  V  C  R  G  S  T  G  G
    --------------------------------------------------->
 +2                                 V  Q  R  E  H  R  R  I  A  A  S  P  P  A  A  L  A
                                    ]--------------------------------------------------
 +1 W  S  T  M  R  S  V  T  V  C  A  E  G  A  Q  E  D  S  R  I  T  T  S  S  S  C
    -------------------------------------------------------------------------------
321 CTGGAGCACC ATGAGGAGTG TGACTGTGTG TGCAGAGGGA GCACAGGAGG ATAGCCGCAT CACCACCAGC AGCTCTTGCC
    GACCTCGTGG TACTCCTCAC ACTGACACAC ACGTCTCCCT CGTGTCCTCC TATCGGCGTA GTGGTGGTCG TCGAGAACGG

+2 Q  S  C  A  V  Q  W  L  I  L  L  E  N  V  C  V  I  S  I  L  N  L  S  C  L  L  Q
    ----------------------------------------------------------------------------------
 +1 P  E  L  C  S  A  V  A  D  S  I  R  E  R  M  R  Y  L  H  P
    ----------------------------------------------------------->
401 CAGAGCTGTG CAGTGCAGTG GCTGATTCTA TTAGAGAACG TATGCGTTAT CTCCATCCTT AATCTCAGTT GTTTGCTTCA
    GTCTCGACAC GTCACGTCAC CGACTAAGAT AATCTCTTGC ATACGCAATA GAGGTAGGAA TTAGAGTCAA CAAACGAAGT
```

Fig. 18-1

```
     +2   G  P  F  I  F  R  I  Y  S  A  F
         ------------------------------------>
 481 AGGACCTTTC ATCTTCAGGA TTTACAGTGC ATTCTGAAAG AGGAGACATC AAACAGAATT AGGAGTTGTG CAACAGCTCT
     TCCTGGAAAG TAGAAGTCCT AAATGTCACG TAAGACTTTC TCCTCTGTAG TTTGTCTTAA TCCTCAACAC GTTGTCGAGA

561 TTTGAGAGGA GGCCTAAAGG ACAGGAGAAA AGGTCTTCAA TCGTGGAAAG AAAATTAAAT GTTGTATTAA ATAGATCACC
     AAACTCTCCT CCGGATTTCC TGTCCTCTTT TCCAGAAGTT AGCACCTTTC TTTTAATTTA CAACATAATT TATCTAGTGG

641 AGCTAGTTTC AGAGTTACCA TGTACGTATT CCACTAGCTG GGTTCTGTAT TTCAGTTCTT TCGATACGGC TTAGGGTAAT
     TCGATCAAAG TCTCAATGGT ACATGCATAA GGTGATCGAC CCAAGACATA AAGTCAAGAA AGCTATGCCG AATCCCATTA

721 GTCAGTACAG GAAAAAAACT GTGCAAGTGA GCACCTGATT CCGTTGCCTT GGCTTAACTC TAAAGCTCCA TGTCCTGGGC
     CAGTCATGTC CTTTTTTTGA CACGTTCACT CGTGGACTAA GGCAACGGAA CCGAATTGAG ATTTCGAGGT ACAGGACCCG

801 CTAAAATCGT ATAAAATCTG GATTTTTTTN TTTTTTTTTG CGCATATTCA CATATGTAAA CCAGAACATT CTATGTACTA
     GATTTTAGCA TATTTTAGAC CTAAAAAAAN AAAAAAAAAC GCGTATAAGT GTATACATTT GGTCTTGTAA GATACATGAT

881 CAAACCTGGT TTTTAAAAAG GAACTATGTT GCTATGAATT AAACTTGTGT CGTGCTGATA GGACAGACTG GATTTTTCAT
     GTTTGGACCA AAAATTTTTC CTTGATACAA CGATACTTAA TTTGAACACA GCACGACTAT CCTGTCTGAC CTAAAAAGTA
  -3           <---------------------------------------------------------------------------

961 ATTTCTTATT AAAATTTCTG CCATTTAGAA GAAGAGAACT ACATTCATGG TTTGGAAGAG ATAAACCTGA AAAGAAGAGT
     TAAAGAATAA TTTTAAAGAC GGTAAATCTT CTTCTCTTGA TGTAAGTACC AAACCTTCTC TATTTGGACT TTTCTTCTCA
  -3 ---------------------------------------------------------------------------------------

1041 GGCCTTATCT TCACTTTATC GATAAGTCAG TTTATTTGTT TCATTGTGTA CATTTTTATA TTCTCCTTTT GACATTATAA
     CCGGAATAGA AGTGAAATAG CTATTCAGTC AAATAAACAA AGTAACACAT GTAAAAATAT AAGAGGAAAA CTGTAATATT
  -3 --------------[

1121 CTGTTGGCTT TTCTAATCTT GTTAAATATA TCTATTTTTA CCAAAGGTAT TTAATATTCT TTTTTATGAC AACTTAGATC
     GACAACCGAA AAGATTAGAA CAATTTATAT AGATAAAAAT GGTTTCCATA AATTATAAGA AAAAATACTG TTGAATCTAG

1201 AACTATTTTT AGCTTGGTAA ATTTTTCTAA ACACAATTGT TATAGCCAGA GGAACAAAGA TGATATAAAA TATTGTTGCT
     TTGATAAAAA TCGAACCATT TAAAAAGATT TGTGTTAACA ATATCGGTCT CCTTGTTTCT ACTATATTTT ATAACAACGA

1281 CTGACAAAAA TACATGTATT TCATTCTCGT ATGGTGCTAG AGTTAGATTA ATCTGCATTT TAAAAAACTG AATTGGAATA
     GACTGTTTTT ATGTACATAA AGTAAGAGCA TACCACGATC TCAATCTAAT TAGACGTAAA ATTTTTTGAC TTAACCTTAT

1361 GAATTGGTAA GTTGCAAAGA CTTTTTGAAA ATAATTAAAT TATCATATCT TCCATTCCTG TTATTGGAGA TGAAAATAAA
     CTTAACCATT CAACGTTTCT GAAAAACTTT TATTAATTTA ATAGTATAGA AGGTAAGGAC AATAACCTCT ACTTTTATTT
```

Fig. 18-2

```
1441  AAGCAACTTA TGAAAGTAGA CATTCAGATC CAGCCATTAC TAACCTATTC CTTTTTTGGG GAAATCTGAG CCTAGCTCAG
      TTCGTTGAAT ACTTTCATCT GTAAGTCTAG GTCGGTAATG ATTGGATAAG GAAAAAACCC CTTTAGACTC GGATCGAGTC

1521  AAAAACATAA AGCACCTTGA AAAAGACTTG GCAGCTTCCT GATAAAGCGT GCTGTGCTGT GCAGTAGGAA CACATCCTAT
      TTTTTGTATT TCGTGGAACT TTTTCTGAAC CGTCGAAGGA CTATTTCGCA CGACACGACA CGTCATCCTT GTGTAGGATA

1601  TTATTGTGAT GTTGTGGTTT TATTATCTTA AACTCTGTTC CATACACTTG TATAAATACA TGGATATTTT TATGTACAGA
      AATAACACTA CAACACCAAA ATAATAGAAT TTGAGACAAG GTATGTGAAC ATATTTATGT ACCTATAAAA ATACATGTCT

1681  AGTATGTCTC TTAACCAGTT CACTTATTGT ACCTGG
      TCATACAGAG AATTGGTCAA GTGAATAACA TGGACC
```

Fig. 18-3

DNA AND POLYPEPTIDE SEQUENCE USED FOR MAMMALIAN CELL EXPRESSION

```
+1                m  s  l  f  g  l  l  l  l  t  s  a  l  a  g  q  r
1    GGATCCAAAA TGAGCCTCTT CGGGCTTCTC CTGCTGACAT CTGCCCTGGC CGGCCAGAGA

+1    q  g  t  q  a  E  S    N  L  S    S  K  F  Q    F  S  S    N  K  E
61   CAGGGGACTC AGGCGGAATC CAACCTGAGT AGTAAAGTTC CAGTTTTCCA GCAACAAGGA

+1    Q  N  G  V    Q  D  P    Q  H  E    R  I  I  T    V  S  T    N  G  S
121  ACAGAACGGA GTACAAGATC CTCAGCATGA GAGAATTATT ACTGTGTCTA CTAATGGAAG

+1    I  H  S  P    R  F  P    H  T  Y    P  R  N  T    V  L  V    W  R  L
181  TATTCACAGC CCAAGGTTTC CTCATACTTA TCCAAGAAAT ACGGTCTTGG TATGGAGATT

+1    V  A  V  E    E  N  V    W  I  Q    L  T  F  D    E  R  F    G  L  E
241  AGTAGCAGTA GACGAAAATG TATGGATACA ACTTACGTTT GATGAAAGAT TTGGGCTTGA

+1    D  P  E  D    D  I  C    K  Y  D    F  V  Z  V    E  E  P    S  D  G
301  AGACCCAGAA GATGACATAT GCAAGTATGA TTTTGTAGAA GTTGACAAAC CCAGTGATGG

+1    T  I  L  G    R  W  C    G  S  G    T  V  P  G    K  Q  I    S  K  G
361  AACTATATTA GGGCCCTGGT GTGGTTCTGG TACTGTACCA GGAAAACAGA TTTCTAAAGG

+1    N  Q  I  R    I  R  F    V  S  D    E  Y  F  P    S  E  P    G  F  C
421  AAATCAAATT AGGATAAGAT TTGTATCTGA TGAATATTTT CCTTCTGPAC CAGGGTTCTG

+1    I  H  Y  N    I  V  M    P  Q  F    T  E  A  V    S  P  S    V  L  P
481  CATCCACTAC AACATTGTCA TGCCACAATT CACAGAAGCT GTGAGTCCTT CAGTGCTACC

+1    P  S  A  L    P  L  D    L  L  N    N  A  I  T    A  F  S    T  L  E
541  CCCTTCAGCT TTGCCACTTG GACCTGCTTA ATAATGCTAT AACTGCCTTT AGTACCTTCG

+1    D  L  I  R    Y  L  E    P  E  R    W  Q  L  D    L  E  D    L  Y  R
601  AAGACCTTAT TCGATATCTT GAACCAGAGA GXTGGCAGTT GGACTTAGAA GATCTATATA

+1    P  T  W  Q    L  L  G    K  A  F    V  F  G  R    K  S  R    V  V  D
661  GGCCAACTTG GCAACTTCTT GGCAAGGCTT TTGTTTTTGG AAGAAAATCC AGAGTGGTGG

+1    L  N  L  L    T  E  E    V  R  L    Y  S  C  T    P  R  N    F  S  V
721  ATCTGAACCT TCTAACAGAG GAGGTAAGXT TATACAGCTG CACACCTCGT AACTTCTCAG

+1    S  I  R  E    E  L  K    R  T  D    T  I  F  W    P  G  C    L  L  V
781  TGTCCATAAG GGAAGAACTT AAAGAGAACC GATACCATTT TCTGGCCAGG TTGTCTCCTG
```

Fig. 19-1

```
+1      K   R   C   G       G   N   C       A   C   C       L   H   N   C       N   E   C       Q   C   V
841     GTTAAACGCT  GTGGTGGGAA  CTGTGCCTGT  TGTCTCCACA  ATTGCAATGA  ATGTCAATGT

+1      P   S   K   V       T   K   K       Y   H   E       V   L   Q       L   R   P   K       T   G   V
901     GTCCCAAGCA  AAGTTACTAA  AAAATACCAC  GAGGTCCTTC  AGTTGAGACC  AAAGACCGGT

+1      R   G   L   H       K   S       T   D   V       A   L   E   H       H   E   E       C   G   C
961     GTCAGGGGAT  TGCACAAATC  ACTCACCGAC  GTGGCCCTGG  AGCACCATGA  GGAGTGTGAC

+1      V   C   R   G       S   T   G       G   S   R       G   P   F   E       C   K   P       I   P   N
1021    TGTGTGTGCA  GAGGGAGCAC  AGGAGGATCT  AGAGGGCCCT  TCGAAGGTAA  GCCTATCCCT

+1      P   L   L   G       L   D   S       T   R   T       G   H   H   H       H   H   H
1081    AACCCTCTCC  TCGGTCTCGA  TTCTACGCGT  ACCGGTCATC  ATCACCATCA  CCATTGA
```

Fig. 19-2

DNA AND POLYPEPTIDE SEQUENCE USED FOR BACULOVIRUS/INSECT CELL EXPRESSION

```
1     GAATTCAAAG GCCTGTATTT TACTGTTTTC GTAACAGTTT TGTAATAAAA AAACCTATAA

+3         m  k  f    l  v  n     v  a  l     v  f  m  v    v  y  i     s  y  i
61    ATATGAAATT CTTAGTCAAC GTTGCCCTTG TTTTTATGGT CGTATACATT TCTTACATCT

+3     y  a  D  P    E  S  H     H  H  H  H    E  S     N  L  S     S  K  F
121   ATGCGGATCC GGAGTCTCAC CATCACCACC ATCATGAATC AACCTGAGT AGTAAATTCC

+3     Q  F  S  S    N  K  E     Q  N  G     V  Q  D  P    Q  H  E    R  I  I
181   AGTTTTCCAG CAACAAGGAA CAGAACGGAG TACAAGATCC TCAGCATGAG AGAATTATTA

+3     T  V  S  T    N  G  S     I  H  S     P  R  F  P    H  T  Y    P  R  N
241   CTGTGTCTAC TAATGGAAGT ATTCACAGCC CAAGGTTTCC TCATACTTAT CCAAGAAATA

+3     T  V  L  V    W  R  L     V  A  V     E  E  N  V    W  I  Q    L  T  F
301   CGGTCTTGGT ATGGAGATTA GTAGCAGTAG AGGAAAATGT ATGGATACAA CTTACGTTTG

+3     D  E  R  F    G  L  E     D  P  G     D  D  I  C    K  Y  D    F  V  G
361   ATGAAAGATT TGGGCTTGAA GACCCAGAAG ATGACATATG CAAGTATGAT TTTGTAGAAG

+3     V  E  E  P    S  D  G     T  I  L     G  R  W  C    G  S  G    T  V  P
421   TTGAGGAACC CAGTGATGGA ACTATATTAG GGCGCTGGTG TGGTTCTGGT ACTGTACCAG

+3     G  K  E  I    S  K  G     N  Q  I     R  I  R  F    V  S  D    E  Y  F
481   GAAAACAGAT TTCTAAAGGA AATCAAATTA GGATAAGATT TGTATCTGAT GAATATTTTC

+3     P  S  E  P    G  F  C     I  H  Y     N  I  V  M    P  Q  F    T  E  A
541   CTTCTGAACC AGGGTTCTGC ATCCACTACA ACATTGTCAT GCCACAATTC ACAGAAGCTG

+3     V  S  P  S    V  L  P     P  S  A     L  P  L  D    L  L  N    N  A  I
601   TGAGTCCTTC AGTGCTACCC CCTTCAGCTT TGCCACTGGA CCTGCTTAAT AATGCTATAA

+3     T  A  F  S    T  L  E     D  L  I     R  Y  L  E    P  E  R    W  Q  L
661   CTGCCTTTAG TACCTTGGAA GACCTTATTC GATATCTTGA ACCAGAGAGA TGGCAGTTGG

+3     D  L  E  D    L  Y  R     P  T  W     Q  L  L  G    K  A  F    V  F  G
721   ACTTAGAAGA TCTATATAGG CCAACTTGGC AACTTCTTGG CAAGGCTTTT GTTTTTGGAA
```

Fig. 20-1

```
+3    R   K   S   R      V   V   D      L   R   L      L   T   E   E      V   R   L      Y   S   C
781   GAAAATCCAG  AGTGGTGGAT  CTGAACCTTC  TAACAGAGGA  GGTAAGATTA  TACAGCTGCA

+3    T   P   R   N      F   S   V      S   I   R      E   E   L   K      R   T   D      T   I   F
841   CACCTCGTAA  CTTCTCAGTG  TCCATAAGGG  AAGAACTAAA  GAGAACCGAT  ACCATTTTCT

+3    W   P   G   C      L   L   V      K   R   C      G   G   N   C      A   C   C      L   H   N
901   GGCCAGGTTG  TCTCCTGGTT  AAACGCTGTG  GTGGGAACTG  TGCCTGTTGT  CTCCACAATT

+3    C   N   E   C      Q   C   V      P   S   K      V   T   K   K      Y   H   E      V   L   Q
961   GCAATGAATG  TCAATGTGTC  CCAAGCAAAG  TTACTAAAAA  ATACCACGAG  GTCCTTCAGT

+3    L   R   P   K      T   G   V      R   G   L      H   K   S   L      T   D   V      A   L   E
1021  TGAGACCAAA  GACCGGTGTC  AGGGGATTGC  ACAAATCACT  CACCGACGTG  GCCCTGGAGC

+3    H   H   E   E      C   D   C      V   C   R      G   S   T   G      G
1081  accatgagga  gtgtgactgt  gtgtgcagag  ggagcacagg  aggatagctc  taga
```

Fig. 20-2

DNA AND POLYPEPTIDE SEQUENCE USED FOR E.coli EXPRESSION

```
+ 3        Q  T  N     S  S  S     N  N  N     N  N  N     N  N  N     L  G  I
1     CGCAGACTAA TTCGAGCTCG AACAACAACA ACAATAACAA TAACAACAAC CTCGGGATCG

E  G  R  I     S  E  F     E  S  N     L  S  S  K     F  Q  F     S  S  N
61    AGGGAAGGAT TTCAGAATTC GAATCCAACC TGAGTAGTAA ATTCCAGTTT TCCAGCAACA

+ 3        K  E  Q     G  V  Q     D  P  Q     H  E  R  I     I  T  V     S  T  N
121   AGGAACAGAA CCGAGTACAA GATCCTCAGC ATGAGAGAAT TATTACTGTG TCTACTAATG

+ 3        G  S  I  H     S  P  R     F  P  H     T  Y  P  R     N  T  V     L  V  W
181   GAAGTATTCA CAGCCCAAGG TTTCCTCATA CTTATCCAAG AAqTACGGTC TTGGTATGGA

+ 3        R  L  V  A     V  E  E     N  V  W     I  Q  L  T     I  D  E     R  F  G
241   GATTAGTXGC AGTAGAGGAA AATGTATGGA TACAACTTAC GTTTGATGAA AGATTTGGGC

+ 3        L  E  D  P     E  D  D     I  C  K     Y  D  F  V     E  V  E     E  P  S
301   TTGAAGACCC AGAAGATGAC ATATGCAAGT ATGATTTTGT AGAAGTTGAG GAACCCAGTG

+ 3        D  G  T  I     L  G  R     W  C  G     S  G  T  V     P  G  K     Q  I  S
361   ATGGAACTAT ATTAGGGCGC TGGTGTGGTT CTGGTACTGT ACCAGGAAAA CAGATTTCTA

+ 3        K  G  S  Q     I  R  I     R  F  V     S  D  E  Y     F  P  S     E  P  G
421   AAGGAAATCA AATTAGGATA AGATTTGTAT CTGATGAATA TTTTCCTTCT GAACCAGGGT

+ 3        F  C  I  H     Y  N  I     V  M  P     Q  F  T  E     A  V  S     P  S  V
481   TCTGCATCCA CTACAACATT GTCATGCCAC AATTCACAGA AGCTGTGAGT CCTTCAGTGC

+ 3        L  P  P  S     A  L  P     L  D  L     L  N  N  A     I  T  A     F  S  T
541   TACCCCCTTC AGZTTTGCCA CTGGACCTGC TTAATAATGC TATAACTGCC TTTAGTACCT

+ 3        L  E  D  L     I  R  Y     L  E  P     E  R  W  Q     L  D  L     E  D  L
601   TGGAAGACCT TATTCGATAT CTTGAACCAG AGAGATGGCA GTTGGACTTA GAAGATCTAT

+ 3        Y  R  P  T     W  Q  L     L  G  K     A  F  V  F     G  R  K     S  R  V
661   ATAGGCCAAC TTGGCAACTT CTTGGCAAGG CTTTTGTTTT TGGAAGAAAA TCCAGAGTGG

+ 3        V  D  L  N     L  L  T     E  E  V     R  L  Y  S     C  T  P     R  N  F
721   TGGATCCGAA CCTTCTAACA GAGGAGGTAA GATTATACAG CTGCACACCT CGTAACTTCT

+ 3        S  V  S  I     R  E  E     L  K  R     T  D  T  I     F  W  P     G  C  L
781   CAGTGTCCAT AAGGGAAGAA CTAAAGAGAA CCGATACCAT TTTCTGGCCA GGTTGTCTCC
```

Fig. 21-1

```
   +3   L   V   K   R    C   G   G    N   C   A    C   C   L   E    N   C   N    E   C   Q
  841   TGGTTAAACG  CTGCGGTGGG  AACTGTGCCT  GTTGTCTCCA  CAATTGCAAT  GAATGTCAAT

+3   C   V   I   S    K   V   T    K   K   Y    H   E   V   L    Q   L   R    P   K   T
  901   GTGTCCCAAG  CAAAGTTACT  AAAAAATACC  ACGAGGTCCT  TCAGTTGAGA  CCAAAGACCG

+3   G   V   R    G   L   H   K    S   L   T    D   V   A   L    E   H   H    E   E   C
  961   GTGTCAGGGG  ATTGCACAAA  TCACTCACCG  ACGTGGCCCT  GGAGCACCAT  GAGGAGTGTG

+3   D   C   V   C    R   G   S    T   G   G    H   H   H   H    H   H   *
 1021   ACTGTGTGTG  CAGAGGGAGC  ACAGGAGGAC  ATCATCACCA  TCACCATTGA  TCTAGAGTCG

1081   ACCTGCAGGC  AAGCTT
```

Fig. 21-2

DNA AND POLYPEPTIDE SEQUENCE USED FOR E.coli
EXPRESSION OF THE PDGF-LIKE DOMAIN

```
+ 3                  M   R   G   S   H   H   H   H   H   G   M   A   S   M
1    AAGGAGATAT ACATATGCGG GGTTCTCATC ATCATCATCA TCATGGTATG GCTAGCATGA

+ 3   T   G   O   O   M   G   R   D   L   Y   D   D   D   D   K   D   P   G   R
61   CTGGTGGACA GCAAATGGGT CGGGATCTGT ACGACGATGA CGATAAGGAT CCGCGAAGAA

+ 3   K   S   R   V   V   D   L   N   L   L   T   E   E   V   R   L   Y   S   C   T
121  AATCCAGAGT GGTGGATCTG AACCTTCTAA CAGAGGAGGT AAGATTATAC AGCTGCACAC

+ 3   P   R   N   F   S   V   S   I   R   E   E   L   K   R   T   D   T   I   F   W
101  CTCGTAACTT CTCAGTGTCC ATAAGGGAAG AACTAAAGAG AACCGATACC ATTTTCTGGC

+ 3   P   G   C   L   L   V   K   R   C   G   G   N   C   A   C   C   L   H   N   C
241  CAGGTTGTCT CCTGGTTAAA CGCTGTGGTG GGAACTGTGC CTGTTGTCTC CACAATTGCA

+ 3   N   E   C   Q   C   V   P   S   K   V   T   K   K   Y   H   E   V   L   Q   L
301  ATGAATGTCA ATGTGTCCCA AGCAAAGTTA CTAAAAAATA CCACGAGGTC CTTCAGTTGA

+ 3   R   P   K   T   G   V   R   G   L   H   K   S   L   T   D   V   A   L   E   H
361  GACCAAAGAC CCGTGTCAGG CGATTGCACA AATCACTCAC CGACGTGGCC CTGGAGCACC

+ 3   H   E   E   C   D   C   V   C   R   G   S   T   G   G
421  ATGAGGAGTG TGACTGTGTG TGCAGAGGGA GCACAGGAGG ATAATGAATT CGAAGCTTGA

481  TCCGGCTGCT AACAAAGCCC
```

Fig. 24

EXPRESSION OF PDGF DOMAIN IN E.coli

DNA AND POLYPEPTIDE SEQUENCE USED FOR E.coli
EXPRESSION OF THE CUB-LIKE DOMAIN

```
+ 2        M   A   M   D   I   G   I   N   S   D   P   E   S   H   H   H   H   H
  1    GGCGATGGCC ATGGATATCG AATTAATTC GGATCCGGAG TCTCACCATC ACCACCATCA

+2         E   S   N   L   S   S   K   F   Q   F   S   S   N   K   E   Q   N   G   V   Q
 61    TGAATCCAAC CTGAGTAGTA AATTCCAGTT TTCCAGCAAC AAGGAACAGA ACGGAGTACA

+2         D   P   Q   H   E   R   I   I   T   V   S   T   N   G   S   I   H   S   P   R
121    AGATCCTCAG CATGAGAGAA TTATTACTGT GTCTACTAAT GGAAGTATTC ACAGCCCAAG

+2         F   P   H   T   Y   P   R   N   T   V   L   W   R   L   V   A   V   E   E
181    GTTTCCTCAT ACTTATCCAA GAAATACGGT CTTGGTATGG AGATTAGTAG CAGTAGACGA

+2         N   V   W   I   Q   L   T   F   D   E   R   F   G   L   E   D   P   E   D   D
241    AAATGTATGG ATACAACTTA CGTTTGATGA AGATTTGGG CTTGAAGACC CAGAAGATGA

+ 2        I   C   K   V   D   F   V   E   V   E   E   P   S   D   G   T   I   L   G   R
301    CATATGCAAG TATGATTTTG TAGAAGTTGA GGAACCCAGT GATGGAACTA TATTAGGGCG

+2         W   C   G   S   G   T   V   P   G   K   Q   I   S   K   G   N   Q   I   R   I
361    CTGGTGTGGT TCTGGTACTG TACCAGGAAA ACAGATTTCT AAAGGAAATC AAATTAGGAT

+ 2        R   F   V   S   D   E   Y   F   P   S   E   P   G   F   C   I   H   Y   N   I
421    AAGATTTGTA TCTGATGAAT ATTTTCCTTC TGAACCAGGG TTCTGCATCC ACTACAACAT

+2         V   M   P   C   F   T   E   A   V
491    TGTCATGCCA CAATTCACAG AAGCTGTGTA GTCGAGCTCC GTCGACAAGC TTGCGGCCGC

541    ACTCGAGCAC
```

Fig. 26

GENOMIC DNA SEQUENCES OF 2 EXONS DETERMINED BY SEQUENCING tttcttttataccatatagtggtggatctgaaccagGGTTCTGCATCCACTACAACATTGTC
ATGCCACAATTCACAGAAGCTGTGAGTCCTTCAGTGCTACCCCCTTCAGCTTTGCCACTGGA
CCTGCTTAATAATGCTATAACTGCCTTTAGTACCTTGGAAGACCTTATTCGATATCTTGAAC
CAGAGAGATGGCAGTTGGACTTAGAAGATCTATATAGGCCAACTTGGCAACTTCTTGGCAAG
GCTTTTGTTTTTGGAAGAAAATCCAGAGTGGTGGATCTGAACCTTCTAACAGAGGAGGTAAG
ATTATACAGCTGCACACCTCGTAACTTCTCAGTGTCCATAAGGGAAGAACTAAAGAGAACCG
ATACCATTTTCTGGCCAGGTTGTCTCCTGGTTAAACGCTGTGGTGGGAACTGTGCCTGTTGT
CTCCACAATTGCAATGAATGTCAATGTGTCCCAAGCAAAGTTACTAAAAAATACCACGAGgt
aggtatacaattttcttttggtttccttcgggtattttatgtctt aaagccagtcatagacattcgttgattttaaaagtggcttactcttattccctttcagGTC
CTTCAGTTGAGACCAAAGACCGGTGTCAGGGGATTGCACAAATCACTCACCGACGTGGCCCT
GGAGCACCATGAGGAGTGTGACTGTGTGTGCAGAGGGAGCACAGGAGGATAGCCGCATCACC
ACCAGCAGCTCTTGCCCAGAGCTGTGCAGTGCAGTGGCTGATTCTATTAGAGAACGTATGCG
TTATCTCCATCCTTAATCTCAGTTGTTTGCTTCAAGGACCTTTCATCTTCAGGATTTACAGT
GCATTCTGAAAGAGGAGACATCAAACAGAATTAGGAGTTGTGCAACAGCTCTTTTGAGAGGA
GGCCTAAAGGACAGGAGAAAAGGTCTTCAATCGTGGAAAGAAAATTAAATGTTGTATTAAAT
AGATCACCAGCTAGTTTCAGAGTTACCATGTACGTATTCCACTAGCTGGGTTCTGTATTTCA
GTTCTTTCGATACGGCTTAGGGTAATGTCAGTACAGGAAAAAAACTGTGCAAGTGAGCACCT
GATTCCGTTGCCTTGGCTTAACTCTAAAGCTCCATGTCCTGGGCCTAAAATCGTATAAAATC
TGGATTTTTTTTTTTTTTTTGCGCATATTCACATATGTAAACCAGAACATTCTATGTACTA
CAAACCTGGTTTTTAAAAAGGAACTATGTTGCTATGAATTAAACTTGTGTCATGCTGATAGG
ACAGACTGGATTTTTCATATTTCTTATTAAAATTTCTGCCATTTAGAAGAAGAGAACTACAT
TCATGGTTTGGAAGAGATAAACCTGAAAAGAAGAGTGGCCTTATCTTCACTTTATCGATAAG
TCAGTTTATTTGTTTCATTGTGTACATTTTTATATTCTCCTTTTGACATTATAACTGTTGGC
TTTTCTAATCTTGTTAAATATATCTATTTTTACCAAAGGTATTTAATATTCTTTTTTATGAC
AACTTAGATCAACTATTTTTAGCTTGGTAAATTTTTCTAAACACAATTGTTATAGCCAGAGG
AACAAAGATGATATAAAATATTGTTGCTCTGACAAAAATACATGTATTTCATTCTCGTATGG
TGCTAGAGTTAGATTAATCTGCATTTTAAAAAACTGAATTGGAATAGAATTGGTAAGTTGCA
AAGACTTTTTGAAAATAATTAAATTATCATATCTTCCATTCCTGTTATTGGAGATGAAAATA
AAAAGCAACTTATGAAAGTAGACATTCAGATCCAGCCATTACTAACCTATTCCTTTTTTGGG
GAAATCTGAGCCTAGCTCAGAAAAACATAAAGCACCTTGAAAAAGACTTGGCAGCTTCCTGA
TAAAGCGTGCTGTGCTGTGCAGTAGGAACACATCCTATTTATTGTGATGTTGTGGTTTTATT
ATCTTAAACTCTGTTCCATACACTTGTATAAATACATGGATATTTTTATGTACAGAAGTATG
TCTCTTAACCAGTTCACTTATTGTACTCTGGCAATTTAAAAGAAAATCAGTAAAATATTTTG
CTTGTAAAATGCTTAATATCGTGCCTAGGTTATGTGGTGACTATTTGAATCAAAAATGTATT
GAATCATCAAATAAAAGAATGTGGCTATTTTGGGGAGAAAATTatgtgtgtgtgctcaag
atttatttcttggactctgagaaaatgaaagataaa

Fig. 30A

LOCATION OF SPLICE SITES WITHIN THE cDNA SEQUENCE

```
  1  GAATTCGCCC TTTTGTTTAA ACCTTGGGAA CTGGTTCAGG TCCAGGTTTT GCTTTGATCC

61  TTTTCAAAAA CTGGAGACAC AGAAGAGGGC TCTAGGAAAA AGTTTTGGAT GGGATTATGT

121  GGAAACTACC CTGCGATTCT CTGCTGCCAG AGCAGGCTCG GCGCTTCCAC CCCAGTGCAG

181  CCTTCCCCTG GCGGTGGTGA AAGAGACTCG GGAGTCGCTG CTTCCAAAGT GCCCGCCGTG

+3                                   M  S  L  F  G  L  L  L  L  T  S
241  AGTGAGCTCT CACCCCAGTC AGCCAAATGA GCCTCTTCGG GCTTCTCCTG CTGACATCTG

+3 A  L  A  G  Q  R  Q  G  T  Q  A  E  S  N  L  S  S  K  F  Q
301  CCCTGGCCGG CCAGAGACAG GGGACTCAGG CGGAATCCAA CCTGAGTAGT AAATTCCAGT

+3 F  S  S  N  K  E  Q  N  G  V  Q  D  P  Q  H  E  R  I  I  T
361  TTTCCAGCAA CAAGGAACAG AACGGAGTAC AAGATCCTCA GCATGAGAGA ATTATTACTG

+3 V  S  T  N  G  S  I  H  S  P  R  F  P  H  T  Y  P  R  N  T
421  TGTCTACTAA TGGAAGTATT CACAGCCCAA GGTTTCCTCA TACTTATCCA AGAAATACGG

+3 V  L  V  W  R  L  V  A  V  E  E  N  V  W  I  Q  L  T  F  D
481  TCTTGGTATG GAGATTAGTA GCAGTAGAGG AAAATGTATG GATACAACTT ACGTTTGATG

+3 E  R  F  G  L  E  D  P  E  D  D  I  C  K  Y  D  F  V  E  V
541  AAAGATTTGG GCTTGAAGAC CCAGAAGATG ACATATGCAA GTATGATTTT GTAGAAGTTG

+3 E  E  P  S  D  G  T  I  L  G  R  W  C  G  S  G  T  V  P  G
601  AGGAACCCAG TGATGGAACT ATATTAGGGC GCTGGTGTGG TTCTGGTACT GTACCAGGAA

+3 K  Q  I  S  K  G  N  Q  I  R  I  R  F  V  S  D  E  Y  F  P
661  AACAGATTTC TAAAGGAAAT CAAATTAGGA TAAGATTTGT ATCTGATGAA TATTTTCCTT

+3 S  E  P |G  F  C  I  H  Y  N  I  V  M  P  Q  F  T  E  A  V
721  CTGAACCAG|G TTCTGCATC CACTACAACA TTGTCATGCC ACAATTCACA GAAGCTGTGA

+3 S  P  S  V  L  P  P  S  A  L  P  L  D  L  N  N  A  I  T
781  GTCCTTCAGT GCTACCCCCT TCAGCTTTGC CACTGGACCT GCTTAATAAT GCTATAACTG

+3 A  F  S  T  L  E  D  L  I  R  Y  L  E  P  E  R  W  Q  L  D
841  CCTTTAGTAC CTTGGAAGAC CTTATTCGAT ATCTTGAACC AGAGAGATGG CAGTTGGACT

+3 L  E  D  L  Y  R  P  T  W  Q  L  G  K  A  F  V  F  G  R
901  TAGAAGATCT ATATAGGCCA ACTTGGCAAC TTCTTGGCAA GGCTTTTGTT TTTGGAAGAA

+3 K  S  R  V  V  D  L  N  L  L  T  E  E |V  R  L  Y  S  C  T
961  AATCCAGAGT GGTGGATCTG AACCTTCTAA CAGAGGAG|GT AAGATTATAC AGCTGCACAC
```

Fig. 30B-1

```
     +3 P   R   N   F   S   V   S   I   R   E   E   L   K   R   T   D   T   I   F   W
1021    CTCGTAACTT CTCAGTGTCC ATAAGGGAAG AACTAAAGAG AACCGATACC ATTTTCTGGC

+3 P   G   C   L   L   V   K   R   C   G   G   N   C   A   C   C   L   H   N   C
1081    CAGGTTGTCT CCTGGTTAAA CGCTGTGGTG GGAACTGTGC CTGTTGTCTC CACAATTGCA

+3 N   E   C   Q   C   V   P   S   K   V   T   K   K   Y   H   E   V   L   Q   L
1141    ATGAATGTCA ATGTGTCCCA AGCAAAGTTA CTAAAAAATA CCACGAGGTC CTTCAGTTGA

+3 R   P   K   T   G   V   R   G   L   H   K   S   L   T   D   V   A   L   E   H
1201    GACCAAAGAC CGGTGTCAGG GGATTGCACA AATCACTCAC CGACGTGGCC CTGGAGCACC

+3 H   E   E   C   D   C   V   C   R   G   S   T   G   G
1261    ATGAGGAGTG TGACTGTGTG TGCAGAGGGA GCACAGGAGG ATAGCCGCAT CACCACCAGC
1321    AGCTCTTGCC CAGAGCTGTG CAGTGCAGTG GCTGATTCTA TTAGAGAACG TATGCGTTAT
1381    CTCCATCCTT AATCTCAGTT GTTTGCTTCA AGGACCTTTC ATCTTCAGGA TTTACAGTGC
1441    ATTCTGAAAG AGGAGACATC AAACAGAATT GGAGTTGTG CAACAGCTCT TTTGAGAGGA
1501    GGCCTAAAGG ACAGGAGAAA AGGTCTTCAA TCGTGGAAAG AAAATTAAAT GTTGTATTAA
1561    ATAGATCACC AGCTAGTTTC AGAGTTACCA TGTACGTATT CCACTAGCTG GGTTCTGTAT
1621    TTCAGTTCTT TCGATACGGC TTAGGGTAAT GTCAGTACAG GAAAAAAACT GTGCAAGTGA
1681    GCACCTGATT CCGTTGCCTT GCTTAACTCT AAAGCTCCAT GTCCTGGGCC TAAAATCGTA
1741    TAAAATCTGG ATTTTTTTTT TTTTTTTTG CTCATATTCA CATATGTAAA CCAGAACATT
1801    CTATGTACTA CAAACCTGGT TTTTAAAAAG GAACTATGTT GCTATGAATT AAACTTGTGT
1861    CATGCTGATA GGACAGACTG GATTTTTCAT ATTTCTTATT AAAATTTCTG CCATTTAGAA
1921    GAAGAGAACT ACATTCATGG TTTGGAAGAG ATAAACCTGA AAGAAGAGT GGCCTTATCT
1981    TCACTTTATC GATAAGTCAG TTTATTTGTT TCATTGTGTA CATTTTTATA TTCTCCTTTT
2041    GACATTATAA CTGTTGGCTT TTCTAATCTT GTTAAATATA TCTATTTTTA CCAAAGGTAT
2101    TTAATATTCT TTTTTATGAC AACTTAGATC AACTATTTTT AGCTTGGTAA ATTTTTCTAA
2161    ACACAATTGT TATAGCCAGA GGAACAAAGA TGATATAAAA TATTGTTGCT CTGACAAAAA
2221    TACATGTATT TCATTCTCGT ATGGTGCTAG AGTTAGATTA ATCTGCATTT TAAAAAACTG
2281    AATTGGAATA GAATTGGTAA GTTGCAAAGA CTTTTTGAAA ATAATTAAAT TATCATATCT
2341    TCCATTCCTG TTATTGGAGA TGAAAATAAA AAGCAACTTA TGAAAGTAGA CATTCAGATC
2401    CAGCCATTAC TAACCTATTC CTTTTTTGGG GAAATCTGAG CCTAGCTCAG AAAAACATAA
2461    AGCACCTTGA AAAAGACTTG GCAGCTTCCT GATAAAGCGT GCTGTGCTGT GCAGTAGGAA
2521    CACATCCTAT TTATTGTGAT GTTGTGGTTT TATTATCTTA AACTCTGTTC CATACACTTG
2581    TATAAATACA TGGATATTTT TATGTACAGA AGTATGTCTC TTAACCAGTT CACTTATTGT
2641    ACCTGGAAGG GCGAATTCTG CAGATATC
```

Fig. 30B-2

SEQUENCE LISTING

```
<160> NUMBER OF SEQ ID NOS: 130

<210> SEQ ID NO 1
<211> LENGTH: 323
<212> TYPE: PRT
<213> ORGANISM: Homo sapiens

<400> SEQUENCE: 1

Glu Ser Asn Leu Ser Ser Lys Phe Gln Phe Ser Ser Asn Lys Glu Gln
 1               5                  10                  15

Tyr Gly Val Gln Asp Pro Gln His Glu Arg Ile Ile Thr Val Ser Thr
            20                  25                  30

Asn Gly Ser Ile His Ser Pro Arg Phe Pro His Thr Tyr Pro Arg Asn
        35                  40                  45

Thr Val Leu Val Trp Arg Leu Val Ala Val Glu Glu Asn Val Trp Ile
    50                  55                  60
```

```
Gln Leu Thr Phe Asp Glu Arg Phe Gly Leu Glu Asp Pro Glu Asp Asp
 65                  70                  75                  80

Ile Cys Lys Tyr Asp Phe Val Glu Val Glu Pro Ser Asp Gly Thr
                 85                  90                  95

Ile Leu Gly Arg Trp Cys Gly Ser Gly Thr Val Pro Gly Lys Gln Ile
                100                 105                 110

Ser Lys Gly Asn Gln Ile Arg Ile Arg Phe Val Ser Asp Glu Tyr Phe
                115                 120                 125

Pro Ser Glu Pro Gly Phe Cys Ile His Tyr Asn Ile Val Met Pro Gln
                130                 135                 140

Phe Thr Glu Ala Val Ser Pro Ser Val Leu Pro Pro Ser Ala Leu Pro
145                 150                 155                 160

Leu Asp Leu Leu Asn Asn Ala Ile Thr Ala Phe Ser Thr Leu Glu Asp
                165                 170                 175

Leu Ile Arg Tyr Leu Glu Pro Glu Arg Trp Gln Leu Asp Leu Glu Asp
                180                 185                 190

Leu Tyr Arg Pro Thr Trp Gln Leu Leu Gly Lys Ala Phe Val Phe Gly
                195                 200                 205

Arg Lys Ser Arg Val Val Asp Leu Asn Leu Leu Thr Glu Glu Val Arg
                210                 215                 220

Leu Tyr Ser Cys Thr Pro Arg Asn Phe Ser Val Ser Ile Arg Glu Glu
225                 230                 235                 240

Leu Lys Arg Thr Asp Thr Ile Phe Trp Pro Gly Cys Leu Leu Val Lys
                245                 250                 255

Arg Cys Gly Gly Asn Cys Ala Cys Cys Leu His Asn Cys Asn Glu Cys
                260                 265                 270

Gln Cys Val Pro Ser Lys Val Thr Lys Lys Tyr His Glu Val Leu Gln
                275                 280                 285

Leu Arg Pro Lys Thr Gly Val Arg Gly Leu His Lys Ser Leu Thr Asp
                290                 295                 300

Val Ala Leu Glu His His Glu Glu Cys Asp Cys Val Cys Arg Gly Ser
305                 310                 315                 320

Thr Gly Gly

<210> SEQ ID NO 2
<211> LENGTH: 345
<212> TYPE: PRT
<213> ORGANISM: Homo sapiens

<400> SEQUENCE: 2

Met Ser Leu Phe Gly Leu Leu Leu Leu Thr Ser Ala Leu Ala Gly Gln
  1               5                  10                  15

Arg Gln Gly Thr Gln Ala Glu Ser Asn Leu Ser Ser Lys Phe Gln Phe
                 20                  25                  30

Ser Ser Asn Lys Glu Gln Tyr Gly Val Gln Asp Pro Gln His Glu Arg
                 35                  40                  45

Ile Ile Thr Val Ser Thr Asn Gly Ser Ile His Ser Pro Arg Phe Pro
                 50                  55                  60

His Thr Tyr Pro Arg Asn Thr Val Leu Val Trp Arg Leu Val Ala Val
 65                  70                  75                  80

Glu Glu Asn Val Trp Ile Gln Leu Thr Phe Asp Glu Arg Phe Gly Leu
                 85                  90                  95

Glu Asp Pro Glu Asp Asp Ile Cys Lys Tyr Asp Phe Val Glu Val Glu
                100                 105                 110
```

-continued

```
Glu Pro Ser Asp Gly Thr Ile Leu Gly Arg Trp Cys Gly Ser Gly Thr
            115                 120                 125

Val Pro Gly Lys Gln Ile Ser Lys Gly Asn Gln Ile Arg Ile Arg Phe
        130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
        275                 280                 285

His Asn Cys Asn Glu Cys Gln Cys Val Pro Ser Lys Val Thr Lys Lys
    290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
            340                 345
```

<210> SEQ ID NO 3
<211> LENGTH: 1035
<212> TYPE: DNA
<213> ORGANISM: Homo sapiens

<400> SEQUENCE: 3

| | | | | | |
|---|---|---|---|---|---|
| atgagcctct | tcgggcttct | cctgctgaca | tctgccctgg | ccggccagag | acaggggact | 60 |
| caggcggaat | ccaacctgag | tagtaaattc | cagttttcca | gcaacaagga | acagaacgga | 120 |
| gtacaagatc | ctcagcatga | gaattatt | actgtgtcta | ctaatggaag | tattcacagc | 180 |
| ccaaggtttc | ctcatactta | tccaagaaat | acggtcttgg | tatggagatt | agtagcagta | 240 |
| gaggaaaatg | tatggataca | acttacgttt | gatgaaagat | ttgggcttga | agacccagaa | 300 |
| gatgacatat | gcaagtatga | ttttgtagaa | gttgaggaac | ccagtgatgg | aactatatta | 360 |
| ggcgctggt | gtggttctgg | tactgtacca | ggaaaacaga | tttctaaagg | aaatcaaatt | 420 |
| aggataagat | ttgtatctga | tgaatatttt | ccttctgaac | agggttctg | catccactac | 480 |
| aacattgtca | tgccacaatt | cacagaagct | gtgagtcctt | cagtgctacc | ccttcagct | 540 |
| ttgccactgg | acctgcttaa | taatgctata | actgccttta | gtaccttgga | agaccttatt | 600 |
| cgatatcttg | aaccagagag | atggcagttg | gacttagaag | atctatatag | gccaacttgg | 660 |
| caacttcttg | gcaaggcttt | tgttttttgga | agaaaatcca | gagtggtgga | tctgaacctt | 720 |
| ctaacagagg | aggtaagatt | atacagctgc | acacctcgta | acttctcagt | gtccataagg | 780 |

-continued

| | |
|---|---|
| gaagaactaa agagaaccga taccattttc tggccaggtt gtctcctggt taaacgctgt | 840 |
| ggtgggaact gtgcctgttg tctccacaat tgcaatgaat gtcaatgtgt cccaagcaaa | 900 |
| gttactaaaa aataccacga ggtccttcag ttgagaccaa agaccggtgt caggggattg | 960 |
| cacaaatcac tcaccgacgt ggccctggag caccatgagg agtgtgactg tgtgtgcaga | 1020 |
| gggagcacag gagga | 1035 |

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 4
aaaatgtatg gatacaactt ac        22

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 5
gtttgatgaa agatttgggc ttg       23

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 6
tttctaaagg aaatcaaatt ag        22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 7
gataagattt gtatctgatg            20

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 8
gatgtctcct ctttcag               17

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 9
gcacaactcc taattctg                                              18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 10
agcacctgat tccgttgc                                              18

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 11
tagtacatag aatgttctgg                                            20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 12
aagagacata cttctgtac                                             19

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 13
ccaggtacaa taagtgaact g                                          21

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 14
cctttagaaa tctgttttcc tggtacag                                   28

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 15
ggaaaatatt catcagatac aaatcttatc c                               31

<210> SEQ ID NO 16
<211> LENGTH: 22
<212> TYPE: DNA

```
<213> ORGANISM: Artificial Sequence
<220> FEATURE:
<223> OTHER INFORMATION: Description of Artificial Sequence:primer

<400> SEQUENCE: 16
ggtccagtgg caaagctgaa gg                                              22

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 17
ctggttcaag atatcgaata aggtcttcc                                       29

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 18
tttgtttaaa ccttgggaaa ctgg                                            24

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 19
gtccaggttt tgctttgatc c                                               21

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 20
aattggatcc gagagtggtg gatctgaacc                                      30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 21
aattggatcc gggaagaaaa tccagagtgg                                      30

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence:primer

<400> SEQUENCE: 22
ggttgaattc attattttttt agtaactttg cttgggacac                          40
```

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 23
aattgaattc attatcctcc tgtgctccct c                               31

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: primer

<400> SEQUENCE: 24
aattggatcc ggagtctcac catcaccacc atcatgaatc caacctgagt agtaaattcc   60

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 25
aattgaattc gctatcctcc tgtgctccct ctgc                            34

<210> SEQ ID NO 26
<211> LENGTH: 111
<212> TYPE: PRT
<213> ORGANISM: Homo sapiens

<400> SEQUENCE: 26

Gly Val Gln Asp Pro Gln His Glu Arg Ile Ile Thr Val Ser Thr Asn
 1               5                  10                  15

Gly Ser Ile His Ser Pro Arg Phe Pro His Thr Tyr Pro Arg Asn Thr
            20                  25                  30

Val Leu Val Trp Arg Leu Val Ala Val Glu Glu Asn Val Trp Ile Gln
        35                  40                  45

Leu Thr Phe Asp Glu Arg Phe Gly Leu Glu Asp Pro Glu Asp Asp Ile
    50                  55                  60

Cys Lys Tyr Asp Phe Val Glu Val Glu Glu Pro Ser Asp Gly Thr Ile
 65                  70                  75                  80

Leu Gly Arg Trp Cys Gly Ser Gly Thr Val Pro Gly Lys Gln Ile Ser
                85                  90                  95

Lys Gly Asn Gln Ile Arg Ile Arg Phe Val Ser Asp Glu Tyr Phe
            100                 105                 110

<210> SEQ ID NO 27
<211> LENGTH: 168
<212> TYPE: PRT
<213> ORGANISM: Homo sapiens

<400> SEQUENCE: 27

Met Ala Met Asp Ile Gly Ile Asn Ser Asp Pro Glu Ser His His His
 1               5                  10                  15

His His His Glu Ser Asn Leu Ser Ser Lys Phe Gln Phe Ser Ser Asn
            20                  25                  30

```
Lys Glu Gln Asn Gly Val Gln Asp Pro Gln His Glu Arg Ile Ile Thr
            35                  40                  45

Val Ser Thr Asn Gly Ser Ile His Ser Pro Arg Phe Pro His Thr Tyr
 50                  55                  60

Pro Arg Asn Thr Val Leu Val Trp Arg Leu Val Ala Val Glu Glu Asn
 65                  70                  75                  80

Val Trp Ile Gln Leu Thr Phe Asp Glu Arg Phe Gly Leu Glu Asp Pro
                 85                  90                  95

Glu Asp Asp Ile Cys Lys Tyr Asp Phe Val Glu Val Glu Pro Ser
            100                 105                 110

Asp Gly Thr Ile Leu Gly Arg Trp Cys Gly Ser Gly Thr Val Pro Gly
            115                 120                 125

Lys Gln Ile Ser Lys Gly Asn Gln Ile Arg Ile Arg Phe Val Ser Asp
            130                 135                 140

Glu Tyr Phe Pro Ser Glu Pro Gly Phe Cys Ile His Tyr Asn Ile Val
145                 150                 155                 160

Met Pro Gln Phe Thr Glu Ala Val
                165

<210> SEQ ID NO 28
<211> LENGTH: 504
<212> TYPE: DNA
<213> ORGANISM: Homo sapiens

<400> SEQUENCE: 28
atggccatgg atatcggaat taattcggat ccggagtctc accatcacca ccatcatgaa     60
tccaacctga gtagtaaatt ccagtttttcc agcaacaagg aacagaacgg agtacaagat    120
cctcagcatg agagaattat tactgtgtct actaatggaa gtattcacag cccaaggttt    180
cctcatactt atccaagaaa tacggtcttg gtatggagat tagtagcagt gaggaaaat     240 gtatggatac aacttacgtt tgatgaaaga tttgggcttg aagacccaga agatgacata    300
tgcaagtatg attttgtaga agttgaggaa cccagtgatg aactatatt agggcgctgg     360 tgtggttctg gtactgtacc aggaaaacag atttctaaag gaaatcaaat taggataaga    420
tttgtatctg atgaatattt tccttctgaa ccagggttct gcatccacta caacattgtc    480
atgccacaat tcacagaagc tgtg                                            504

<210> SEQ ID NO 29
<211> LENGTH: 132
<212> TYPE: PRT
<213> ORGANISM: Homo sapiens

<400> SEQUENCE: 29

Asp Leu Tyr Arg Pro Thr Trp Gln Leu Leu Gly Lys Ala Phe Val Phe
 1               5                  10                  15

Gly Arg Lys Ser Arg Val Val Asp Leu Asn Leu Leu Thr Glu Val
             20                  25                  30

Arg Leu Tyr Ser Cys Thr Pro Arg Asn Phe Ser Val Ser Ile Arg Glu
             35                  40                  45

Glu Leu Lys Arg Thr Asp Thr Ile Phe Trp Pro Gly Cys Leu Leu Val
         50                  55                  60

Lys Arg Cys Gly Gly Asn Cys Ala Cys Cys Leu His Asn Cys Asn Glu
 65                  70                  75                  80

Cys Gln Cys Val Pro Ser Lys Val Thr Lys Lys Tyr His Glu Val Leu
                 85                  90                  95
```

```
Gln Leu Arg Pro Lys Thr Gly Val Arg Gly Leu His Lys Ser Leu Thr
            100                 105                 110

Asp Val Ala Leu Glu His His Glu Glu Cys Asp Cys Val Cys Arg Gly
        115                 120                 125

Ser Thr Gly Gly
    130

<210> SEQ ID NO 30
<211> LENGTH: 300
<212> TYPE: DNA
<213> ORGANISM: Artificial Sequence
<220> FEATURE:
<221> NAME/KEY: misc_feature
<222> LOCATION: (41) (41)
<223> OTHER INFORMATION: n is a, c, g, t, or u
<220> FEATURE:
<221> NAME/KEY: misc_feature
<222> LOCATION: (293) (293)
<223> OTHER INFORMATION: n is a, c, g, t, or u
<220> FEATURE:
<223> OTHER INFORMATION: Description of Artificial Sequence: Human EST

<400> SEQUENCE: 30
cacaaatcac tcaccgacgt ggccctggag caccatgagg ngtgtgactg tgtgtgcaga      60
gggagcacag gaggatagcc gcatcaccac cagcagctct tgcccagagc tgtgcagtgc     120
agtggctgat tctattagag aacgtatgcg ttatctccat ccttaatctc agttgtttgc     180
ttcaaggacc tttcatcttc aggatttaca gtgcattctg aaagaggaga catcaaacag     240
aattaggagt tgtgcaacag ctcttttgag aggaggctaa aggacaggag aanaggtctt     300

<210> SEQ ID NO 31
<211> LENGTH: 284
<212> TYPE: DNA
<213> ORGANISM: Artificial Sequence
<220> FEATURE:
<223> OTHER INFORMATION: Description of Artificial Sequence:Human  EST

<400> SEQUENCE: 31
tgcagtgcag tggctgattc tattagagaa cgtatgcgtt atctccatcc ttaatctcag      60
ttgtttgctt caaggacctt tcatcttcag gatttacagt gcattctgaa agaggagaca     120
tcaaacagaa ttaggagttg tgcaacagct cttttgagag gaggcctaaa ggacaggaga     180
aaaggtcttc aatcgtggaa agaaaattaa atgttgtatt aaatagatca ccagctagtt     240
tcagagttac catgtacgta ttccactagc tgggttctgt attt                      284

<210> SEQ ID NO 32
<211> LENGTH: 275
<212> TYPE: DNA
<213> ORGANISM: Artificial Sequence
<220> FEATURE:
<223> OTHER INFORMATION: Description of Artificial Sequence: Human EST

<400> SEQUENCE: 32
cacgaggtcc ttcagttgag accaaagacc ggtgtcaggg gattgcacaa atcactcacc      60
gacgtggccc tggagcacca tgaggagtgt gactgtgtgt gcagagggag cacagggggga    120 tagccgcatc accaccagca gctcttgccc agagctgtgc agtgcagtgg ctgattctat     180
tagagaacgt atgcgttatc tccatcctta atctcagttg tttgcttcaa ggacctttca     240
tcttcaggat ttacagtgca ttctgaaaga ggaga                                275
```

-continued

```
<210> SEQ ID NO 33
<211> LENGTH: 278
<212> TYPE: DNA
<213> ORGANISM: Artificial Sequence
<220> FEATURE:
<221> NAME/KEY: misc_feature
<222> LOCATION: (248) (248)
<223> OTHER INFORMATION: n is a, c, g, t, or u
<220> FEATURE:
<223> OTHER INFORMATION: Description of Artificial Sequence: Human EST

<400> SEQUENCE: 33
ggaggatagc cgcatcacca ccagcagctc ttgcccagag ctgtgcagtg cagtggctga      60
ttctattaga gaacgtatgc gttatctcca tccttaatct cagttgtttg cttcaaggac     120
ctttcatctt caggatttac agtgcattct gaaagaggag acatcaaaca gaattaggag     180
ttgtgcaaca gctcttttga gaggaggcct aaaggacagg agaaaggtc ttcaatcgtg      240 gaaagaanat taaatgttgt attaaataga caccagct                            278

<210> SEQ ID NO 34
<211> LENGTH: 275
<212> TYPE: DNA
<213> ORGANISM: Artificial Sequence
<220> FEATURE:
<223> OTHER INFORMATION: Description of Artificial Sequence: Human EST

<400> SEQUENCE: 34
ggaggatagc cgcatcacca ccagcagctc ttgcccagag ctgtgcagtg cagtggctga      60
ttctattaga gaacgtatgc gttatctcca tccttaatct cagttgtttg cttcaaggac     120
ctttcatctt caggatttac atgcattctg aaagaggaga catcaaacag aattaggagt     180
tgtgcaacag ctcttttgag aggaggccta aaggacagga gaaaggtct tcaatcgtgg      240 aaagaaaatt aaatgttgta ttaaatagat cacca                              275

<210> SEQ ID NO 35
<211> LENGTH: 261
<212> TYPE: DNA
<213> ORGANISM: Artificial Sequence
<220> FEATURE:
<223> OTHER INFORMATION: Description of Artificial Sequence: Human EST

<400> SEQUENCE: 35
gagaaccgat accattttct ggccaggttg tctcctggtt aaacgctgtg gtgggaactg      60
tgcctgttgt ctccacaatt gcaatgaatg tcaatgtgtc ccaagcaaag ttactaaaaa     120
ataccacgag gtccttcagt tgagaccaaa gaccggtgtc aggggattgc acaaatcact     180
caccgacgtg gccctggagc accatgagga gtgtgactgt gtgtgcagag ggagcacagg     240
aggatagccg catcaccacc a                                             261

<210> SEQ ID NO 36
<211> LENGTH: 279
<212> TYPE: DNA
<213> ORGANISM: Artificial Sequence
<220> FEATURE:
<223> OTHER INFORMATION: Description of Artificial Sequence: Human EST

<400> SEQUENCE: 36
agaaaatcca gagtggtgga tctgaacctt ctaacagagg aggtaagatt atacagctgc      60
acacctcgta acttctcagt gtccataagg gaagaactaa agagaaccga taccattttc     120
tggccaggtt gtctcctggt taaacgctgt ggtgggaact gtgcctgttg tctccacaat     180
```

```
tgcaatgaat gtcaatgtgt cccaagcaaa gttactaaaa ataccacga ggtccttcag    240 ttgagaccaa agaccggtgt caggggattg cacaaatca                          279
```

<210> SEQ ID NO 37
<211> LENGTH: 262
<212> TYPE: DNA
<213> ORGANISM: Artificial Sequence
<220> FEATURE:
<223> OTHER INFORMATION: Description of Artificial Sequence: Human EST

<400> SEQUENCE: 37

```
aggaaatcaa attaggataa gatttgtatc tgatgaatat tttccttctg aaccttctaa    60
cagaggaggt aagattatac agctgcacac ctcgtaactt ctcagtgtcc ataagggaag   120
aactaaagag aaccgatacc attttctggc caggttgtct cctggttaaa cgctgtggtg   180
ggaactgtgc ctgttgtctc ccacaattgc aatgaatgtc aatgtgtccc aagcaaagtt   240
actaaaaaat accacgaggt cc                                            262
```

<210> SEQ ID NO 38
<211> LENGTH: 289
<212> TYPE: DNA
<213> ORGANISM: Artificial Sequence
<220> FEATURE:
<221> NAME/KEY: misc_feature
<222> LOCATION: (35) (35)
<223> OTHER INFORMATION: n is a, c, g, t, or u
<220> FEATURE:
<221> NAME/KEY: misc_feature
<222> LOCATION: (51) (51)
<223> OTHER INFORMATION: n is a, c, g, t, or u
<220> FEATURE:
<221> NAME/KEY: misc_feature
<222> LOCATION: (125) (125)
<223> OTHER INFORMATION: n is a, c, g, t, or u
<220> FEATURE:
<223> OTHER INFORMATION: Description of Artificial Sequence: Human EST

<400> SEQUENCE: 38

```
atttcatctt caggatttac agtgcattct gaaanaggag aaatcaaaca naattaggag    60
ttgtgcaaca gctcttttga gaggaggcct aaaggacagg agaaaaggtc ttcaatcgtg   120
gaaanaaaat taaatgttgt attaaataga tcaccagcta gtttcagagt taccatgtac   180
gtattccact agctgggttc tgtatttcag ttctttcgat acggcttagg gtaatgtcag   240
tacaggaaaa aaactgtgca agtgagcacc tgattccgtt gccttgctt               289
```

<210> SEQ ID NO 39
<211> LENGTH: 245
<212> TYPE: DNA
<213> ORGANISM: Artificial Sequence
<220> FEATURE:
<223> OTHER INFORMATION: Description of Artificial Sequence: Human EST

<400> SEQUENCE: 39

```
caaagttact aaaaaatacc acgaggtcct tcagttgaga ccaaagaccg gtgtcagggg    60
attgcacaaa tcactcaccg acgtggccct ggagcaccat gaggagtgtg actgtgtgtg   120 cagggagc acaggaggat agccgcatca ccaccagcag ctcttgccca gagctgtgca    180
gtgcagtggc tgattctatt agagaacgta tgcgttatct ccatccttaa tctcagttgt   240
ttgct                                                                245
```

<210> SEQ ID NO 40
<211> LENGTH: 247

```
<212> TYPE: DNA
<213> ORGANISM: Artificial Sequence
<220> FEATURE:
<221> NAME/KEY: misc_feature
<222> LOCATION: (2)  (2)
<223> OTHER INFORMATION: n is a, c, g, t, or u
<220> FEATURE:
<221> NAME/KEY: misc_feature
<222> LOCATION: (86)  (86)
<223> OTHER INFORMATION: n is a, c, g, t, or u
<220> FEATURE:
<221> NAME/KEY: misc_feature
<222> LOCATION: (191)  (191)
<223> OTHER INFORMATION: n is a, c, g, t, or u
<220> FEATURE:
<223> OTHER INFORMATION: Description of Artificial Sequence: Human EST

<400> SEQUENCE: 40
angagttgcc cagagctgtg cagtgcagtg gctgattcta ttagagaacg tatgcgttat      60
ctccatcctt aatctcagtt gtttgnttca aggacctttc atcttcagga tttacagtgc     120
attctgaaag aggagacatc aaacagaatt aggagttgtg caacagctct tttgagagga     180
ggcctaaagg ncaggagaaa aggtcttcaa tcgtggaaag aaaattaaat gttgtattaa     240
atagatc                                                              247

<210> SEQ ID NO 41
<211> LENGTH: 232
<212> TYPE: DNA
<213> ORGANISM: Artificial Sequence
<220> FEATURE:
<223> OTHER INFORMATION: Description of Artificial Sequence: Human EST

<400> SEQUENCE: 41
aggaaatcaa attaggataa gatttgtatc tgatgaatat tttccttctg aaccttctaa      60
cagaggaggt aagattatac agctgcacac ctcgtaactt ctcagtgtcc ataagggaag     120
aactaaagag aaccgatacc attttctggc caggttgtct cctggttaaa cgctgtggtg     180
ggaactgtgc ctgttgtctc cacaattgca atgaatgtca atgtgtccca ag             232

<210> SEQ ID NO 42
<211> LENGTH: 253
<212> TYPE: DNA
<213> ORGANISM: Artificial Sequence
<220> FEATURE:
<223> OTHER INFORMATION: Description of Artificial Sequence: Human EST

<400> SEQUENCE: 42
gtgcattctg aaagaggaga catcaaacag aattaggagt tgtgcaacag ctcttttgag      60
aggaggccta aggacagga gaaaggtct tcaatcgtgg aaagaaaatt aaatgttgta     120
ttaaatagat caccagctag tttcagagtt accatgtacg tattccacta gctgggttct     180
gtatttcagt tctttcgata cggcttaggg taatgtcagt acaggaaaaa aactgtgcaa     240
gtgagcacct gat                                                      253

<210> SEQ ID NO 43
<211> LENGTH: 265
<212> TYPE: DNA
<213> ORGANISM: Artificial Sequence
<220> FEATURE:
<221> NAME/KEY: misc_feature
<222> LOCATION: (238)  (238)
<223> OTHER INFORMATION: n is a, c, g, t, or u
<220> FEATURE:
<221> NAME/KEY: misc_feature
<222> LOCATION: (246)  (247)
```

<223> OTHER INFORMATION: n is a, c, g, t, or u
<220> FEATURE:
<221> NAME/KEY: misc_feature
<222> LOCATION: (252)..(252)
<223> OTHER INFORMATION: n is a, c, g, t, or u
<220> FEATURE:
<221> NAME/KEY: misc_feature
<222> LOCATION: (257)..(257)
<223> OTHER INFORMATION: n is a, c, g, t, or u
<220> FEATURE:
<223> OTHER INFORMATION: Description of Artificial Sequence: Human EST

<400> SEQUENCE: 43
tgcaacagct cttttgagag gaggcctaaa ggacaggaga aaaggtcttc aatcgtggaa      60
agaaaattaa atgttgtatt aaatagatca ccagctagtt tcagagttac catgtacgta     120
ttccactagc tgggttctgt atttcagttc tttcgatacg gcttagggta atgtcagtac     180
aggaaaaaaa ctgtgcaagt gagcacctga ttccgttgcc ttgcttaacc ctaaagcncc     240
atgtcnnggg cnaaaancga aaat                                            265

<210> SEQ ID NO 44
<211> LENGTH: 291
<212> TYPE: DNA
<213> ORGANISM: Artificial Sequence
<220> FEATURE:
<221> NAME/KEY: misc_feature
<222> LOCATION: (61)..(61)
<223> OTHER INFORMATION: n is a, c, g, t, or u
<220> FEATURE:
<221> NAME/KEY: misc_feature
<222> LOCATION: (66)..(66)
<223> OTHER INFORMATION: n is a, c, g, t, or u
<220> FEATURE:
<221> NAME/KEY: misc_feature
<222> LOCATION: (88)..(88)
<223> OTHER INFORMATION: n is a, c, g, t, or u
<220> FEATURE:
<221> NAME/KEY: misc_feature
<222> LOCATION: (141)..(141)
<223> OTHER INFORMATION: n is a, c, g, t, or u
<220> FEATURE:
<221> NAME/KEY: misc_feature
<222> LOCATION: (155)..(155)
<223> OTHER INFORMATION: n is a, c, g, t, or u
<220> FEATURE:
<221> NAME/KEY: misc_feature
<222> LOCATION: (172)..(172)
<223> OTHER INFORMATION: n is a, c, g, t, or u
<220> FEATURE:
<221> NAME/KEY: misc_feature
<222> LOCATION: (177)..(177)
<223> OTHER INFORMATION: n is a, c, g, t, or u
<220> FEATURE:
<221> NAME/KEY: misc_feature
<222> LOCATION: (227)..(227)
<223> OTHER INFORMATION: n is a, c, g, t, or u
<220> FEATURE:
<221> NAME/KEY: misc_feature
<222> LOCATION: (229)..(229)
<223> OTHER INFORMATION: n is a, c, g, t, or u
<220> FEATURE:
<221> NAME/KEY: misc_feature
<222> LOCATION: (274)..(274)
<223> OTHER INFORMATION: n is a, c, g, t, or u
<220> FEATURE:
<223> OTHER INFORMATION: Description of Artificial Sequence: Human EST

<400> SEQUENCE: 44
ccttaatctc agttgtttgc ttcaaggacc tttcatcttc aggatttaca gtgcattctg      60
naagangaga catcaaacag aattaggngt tgtgcaaaag ctcttttgag aggaggccta     120
aaggacagga gaaaaggtct ncaatcgtgg aaagnaaatt aaatgttgta tnaaatngat     180

```
caccagctag tttcagagtt accatgtacg tattccacta gctgggncng tattcagtct      240
ttcggaacgg cttagggtaa tgtcagtaca gganaaaaac tgtgcagtga g              291
```

```
<210> SEQ ID NO 45
<211> LENGTH: 279
<212> TYPE: DNA
<213> ORGANISM: Artificial Sequence
<220> FEATURE:
<221> NAME/KEY: misc_feature
<222> LOCATION: (205)  (205)
<223> OTHER INFORMATION: n is a, c, g, t, or u
<220> FEATURE:
<221> NAME/KEY: misc_feature
<222> LOCATION: (240)  (240)
<223> OTHER INFORMATION: n is a, c, g, t, or u
<220> FEATURE:
<221> NAME/KEY: misc_feature
<222> LOCATION: (254)  (254)
<223> OTHER INFORMATION: n is a, c, g, t, or u
<220> FEATURE:
<223> OTHER INFORMATION: Description of Artificial Sequence: Human EST

<400> SEQUENCE: 45
attaaataga tcaccagcta gtttcagagt taccatgtac gtattccact agctgggttc       60
tgtatttcag ttctttcgat acggcttagg gtaatgtcag tacaggaaaa aaactgtgca      120
agtgagcacc tgattccgtt gccttggctt aactctaaag ctccatgtcc tgggcctaaa      180
atcgtataaa atctggattt ttttnttttt ttttgcgcat attcacatat gtaaaccagn      240
acattctatg tacnacaaac ctggtttta aaaggaac                               279
```

```
<210> SEQ ID NO 46
<211> LENGTH: 181
<212> TYPE: DNA
<213> ORGANISM: Artificial Sequence
<220> FEATURE:
<223> OTHER INFORMATION: Description of Artificial Sequence: Human EST

<400> SEQUENCE: 46
ggctagtttc agagttacca tgtacgtatt ccactagctg ggttctgtat ttcagttctt       60
tcgatacggc ttagggtaat gtcagtacag gaaaaaaact gtgcaagtga gcacctgatt      120
ccgttgcctt gcttaactct aaagctccat gtcctgggcc taaaatcgta taaatctgg       180 a                                                                      181
```

```
<210> SEQ ID NO 47
<211> LENGTH: 184
<212> TYPE: DNA
<213> ORGANISM: Artificial Sequence
<220> FEATURE:
<221> NAME/KEY: misc_feature
<222> LOCATION: (54)  (54)
<223> OTHER INFORMATION: n is a, c, g, t, or u
<220> FEATURE:
<223> OTHER INFORMATION: Description of Artificial Sequence: Human EST

<400> SEQUENCE: 47
aatagatcac cagctagttt cagagttacc atgtacgtat tccactagct gggntctgta       60
tttcagttcc tttcgatacg gcttagggta atgtcagtac aggaaaaaag ctgtgcaagt      120
gagcacctga ttccgttgcc ttgcttaact ctaaagctcc atgtcctggg cctaaaatcg      180
tata                                                                   184
```

```
<210> SEQ ID NO 48
```

<211> LENGTH: 290
<212> TYPE: DNA
<213> ORGANISM: Artificial Sequence
<220> FEATURE:
<223> OTHER INFORMATION: Description of Artificial Sequence: Human EST

<400> SEQUENCE: 48

```
aaaggaacta tgttgctatg aattaaactt gtgtcgtgct gataggacag actggatttt      60
tcatatttct tattaaaatt tctgccattt agaagaagag aactacattc atggtttgga     120
agagataaac ctgaaaagaa gagtggcctt atcttcactt tatcgataag tcagtttatt     180
tgtttcattg tgtacatttt tatattctcc ttttgacatt ataactgttg gcttttctaa    240
tcttgttaaa tatatctatt tttaccaaag gtatttaata ttctttttta               290
```

<210> SEQ ID NO 49
<211> LENGTH: 300
<212> TYPE: DNA
<213> ORGANISM: Artificial Sequence
<220> FEATURE:
<221> NAME/KEY: misc_feature
<222> LOCATION: (41) (41)
<223> OTHER INFORMATION: n is a, c, g, t, or u
<220> FEATURE:
<221> NAME/KEY: misc_feature
<222> LOCATION: (293) (293)
<223> OTHER INFORMATION: n is a, c, g, t, or u
<220> FEATURE:
<223> OTHER INFORMATION: Description of Artificial Sequence: Human EST

<400> SEQUENCE: 49

```
cacaaatcac tcaccgacgt ggccctggag caccatgagg ngtgtgactg tgtgtgcaga      60
gggagcacag gaggatagcc gcatcaccac cagcagctct tgcccagagc tgtgcagtgc     120
agtggctgat tctattagag aacgtatgcg ttatctccat ccttaatctc agttgtttgc    180
ttcaaggacc tttcatcttc aggatttaca gtgcattctg aaagaggaga catcaaacag    240
aattaggagt tgtgcaacag ctctttgag aggaggctaa aggacaggag aanaggtctt    300
```

<210> SEQ ID NO 50
<211> LENGTH: 284
<212> TYPE: DNA
<213> ORGANISM: Artificial Sequence
<220> FEATURE:
<223> OTHER INFORMATION: Description of Artificial Sequence: Human EST

<400> SEQUENCE: 50

```
tgcagtgcag tggctgattc tattagagaa cgtatgcgtt atctccatcc ttaatctcag      60
ttgtttgctt caaggacctt tcatcttcag gatttacagt gcattctgaa agaggagaca    120
tcaaacagaa ttaggagttg tgcaacagct cttttgagag gaggcctaaa ggacaggaga    180
aaaggtcttc aatcgtggaa agaaaattaa atgttgtatt aaatagatca ccagctagtt    240
tcagagttac catgtacgta ttccactagc tgggttctgt attt                      284
```

<210> SEQ ID NO 51
<211> LENGTH: 301
<212> TYPE: DNA
<213> ORGANISM: Artificial Sequence
<220> FEATURE:
<221> NAME/KEY: misc_feature
<222> LOCATION: (47) (47)
<223> OTHER INFORMATION: n is a, c, g, t, or u
<220> FEATURE:
<221> NAME/KEY: misc_feature
<222> LOCATION: (253) (253)
<223> OTHER INFORMATION: n is a, c, g, t, or u
<220> FEATURE:
<223> OTHER INFORMATION: Description of Artificial Sequence: Human EST

<400> SEQUENCE: 51

```
cttgttaaat atatctattt ttaccaaagg tatttaatat tctttantta tgacaactta      60
gatcaactat ttttagcttg gtaaattttt ctaaacacaa ttgttatagc cagaggaaca     120
aagatgatat aaaatattgt tgctctgaca aaaatacatg tatttcattc tcgtatggtg    180
ctagagttag attaatctgc attttaaaaa actgaattgg aatagaattg gtaagttgca    240
aagactttt ganaataatt aaattatcat atcttccatt cctgttattg ggggagaaaa     300
t                                                                    301
```

<210> SEQ ID NO 52
<211> LENGTH: 275
<212> TYPE: DNA
<213> ORGANISM: Artificial Sequence
<220> FEATURE:
<223> OTHER INFORMATION: Description of Artificial Sequence: Human EST

<400> SEQUENCE: 52

```
cacgaggtcc ttcagttgag accaaagacc ggtgtcaggg gattgcacaa atcactcacc     60
gacgtggccc tggagcacca tgaggagtgt gactgtgtgt gcagaggggag cacaggggga   120
tagccgcatc accaccagca gctcttgccc agagctgtgc agtgcagtgg ctgattctat    180
tagagaacgt atgcgttatc tccatcctta atctcagttg tttgcttcaa ggacctttca    240
tcttcaggat ttacagtgca ttctgaaaga ggaga                               275
```

<210> SEQ ID NO 53
<211> LENGTH: 288
<212> TYPE: DNA
<213> ORGANISM: Artificial Sequence
<220> FEATURE:
<223> OTHER INFORMATION: Description of Artificial Sequence: Human EST

<400> SEQUENCE: 53

```
ttaaaaagga actatgttgc tatgaattaa acttgtgtca tgctgatagg acagactgga     60
tttttcatat ttcttattaa aatttctgcc atttagaaga agagaactac attcatggtt    120
tggaagagat aaacctgaaa agaagagtgg ccttatcttc actttatcga taagtcagtt    180
tatttgtttc attgtgtaca tttttatatt ctcctttga cattataact gttggctttc    240
taatctgtta aatatatcta ttttaccaa aggtatttaa tattcttt                  288
```

<210> SEQ ID NO 54
<211> LENGTH: 278
<212> TYPE: DNA
<213> ORGANISM: Artificial Sequence
<220> FEATURE:
<221> NAME/KEY: misc_feature
<222> LOCATION: (248)..(248)
<223> OTHER INFORMATION: n is a, c, g, t, or u
<220> FEATURE:
<223> OTHER INFORMATION: Description of Artificial Sequence: Human EST

<400> SEQUENCE: 54

```
ggaggatagc cgcatcacca ccagcagctc ttgcccagag ctgtgcagtg cagtggctga     60
ttctattaga gaacgtatgc gttatctcca tccttaatct cagttgtttg cttcaaggac    120
ctttcatctt caggatttac agtgcattct gaaagaggag acatcaaaca gaattaggag    180
ttgtgcaaca gctctttga gaggaggcct aaaggacagg agaaaaggtc ttcaatcgtg     240
```

```
gaaagaaanat taaatgttgt attaaataga caccagct                              278

<210> SEQ ID NO 55
<211> LENGTH: 275
<212> TYPE: DNA
<213> ORGANISM: Artificial Sequence
<220> FEATURE:
<223> OTHER INFORMATION: Description of Artificial Sequence: Human EST

<400> SEQUENCE: 55
ggaggatagc cgcatcacca ccagcagctc ttgcccagag ctgtgcagtg cagtggctga       60
ttctattaga gaacgtatgc gttatctcca tccttaatct cagttgtttg cttcaaggac      120
ctttcatctt caggatttac atgcattctg aaagaggaga catcaaacag aattaggagt      180
tgtgcaacag ctcttttgag aggaggccta aggacagga gaaaggtct tcaatcgtgg        240 aaagaaaatt aaatgttgta ttaaatagat cacca                                 275

<210> SEQ ID NO 56
<211> LENGTH: 261
<212> TYPE: DNA
<213> ORGANISM: Artificial Sequence
<220> FEATURE:
<223> OTHER INFORMATION: Description of Artificial Sequence: Human EST

<400> SEQUENCE: 56
gagaaccgat accattttct ggccaggttg tctcctggtt aaacgctgtg gtgggaactg       60
tgcctgttgt ctccacaatt gcaatgaatg tcaatgtgtc ccaagcaaag ttactaaaaa      120
ataccacgag gtccttcagt tgagaccaaa gaccggtgtc aggggattgc acaaatcact      180
caccgacgtg gccctggagc accatgagga gtgtgactgt gtgtgcagag ggagcacagg      240
aggatagccg catcaccacc a                                                261

<210> SEQ ID NO 57
<211> LENGTH: 279
<212> TYPE: DNA
<213> ORGANISM: Artificial Sequence
<220> FEATURE:
<223> OTHER INFORMATION: Description of Artificial Sequence: Human EST

<400> SEQUENCE: 57
agaaaatcca gagtggtgga tctgaacctt ctaacagagg aggtaagatt atacagctgc       60
acacctcgta acttctcagt gtccataagg gaagaactaa agagaaccga taccattttc      120
tggccaggtt gtctcctggt taaacgctgt ggtgggaact gtgcctgttg tctccacaat      180
tgcaatgaat gtcaatgtgt cccaagcaaa gttactaaaa ataccacga ggtccttcag      240 ttgagaccaa agaccggtgt caggggattg cacaaatca                             279

<210> SEQ ID NO 58
<211> LENGTH: 259
<212> TYPE: DNA
<213> ORGANISM: Artificial Sequence
<220> FEATURE:
<223> OTHER INFORMATION: Description of Artificial Sequence: Human EST

<400> SEQUENCE: 58
agatgatata aaatattgtt gctctgacaa aaatacatgt atttcattct cgtatggtgc       60
tagagttaga ttaatctgca ttttaaaaaa ctgaattgga atagaattgg taagttgcaa      120 agacttttttg aaaataatta aattatcata tcttccattc ctgttattgg agatgaaaat    180
aaaaagcaac ttatgaaagt agacattcag atccagccat tactaaccta ttccttttt      240
```

```
ggggaaatct gagcctagc                                                259
```

<210> SEQ ID NO 59
<211> LENGTH: 284
<212> TYPE: DNA
<213> ORGANISM: Artificial Sequence
<220> FEATURE:
<223> OTHER INFORMATION: Description of Artificial Sequence: Human EST

<400> SEQUENCE: 59

```
tttttaaaaa ggaactatgt tgctatgaat taaacttgtg tcgtgctgat aggacagact    60 ggattttca tatttcttat taaaatttct gccatttaga agaagagaac tacattcatg    120
gtttggaaga gataaacctg aaaagaagag tggcctatct tcactttatc gataagtcag   180
tttatttgtt tcattgtgta cattttata ttctcctttg acatataact gttggctttt    240
ctaatctgtt aaatatatct attttacca aggtatttta atat                     284
```

<210> SEQ ID NO 60
<211> LENGTH: 262
<212> TYPE: DNA
<213> ORGANISM: Artificial Sequence
<220> FEATURE:
<223> OTHER INFORMATION: Description of Artificial Sequence: Human EST

<400> SEQUENCE: 60

```
aggaaatcaa attaggataa gatttgtatc tgatgaatat tttccttctg aaccttctaa    60
cagaggaggt aagattatac agctgcacac ctcgtaactt ctcagtgtcc ataagggaag   120
aactaaagag aaccgatacc attttctggc caggttgtct cctggttaaa cgctgtggtg   180
ggaactgtgc ctgttgtctc ccacaattgc aatgaatgtc aatgtgtccc aagcaaagtt   240
actaaaaaat accacgaggt cc                                            262
```

<210> SEQ ID NO 61
<211> LENGTH: 289
<212> TYPE: DNA
<213> ORGANISM: Artificial Sequence
<220> FEATURE:
<221> NAME/KEY: misc_feature
<222> LOCATION: (35) (35)
<223> OTHER INFORMATION: n is a, c, g, t, or u
<220> FEATURE:
<221> NAME/KEY: misc_feature
<222> LOCATION: (51) (51)
<223> OTHER INFORMATION: n is a, c, g, t, or u
<220> FEATURE:
<221> NAME/KEY: misc_feature
<222> LOCATION: (125) (125)
<223> OTHER INFORMATION: n is a, c, g, t, or u
<220> FEATURE:
<223> OTHER INFORMATION: Description of Artificial Sequence: Human EST

<400> SEQUENCE: 61

```
atttcatctt caggatttac agtgcattct gaaanaggag aaatcaaaca naattaggag    60
ttgtgcaaca gctcttttga gaggaggcct aaaggacagg agaaaaggtc ttcaatcgtg   120
gaaanaaaat taaatgttgt attaaataga tcaccagcta gtttcagagt taccatgtac   180
gtattccact agctgggttc tgtatttcag ttctttcgat acggcttagg gtaatgtcag   240
tacaggaaaa aaactgtgca agtgagcacc tgattccgtt gccttgctt                289
```

<210> SEQ ID NO 62
<211> LENGTH: 251
<212> TYPE: DNA

<213> ORGANISM: Artificial Sequence
<220> FEATURE:
<221> NAME/KEY: misc_feature
<222> LOCATION: (10)..(10)
<223> OTHER INFORMATION: n is a, c, g, t, or u
<220> FEATURE:
<221> NAME/KEY: misc_feature
<222> LOCATION: (246)..(246)
<223> OTHER INFORMATION: n is a, c, g, t, or u
<220> FEATURE:
<223> OTHER INFORMATION: Description of Artificial Sequence: Human EST

<400> SEQUENCE: 62

```
ttagcttggn aaatttttct aaacacaatt gttatagcca gaggaacaaa gatgatataa      60
aatattgttg ctctgacaaa aatacatgta tttcattctc gtatggtgct agagttagat     120
taatctgcat tttaaaaaac tgaattggaa tagaattggt aagttgcaaa gacttttga     180
aaataattaa attatcatat cttccattcc tgttattgga gatgaaaata aaaagcaact     240
tatganagta g                                                          251
```

<210> SEQ ID NO 63
<211> LENGTH: 252
<212> TYPE: DNA
<213> ORGANISM: Artificial Sequence
<220> FEATURE:
<221> NAME/KEY: misc_feature
<222> LOCATION: (250)..(250)
<223> OTHER INFORMATION: n is a, c, g, t, or u
<220> FEATURE:
<223> OTHER INFORMATION: Description of Artificial Sequence: Human EST

<400> SEQUENCE: 63

```
cttttttatg acaacttaga tcaactattt ttagcttggt aaatttttct aaacacaatt      60
gttatagcca gaggaacaaa gatgatataa aatattgttg ctctgacaaa aatacatgta     120
tttcattctc gtatggtgct agagttagat taatctgcat tttaaaaaac tgaattggaa     180
tagaattggt aagttgcaaa ggcttttttga aaataattaa attatcatat cttccattcc     240
tgttattggn gg                                                          252
```

<210> SEQ ID NO 64
<211> LENGTH: 245
<212> TYPE: DNA
<213> ORGANISM: Artificial Sequence
<220> FEATURE:
<223> OTHER INFORMATION: Description of Artificial Sequence: Human EST

<400> SEQUENCE: 64

```
caaagttact aaaaaatacc acgaggtcct tcagttgaga ccaaagaccg gtgtcagggg      60
attgcacaaa tcactcaccg acgtggccct ggagcaccat gaggagtgtg actgtgtgtg     120
cagagggagc acaggaggat agccgcatca ccaccagcag ctcttgccca gagctgtgca     180
gtgcagtggc tgattctatt agagaacgta tgcgttatct ccatccttaa tctcagttgt     240
ttgct                                                                  245
```

<210> SEQ ID NO 65
<211> LENGTH: 245
<212> TYPE: DNA
<213> ORGANISM: Artificial Sequence
<220> FEATURE:
<223> OTHER INFORMATION: Description of Artificial Sequence: Human EST

<400> SEQUENCE: 65

```
agataaacct gaaagaaga gtggccttat cttcacttta tcgataagtc agtttatttg      60
```
tttcattgtg tacatttta tattctcctt ttgacattat aactgttggc ttttctaatc 120
ttgttaaata tatctatttt taccaaaggt atttaatatt cttttttatg acaacttaga 180
tcaactattt ttagcttggt aaattttct aaacacaatt gttatagcca gaggaacaaa 240
gatga 245

```
<210> SEQ ID NO 66
<211> LENGTH: 243
<212> TYPE: DNA
<213> ORGANISM: Artificial Sequence
<220> FEATURE:
<223> OTHER INFORMATION: Description of Artificial Sequence: Human EST
```

<400> SEQUENCE: 66 ctggatttttt catatttctt attaaaattt ctgccattta gaagaagaga actacattca 60
tggtttggaa gagataaacc tgaaaagaag agtggcctta tcttcacttt atcgataagt 120
cagtttattt gtttcattgt gtacattttt atattctcct tttgacatta taactgttgg 180
cttttctaat cttgttaaat atatctatttt ttaccaaagg tatttaatat tcttttttat 240
gac 243

```
<210> SEQ ID NO 67
<211> LENGTH: 244
<212> TYPE: DNA
<213> ORGANISM: Artificial Sequence
<220> FEATURE:
<221> NAME/KEY: misc_feature
<222> LOCATION: (64)..(64)
<223> OTHER INFORMATION: n is a, c, g, t, or u
<220> FEATURE:
<221> NAME/KEY: misc_feature
<222> LOCATION: (215)..(215)
<223> OTHER INFORMATION: n is a, c, g, t, or u
<220> FEATURE:
<223> OTHER INFORMATION: Description of Artificial Sequence: Human EST
```

<400> SEQUENCE: 67
gctcatattc acatatgtaa accagaacat tctatgtact acaaacctgg ttttaaaaa 60 gganctatgt tgctatgaat taaacttgtg tcgtgctgat aggacagact ggattttca 120 tatttcttat taaaatttct gccatttaga agaagagaac tacattcatg gtttggaaga 180
gataaacctg aaaagaagag tggccttatc ttcantttat cgataagtca gtttatttgt 240
ttca 244

```
<210> SEQ ID NO 68
<211> LENGTH: 247
<212> TYPE: DNA
<213> ORGANISM: Artificial Sequence
<220> FEATURE:
<221> NAME/KEY: misc_feature
<222> LOCATION: (2)..(2)
<223> OTHER INFORMATION: n is a, c, g, t, or u
<220> FEATURE:
<221> NAME/KEY: misc_feature
<222> LOCATION: (86)..(86)
<223> OTHER INFORMATION: n is a, c, g, t, or u
<220> FEATURE:
<221> NAME/KEY: misc_feature
<222> LOCATION: (191)..(191)
<223> OTHER INFORMATION: n is a, c, g, t, or u
<220> FEATURE:
<223> OTHER INFORMATION: Description of Artificial Sequence: Human EST
```

<400> SEQUENCE: 68

-continued

```
angagttgcc cagagctgtg cagtgcagtg gctgattcta ttagagaacg tatgcgttat      60
ctccatcctt aatctcagtt gtttgnttca aggacctttc atcttcagga tttacagtgc     120
attctgaaag aggagacatc aaacagaatt aggagttgtg caacagctct tttgagagga     180
ggcctaaagg ncaggagaaa aggtcttcaa tcgtggaaag aaaattaaat gttgtattaa     240
atagatc                                                               247
```

<210> SEQ ID NO 69
<211> LENGTH: 233
<212> TYPE: DNA
<213> ORGANISM: Artificial Sequence
<220> FEATURE:
<223> OTHER INFORMATION: Description of Artificial Sequence: Human EST

<400> SEQUENCE: 69

```
aaagatgata taaatattg ttgctctgac aaaaatacat gtatttcatt ctcgtatggt       60
gctagagtta gattaatctg cattttaaaa aactgaattg gaatagaatt ggtaagttgc     120
aaagactttt tgaaaataat taaattatca tatcttccat tcctgttatt ggagatgaaa     180
ataaaaagca acttatgaaa gtagacattc agatccagcc attactaacc tat            233
```

<210> SEQ ID NO 70
<211> LENGTH: 232
<212> TYPE: DNA
<213> ORGANISM: Artificial Sequence
<220> FEATURE:
<223> OTHER INFORMATION: Description of Artificial Sequence: Human EST

<400> SEQUENCE: 70

```
aggaaatcaa attaggataa gatttgtatc tgatgaatat tttccttctg aaccttctaa      60
cagaggaggt aagattatac agctgcacac ctcgtaactt ctcagtgtcc ataagggaag     120
aactaaagag aaccgatacc attttctggc caggttgtct cctggttaaa cgctgtggtg     180
ggaactgtgc ctgttgtctc cacaattgca atgaatgtca atgtgtccca ag             232
```

<210> SEQ ID NO 71
<211> LENGTH: 253
<212> TYPE: DNA
<213> ORGANISM: Artificial Sequence
<220> FEATURE:
<223> OTHER INFORMATION: Description of Artificial Sequence: Human EST

<400> SEQUENCE: 71

```
gtgcattctg aaagaggaga catcaaacag aattaggagt tgtgcaacag ctcttttgag      60
aggaggccta aggacagga gaaaggtct tcaatcgtgg aaagaaaatt aaatgttgta     120
ttaaatagat caccagctag tttcagagtt accatgtacg tattccacta gctgggttct    180
gtatttcagt tctttcgata cggcttaggg taatgtcagt acaggaaaaa aactgtgcaa     240
gtgagcacct gat                                                        253
```

<210> SEQ ID NO 72
<211> LENGTH: 233
<212> TYPE: DNA
<213> ORGANISM: Artificial Sequence
<220> FEATURE:
<221> NAME/KEY: misc_feature
<222> LOCATION: (48)  (48)
<223> OTHER INFORMATION: n is a, c, g, t, or u
<220> FEATURE:
<223> OTHER INFORMATION: Description of Artificial Sequence: Human EST

<400> SEQUENCE: 72

```
tgtacatttt tatattctcc ttttgacatt ataactgttg gcttttcnaa tcttgttaaa        60
tatatctatt tttaccaaag gtatttaata ttcttttta tgacaactta gatcaactat        120
ttttagcttg gtaaattttt ctaaacacaa ttgttatagc cagaggaaca aagatgatat       180
aaaatattgt tgctctgaca aaaatacatg tatttcattc tcgtatggtg cta             233
```

<210> SEQ ID NO 73
<211> LENGTH: 250
<212> TYPE: DNA
<213> ORGANISM: Artificial Sequence
<220> FEATURE:
<221> NAME/KEY: misc_feature
<222> LOCATION: (53) (53)
<223> OTHER INFORMATION: n is a, c, g, t, or u
<220> FEATURE:
<223> OTHER INFORMATION: Description of Artificial Sequence: Human EST

<400> SEQUENCE: 73

```
cacaattgtt atagccagag gaacaaagat gatataaaat attgttgctc tgncaaaaat        60
acatgtattt cattctcgta tggtgctaga gttagattaa tctgcatttt aaaaaactga       120
attggaatag aattggtaag ttgcaaagac tttttgaaaa taattaaatt atcatatctt       180
ccattcctgt tattggagat gaaaataaaa agcaacttat gaaagtaaat tcagatccac       240
cattactaac                                                              250
```

<210> SEQ ID NO 74
<211> LENGTH: 247
<212> TYPE: DNA
<213> ORGANISM: Artificial Sequence
<220> FEATURE:
<223> OTHER INFORMATION: Description of Artificial Sequence: Human EST

<400> SEQUENCE: 74

```
atttcattct cgtatggtgc tagagttaga ttaatctgca ttttaaaaaa ctgaattgga        60
atagaattgg taagttgcaa agacttttg aaaataatta aattatcata tcttccattc       120
ctgttattgg agatgaaaat aaaaagcaac ttatgaaagt agacattcag atccagccat       180
tactaaccta ttccttttt ggggaaatct gagcctagct cagaaaaaca taaagcacct       240
tgaaaaa                                                                 247
```

<210> SEQ ID NO 75
<211> LENGTH: 265
<212> TYPE: DNA
<213> ORGANISM: Artificial Sequence
<220> FEATURE:
<221> NAME/KEY: misc_feature
<222> LOCATION: (238) (238)
<223> OTHER INFORMATION: n is a, c, g, t, or u
<220> FEATURE:
<221> NAME/KEY: misc_feature
<222> LOCATION: (246) (247)
<223> OTHER INFORMATION: n is a, c, g, t, or u
<220> FEATURE:
<221> NAME/KEY: misc_feature
<222> LOCATION: (252) (252)
<223> OTHER INFORMATION: n is a, c, g, t, or u
<220> FEATURE:
<221> NAME/KEY: misc_feature
<222> LOCATION: (257) (257)
<223> OTHER INFORMATION: n is a, c, g, t, or u
<220> FEATURE:
<223> OTHER INFORMATION: Description of Artificial Sequence: Human EST

<400> SEQUENCE: 75

```
tgcaacagct cttttgagag gaggcctaaa ggacaggaga aaaggtcttc aatcgtggaa      60
agaaaattaa atgttgtatt aaatagatca ccagctagtt tcagagttac catgtacgta     120
ttccactagc tgggttctgt atttcagttc tttcgatacg gcttagggta atgtcagtac     180
aggaaaaaaa ctgtgcaagt gagcacctga ttccgttgcc ttgcttaacc ctaaagcncc     240
atgtcnnggg cnaaaancga aaat                                            265
```

```
<210> SEQ ID NO 76
<211> LENGTH: 251
<212> TYPE: DNA
<213> ORGANISM: Artificial Sequence
<220> FEATURE:
<221> NAME/KEY: misc_feature
<222> LOCATION: (134)..(134)
<223> OTHER INFORMATION: n is a, c, g, t, or u
<220> FEATURE:
<221> NAME/KEY: misc_feature
<222> LOCATION: (157)..(157)
<223> OTHER INFORMATION: n is a, c, g, t, or u
<220> FEATURE:
<223> OTHER INFORMATION: Description of Artificial Sequence: Human EST

<400> SEQUENCE: 76
```

```
tttctaaaca caattgttat agccagagga acaaagatga tataaaatat tgttgctctg      60
acaaaaatac atgtatttca ttctcgtatg gtgctagagt tagattaatc tgcattttaa     120
aaaactgaat tggnatagaa ttggtaagtt gcaaagncTT tttgaaaata attaaattat     180
catatcttcc attcctgtta ttggaggatg gaaaataaaa agcaacttat ggaaagtagg     240
acattcagat c                                                          251
```

```
<210> SEQ ID NO 77
<211> LENGTH: 291
<212> TYPE: DNA
<213> ORGANISM: Artificial Sequence
<220> FEATURE:
<221> NAME/KEY: misc_feature
<222> LOCATION: (61)..(61)
<223> OTHER INFORMATION: n is a, c, g, t, or u
<220> FEATURE:
<221> NAME/KEY: misc_feature
<222> LOCATION: (66)..(66)
<223> OTHER INFORMATION: n is a, c, g, t, or u
<220> FEATURE:
<221> NAME/KEY: misc_feature
<222> LOCATION: (88)..(88)
<223> OTHER INFORMATION: n is a, c, g, t, or u
<220> FEATURE:
<221> NAME/KEY: misc_feature
<222> LOCATION: (141)..(141)
<223> OTHER INFORMATION: n is a, c, g, t, or u
<220> FEATURE:
<221> NAME/KEY: misc_feature
<222> LOCATION: (155)..(155)
<223> OTHER INFORMATION: n is a, c, g, t, or u
<220> FEATURE:
<221> NAME/KEY: misc_feature
<222> LOCATION: (172)..(172)
<223> OTHER INFORMATION: n is a, c, g, t, or u
<220> FEATURE:
<221> NAME/KEY: misc_feature
<222> LOCATION: (177)..(177)
<223> OTHER INFORMATION: n is a, c, g, t, or u
<220> FEATURE:
<221> NAME/KEY: misc_feature
<222> LOCATION: (227)..(227)
<223> OTHER INFORMATION: n is a, c, g, t, or u
<220> FEATURE:
<221> NAME/KEY: misc_feature
<222> LOCATION: (229)..(229)
<223> OTHER INFORMATION: n is a, c, g, t, or u
```

```
<220> FEATURE:
<221> NAME/KEY: misc_feature
<222> LOCATION: (274) (274)
<223> OTHER INFORMATION: n is a, c, g, t, or u
<220> FEATURE:
<223> OTHER INFORMATION: Description of Artificial Sequence: Human EST

<400> SEQUENCE: 77
ccttaatctc agttgtttgc ttcaaggacc tttcatcttc aggatttaca gtgcattctg      60
naagangaga catcaaacag aattaggngt tgtgcaaaag ctcttttgag aggaggccta     120
aaggacagga gaaaaggtct ncaatcgtgg aaagnaaatt aaatgttgta tnaaatngat    180
caccagctag tttcagagtt accatgtacg tattccacta gctgggncng tattcagtct    240
ttcggaacgg cttagggtaa tgtcagtaca gganaaaaac tgtgcagtga g            291

<210> SEQ ID NO 78
<211> LENGTH: 253
<212> TYPE: DNA
<213> ORGANISM: Artificial Sequence
<220> FEATURE:
<221> NAME/KEY: misc_feature
<222> LOCATION: (84) (84)
<223> OTHER INFORMATION: n is a, c, g, t, or u
<220> FEATURE:
<221> NAME/KEY: misc_feature
<222> LOCATION: (143) (143)
<223> OTHER INFORMATION: n is a, c, g, t, or u
<220> FEATURE:
<223> OTHER INFORMATION: Description of Artificial Sequence: Human EST

<400> SEQUENCE: 78
gtactacaaa cctggttttt aaaaaggaac tatgttgcta tgaattaaac ttgtgtccat     60
gctgatagga cagactggat tttncatatt tcttattaaa atttctgcca tttagaagaa    120
gagaactaca ttcatggttt ggnagagata aacctgaaaa gaagagtggc cttatcttca    180
ctttatcgat aagtcagttt atttgtttca tgtgtacatt tttatattct cctttgacat    240
ataacgtggc ttt                                                        253

<210> SEQ ID NO 79
<211> LENGTH: 204
<212> TYPE: DNA
<213> ORGANISM: Artificial Sequence
<220> FEATURE:
<221> NAME/KEY: misc_feature
<222> LOCATION: (190) (190)
<223> OTHER INFORMATION: n is a, c, g, t, or u
<220> FEATURE:
<223> OTHER INFORMATION: Description of Artificial Sequence: Human EST

<400> SEQUENCE: 79
ttatattctc cttttgacat tataactgtt ggcttttcta atcttgttaa atatatctat     60
ttttaccaaa ggtatttaat attctttttt atgacaactt agatcaacta ttttagctt    120 ggtaaatttt tctaaacaca attgttatag ccagaggaac aaagatgata taaaatattg   180
ttgctctgan aaaaatacat gtat                                           204

<210> SEQ ID NO 80
<211> LENGTH: 303
<212> TYPE: DNA
<213> ORGANISM: Artificial Sequence
<220> FEATURE:
<221> NAME/KEY: misc_feature
<222> LOCATION: (2) (2)
<223> OTHER INFORMATION: n is a, c, g, t, or u
<220> FEATURE:
```

<221> NAME/KEY: misc_feature
<222> LOCATION: (87)..(104)
<223> OTHER INFORMATION: n is a, c, g, t, or u
<220> FEATURE:
<221> NAME/KEY: misc_feature
<222> LOCATION: (267)..(267)
<223> OTHER INFORMATION: n is a, c, g, t, or u
<220> FEATURE:
<221> NAME/KEY: misc_feature
<222> LOCATION: (272)..(272)
<223> OTHER INFORMATION: n is a, c, g, t, or u
<220> FEATURE:
<221> NAME/KEY: misc_feature
<222> LOCATION: (300)..(300)
<223> OTHER INFORMATION: n is a, c, g, t, or u
<220> FEATURE:
<223> OTHER INFORMATION: Description of Artificial Sequence: Human EST

<400> SEQUENCE: 80
anactgtgca agtgagcacc tgattccgtt gccttgctta actctaaagc tccatgtcct      60
gggcctaaaa tcgtataaaa tctggannnn nnnnnnnnnn nnnngctcat attcacatat     120
gtaaaccaga acattctatg tactacaaac ctggttttta aaaggaact atgttgctat      180 gaattaaact tgtgtcgtgc tgataggaca gactggattt tcatatttc ttattaaaat      240 ttctgccatt agaagaagag aactacnttc anggtttgga agagataacc ctgaaaagan    300
ggg                                                                    303

<210> SEQ ID NO 81
<211> LENGTH: 228
<212> TYPE: DNA
<213> ORGANISM: Artificial Sequence
<220> FEATURE:
<221> NAME/KEY: misc_feature
<222> LOCATION: (112)..(112)
<223> OTHER INFORMATION: n is a, c, g, t, or u
<220> FEATURE:
<221> NAME/KEY: misc_feature
<222> LOCATION: (132)..(132)
<223> OTHER INFORMATION: n is a, c, g, t, or u
<220> FEATURE:
<223> OTHER INFORMATION: Description of Artificial Sequence: Human EST

<400> SEQUENCE: 81
gctcatattc acatatgtaa accagaacat tctatgtact acaaacctgg tttttaaaaa      60
ggaactattt gctatgaatt aaacttgtgt cgtgctgata ggacagactg gnttttcat     120 atttcttatt anaatttctg ccattagaag aagagaacta cattcatggt ttggaagaga    180
taaacctgaa aagaagagtg gcctatttca ctttatcgat aagtcagt                  228

<210> SEQ ID NO 82
<211> LENGTH: 193
<212> TYPE: DNA
<213> ORGANISM: Artificial Sequence
<220> FEATURE:
<220> FEATURE:
<223> OTHER INFORMATION: Description of Artificial Sequence: Human EST

<400> SEQUENCE: 82
gctcatattc acatatgtaa accagaacat tctatgtact acaaacctgg tttttaaaaa      60
ggaactatgt tgctatgaat taaacttgtg tcgtgctgat aggacagact ggattttca     120 tatttcttat taaatttct gccatttaga agaagagaac tacattcatg gtttggaaga    180
gataaacctg aaa                                                         193

<210> SEQ ID NO 83

```
<211> LENGTH: 282
<212> TYPE: DNA
<213> ORGANISM: Artificial Sequence
<220> FEATURE:
<221> NAME/KEY: misc_feature
<222> LOCATION: (42)..(42)
<223> OTHER INFORMATION: n is a, c, g, t, or u
<220> FEATURE:
<221> NAME/KEY: misc_feature
<222> LOCATION: (94)..(94)
<223> OTHER INFORMATION: n is a, c, g, t, or u
<220> FEATURE:
<221> NAME/KEY: misc_feature
<222> LOCATION: (235)..(235)
<223> OTHER INFORMATION: n is a, c, g, t, or u
<220> FEATURE:
<221> NAME/KEY: misc_feature
<222> LOCATION: (269)..(269)
<223> OTHER INFORMATION: n is a, c, g, t, or u
<220> FEATURE:
<223> OTHER INFORMATION: Description of Artificial Sequence: Human EST

<400> SEQUENCE: 83
aaaaaactga attggaatag aattggtaag ttgcaaagac tntttgaaaa taattaaatt    60
atcatatctt ccattcctgt tattggagat gaanataaaa agcaacttat gaaagtagac   120
attcagatcc agccattact aacctattcc tttttggggg aaatctgagc ctagctcaga   180
aaaacataaa gcaccttgaa aaagacttgg cagcttcctg ataaagcgtg ctgtntgtca   240
gtaggaacac atcctattta ttgtgatgnt gtggtttatt at                      282

<210> SEQ ID NO 84
<211> LENGTH: 279
<212> TYPE: DNA
<213> ORGANISM: Artificial Sequence
<220> FEATURE:
<221> NAME/KEY: misc_feature
<222> LOCATION: (205)..(205)
<223> OTHER INFORMATION: n is a, c, g, t, or u
<220> FEATURE:
<221> NAME/KEY: misc_feature
<222> LOCATION: (240)..(240)
<223> OTHER INFORMATION: n is a, c, g, t, or u
<220> FEATURE:
<221> NAME/KEY: misc_feature
<222> LOCATION: (254)..(254)
<223> OTHER INFORMATION: n is a, c, g, t, or u
<220> FEATURE:
<223> OTHER INFORMATION: Description of Artificial Sequence: Human EST

<400> SEQUENCE: 84
attaaataga tcaccagcta gtttcagagt taccatgtac gtattccact agctgggttc    60
tgtatttcag ttctttcgat acggcttagg gtaatgtcag tacaggaaaa aaactgtgca   120
agtgagcacc tgattccgtt gccttggctt aactctaaag ctccatgtcc tgggcctaaa   180
atcgtataaa atctggattt ttttntttt ttttgcgcat attcacatat gtaaaccagn    240
acattctatg tacnacaaac ctggttttta aaaaggaac                          279

<210> SEQ ID NO 85
<211> LENGTH: 181
<212> TYPE: DNA
<213> ORGANISM: Artificial Sequence
<220> FEATURE:
<223> OTHER INFORMATION: Description of Artificial Sequence: Human EST

<400> SEQUENCE: 85
ggctagtttc agagttacca tgtacgtatt ccactagctg ggttctgtat ttcagttctt    60
tcgatacggc ttagggtaat gtcagtacag gaaaaaaact gtgcaagtga gcacctgatt   120
```

```
ccgttgcctt gcttaactct aaagctccat gtcctgggcc taaaatcgta taaaatctgg    180
a                                                                    181

<210> SEQ ID NO 86
<211> LENGTH: 269
<212> TYPE: DNA
<213> ORGANISM: Artificial Sequence
<220> FEATURE:
<223> OTHER INFORMATION: Description of Artificial Sequence: Human EST

<400> SEQUENCE: 86
tggtaagttg caaagacttt tgaaaataa ttaaattatc atatcttcca ttcctgttat     60
tggagatgaa ataaaaagc aacttatgaa agtagacatt cagatccagc cattactaac   120
ctattccttt tttggggaaa tctgagccta gctcagaaaa acataaagca ccttgaaaaa   180
gacttggcag cttcctgata aagcgtgctg tgctgtgcag tagggaacac atcctattta   240
ttgtgatgtt gtggtttata tcctaaacc                                    269

<210> SEQ ID NO 87
<211> LENGTH: 184
<212> TYPE: DNA
<213> ORGANISM: Artificial Sequence
<220> FEATURE:
<221> NAME/KEY: misc_feature
<222> LOCATION: (54)..(54)
<223> OTHER INFORMATION: n is a, c, g, t, or u
<220> FEATURE:
<223> OTHER INFORMATION: Description of Artificial Sequence: Human EST

<400> SEQUENCE: 87
aatagatcac cagctagttt cagagttacc atgtacgtat tccactagct gggntctgta     60
tttcagttcc tttcgatacg gcttagggta atgtcagtac aggaaaaaag ctgtgcaagt   120
gagcacctga ttccgttgcc ttgcttaact ctaaagctcc atgtcctggg cctaaaatcg   180
tata                                                                184

<210> SEQ ID NO 88
<211> LENGTH: 164
<212> TYPE: DNA
<213> ORGANISM: Artificial Sequence
<220> FEATURE:
<221> NAME/KEY: misc_feature
<222> LOCATION: (31)..(31)
<223> OTHER INFORMATION: n is a, c, g, t, or u
<220> FEATURE:
<221> NAME/KEY: misc_feature
<222> LOCATION: (53)..(53)
<223> OTHER INFORMATION: n is a, c, g, t, or u
<220> FEATURE:
<221> NAME/KEY: misc_feature
<222> LOCATION: (88)..(89)
<223> OTHER INFORMATION: n is a, c, g, t, or u
<220> FEATURE:
<221> NAME/KEY: misc_feature
<222> LOCATION: (116)..(116)
<223> OTHER INFORMATION: n is a, c, g, t, or u
<220> FEATURE:
<221> NAME/KEY: misc_feature
<222> LOCATION: (119)..(119)
<223> OTHER INFORMATION: n is a, c, g, t, or u
<220> FEATURE:
<221> NAME/KEY: misc_feature
<222> LOCATION: (121)..(121)
<223> OTHER INFORMATION: n is a, c, g, t, or u
<220> FEATURE:
<223> OTHER INFORMATION: Description of Artificial Sequence: Human EST
```

```
<400> SEQUENCE: 88
agataaacct gaaaagaaga gtggccttat nttcacttta tcgataagtc agnttatttg      60
tttcattgtg tacatttnna tattctcctt ttgacattat aactgntggc ttttctaanc     120
ntgttaaata tatctatttt taccaaaggt atttaatatt cttt                      164

<210> SEQ ID NO 89
<211> LENGTH: 143
<212> TYPE: DNA
<213> ORGANISM: Artificial Sequence
<220> FEATURE:
<223> OTHER INFORMATION: Description of Artificial Sequence: Human EST

<400> SEQUENCE: 89
tatggtgcta gagttagatt aatctgcatt ttaaaaaact gaattggaat agaattggta      60
agttgcaaag acttttttgaa ataattaaa ttatcatatc ttccattcct gttattggag    120
atgaaaataa aaagcaactt atg                                            143

<210> SEQ ID NO 90
<211> LENGTH: 164
<212> TYPE: DNA
<213> ORGANISM: Artificial Sequence
<220> FEATURE:
<221> NAME/KEY: misc_feature
<222> LOCATION: (7)   (7)
<223> OTHER INFORMATION: n is a, c, g, t, or u
<220> FEATURE:
<221> NAME/KEY: misc_feature
<222> LOCATION: (35)  (35)
<223> OTHER INFORMATION: n is a, c, g, t, or u
<220> FEATURE:
<221> NAME/KEY: misc_feature
<222> LOCATION: (51)  (51)
<223> OTHER INFORMATION: n is a, c, g, t, or u
<220> FEATURE:
<221> NAME/KEY: misc_feature
<222> LOCATION: (132) (132)
<223> OTHER INFORMATION: n is a, c, g, t, or u
<220> FEATURE:
<221> NAME/KEY: misc_feature
<222> LOCATION: (141) (141)
<223> OTHER INFORMATION: n is a, c, g, t, or u
<220> FEATURE:
<221> NAME/KEY: misc_feature
<222> LOCATION: (145) (146)
<223> OTHER INFORMATION: n is a, c, g, t, or u
<220> FEATURE:
<223> OTHER INFORMATION: Description of Artificial Sequence: Human EST

<400> SEQUENCE: 90 tttttttnttt tgctcatatt cacatatgta aaccngaaca ttctatgtac nacaaacctg    60
gtttttaaaa aggaactatg ttgctatgaa ttaaacttgt gtcgtgctga taggacagac   120
tggatttttc anatttctta ntaannttttc tgccatttag aaga                    164

<210> SEQ ID NO 91
<211> LENGTH: 244
<212> TYPE: DNA
<213> ORGANISM: Artificial Sequence
<220> FEATURE:
<221> NAME/KEY: misc_feature
<222> LOCATION: (98)  (115)
<223> OTHER INFORMATION: n is a, c, g, t, or u
<220> FEATURE:
<223> OTHER INFORMATION: Description of Artificial Sequence: Human EST

<400> SEQUENCE: 91
gtacaggaaa aaaactgtgc aagtgagcac ctgattccgt tgccttgctt aactctaaag     60
```

```
ctccatgtcc tgggcctaaa atcgtataaa atctggannn nnnnnnnnnn nnnnngctca    120
tattcacata tgtaaaccag aacattctat gtactacaaa cctggttttt aaaaaggaac    180
tatgttgcta tgaattaaac ttgtgtcgtg ctgataggac agactggatt tttcatattt    240
ctta                                                                 244
```

```
<210> SEQ ID NO 92
<211> LENGTH: 254
<212> TYPE: DNA
<213> ORGANISM: Artificial Sequence
<220> FEATURE:
<221> NAME/KEY: misc_feature
<222> LOCATION: (16)..(16)
<223> OTHER INFORMATION: n is a, c, g, t, or u
<220> FEATURE:
<221> NAME/KEY: misc_feature
<222> LOCATION: (20)..(20)
<223> OTHER INFORMATION: n is a, c, g, t, or u
<220> FEATURE:
<221> NAME/KEY: misc_feature
<222> LOCATION: (26)..(26)
<223> OTHER INFORMATION: n is a, c, g, t, or u
<220> FEATURE:
<221> NAME/KEY: misc_feature
<222> LOCATION: (52)..(52)
<223> OTHER INFORMATION: n is a, c, g, t, or u
<220> FEATURE:
<221> NAME/KEY: misc_feature
<222> LOCATION: (61)..(61)
<223> OTHER INFORMATION: n is a, c, g, t, or u
<220> FEATURE:
<221> NAME/KEY: misc_feature
<222> LOCATION: (144)..(144)
<223> OTHER INFORMATION: n is a, c, g, t, or u
<220> FEATURE:
<221> NAME/KEY: misc_feature
<222> LOCATION: (225)..(225)
<223> OTHER INFORMATION: n is a, c, g, t, or u
<220> FEATURE:
<221> NAME/KEY: misc_feature
<222> LOCATION: (236)..(236)
<223> OTHER INFORMATION: n is a, c, g, t, or u
<220> FEATURE:
<221> NAME/KEY: misc_feature
<222> LOCATION: (240)..(240)
<223> OTHER INFORMATION: n is a, c, g, t, or u
<220> FEATURE:
<221> NAME/KEY: misc_feature
<222> LOCATION: (242)..(242)
<223> OTHER INFORMATION: n is a, c, g, t, or u
<220> FEATURE:
<223> OTHER INFORMATION: Description of Artificial Sequence: Human EST

<400> SEQUENCE: 92
gcaaagactt tttganaatn attaanttat catatcttcc attcctgtta tnggagatga     60
naataaaaag caacttatga agtagacat tcagatccag ccattactaa cctattcctt    120
ttttggggaa atctgagcct agcncagaaa aacataaagc accttgaaaa agacttggca    180
gcttcctgat aaagcgtgct gtgctgtgca gtaggaacac atccnattta ttgtgntgtn    240
gnggttttat gatc                                                      254
```

```
<210> SEQ ID NO 93
<211> LENGTH: 243
<212> TYPE: DNA
<213> ORGANISM: Artificial Sequence
<220> FEATURE:
<221> NAME/KEY: misc_feature
<222> LOCATION: (103)..(120)
<223> OTHER INFORMATION: n is a, c, g, t, or u
<220> FEATURE:
```

<223> OTHER INFORMATION: Description of Artificial Sequence: Human EST

<400> SEQUENCE: 93

```
tgtcagtaca ggaaaaaaac tgtgcaagtg agcacctgat tccgttgcct tgcttaactc    60
taaagctcca tgtcctgggc ctaaaatcgt ataaaatctg gannnnnnnn nnnnnnnnnn   120
gctcatattc acatatgtaa accagaacat tctatgtact acaaacctgg tttttaaaaa   180
ggaactatgt tgctatgaat taaacttgtg tcatgctgat aggacagact ggattttca    240
tat                                                                 243
```

<210> SEQ ID NO 94
<211> LENGTH: 244
<212> TYPE: DNA
<213> ORGANISM: Artificial Sequence
<220> FEATURE:
<221> NAME/KEY: misc_feature
<222> LOCATION: (36)..(36)
<223> OTHER INFORMATION: n is a, c, g, t, or u
<220> FEATURE:
<223> OTHER INFORMATION: Description of Artificial Sequence: Human EST

<400> SEQUENCE: 94

```
aattatcata tcttccattc ctgttattgg agatgnaaat aaaaagcaac ttatgaaagt    60
agacattcag atccagccat tactaaccta ttccttttt ggggaaatct gagcctagct   120
cagaaaaaca taaagcacct tgaaaaagac tgtcagcttc ctgataaagc gtgctgtgct   180
gtgcagtagg aacacatcct atttattgtg atgttgtggt tttattatct taaactcgtt   240
ccat                                                                244
```

<210> SEQ ID NO 95
<211> LENGTH: 152
<212> TYPE: DNA
<213> ORGANISM: Artificial Sequence
<220> FEATURE:
<221> NAME/KEY: misc_feature
<222> LOCATION: (2)..(2)
<223> OTHER INFORMATION: n is a, c, g, t, or u
<220> FEATURE:
<221> NAME/KEY: misc_feature
<222> LOCATION: (16)..(16)
<223> OTHER INFORMATION: n is a, c, g, t, or u
<220> FEATURE:
<221> NAME/KEY: misc_feature
<222> LOCATION: (33)..(34)
<223> OTHER INFORMATION: n is a, c, g, t, or u
<220> FEATURE:
<221> NAME/KEY: misc_feature
<222> LOCATION: (82)..(82)
<223> OTHER INFORMATION: n is a, c, g, t, or u
<220> FEATURE:
<221> NAME/KEY: misc_feature
<222> LOCATION: (97)..(97)
<223> OTHER INFORMATION: n is a, c, g, t, or u
<220> FEATURE:
<221> NAME/KEY: misc_feature
<222> LOCATION: (108)..(108)
<223> OTHER INFORMATION: n is a, c, g, t, or u
<220> FEATURE:
<221> NAME/KEY: misc_feature
<222> LOCATION: (125)..(125)
<223> OTHER INFORMATION: n is a, c, g, t, or u
<220> FEATURE:
<221> NAME/KEY: misc_feature
<222> LOCATION: (127)..(127)
<223> OTHER INFORMATION: n is a, c, g, t, or u
<220> FEATURE:
<221> NAME/KEY: misc_feature
<222> LOCATION: (137)..(137)
<223> OTHER INFORMATION: n is a, c, g, t, or u

```
<220> FEATURE:
<223> OTHER INFORMATION: Description of Artificial Sequence: Human EST

<400> SEQUENCE: 95
anagatgata taaaanattg ttgctctgac aannatacat gtatttcatt ctcgtatggt      60
gctagagtta gattaatctg cnttttaaaa aactganttg gaatagantt ggtaagttgc     120
aaagncnttt gaaaatnatt aagttatcag at                                   152

<210> SEQ ID NO 96
<211> LENGTH: 292
<212> TYPE: DNA
<213> ORGANISM: Artificial Sequence
<220> FEATURE:
<223> OTHER INFORMATION: Description of Artificial Sequence: Human EST

<400> SEQUENCE: 96
ttccattcct gttattggag atgaaaataa aaagcaactt atgaaagtag acattcagat      60
ccagccatta ctaacctatt cctttttggg ggaaatctga gcctagctca gaaaaacata    120
aagcaccttg aaaagacttg gcagcttcc tgataaagcg tgctgtgctg tgcagtagga     180
acacatccta tttattgtga tgttgtggtt ttattatcta aactctgttc catacacttg    240
tataaataca tggatatttt tatgtacaga agtatgtctc ttaaccagtt ca            292

<210> SEQ ID NO 97
<211> LENGTH: 308
<212> TYPE: DNA
<213> ORGANISM: Artificial Sequence
<220> FEATURE:
<221> NAME/KEY: misc_feature
<222> LOCATION: (46) (46)
<223> OTHER INFORMATION: n is a, c, g, t, or u
<220> FEATURE:
<223> OTHER INFORMATION: Description of Artificial Sequence: Human EST

<400> SEQUENCE: 97
cttccattcc tgttattgga gatgaaaata aaaagcaact tatganagta gacattcaga      60
tccagccatt actaacctat tccttttttg gggaaatctg agcctagctc agaaaaacat    120
aaagcacctt gaaaaagact tggcagcttc ctgataaagc gtgctgtgct gtgcagtagg    180
aacacatcct atttattgtg atgttgtggt tttattatct aaactctgt tccatacact     240 tgtataaaata catggatatt tttatgtaca gaagtatgtc tcttaaccag ttcacttatt   300
gtacctgg                                                             308

<210> SEQ ID NO 98
<211> LENGTH: 1878
<212> TYPE: DNA
<213> ORGANISM: Homo sapiens

<400> SEQUENCE: 98
aaaatgtatg gatacaactt acgtttgatg aaagatttgg gcttgaagac ccagaagatg      60
acatatgcaa gtatgatttt gtagaagttg aggaacccag tgatggaact atattagggc    120
gctggtgtgg ttctggtact gtaccaggaa aacagatttc taaggaaat caaattagga    180 taagatttgt atctgatgaa tattttcctt ctgaaccttc taacagagga ggtaagatta    240
tacagctgca cacctcgtaa cttctcagtg tccataaggg aagaactaaa gagaaccgat    300
accattttct ggccaggttg tctcctggtt aaacgctgtg gtgggaactg tgcctgttgt    360
ctccacaatt gcaatgaatg tcaatgtgtc ccaagcaaag ttactaaaaa ataccacgag    420
```

-continued

```
gtccttcagt tgagaccaaa gaccggtgtc aggggattgc acaaatcact caccgacgtg      480
gccctggagc accatgagga gtgtgactgt gtgtgcagag ggagcacagg aggatagccg      540
catcaccacc agcagctctt gcccagagct gtgcagtgca gtggctgatt ctattagaga      600
acgtatgcgt tatctccatc cttaatctca gttgtttgct tcaaggacct ttcatcttca      660
ggatttacag tgcattctga agaggagaca tcaaacagaa ttaggagttg tgcaacagc       720 tcttttgaga ggaggcctaa aggacaggag aaaaggtctt caatcgtgga agaaaatta      780 aatgttgtat taaatagatc accagctagt ttcagagtta ccatgtacgt attccactag     840
ctgggttctg tatttcagtt ctttcgatac ggcttagggt aatgtcagta caggaaaaaa     900
actgtgcaag tgagcacctg attccgttgc cttgcttaac tctaaagctc catgtcctgg     960
gcctaaaatc gtataaaatc tggattttt ttttttttt tgctcatatt cacatatgta     1020
aaccagaaca ttctatgtac tacaaacctg ttttttaaaa aggaactatg ttgctatgaa    1080
ttaaacttgt gtcgtgctga taggacagac tggattttc atatttctta ttaaaatttc     1140
tgccatttag aagaagagaa ctacattcat ggtttggaag agataaacct gaaaagaaga    1200
gtggccttat cttcacttta tcgataagtc agtttatttg tttcattgtg tacatttta    1260 tattctcctt ttgacattat aactgttggc ttttctaatc ttgttaaata tatctatttt   1320
taccaaaggt atttaatatt ctttttatg acaacttaga tcaactatttt ttagcttggt   1380 aaattttct aaacacaatt gttatagcca gaggaacaaa gatgatataa atattgttg    1440 ctctgacaaa aatacatgta tttcattctc gtatggtgct agagttagat taatctgcat    1500
tttaaaaaac tgaattggaa tagaattggt aagttgcaaa gacttttga aaataattaa    1560 attatcatat cttccattcc tgttattgga gatgaaaata aaaagcaact tatgaaagta    1620
gacattcaga tccagccatt actaacctat tcctttttg gggaaatctg agcctagctc    1680
agaaaaacat aaagcacctt gaaaaagact tggcagcttc ctgataaagc gtgctgtgct    1740
gtgcagtagg aacacatcct atttattgtg atgttgtggt tttattatct taaactctgt    1800
tccatacact tgtataaata catggatatt tttatgtaca gaagtatgtc tcttaaccag    1860
ttcacttatt gtacctgg                                                   1878
```

<210> SEQ ID NO 99
<211> LENGTH: 113
<212> TYPE: PRT
<213> ORGANISM: Homo sapiens

<400> SEQUENCE: 99

```
Met Asn Ile Phe Leu Leu Asn Leu Leu Thr Glu Glu Val Arg Leu Tyr
1               5                   10                  15

Ser Cys Thr Pro Arg Asn Phe Ser Val Ser Ile Arg Glu Glu Leu Lys
            20                  25                  30

Arg Thr Asp Thr Ile Phe Trp Pro Gly Cys Leu Leu Val Lys Arg Cys
        35                  40                  45

Gly Gly Asn Cys Ala Cys Cys Leu His Asn Cys Asn Glu Cys Gln Cys
    50                  55                  60

Val Pro Ser Lys Val Thr Lys Lys Tyr His Glu Val Leu Gln Leu Arg
65                  70                  75                  80

Pro Lys Thr Gly Val Arg Gly Leu His Lys Ser Leu Thr Asp Val Ala
                85                  90                  95

Leu Glu His His Glu Glu Cys Asp Cys Val Cys Arg Gly Ser Thr Gly
            100                 105                 110
```

Gly

<210> SEQ ID NO 100
<211> LENGTH: 2475
<212> TYPE: DNA
<213> ORGANISM: Homo sapiens

<400> SEQUENCE: 100

| | | | | | |
|---|---|---|---|---|---|
| tgccagagca | ggtgggcgct | tccacccag | tgcagccttc | ccctggcggt | ggtgaaagag | 60 |
| actcgggagt | cgctgcttcc | aaagtgcccg | ccgtgagtga | gctctcaccc | cagtcagcca | 120 |
| aatgagcctc | ttcgggcttc | tcctgctgac | atctgccctg | gccggccaga | gacaggggac | 180 |
| tcaggcggaa | tccaacctga | gtagtaaatt | ccagttttcc | agcaacaagg | aacagaacgg | 240 |
| agtacaagat | cctcagcatg | agagaattat | tactgtgtct | actaatggaa | gtattcacag | 300 |
| cccaaggttt | cctcatactt | atccaagaaa | tacggtcttg | gtatggagat | tagtagcagt | 360 |
| agaggaaaat | gtatggatac | aacttacgtt | tgatgaaaga | tttgggcttg | aagacccaga | 420 |
| agatgacata | tgcaagtatg | attttgtaga | agttgaggaa | cccagtgatg | gaactatatt | 480 |
| agggcgctgg | tgtggttctg | gtactgtacc | aggaaaacag | atttctaaag | gaaatcaaat | 540 |
| taggataaga | tttgtatctg | atgaatattt | tccttctgaa | ccagggttct | gcatccacta | 600 |
| caacattgtc | atgccacaat | tcacagaagc | tgtgagtcct | tcagtgctac | ccccttcagc | 660 |
| tttgccactg | gacctgctta | ataatgctat | aactgccttt | agtaccttgg | aagacctttat | 720 |
| tcgatatctt | gaaccagaga | gatggcagtt | ggacttagaa | gatctatata | ggccaacttg | 780 |
| gcaacttctt | ggcaaggctt | ttgttttttgg | aagaaaatcc | agagtggtgg | atctgaacct | 840 |
| tctaacagag | gaggtaagat | tatacagctg | cacacctcgt | aacttctcag | tgtccataag | 900 |
| ggaagaacta | agagaaccg | ataccatttt | ctggccaggt | tgtctcctgg | ttaaacgctg | 960 |
| tggtgggaac | tgtgcctgtt | gtctccacaa | ttgcaatgaa | tgtcaatgtg | tcccaagcaa | 1020 |
| agttactaaa | aaataccacg | aggtccttca | gttgagacca | agaccggtg | tcagggatt | 1080 |
| gcacaaaatca | ctcaccgacg | tggccctgga | gcaccatgag | gagtgtgact | gtgtgtgcag | 1140 |
| agggagcaca | ggaggatagc | cgcatcacca | ccagcagctc | ttgcccagag | ctgtgcagtg | 1200 |
| cagtggctga | ttctattaga | gaacgtatgc | gttatctcca | tccttaatct | cagttgtttg | 1260 |
| cttcaaggac | ctttcatctt | caggatttac | agtgcattct | gaaagaggag | acatcaaaca | 1320 |
| gaattaggag | ttgtgcaaca | gctcttttga | gaggaggcct | aaaggacagg | agaaaaggtc | 1380 |
| ttcaatcgtg | gaaagaaaat | taaatgttgt | attaaataga | tcaccagcta | gtttcagagt | 1440 |
| taccatgtac | gtattccact | agctgggttc | tgtatttcag | ttctttcgat | acggcttagg | 1500 |
| gtaatgtcag | tacaggaaaa | aaactgtgca | agtgagcacc | tgattccgtt | gccttgctta | 1560 |
| actctaaagc | tccatgtcct | gggcctaaaa | tcgtataaaa | tctggatttt | tttttttttt | 1620 |
| tttgctcata | ttcacatatg | taaaccgaaa | cattctatgt | actacaaacc | tggttttaa | 1680 |
| aaaggaacta | tgttgctatg | aattaaactt | gtgtcgtgct | gataggacag | actggatttt | 1740 |
| tcatatttct | tattaaaatt | tctgccattt | agaagaagag | aactacattc | atggtttgga | 1800 |
| agagataaac | ctgaaaagaa | gagtggcctt | atcttcactt | tatcgataag | ccagtttatt | 1860 |
| tgtttcattg | tgtacatttt | tatattctcc | ttttgacatt | ataactgttg | gcttttctaa | 1920 |
| tcttgttaaa | tatatctatt | tttaccaaag | gtatttaata | ttcttttta | tgacaactta | 1980 |
| gatcaactat | ttttagcttg | gtaaattttt | ctaaacacaa | ttgttatagc | cagaggaaca | 2040 |
| aagatgatat | aaaatattgt | tgctctgaca | aaaatacatg | tatttcattc | tcgtatggtg | 2100 |

```
ctagagttag attaatctgc attttaaaaa actgaattgg aatagaattg gtaagttgca      2160 aagactttt  gaaataatt  aaattatcat atcttccatt cctgttattg gagatgaaaa      2220
taaaaagcaa cttatgaaag tagacattca gatccagcca ttactaacct attccttttt      2280
tggggaaatc tgagcctagc tcagaaaaac ataaagcacc ttgaaaaaga cttggcagct      2340
tcctgataaa gcgtgctgtg ctgtgcagta ggaacacatc ctatttattg tgatgttgtg      2400
gttttattat cttaaactct gttccataca cttgtataaa tacatggata tttttatgta      2460
cagaagtatg tctct                                                       2475
```

<210> SEQ ID NO 101
<211> LENGTH: 345
<212> TYPE: PRT
<213> ORGANISM: Homo sapiens

<400> SEQUENCE: 101

```
Met Ser Leu Phe Gly Leu Leu Leu Thr Ser Ala Leu Ala Gly Gln
1               5                   10                  15

Arg Gln Gly Thr Gln Ala Glu Ser Asn Leu Ser Ser Lys Phe Gln Phe
            20                  25                  30

Ser Ser Asn Lys Glu Gln Asn Gly Val Gln Asp Pro Gln His Glu Arg
        35                  40                  45

Ile Ile Thr Val Ser Thr Asn Gly Ser Ile His Ser Pro Arg Phe Pro
    50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
        275                 280                 285

His Asn Cys Asn Glu Cys Gln Cys Val Pro Ser Lys Val Thr Lys Lys
    290                 295                 300
```

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
            340                 345

<210> SEQ ID NO 102
<211> LENGTH: 2776
<212> TYPE: DNA
<213> ORGANISM: Homo sapiens

<400> SEQUENCE: 102

| | | | | | |
|---|---|---|---|---|---|
| atttgtttaa | accttgggaa | actggttcag | gtccaggttt | tgctttgatc | cttttcaaaa | 60 |
| actggagaca | cagaagaggg | cttctaggaa | aaagttttgg | gatgggatta | tgtggaaact | 120 |
| accctgcgat | tctctgctgc | cagagcaggc | tcggcgcttc | cacccagtg | cagccttccc | 180 |
| ctggcggtgg | tgaaagagac | tcgggagtcg | ctgcttccaa | agtgcccgcc | gtgagtgagc | 240 |
| tctcacccca | gtcagccaaa | tgagcctctt | cgggcttctc | ctgctgacat | ctgccctggc | 300 |
| cggccagaga | caggggactc | aggcggaatc | caacctgagt | agtaaattcc | agttttccag | 360 |
| caacaaggaa | cagtacggag | tacaagatcc | tcagcatgag | agaattatta | ctgtgtctac | 420 |
| taatggaagt | attcacagcc | caaggtttcc | tcatacttat | ccaagaaata | cggtcttggt | 480 |
| atggagatta | gtagcagtag | aggaaaatgt | atggatacaa | cttacgtttg | atgaaagatt | 540 |
| tgggcttgaa | gacccagaag | atgacatatg | caagtatgat | tttgtagaag | ttgaggaacc | 600 |
| cagtgatgga | actatattag | ggcgctggtg | tggttctggt | actgtaccag | gaaaacagat | 660 |
| ttctaaagga | aatcaaatta | ggataagatt | tgtatctgat | gaatattttc | cttctgaacc | 720 |
| agggttctgc | atccactaca | acattgtcat | gccacaattc | acagaagctg | tgagtccttc | 780 |
| agtgctaccc | ccttcagctt | tgccactgga | cctgcttaat | aatgctataa | ctgcctttag | 840 |
| taccttggaa | gaccttattc | gatatcttga | accagagaga | tggcagttgg | acttagaaga | 900 |
| tctatatagg | ccaacttggc | aacttcttgg | caaggctttt | gtttttggaa | gaaaatccag | 960 |
| agtggtggat | ctgaaccttc | taacagagga | ggtaagatta | tacagctgca | cacctcgtaa | 1020 |
| cttctcagtg | tccataaggg | aagaactaaa | gagaaccgat | accatttcct | ggccaggttg | 1080 |
| tctcctggtt | aaacgctgtg | gtgggaactg | tgcctgttgt | ctccacaatt | gcaatgaatg | 1140 |
| tcaatgtgtc | ccaagcaaag | ttactaaaaa | ataccacgag | gtccttcagt | tgagaccaaa | 1200 |
| gaccggtgtc | aggggattgc | acaaatcact | caccgacgtg | gccctggagc | accatgagga | 1260 |
| gtgtgactgt | gtgtgcagag | ggagcacagg | aggatagccg | catcaccacc | agcagctctt | 1320 |
| gcccagagct | gtgcagtgca | gtggctgatt | ctattagaga | acgtatgcgt | tatctccatc | 1380 |
| cttaatctca | gttgtttgct | tcaaggacct | ttcatcttca | ggatttacag | tgcattctga | 1440 |
| aagaggagac | atcaaacaga | attaggagtt | gtgcaacagc | tcttttgaga | ggaggcctaa | 1500 |
| aggacaggag | aaaaggtctt | caatcgtgga | agaaaatta | aatgttgtat | taaatagatc | 1560 |
| accagctagt | ttcagagtta | ccatgtacgt | attccactag | ctgggttctg | tatttcagtt | 1620 |
| cttttcgatac | ggcttagggt | aatgtcagta | caggaaaaaa | actgtgcaag | tgagcacctg | 1680 |
| attccgttgc | cttggcttaa | ctctaaagct | ccatgtcctg | ggcctaaaat | cgtataaaat | 1740 |
| ctggattttt | ttttttttt | ttgcgcatat | tcacatatgt | aaaccagaac | attctatgta | 1800 |
| ctacaaacct | ggttttaaa | aaggaactat | gttgctatga | attaaacttg | tgtcatgctg | 1860 |

```
ataggacaga ctggattttt catatttctt attaaaattt ctgccattta gaagaagaga   1920
actacattca tggtttggaa gagataaacc tgaaagaag agtggcctta tcttcacttt    1980
atcgataagt cagtttattt gtttcattgt gtacatttt atattctcct tttgacatta    2040
taactgttgg cttttctaat cttgttaaat atatctattt ttaccaaagg tatttaatat   2100
tcttttttat gacaacttag atcaactatt tttagcttgg taaattttc taaacacaat    2160 tgttatagcc agaggaacaa agatgatata aatattgtt gctctgacaa aaatacatgt    2220
atttcattct cgtatggtgc tagagttaga ttaatctgca ttttaaaaaa ctgaattgga   2280
atagaattgg taagttgcaa agacttttg aaaataatta aattatcata tcttccattc    2340
ctgttattgg agatgaaaat aaaaagcaac ttatgaaagt agacattcag atccagccat   2400
tactaaccta ttccttttt ggggaaatct gagcctagct cagaaaaaca taaagcacct    2460
tgaaaaagac ttggcagctt cctgataaag cgtgctgtgc tgtgcagtag gaacacatcc   2520
tatttattgt gatgttgtgg ttttattatc ttaaactctg ttccatacac ttgtataaat   2580
acatggatat ttttatgtac agaagtatgt ctcttaacca gttcacttat tgtactctgg   2640
caatttaaaa gaaatcagt aaaatatttt gcttgtaaaa tgcttaatat cgtgcctagg    2700
ttatgtggtg actatttgaa tcaaaaatgt attgaatcat caaataaaag aatgtggcta   2760
ttttggggag aaaatt                                                    2776
```

<210> SEQ ID NO 103
<211> LENGTH: 345
<212> TYPE: PRT
<213> ORGANISM: Homo sapiens

<400> SEQUENCE: 103

```
Met Ser Leu Phe Gly Leu Leu Leu Thr Ser Ala Leu Ala Gly Gln
1               5                   10                  15

Arg Gln Gly Thr Gln Ala Glu Ser Asn Leu Ser Ser Lys Phe Gln Phe
            20                  25                  30

Ser Ser Asn Lys Glu Gln Tyr Gly Val Gln Asp Pro Gln His Glu Arg
        35                  40                  45

Ile Ile Thr Val Ser Thr Asn Gly Ser Ile His Ser Pro Arg Phe Pro
    50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
        195                 200                 205
```

```
Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Leu Lys Arg Thr Asp Thr Ile Phe Trp Pro
            260                 265                 270

Gly Cys Leu Leu Val Lys Arg Cys Gly Asn Cys Ala Cys Cys Leu
            275                 280                 285

His Asn Cys Asn Glu Cys Gln Cys Val Pro Ser Lys Val Thr Lys Lys
    290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
            340                 345

<210> SEQ ID NO 104
<211> LENGTH: 1473
<212> TYPE: DNA
<213> ORGANISM: Homo sapiens

<400> SEQUENCE: 104
tttgtttaaa ccttgggaaa ctggttcagg tccaggtttt gctttgatcc ttttcaaaaa    60
ctggagacac agaagagggc tctaggaaaa agttttggat gggattatgt ggaaactacc   120
ctgcgattct ctgctgccag agcaggctcg gcgcttccac cccagtgcag ccttcccctg   180
gcggtggtga agagactcg ggagtcgctg cttccaaagt gcccgccgtg agtgagctct    240
caccccagtc agccaaatga gcctcttcgg gcttctcctg ctgacatctg ccctggccgg   300
ccagagacag gggactcagg cggaatccaa cctgagtagt aaattccagt tttccagcaa   360
caaggaacag aacggagtac aagatcctca gcatgagaga attattactg tgtctactaa   420
tggaagtatt cacagcccaa ggtttcctca tacttatcca agaaatacgg tcttggtatg   480
gagattagta gcagtagagg aaaatgtatg gatacaactt acgtttgatg aaagatttgg   540
gcttgaagac ccagaagatg acatatgcaa gtatgatttt gtagaagttg aggaacccag   600
tgatggaact atattagggc gctggtgtgg ttctggtact gtaccaggaa aacagatttc   660
taaaggaaat caaattagga taagatttgt atctgatgaa tattttcctt ctgaaccagg   720
gttctgcatc cactacaaca ttgtcatgcc acaattcaca gaagctgtga gtccttcagt   780
gctaccccct tcagctttgc cactggacct gcttaataat gctataactg cctttagtac   840 cttgaagac cttattcgat atcttgaacc agagagatgg cagttggact agaagatct    900 ataggcca acttggcaac ttcttggcaa ggcttttgtt tttggaagaa atccagagt     960 ggtggatctg aaccttctaa cagaggaggt aagattatac agctgcacac ctcgtaactt  1020
ctcagtgtcc ataagggaag aactaaagag aaccgatacc attttctggc caggttgtct  1080
cctggttaaa cgctgtggtg ggaactgtgc ctgttgtctc cacaattgca atgaatgtca  1140
atgtgtccca agcaaagtta ctaaaaaata ccacgaggtc cttcagttga gaccaaagac  1200
cggtgtcagg ggattgcaca aatcactcac gacgtggcc ctgagcacc atgaggagtg    1260 tgactgtgtg tgcagaggga gcacaggagg atagccgcat caccaccagc agctcttgcc  1320
```

```
cagagctgtg cagtgcagtg gctgattcta ttagagaacg tatgcgttat ctccatcctt    1380
aatctcagtt gtttgcttca aggacctttc atcttcagga tttacagtgc attctgaaag    1440
aggagacatc aaacagaatt aggagttgtg caa                                  1473
```

<210> SEQ ID NO 105
<211> LENGTH: 215
<212> TYPE: PRT
<213> ORGANISM: Homo sapiens

<400> SEQUENCE: 105

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Arg Arg Lys His
                165                 170                 175

Leu Phe Val Gln Asp Pro Gln Thr Cys Lys Cys Ser Cys Lys Asn Thr
            180                 185                 190

Asp Ser Arg Cys Lys Ala Arg Gln Leu Glu Leu Asn Glu Arg Thr Cys
        195                 200                 205

Arg Cys Asp Lys Pro Arg Arg
    210                 215
```

<210> SEQ ID NO 106
<211> LENGTH: 149
<212> TYPE: PRT
<213> ORGANISM: Homo sapiens

<400> SEQUENCE: 106

```
Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
                20                  25                  30

Asn Gly Ser Ser Glu Val Glu Val Val Pro Phe Gln Glu Val Trp Gly
            35                  40                  45

Arg Ser Tyr Cys Arg Ala Leu Glu Arg Leu Val Asp Val Val Ser Glu
        50                  55                  60

Tyr Pro Ser Glu Val Glu His Met Phe Ser Pro Ser Cys Val Ser Leu
65                  70                  75                  80
```

```
Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
        115                 120                 125

Glu Cys Arg Pro Leu Arg Glu Lys Met Lys Pro Glu Arg Cys Gly Asp
    130                 135                 140

Ala Val Pro Arg Arg
145

<210> SEQ ID NO 107
<211> LENGTH: 188
<212> TYPE: PRT
<213> ORGANISM: Homo sapiens

<400> SEQUENCE: 107

Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Ser Pro Arg Pro Leu Cys Pro Arg
    130                 135                 140

Cys Thr Gln His His Gln Arg Pro Asp Pro Arg Thr Cys Arg Cys Arg
145                 150                 155                 160

Cys Arg Arg Arg Ser Phe Leu Arg Cys Gln Gly Arg Gly Leu Glu Leu
                165                 170                 175

Asn Pro Asp Thr Cys Arg Cys Arg Lys Leu Arg Arg
            180                 185

<210> SEQ ID NO 108
<211> LENGTH: 419
<212> TYPE: PRT
<213> ORGANISM: Homo sapiens

<400> SEQUENCE: 108

Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
            20                  25                  30

Glu Ser Gly Leu Asp Leu Ser Asp Ala Glu Pro Asp Ala Gly Glu Ala
        35                  40                  45

Thr Ala Tyr Ala Ser Lys Asp Leu Glu Glu Gln Leu Arg Ser Val Ser
    50                  55                  60
```

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
            115                 120                 125

Thr Gln Cys Met Pro Arg Glu Val Cys Ile Asp Val Gly Lys Glu Phe
        130                 135                 140

Gly Val Ala Thr Asn Thr Phe Phe Lys Pro Pro Cys Val Ser Val Tyr
145                 150                 155                 160

Arg Cys Gly Gly Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
            195                 200                 205

Cys Arg Cys Met Ser Lys Leu Asp Val Tyr Arg Gln Val His Ser Ile
        210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
            275                 280                 285

Glu Thr Cys Gln Cys Val Cys Arg Ala Gly Leu Arg Pro Ala Ser Cys
    290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
        340                 345                 350

Leu Asn Pro Gly Lys Cys Ala Cys Glu Cys Thr Glu Ser Pro Gln Lys
            355                 360                 365

Cys Leu Leu Lys Gly Lys Lys Phe His His Gln Thr Cys Ser Cys Tyr
        370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser

<210> SEQ ID NO 109
<211> LENGTH: 354
<212> TYPE: PRT
<213> ORGANISM: Homo sapiens

<400> SEQUENCE: 109

Met Tyr Arg Glu Trp Val Val Asn Val Phe Met Met Leu Tyr Val
1                5                   10                  15

```
Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
    50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
    130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
        275                 280                 285

Ser Cys Phe Glu Cys Lys Glu Ser Leu Glu Thr Cys Cys Gln Lys His
    290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
            340                 345                 350

Asn Pro

<210> SEQ ID NO 110
<211> LENGTH: 345
<212> TYPE: PRT
<213> ORGANISM: Homo sapiens

<400> SEQUENCE: 110

Met Ser Leu Phe Gly Leu Leu Leu Leu Thr Ser Ala Leu Ala Gly Gln
1               5                   10                  15

Arg Gln Gly Thr Gln Ala Glu Ser Asn Leu Ser Ser Lys Phe Gln Phe
            20                  25                  30
```

```
Ser Ser Asn Lys Glu Gln Asn Gly Val Gln Asp Pro Gln His Glu Arg
        35                  40                  45

Ile Ile Thr Val Ser Thr Asn Gly Ser Ile His Ser Pro Arg Phe Pro
 50                  55                  60

His Thr Tyr Pro Arg Asn Thr Val Leu Val Trp Arg Leu Val Ala Val
65                   70                  75                  80

Glu Glu Asn Val Trp Ile Gln Leu Thr Phe Asp Glu Arg Phe Gly Leu
                 85                  90                  95

Glu Asp Pro Glu Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
            115                 120                 125

Val Pro Gly Lys Gln Ile Ser Lys Gly Asn Gln Ile Arg Ile Arg Phe
            130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
                180                 185                 190

Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
        210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
                260                 265                 270

Gly Cys Leu Leu Val Lys Arg Cys Gly Gly Asn Cys Ala Cys Cys Leu
        275                 280                 285

His Asn Cys Asn Glu Cys Gln Cys Val Pro Ser Lys Val Thr Lys Lys
        290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
                340                 345

<210> SEQ ID NO 111
<211> LENGTH: 167
<212> TYPE: PRT
<213> ORGANISM: Homo sapiens

<400> SEQUENCE: 111

Met Ser Leu Phe Gly Leu Leu Leu Leu Thr Ser Ala Leu Ala Gly Gln
1               5                   10                  15

Arg Gln Gly Thr Gln Ala Glu Ser Asn Leu Ser Ser Lys Phe Gln Phe
                20                  25                  30

Ser Ser Asn Lys Glu Gln Asn Gly Val Gln Asp Pro Gln His Glu Arg
        35                  40                  45

Ile Ile Thr Val Ser Thr Asn Gly Ser Ile His Ser Pro Arg Phe Pro
```

```
              50                  55                  60
His Thr Tyr Pro Arg Asn Thr Val Leu Val Trp Arg Leu Val Ala Val
 65                  70                  75                  80

Glu Glu Asn Val Trp Ile Gln Leu Thr Phe Asp Glu Arg Phe Gly Leu
                 85                  90                  95

Glu Asp Pro Glu Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
            115                 120                 125

Val Pro Gly Lys Gln Ile Ser Lys Gly Asn Gln Ile Arg Ile Arg Phe
130                 135                 140

Val Ser Asp Glu Tyr Phe Pro Ser Glu Pro Ser Asn Arg Gly Gly Lys
145                 150                 155                 160

Ile Ile Gln Leu His Thr Ser
                165

<210> SEQ ID NO 112
<211> LENGTH: 282
<212> TYPE: PRT
<213> ORGANISM: Homo sapiens

<400> SEQUENCE: 112

Met Ser Leu Phe Gly Leu Leu Leu Leu Thr Ser Ala Leu Ala Gly Gln
 1               5                  10                  15

Arg Gln Gly Thr Gln Ala Glu Ser Asn Leu Ser Ser Lys Phe Gln Phe
                20                  25                  30

Ser Ser Asn Lys Glu Gln Asn Gly Val Gln Asp Pro Gln His Glu Arg
             35                  40                  45

Ile Ile Thr Val Ser Thr Asn Gly Ser Ile His Ser Pro Arg Phe Pro
         50                  55                  60

His Thr Tyr Pro Arg Asn Thr Val Leu Val Trp Arg Leu Val Ala Val
 65                  70                  75                  80

Glu Glu Asn Val Trp Ile Gln Leu Thr Phe Asp Glu Arg Phe Gly Leu
                 85                  90                  95

Glu Asp Pro Glu Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
            115                 120                 125

Val Pro Gly Lys Gln Ile Ser Lys Gly Asn Gln Ile Arg Ile Arg Phe
130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
            195                 200                 205

Gln Leu Asp Leu Glu Asp Leu Tyr Arg Pro Thr Trp Gln Leu Leu Gly
            210                 215                 220

Lys Ala Phe Val Phe Gly Arg Lys Ser Arg Val Val Asp Leu Asn Leu
225                 230                 235                 240

Leu Thr Glu Glu Val Leu Gln Leu Arg Pro Lys Thr Gly Val Arg Gly
                245                 250                 255
```

-continued

```
Leu His Lys Ser Leu Thr Asp Val Ala Leu Glu His His Glu Glu Cys
            260                 265                 270
Asp Cys Val Cys Arg Gly Ser Thr Gly Gly
            275                 280
```

<210> SEQ ID NO 113
<211> LENGTH: 822
<212> TYPE: DNA
<213> ORGANISM: Homo sapiens

<400> SEQUENCE: 113

| | | | | | |
|---|---|---|---|---|---|
| aggaaatcaa | attaggataa | gatttgtatc | tgatgaatat | tttccttctg | aaccttctaa | 60 |
| cagaggaggt | aagattatac | agctgcacac | ctcgtaactt | ctcagtgtcc | ataagggaag | 120 |
| aactaaagag | aaccgatacc | attttctggc | caggttgtct | cctggttaaa | cgctgtggtg | 180 |
| ggaactgtgc | ctgttgtctc | cacaattgca | atgaatgtca | atgtgtccca | agcaaagtta | 240 |
| ctaaaaaata | ccacgaggtc | cttcagttga | gaccaaagac | cggtgtcagg | ggattgcaca | 300 |
| aatcactcac | cgacgtggcc | ctggagcacc | atgaggagtg | tgactgtgtg | tgcagaggga | 360 |
| gcacaggagg | atagccgcat | caccaccagc | agctcttgcc | cagagctgtg | cagtgcagtg | 420 |
| gctgattcta | ttagagaacg | tatgcgttat | ctccatcctt | aatctcagtt | gtttgcttca | 480 |
| aggacctttc | atcttcagga | tttacagtgc | attctgaaag | aggagacatc | aaacagaatt | 540 |
| aggagttgtg | caacagctct | tttgagagga | ggcctaaagg | acaggagaaa | aggtcttcaa | 600 |
| tcgtggaaag | aaaattaaat | gttgtattaa | atagatcacc | agctagtttc | agagttacca | 660 |
| tgtacgtatt | ccactagctg | ggttctgtat | ttcagttctt | tcgatacggc | ttagggtaat | 720 |
| gtcagtacag | gaaaaaaact | gtgcaagtga | gcacctgatt | ccgttgcctt | ggcttaactc | 780 |
| taaagctcca | tgtcctgggc | ctaaaatcgt | ataaaatctg | ga | | 822 |

<210> SEQ ID NO 114
<211> LENGTH: 227
<212> TYPE: PRT
<213> ORGANISM: Homo sapiens

<400> SEQUENCE: 114

```
Met Asn Ile Phe Leu Leu Asn Leu Leu Thr Glu Glu Val Arg Leu Tyr
1               5                   10                  15
Ser Cys Thr Pro Arg Asn Phe Ser Val Ser Ile Arg Glu Glu Leu Lys
            20                  25                  30
Arg Thr Asp Thr Ile Phe Trp Pro Gly Cys Leu Leu Val Lys Arg Cys
        35                  40                  45
Gly Gly Asn Cys Ala Cys Cys Leu His Asn Cys Asn Glu Cys Gln Cys
    50                  55                  60
Val Pro Ser Lys Val Thr Lys Lys Tyr His Glu Val Leu Gln Leu Arg
65                  70                  75                  80
Pro Lys Thr Gly Val Arg Gly Leu His Lys Ser Leu Thr Asp Val Ala
                85                  90                  95
Val Ser Gly Asp Cys Thr Asn His Ser Pro Thr Trp Pro Leu Glu His
            100                 105                 110
His Glu Glu Cys Asp Cys Val Cys Arg Gly Ser Thr Gly Gly Val Gln
        115                 120                 125
Arg Glu His Arg Arg Ile Ala Ala Ser Pro Pro Ala Leu Ala Trp
    130                 135                 140
Ser Thr Met Arg Ser Val Thr Val Cys Ala Glu Gly Ala Gln Glu Asp
145                 150                 155                 160
```

```
Ser Arg Ile Thr Thr Ser Ser Cys Gln Ser Cys Ala Val Gln Trp
            165                 170                 175

Leu Ile Leu Leu Glu Asn Val Cys Val Ile Ser Ile Leu Asn Leu Ser
        180                 185                 190

Cys Leu Leu Gln Pro Glu Leu Cys Ser Ala Val Ala Asp Ser Ile Arg
        195                 200                 205

Glu Arg Met Arg Tyr Leu His Pro Gly Pro Phe Ile Phe Arg Ile Tyr
    210                 215                 220

Ser Ala Phe
225

<210> SEQ ID NO 115
<211> LENGTH: 1716
<212> TYPE: DNA
<213> ORGANISM: Homo sapiens
<220> FEATURE:
<221> NAME/KEY: misc_feature
<222> LOCATION: (830)..(830)
<223> OTHER INFORMATION: n is a, c, g, t, or u

<400> SEQUENCE: 115
aggaaatcaa attaggataa gatttgtatc tgatgaatat tttccttctg aaccttctaa      60
cagaggaggt aagattatac agctgcacac ctcgtaactt ctcagtgtcc ataagggaag    120
aactaaagag aaccgatacc attttctggc caggttgtct cctggttaaa cgctgtggtg    180
ggaactgtgc ctgttgtctc cacaattgca atgaatgtca atgtgtccca agcaaagtta    240
ctaaaaaata ccacgaggtc cttcagttga gaccaaagac cggtgtcagg ggattgcaca    300
aatcactcac cgacgtggcc ctggagcacc atgaggagtg tgactgtgtg tgcagaggga    360
gcacaggagg atagccgcat caccaccagc agctcttgcc cagagctgtg cagtgcagtg    420
gctgattcta ttagagaacg tatgcgttat ctccatcctt aatctcagtt gtttgcttca    480
aggacctttc atcttcagga tttacagtgc attctgaaag aggagacatc aaacagaatt    540
aggagttgtg caacagctct tttgagagga ggcctaaagg acaggagaaa aggtcttcaa    600
tcgtggaaag aaaattaaat gttgtattaa atagatcacc agctagtttc agagttacca    660
tgtacgtatt ccactagctg ggttctgtat ttcagttctt tcgatacggc ttagggtaat    720
gtcagtacag gaaaaaaact gtgcaagtga gcacctgatt ccgttgcctt ggcttaactc    780
taaagctcca tgtcctgggc ctaaaatcgt ataaaatctg gatttttttn tttttttttg    840
cgcatattca catatgtaaa ccagaacatt ctatgtacta caaacctggt ttttaaaaag    900
gaactatgtt gctatgaatt aaacttgtgt cgtgctgata ggacagactg gattttttcat   960 atttcttatt aaaatttctg ccatttagaa gaagagaact acattcatgg tttggaagag   1020
ataaacctga aaagaagagt ggccttatct tcactttatc gataagtcag tttatttgtt   1080
tcattgtgta catttttata ttctcctttt gacattataa ctgttggctt ttctaatctt   1140
gttaaatata tctattttta ccaaaggtat ttaatattct tttttatgac aacttagatc   1200
aactattttt agcttggtaa attttttctaa acacaattgt tatagccaga ggaacaaaga   1260
tgatataaaa tattgttgct ctgacaaaaa tacatgtatt tcattctcgt atggtgctag   1320
agttagatta atctgcattt taaaaaactg aattggaata gaattggtaa gttgcaaaga   1380
ctttttgaaa ataattaaat tatcatatct tccattcctg ttattggaga tgaaaataaa   1440
aagcaactta tgaaagtaga cattcagatc cagccattac taacctattc cttttttggg   1500
gaaatctgag cctagctcag aaaaacataa agcaccttga aaaagacttg gcagcttcct   1560
```

-continued

```
gataaagcgt gctgtgctgt gcagtaggaa cacatcctat ttattgtgat gttgtggttt      1620
tattatctta aactctgttc catacacttg tataaataca tggatatttt tatgtacaga      1680
agtatgtctc ttaaccagtt cacttattgt acctgg                                1716
```

<210> SEQ ID NO 116
<211> LENGTH: 227
<212> TYPE: PRT
<213> ORGANISM: Homo sapiens

<400> SEQUENCE: 116

```
Met Asn Ile Phe Leu Leu Asn Leu Leu Thr Glu Glu Val Arg Leu Tyr
1               5                   10                  15

Ser Cys Thr Pro Arg Asn Phe Ser Val Ser Ile Arg Glu Glu Leu Lys
            20                  25                  30

Arg Thr Asp Thr Ile Phe Trp Pro Gly Cys Leu Leu Val Lys Arg Cys
        35                  40                  45

Gly Gly Asn Cys Ala Cys Cys Leu His Asn Cys Asn Glu Cys Gln Cys
    50                  55                  60

Val Pro Ser Lys Val Thr Lys Lys Tyr His Glu Val Leu Gln Leu Arg
65                  70                  75                  80

Pro Lys Thr Gly Val Arg Gly Leu His Lys Ser Leu Thr Asp Val Ala
                85                  90                  95

Val Ser Gly Asp Cys Thr Asn His Ser Pro Thr Trp Pro Leu Glu His
            100                 105                 110

His Glu Glu Cys Asp Cys Val Cys Arg Gly Ser Thr Gly Gly Val Gln
        115                 120                 125

Arg Glu His Arg Arg Ile Ala Ala Ser Pro Pro Ala Ala Leu Ala Trp
    130                 135                 140

Ser Thr Met Arg Ser Val Thr Val Cys Ala Glu Gly Ala Gln Glu Asp
145                 150                 155                 160

Ser Arg Ile Thr Thr Ser Ser Cys Gln Ser Cys Ala Val Gln Trp
                165                 170                 175

Leu Ile Leu Leu Glu Asn Val Cys Val Ile Ser Ile Leu Asn Leu Ser
            180                 185                 190

Cys Leu Leu Gln Pro Glu Leu Cys Ser Ala Val Ala Asp Ser Ile Arg
        195                 200                 205

Glu Arg Met Arg Tyr Leu His Pro Gly Pro Phe Ile Phe Arg Ile Tyr
    210                 215                 220

Ser Ala Phe
225
```

<210> SEQ ID NO 117
<211> LENGTH: 1134
<212> TYPE: DNA
<213> ORGANISM: Homo sapiens

<400> SEQUENCE: 117

```
ggatccaaaa tgagcctctt cgggcttctc ctgctgacat ctgccctggc cggccagaga      60
caggggactc aggcggaatc caacctgagt agtaaattcc agttttccag caacaaggaa     120
cagaacggag tacaagatcc tcagcatgag agaattatta ctgtgtctac taatggaagt     180
attcacagcc aaggtttcc tcatacttat ccaagaaata cggtcttggt atggagatta     240
gtagcagtag aggaaaatgt atggatacaa cttacgtttg atgaaagatt tgggcttgaa     300
gacccagaag atgacatatg caagtatgat tttgtagaag ttgaggaacc cagtgatgga     360
```

```
actatattag ggcgctggtg tggttctggt actgtaccag gaaaacagat ttctaaagga      420
aatcaaatta ggataagatt tgtatctgat gaatattttc cttctgaacc agggttctgc      480
atccactaca acattgtcat gccacaattc acagaagctg tgagtccttc agtgctaccc      540
ccttcagctt tgccactgga cctgcttaat aatgctataa ctgcctttag taccttggaa      600
gaccttattc gatatcttga accagagaga tggcagttgg acttagaaga tctatatagg      660
ccaacttggc aacttcttgg caaggctttt gttttggaa gaaaatccag agtggtggat       720
ctgaaccttc taacagagga ggtaagatta tacagctgca cacctcgtaa cttctcagtg      780
tccataaggg aagaactaaa gagaaccgat accattttct ggccaggttg tctcctggtt      840
aaacgctgtg gtgggaactg tgcctgttgt ctccacaatt gcaatgaatg tcaatgtgtc      900
ccaagcaaag ttactaaaaa ataccacgag gtccttcagt tgagaccaaa gaccggtgtc      960 agggattgc acaaatcact caccgacgtg gccctggagc accatgagga gtgtgactgt     1020
gtgtgcagag ggagcacagg aggatctaga gggcccttcg aaggtaagcc tatccctaac     1080
cctctcctcg gtctcgattc tacgcgtacc ggtcatcatc accatcacca ttga           1134
```

<210> SEQ ID NO 118
<211> LENGTH: 374
<212> TYPE: PRT
<213> ORGANISM: Homo sapiens

<400> SEQUENCE: 118

```
Met Ser Leu Phe Gly Leu Leu Leu Thr Ser Ala Leu Ala Gly Gln
1               5                   10                  15

Arg Gln Gly Thr Gln Ala Glu Ser Asn Leu Ser Ser Lys Phe Gln Phe
            20                  25                  30

Ser Ser Asn Lys Glu Gln Asn Gly Val Gln Asp Pro Gln His Glu Arg
        35                  40                  45

Ile Ile Thr Val Ser Thr Asn Gly Ser Ile His Ser Pro Arg Phe Pro
    50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240
```

```
Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Val Lys Arg Cys Gly Asn Cys Ala Cys Cys Leu
        275                 280                 285

His Asn Cys Asn Glu Cys Gln Cys Val Pro Ser Lys Val Thr Lys Lys
    290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly Ser Arg Gly Pro Phe Glu Gly
                340                 345                 350

Lys Pro Ile Pro Asn Pro Leu Leu Gly Leu Asp Ser Thr Arg Thr Gly
            355                 360                 365

His His His His His His
    370

<210> SEQ ID NO 119
<211> LENGTH: 1134
<212> TYPE: DNA
<213> ORGANISM: Homo sapiens

<400> SEQUENCE: 119
gaattcaaag gcctgtattt tactgttttc gtaacagttt tgtaataaaa aaacctataa       60
atatgaaatt cttagtcaac gttgcccttg tttttatggt cgtatacatt tcttacatct      120
atgcggatcc ggagtctcac catcaccacc atcatgaatc caacctgagt agtaaattcc      180
agttttccag caacaaggaa cagaacggag tacaagatcc tcagcatgag agaattatta      240
ctgtgtctac taatggaagt attcacagcc caaggtttcc tcatacttat ccaagaaata      300
cggtcttggt atggagatta gtagcagtag aggaaaatgt atggatacaa cttacgtttg      360
atgaaagatt tgggcttgaa gacccagaag atgacatatg caagtatgat tttgtagaag      420
ttgaggaacc cagtgatgga actatattag ggcgctggtg tggttctggt actgtaccag      480
gaaaacagat ttctaaagga aatcaaatta ggataagatt tgtatctgat gaatattttc      540
cttctgaacc agggttctgc atccactaca acattgtcat gccacaattc acagaagctg      600
tgagtccttc agtgctaccc ccttcagctt tgccactgga cctgcttaat aatgctataa      660
ctgcctttag taccttggaa gaccttattc gatatcttga accagagaga tggcagttgg      720
acttagaaga tctatatagg ccaacttggc aacttcttgg caaggctttt gttttttggaa      780 gaaaatccag agtggtggat ctgaaccttc taacagagga ggtaagatta tacagctgca      840
cacctcgtaa cttctcagtg tccataaggg aagaactaaa gagaaccgat accatttttct      900 ggccaggttg tctcctggtt aaacgctgtg gtgggaactg tgcctgttgt ctccacaatt      960
gcaatgaatg tcaatgtgtc ccaagcaaag ttactaaaaa ataccacgag gtccttcagt     1020
tgagaccaaa gaccggtgtc agggggattgc acaaatcact caccgacgtg gccctggagc     1080
accatgagga gtgtgactgt gtgtgcagag ggagcacagg aggatagctc taga           1134

<210> SEQ ID NO 120
<211> LENGTH: 354
<212> TYPE: PRT
<213> ORGANISM: Homo sapiens
```

<400> SEQUENCE: 120

| Met | Lys | Phe | Leu | Val | Asn | Val | Ala | Leu | Val | Phe | Met | Val | Val | Tyr | Ile |
| 1 | | | | 5 | | | | | 10 | | | | | 15 | |

Ser Tyr Ile Tyr Ala Asp Pro Glu Ser His His His His His Glu
            20                  25                  30
Ser Asn Leu Ser Ser Lys Phe Gln Phe Ser Ser Asn Lys Glu Gln Asn
        35                  40                  45
Gly Val Gln Asp Pro Gln His Glu Arg Ile Ile Thr Val Ser Thr Asn
50                  55                  60
Gly Ser Ile His Ser Pro Arg Phe Pro His Thr Tyr Pro Arg Asn Thr
65                  70                  75                  80
Val Leu Val Trp Arg Leu Val Ala Val Glu Glu Asn Val Trp Ile Gln
                85                  90                  95
Leu Thr Phe Asp Glu Arg Phe Gly Leu Glu Asp Pro Glu Asp Asp Ile
                100                 105                 110
Cys Lys Tyr Asp Phe Val Glu Val Glu Glu Pro Ser Asp Gly Thr Ile
            115                 120                 125
Leu Gly Arg Trp Cys Gly Ser Gly Thr Val Pro Gly Lys Gln Ile Ser
130                 135                 140
Lys Gly Asn Gln Ile Arg Ile Arg Phe Val Ser Asp Glu Tyr Phe Pro
145                 150                 155                 160
Ser Glu Pro Gly Phe Cys Ile His Tyr Asn Ile Val Met Pro Gln Phe
                165                 170                 175
Thr Glu Ala Val Ser Pro Ser Val Leu Pro Pro Ser Ala Leu Pro Leu
                180                 185                 190
Asp Leu Leu Asn Asn Ala Ile Thr Ala Phe Ser Thr Leu Glu Asp Leu
            195                 200                 205
Ile Arg Tyr Leu Glu Pro Glu Arg Trp Gln Leu Asp Leu Glu Asp Leu
        210                 215                 220
Tyr Arg Pro Thr Trp Gln Leu Leu Gly Lys Ala Phe Val Phe Gly Arg
225                 230                 235                 240
Lys Ser Arg Val Val Asp Leu Asn Leu Leu Thr Glu Glu Val Arg Leu
                245                 250                 255
Tyr Ser Cys Thr Pro Arg Asn Phe Ser Val Ser Ile Arg Glu Glu Leu
            260                 265                 270
Lys Arg Thr Asp Thr Ile Phe Trp Pro Gly Cys Leu Leu Val Lys Arg
        275                 280                 285
Cys Gly Gly Asn Cys Ala Cys Cys Leu His Asn Cys Asn Glu Cys Gln
290                 295                 300
Cys Val Pro Ser Lys Val Thr Lys Lys Tyr His Glu Val Leu Gln Leu
305                 310                 315                 320
Arg Pro Lys Thr Gly Val Arg Gly Leu His Lys Ser Leu Thr Asp Val
                325                 330                 335
Ala Leu Glu His His Glu Glu Cys Asp Cys Val Cys Arg Gly Ser Thr
            340                 345                 350
Gly Gly

<210> SEQ ID NO 121
<211> LENGTH: 1097
<212> TYPE: DNA
<213> ORGANISM: Homo sapiens

<400> SEQUENCE: 121

-continued

```
cgcagactaa ttcgagctcg aacaacaaca acaataacaa taacaacaac ctcgggatcg      60
gagggaagga tttcagaatt cgaatccaac ctgagtagta aattccagtt ttccagcaac     120
aaggaacaga acggagtaca agatcctcag catgagagaa ttattactgt gtctactaat     180
ggaagtattc acagcccaag gtttcctcat acttatccaa gaaatacggt cttggtatgg     240
agattagtag cagtagagga aaatgtatgg atacaactta cgtttgatga aagatttggg     300
cttgaagacc cagaagatga catatgcaag tatgattttg tagaagttga ggaacccagt     360
gatggaacta tattagggcg ctggtgtggt tctggtactg taccaggaaa acagatttct     420
aaaggaaatc aaattaggat aagatttgta tctgatgaat attttccttc tgaaccaggg     480
ttctgcatcc actacaacat tgtcatgcca caattcacag aagctgtgag tccttcagtg     540
ctaccccctt cagctttgcc actggacctg cttaataatg ctataactgc ctttagtacc     600
ttggaagacc ttattcgata tcttgaacca gagagatggc agttggactt agaagatcta     660
tataggccaa cttggcaact tcttggcaag gcttttgttt ttggaagaaa atccagagtg     720
gtggatctga accttctaac agaggaggta agattataca gctgcacacc tcgtaacttc     780
tcagtgtcca taaggaagaa actaaagaga accgatacca ttttctggcc aggttgtctc     840
ctggttaaac gctgtggtgg gaactgtgcc tgttgtctcc acaattgcaa tgaatgtcaa     900
tgtgtcccaa gcaaagttac taaaaaatac cacgaggtcc ttcagttgag accaaagacc     960
ggtgtcaggg gattgcacaa atcactcacc gacgtggccc tggagcacca tgaggagtgt    1020
gactgtgtgt gcagagggag cacaggagga catcatcacc atcaccattg atctagagtc    1080
gacctgcagg caagctt                                                   1097
```

<210> SEQ ID NO 122
<211> LENGTH: 355
<212> TYPE: PRT
<213> ORGANISM: Homo sapiens

<400> SEQUENCE: 122

```
Gln Thr Asn Ser Ser Asn Asn Asn Asn Asn Asn Asn Asn Asn
1               5                   10                  15

Leu Gly Ile Glu Gly Arg Ile Ser Glu Phe Glu Ser Asn Leu Ser Ser
                20                  25                  30

Lys Phe Gln Phe Ser Ser Asn Lys Glu Gln Asn Gly Val Gln Asp Pro
            35                  40                  45

Gln His Glu Arg Ile Ile Thr Val Ser Thr Asn Gly Ser Ile His Ser
        50                  55                  60

Pro Arg Phe Pro His Thr Tyr Pro Arg Asn Thr Val Leu Val Trp Arg
65                  70                  75                  80

Leu Val Ala Val Glu Glu Asn Val Trp Ile Gln Leu Thr Phe Asp Glu
                85                  90                  95

Arg Phe Gly Leu Glu Asp Pro Glu Asp Asp Ile Cys Lys Tyr Asp Phe
            100                 105                 110

Val Glu Val Glu Glu Pro Ser Asp Gly Thr Ile Leu Gly Arg Trp Cys
        115                 120                 125

Gly Ser Gly Thr Val Pro Gly Lys Gln Ile Ser Lys Gly Asn Gln Ile
    130                 135                 140

Arg Ile Arg Phe Val Ser Asp Glu Tyr Phe Pro Ser Glu Pro Gly Phe
145                 150                 155                 160

Cys Ile His Tyr Asn Ile Val Met Pro Gln Phe Thr Glu Ala Val Ser
                165                 170                 175
```

```
Pro Ser Val Leu Pro Ser Ala Leu Pro Leu Asp Leu Leu Asn Asn
        180                 185                 190

Ala Ile Thr Ala Phe Ser Thr Leu Glu Asp Leu Ile Arg Tyr Leu Glu
        195                 200                 205

Pro Glu Arg Trp Gln Leu Asp Leu Glu Asp Leu Tyr Arg Pro Thr Trp
        210                 215                 220

Gln Leu Leu Gly Lys Ala Phe Val Phe Gly Arg Lys Ser Arg Val Val
225                 230                 235                 240

Asp Leu Asn Leu Leu Thr Glu Val Arg Leu Tyr Ser Cys Thr Pro
                245                 250                 255

Arg Asn Phe Ser Val Ser Ile Arg Glu Leu Lys Arg Thr Asp Thr
                260                 265                 270

Ile Phe Trp Pro Gly Cys Leu Leu Val Lys Arg Cys Gly Gly Asn Cys
                275                 280                 285

Ala Cys Cys Leu His Asn Cys Asn Glu Cys Gln Cys Val Pro Ser Lys
        290                 295                 300

Val Thr Lys Lys Tyr His Glu Val Leu Gln Leu Arg Pro Lys Thr Gly
305                 310                 315                 320

Val Arg Gly Leu His Lys Ser Leu Thr Asp Val Ala Leu Glu His His
                325                 330                 335

Glu Glu Cys Asp Cys Val Cys Arg Gly Ser Thr Gly Gly His His His
                340                 345                 350

His His His
        355

<210> SEQ ID NO 123
<211> LENGTH: 500
<212> TYPE: DNA
<213> ORGANISM: Homo sapiens

<400> SEQUENCE: 123
aaggagatat acatatgcgg ggttctcatc atcatcatca tcatggtatg gctagcatga      60
ctggtggaca gcaaatgggt cgggatctgt acgacgatga cgataaggat ccgggaagaa     120
aatccagagt ggtggatctg aaccttctaa cagaggaggt aagattatac agctgcacac     180
ctcgtaactt ctcagtgtcc ataagggaag aactaaagag aaccgatacc attttctggc     240
caggttgtct cctggttaaa cgctgtggtg ggaactgtgc ctgttgtctc cacaattgca     300
atgaatgtca atgtgtccca agcaaagtta ctaaaaaata ccacgaggtc cttcagttga     360
gaccaaagac cggtgtcagg ggattgcaca atcactcac cgacgtggcc ctggagcacc     420
atgaggagtg tgactgtgtg tgcagaggga gcacaggagg ataatgaatt cgaagcttga     480
tccggctgct aacaaagccc                                                 500

<210> SEQ ID NO 124
<211> LENGTH: 149
<212> TYPE: PRT
<213> ORGANISM: Homo sapiens

<400> SEQUENCE: 124

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Gly Arg Lys Ser Arg Val Val Asp Leu Asn Leu Leu Thr Glu Glu
        35                  40                  45
```

```
Val Arg Leu Tyr Ser Cys Thr Pro Arg Asn Phe Ser Val Ser Ile Arg
 50                  55                  60

Glu Glu Leu Lys Arg Thr Asp Thr Ile Phe Trp Pro Gly Cys Leu Leu
65                  70                  75                  80

Val Lys Arg Cys Gly Gly Asn Cys Ala Cys Cys Leu His Asn Cys Asn
                85                  90                  95

Glu Cys Gln Cys Val Pro Ser Lys Val Thr Lys Lys Tyr His Glu Val
            100                 105                 110

Leu Gln Leu Arg Pro Lys Thr Gly Val Arg Gly Leu His Lys Ser Leu
            115                 120                 125

Thr Asp Val Ala Leu Glu His His Glu Glu Cys Asp Cys Val Cys Arg
            130                 135                 140

Gly Ser Thr Gly Gly
145
```

<210> SEQ ID NO 125
<211> LENGTH: 550
<212> TYPE: DNA
<213> ORGANISM: Homo sapiens

<400> SEQUENCE: 125

```
ggcgatggcc atggatatcg aattaattc ggatccggag tctcaccatc accaccatca    60
tgaatccaac ctgagtagta aattccagtt ttccagcaac aaggaacaga acggagtaca   120
agatcctcag catgagagaa ttattactgt gtctactaat ggaagtattc acagcccaag   180
gtttcctcat acttatccaa gaaatacggt cttggtatgg agattagtag cagtagagga   240
aaatgtatgg atacaactta cgtttgatga agatttgggc ttgaagacc agaagatga    300
catatgcaag tatgatttg tagaagttga ggaacccagt gatggaacta ttagggcg    360
ctggtgtggt tctggtactg taccaggaaa acagatttct aaaggaaatc aaattaggat   420
aagatttgta tctgatgaat attttccttc tgaaccaggg ttctgcatcc actcaaacat   480
tgtcatgcca caattcacag aagctgtgta gtcgagctcc gtcgacaagc ttgcggccgc   540
actcgagcac                                                         550
```

<210> SEQ ID NO 126
<211> LENGTH: 168
<212> TYPE: PRT
<213> ORGANISM: Homo sapiens

<400> SEQUENCE: 126

```
Met Ala Met Asp Ile Gly Ile Asn Ser Asp Pro Glu Ser His His His
 1               5                   10                  15

His His His Glu Ser Asn Leu Ser Ser Lys Phe Gln Phe Ser Ser Asn
                20                  25                  30

Lys Glu Gln Asn Gly Val Gln Asp Pro Gln His Glu Arg Ile Ile Thr
            35                  40                  45

Val Ser Thr Asn Gly Ser Ile His Ser Pro Arg Phe Pro His Thr Tyr
 50                  55                  60

Pro Arg Asn Thr Val Leu Val Trp Arg Leu Val Ala Val Glu Glu Asn
65                  70                  75                  80

Val Trp Ile Gln Leu Thr Phe Asp Glu Arg Phe Gly Leu Glu Asp Pro
                85                  90                  95

Glu Asp Asp Ile Cys Lys Tyr Asp Phe Val Glu Val Glu Glu Pro Ser
            100                 105                 110

Asp Gly Thr Ile Leu Gly Arg Trp Cys Gly Ser Gly Thr Val Pro Gly
```

```
                115                 120                 125
Lys Gln Ile Ser Lys Gly Asn Gln Ile Arg Ile Arg Phe Val Ser Asp
        130                 135                 140

Glu Tyr Phe Pro Ser Glu Pro Gly Phe Cys Ile His Tyr Asn Ile Val
145                 150                 155                 160

Met Pro Gln Phe Thr Glu Ala Val
                165

<210> SEQ ID NO 127
<211> LENGTH: 542
<212> TYPE: DNA
<213> ORGANISM: Homo sapiens

<400> SEQUENCE: 127
tttcttttat accatatagt ggtggatctg aaccagggtt ctgcatccac tacaacattg      60
tcatgccaca attcacagaa gctgtgagtc cttcagtgct accccttca gctttgccac      120 tggacctgct aataatgct ataactgcct ttagtacctt ggaagacctt attcgatatc      180
ttgaaccaga gagatggcag ttggacttag aagatctata taggccaact tggcaacttc      240
ttggcaaggc ttttgttttt ggaagaaaat ccagagtggt ggatctgaac cttctaacag      300
aggaggtaag attatacagc tgcacacctc gtaacttctc agtgtccata agggaagaac      360
taaagagaac cgataccatt ttctggccag ttgtctcct ggttaaacgc tgtggtggga      420
actgtgcctg ttgtctccac aattgcaatg aatgtcaatg tgtcccaagc aaagttacta      480
aaaaatacca cgaggtaggt atacaatttt cttttggtt ccttcgggt attttatgtc       540 tt                                                                    542

<210> SEQ ID NO 128
<211> LENGTH: 1710
<212> TYPE: DNA
<213> ORGANISM: Homo sapiens

<400> SEQUENCE: 128
aaagccagtc atagacattc gttgattttt aaaagtggct tactcttatt ccctttcagg      60
tccttcagtt gagaccaaag accggtgtca ggggattgca caaatcactc accgacgtgg     120
ccctggagca ccatgaggag tgtgactgtg tgtgcagagg gagcacagga ggatagccgc     180
atcaccacca gcagctcttg cccagagctg tgcagtgcag tggctgattc tattagagaa     240
cgtatgcgtt atctccatcc ttaatctcag ttgtttgctt caaggacctt tcatcttcag     300
gatttacagt gcattctgaa agaggagaca tcaaacagaa ttaggagttg tgcaacagct     360
cttttgagag gaggcctaaa ggacaggaga aaggtcttc aatcgtggaa agaaaattaa     420
atgttgtatt aaatagatca ccagctagtt tcagagttac catgtacgta ttccactagc     480
tgggttctgt atttcagttc tttcgatacg gctagggta atgtcagtac aggaaaaaaa     540
ctgtgcaagt gagcacctga ttccgttgcc ttggcttaac tctaaagctc catgtcctgg     600
gcctaaaatc gtataaaatc tggattttt ttttttttt tgcgcatatt cacatatgta     660
aaccagaaca ttctatgtac tacaaacctg gtttttaaaa aggaactatg ttgctatgaa     720
ttaaacttgt gtcatgctga taggacagac tggattttc atatttctta ttaaaatttc     780
tgccatttag aagaagagaa ctacattcat ggtttggaag agataaacct gaaaagaaga     840
gtggccttat cttcacttta tcgataagtc agtttatttg tttcattgtg tacattttta     900
tattctcctt ttgacattat aactgttggc ttttctaatc ttgttaaata tatctatttt     960
```

| | |
|---|---:|
| taccaaaggt atttaatatt cttttttatg acaacttaga tcaactattt ttagcttggt | 1020 |
| aaattttttct aaacacaatt gttatagcca gaggaacaaa gatgatataa aatattgttg | 1080 |
| ctctgacaaa aatacatgta tttcattctc gtatggtgct agagttagat taatctgcat | 1140 |
| tttaaaaaac tgaattggaa tagaattggt aagttgcaaa gacttttga aaataattaa | 1200 |
| attatcatat cttccattcc tgttattgga gatgaaaata aaaagcaact tatgaaagta | 1260 |
| gacattcaga tccagccatt actaacctat tcctttttg gggaaatctg agcctagctc | 1320 |
| agaaaaacat aaagcacctt gaaaagact tggcagcttc ctgataaagc gtgctgtgct | 1380 |
| gtgcagtagg aacacatcct atttattgtg atgttgtggt tttattatct aaactctgt | 1440 |
| tccatacact tgtataaata catggatatt tttatgtaca aagtatgtc tcttaaccag | 1500 |
| ttcacttatt gtactctggc aatttaaaag aaaatcagta aaatattttg cttgtaaaat | 1560 |
| gcttaatatc gtgcctaggt tatgtggtga ctatttgaat caaaatgta ttgaatcatc | 1620 |
| aaataaaaga atgtggctat tttggggaga aaattatgtg tgtgtgtgct caagatttat | 1680 |
| ttcttggact ctgagaaaat gaaagataaa | 1710 |

```
<210> SEQ ID NO 129
<211> LENGTH: 2668
<212> TYPE: DNA
<213> ORGANISM: Homo sapiens

<400> SEQUENCE: 129
```

| | |
|---|---:|
| gaattcgccc ttttgtttaa accttgggaa ctggttcagg tccaggtttt gctttgatcc | 60 |
| ttttcaaaaa ctggagacac agaagagggc tctaggaaaa agttttggat gggattatgt | 120 |
| ggaaactacc ctgcgattct ctgctgccag agcaggctcg gcgcttccac cccagtgcag | 180 |
| ccttcccctg gcggtggtga aagagactcg ggagtcgctg cttccaaagt gcccgccgtg | 240 |
| agtgagctct cacccagtc agccaaatga gcctcttcgg gcttctcctg ctgacatctg | 300 |
| ccctggccgg ccagagacag gggactcagg cggaatccaa cctgagtagt aaattccagt | 360 |
| tttccagcaa caaggaacag aacggagtac aagatcctca gcatgagaga attattactg | 420 |
| tgtctactaa tggaagtatt cacagcccaa ggtttcctca tacttatcca agaaatacgg | 480 |
| tcttggtatg gagattagta gcagtagagg aaaatgtatg gatacaactt acgtttgatg | 540 |
| aaagatttgg gcttgaagac ccagaagatg acatatgcaa gtatgatttt gtagaagttg | 600 |
| aggaacccag tgatggaact atattagggc gctggtgtgg ttctggtact gtaccaggaa | 660 |
| aacagatttc taaggaaat caaattagga taagatttgt atctgatgaa tattttcctt | 720 |
| ctgaaccagg gttctgcatc cactacaaca ttgtcatgcc acaattcaca gaagctgtga | 780 |
| gtccttcagt gctaccccct tcagctttgc cactggacct gcttaataat gctataactg | 840 |
| cctttagtac cttggaagac cttattcgat atcttgaacc agagagatgg cagttggact | 900 |
| tagaagatct atataggcca acttggcaac ttcctggcaa ggcttttgtt tttgaagaa | 960 |
| aatccagagt ggtggatctg aaccttctaa cagaggaggt aagattatac agctgcacac | 1020 |
| ctcgtaactt ctcagtgtcc ataagggaag aactaaagag aaccgatacc attttctggc | 1080 |
| caggttgtct cctggttaaa cgctgtggtg ggaactgtgc ctgttgtctc cacaattgca | 1140 |
| atgaatgtca atgtgtccca agcaaagtta ctaaaaaata ccacgaggtc cttcagttga | 1200 |
| gaccaaagac cggtgtcagg ggattgcaca aatcactcac cgacgtggcc ctggagcacc | 1260 |
| atgaggagtg tgactgtgtg tgcagaggga gcacaggagg atagccgcat caccaccagc | 1320 |
| agctcttgcc cagagctgtg cagtgcagtg gctgattcta ttagagaacg tatgcgttat | 1380 |

```
ctccatcctt aatctcagtt gtttgcttca aggacctttc atcttcagga tttacagtgc    1440
attctgaaag aggagacatc aaacagaatt aggagttgtg caacagctct tttgagagga    1500
ggcctaaagg acaggagaaa aggtcttcaa tcgtggaaag aaaattaaat gttgtattaa    1560
atagatcacc agctagtttc agagttacca tgtacgtatt ccactagctg ggttctgtat    1620
ttcagttctt tcgatacggc ttagggtaat gtcagtacag gaaaaaaact gtgcaagtga    1680
gcacctgatt ccgttgcctt gcttaactct aaagctccat gtcctgggcc taaaatcgta    1740
taaaatctgg attttttttt tttttttttg ctcatattca catatgtaaa ccagaacatt    1800
ctatgtacta caaacctggt ttttaaaaag gaactatgtt gctatgaatt aaacttgtgt    1860
catgctgata ggacagactg gattttcat atttcttatt aaaatttctg ccatttagaa    1920
gaagagaact acattcatgg tttggaagag ataaacctga aagaagagt ggcttatct    1980 tcactttatc gataagtcag tttatttgtt tcattgtgta cattttata ttctcctttt    2040 gacattataa ctgttggctt ttctaatctt gttaaatata tctatttta ccaaaggtat    2100 ttaatattct tttttatgac aacttagatc aactattttt agcttggtaa attttctaa    2160 acacaattgt tatagccaga ggaacaaaga tgatataaaa tattgttgct ctgacaaaaa    2220
tacatgtatt tcattctcgt atggtgctag agttagatta atctgcattt taaaaaactg    2280
aattggaata gaattggtaa gttgcaaaga cttttgaaa ataattaaat tatcatatct    2340
tccattcctg ttattggaga tgaaaataaa aagcaactta tgaaagtaga cattcagatc    2400
cagccattac taacctattc ctttttggg gaaatctgag cctagctcag aaaaacataa    2460
agcaccttga aaaagacttg gcagcttcct gataaagcgt gctgtgctgt gcagtaggaa    2520
cacatcctat ttattgtgat gttgtggttt tattatctta aactctgttc catacacttg    2580
tataaataca tggatatttt tatgtacaga agtatgtctc ttaaccagtt cacttattgt    2640
acctggaagg gcgaattctg cagatatc                                       2668
```

<210> SEQ ID NO 130
<211> LENGTH: 345
<212> TYPE: PRT
<213> ORGANISM: Homo sapiens

<400> SEQUENCE: 130

Met Ser Leu Phe Gly Leu Leu Leu Thr Ser Ala Leu Ala Gly Gln
1               5                   10                  15

Arg Gln Gly Thr Gln Ala Glu Ser Asn Leu Ser Ser Lys Phe Gln Phe
                20                  25                  30

Ser Ser Asn Lys Glu Gln Asn Gly Val Gln Asp Pro Gln His Glu Arg
            35                  40                  45

Ile Ile Thr Val Ser Thr Asn Gly Ser Ile His Ser Pro Arg Phe Pro
        50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
    130                 135                 140

```
                              -continued

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
        275                 280                 285

His Asn Cys Asn Glu Cys Gln Cys Val Pro Ser Lys Val Thr Lys Lys
    290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
            340             345
```

VASCULAR ENDOTHELIAL GROWTH FACTOR-X

RELATED APPLICATIONS

This application is a divisional of application Ser. No. 09/468,647 filed Dec. 21, 1999, now U.S. Pat. No. 6,783,953 which claims priority under 35 U.S.C. § 119(e) from U.S. provisional application Ser. No. 60/124,967, filed Mar. 18, 1999, and from U.S. provisional application Ser. No. 60/164,131, filed Nov. 8, 1999.

The present invention is concerned with a novel vascular endothelial growth factor (VEGF) herein designated "VEGF-X", and characterisation of the nucleic acid and amino acid sequences of VEGF-X.

INTRODUCTION

Angiogenesis involves formation and proliferation of new blood vessels, and is an essential physiological process for normal growth and development of tissues in, for example, embryonic development, tissue regeneration and organ and tissue repair. Angiogenesis also features in the growth of human cancers which require continuous stimulation of blood vessel growth. Abnormal angiogenesis is associated with other diseases such as rheumatoid arthritis psoriasis and diabetic retinopathy.

Capillary vessels consist of endothelial cells which carry the genetic information necessary to proliferate to form capillary networks. Angiogenic molecules which can initiate this process have previously been characterised. A highly selective mitogen for vascular enothelial cells is vascular endothelial growth factor (VEGF) (Ferrara et al., "Vascular Endothelial Growth Factor: Basic Biology and Clinical Implications". Regulation of angiogenesis, by I. D. Goldberg and E. M. Rosen 1997 Birkhauser Verlag Basle/Switzerland). VEGF is a potent vasoactive protein which is comprised of a glycosylated cationic 46–49 kd dimer having two 24 kd subunits. It is inactivated by sulfhydryl reducing agents and is resistant to acidic pH and to heating and binds to immobilised heparin.

VEGF-A has four different forms of 121, 165, 189 and 206 amino acids respectively due to alternative splicing. VEGF121 and VEGF165 are soluble and are capable of promoting angiogenesis, whereas VEGF189 and VEGF206 are bound to heparin containing proteoglycans in the cell surface. The temporal and spatial expression of VEGF has been correlated with physiological proliferation of the blood vessels (Gajdusek, C. M., and Carbon, S. J., Cell Physiol., 139: 570–579, (1989)); McNeil, P. L., Muthukrishnan, L., Warder, E., D'Amore, P. A., J. Cell. Biol., 109: 811–822, (1989)). Its high affinity binding sites are localized only on endothelial cells in tissue sections (Jakeman, L. B., et al., Clin. Invest. 89: 244–253 (1989)). The growth factor can be isolated from pituitary cells and several tumor cell lines, and has been implicated in some human gliomas (Plate, K. H. Nature. 359: 845–848, (1992)). The inhibition of VEGF function by anti-VEGF monoclonal antibodies was shown to inhibit tumor growth in immune-deficient mice (Kim, K. J., Nature 362: 841–844, (1993)).

VEGF proteins have been described in the following patents and application all of which are hereby incorporated by reference EP-0,506,477, WO-95/24473, WO-98/28621, WO-90/13649, EP-0,476,983, EP-0,550,296, WO-90/13649, WO-96/26736, WO-96/27007, WO-98/49300, WO-98/36075, WO-96/27007, WO-98/49300, WO-98/10071, WO-98/07832, WO-98/02543, WO-97/05250, WO-91/02058, WO-96/39421, WO-96/39515, WO-98/16551.

The present inventors have now identified a further vascular endothelial growth factor, designated herein as "VEGF-X", and the nucleic acid sequence encoding it, which has potentially significant benefits for the treatment of tumours and other conditions mediated by inappropriate angiogenic activity.

SUMMARY OF THE INVENTION

In the present application, there is provided a novel vascular endothelial growth factor, herein designated "VEGF-X", nucleic acid molecules encoding said growth factor, an expression vector comprising said nucleic acid molecule, a host cell transformed with said vector and compounds which inhibit or enhance angiogenesis. Also provided is the sequence of a CUB domain present in the sequence of VEGF-X which domain itself prevents angiogenesis and which is used to treat diseases associated with inappropriate vascularisation or angiogenesis.

DETAILED DESCRIPTION OF THE INVENTION

Therefore, according to a first aspect of the present invention there is provided a nucleic acid molecule encoding a VEGF-X protein or a functional equivalent, fragment, derivative or bioprecursor thereof, said protein comprising the amino acid sequence from position 23 to 345 of the amino acid sequence illustrated in FIG. 10. Alternatively, the nucleic acid molecule of the invention encodes the complete sequence identified in FIG. 10 and which advantageously includes a signal peptide to express said protein extracellularly. Preferably, the nucleic acid molecule is a DNA and even more preferably a cDNA molecule. Preferably, the nucleic acid molecule comprises the nucleotide sequence from position 257 to 1291 of the nucleotide sequence illustrated in FIG. 9. In a preferred embodiment the nucleic acid is of mammalian origin and even more preferably of human origin.

In accordance with the present invention a functional equivalent should be taken to mean a protein, or a sequence of amino acids that have similar function to the VEGF-X protein of the invention.

Also provided by this aspect of the present invention is a nucleic acid molecule such as an antisense molecule capable of hybridising to the nucleic acid molecules according to the invention under high stringency conditions, which conditions would be well known to those skilled in the art.

Stringency of hybridisation as used herein refers to conditions under which polynucleic acids are stable. The stability of hybrids is reflected in the melting temperature (Tm) of the hybrids. Tm can be approximated by the formula:

$$81.5^\circ C. + 16.6(\log_{10}[Na^+] + 0.41(\% \ G\&C) - 600/l$$

wherein l is the length of the hybrids in nucleotides.

Tm decreases approximately by 1–1.5° C. with every 1% decrease in sequence homology.

The term "stringency" refers to the hybridisation conditions wherein a single-stranded nucleic acid joins with a complementary strand when the purine or pyrimidine bases therein pair with their corresponding base by hydrogen bonding. High stringency conditions favour homologous base pairing whereas low stringency conditions favour non-homologous base pairing.

"Low stringency" conditions comprise, for example, a temperature of about 37° C. or less, a formamide concentration of less than about 50%, and a moderate to low salt (SSC) concentration; or, alternatively, a temperature of about 50° C. or less, and a moderate to high salt (SSPE) concentration, for example 1M NaCl.

"High stringency" conditions comprise, for example, a temperature of about 42° C. or less, a formamide concentration of less than about 20%, and a low salt (SSC) concentration; or, alternatively, a temperature of about 65° C., or less, and a low salt (SSPE) concentration. For example, high stringency conditions comprise hybridization in 0.5 M NaHPO$_4$, 7% sodium dodecyl sulfate (SDS), 1 mM EDTA at 65° C. (Ausubel, F. M. et al. *Current Protocols in Molecular Biology*, Vol. I, 1989; Green Inc. New York, at 2.10.3).

"SSC" comprises a hybridization and wash solution. A stock 20×SSC solution contains 3M sodium chloride, 0.3M sodium citrate, pH 7.0.

"SSPE" comprises a hybridization and wash solution. A 1×SSPE solution contains 180 mM NaCl, 9 mM Na$_2$HPO$_4$ and 1 mM EDTA, pH 7.4.

The nucleic acid capable of hybridising to nucleic acid molecules according to the invention will generally be at least 70%, preferably at least 80 or 90% and more preferably at least 95% homologous to the nucleotide sequences according to the invention.

The antisense molecule capable of hybridising to the nucleic acid according to the invention may be used as a probe or as a medicament or may be included in a pharmaceutical composition with a pharmaceutically acceptable carrier, diluent or excipient therefor.

The term "homologous" describes the relationship between different nucleic acid molecules or amino acid sequences wherein said sequences or molecules are related by partial identity or similarity at one or more blocks or regions within said molecules or sequences.

The present invention also comprises within its scope proteins or polypeptides encoded by the nucleic acid molecules according to the invention or a functional equivalent, derivative or bioprecursor thereof.

Therefore, according to a further aspect of the present invention, there is provided a VEGF-X protein, or a functional equivalent, derivative or bioprecusor thereof, comprising an amino acid sequence from position 23 to 345 of the sequence as illustrated in FIG. 10, or alternatively which amino acid sequence comprises the complete sequence of FIG. 10. A further aspect of the invention comprises a VEGF-X protein, or a functional equivalent, derivative or bioprecusor thereof, encoded by a nucleic acid molecule according to the invention. Preferably, the VEGF-X protein encoded by said nucleic acid molecule comprises the sequence from position 23 to 345 of the amino acid sequence as illustrated in FIG. 10, or which sequence alternatively comprises the sequence of amino acids of FIG. 10.

The DNA molecules according to the invention may, advantageously, be included in a suitable expression vector to express VEGF-X encoded therefrom in a suitable host. Incorporation of cloned DNA into a suitable expression vector for subsequent transformation of said cell and subsequent selection of the transformed cells is well known to those skilled in the art as provided in Sambrook et al. (1989), molecular cloning, a laboratory manual, Cold Spring Harbour Laboratory Press.

An expression vector according to the invention includes a vector having a nucleic acid according to the invention operably linked to regulatory sequences, such as promoter regions, that are capable of effecting expression of said DNA fragments. The term "operably linked" refers to a juxta position wherein the components described are in a relationship permitting them to function in their intended manner. Such vectors may be transformed into a suitable host cell to provide for expression of a polypeptide according to the invention. Thus, in a further aspect, the invention provides a process for preparing polypeptides according to the invention which comprises cultivating a host cell, transformed or transfected with an expression vector as described above under conditions to provide for expression by the vector of a coding sequence encoding the polypeptides, and recovering the expressed polypeptides.

The vectors may be, for example, plasmid, virus or phage vectors provided with an origin of replication, and optionally a promoter for the expression of said nucleotide and optionally a regulator of the promoter.

The vectors may contain one or more selectable markers, such as, for example, ampicillin resistance.

Regulatory elements required for expression include promoter sequences to bind RNA polymerase and transcription initiation sequences for ribosome binding. For example, a bacterial expression vector may include a promoter such as the lac promoter and for translation initiation the Shine-Dalgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art.

Nucleic acid molecules according to the invention may be inserted into the vectors described in an antisense orientation in order to provide for the production of antisense RNA. Antisense RNA or other antisense nucleic acids may be produced by synthetic means.

In accordance with the present invention, a defined nucleic acid includes not only the identical nucleic acid but also any minor base variations including in particular, substitutions in cases which result in a synonymous codon (a different codon specifying the same amino acid residue) due to the degenerate code in conservative amino acid substitutions. The term "nucleic acid sequence" also includes the complementary sequence to any single stranded sequence given regarding base variations.

The present invention also advantageously provides nucleic acid sequences of at least approximately 10 contiguous nucleotides of a nucleic acid according to the invention and preferably from 10 to 50 nucleotides even more preferably, the nucleic acid sequence comprise the sequences illustrated in FIG. 3. These sequences may, advantageously be used as probes or primers to initiate replication, or the like. Such nucleic acid sequences may be produced according to techniques well known in the art, such as by recombinant or synthetic means. They may also be used in diagnostic kits or the like for detecting the presence of a nucleic acid according to the invention. These tests generally comprise contacting the probe with the sample under hybridising conditions and detecting for the presence of any duplex or triplex formation between the probe and any nucleic acid in the sample.

The nucleic acid sequences according to this aspect of the present invention comprise the sequences of nucleotides illustrated in FIGS. 3 and 5.

According to the present invention these probes may be anchored to a solid support. Preferably, they are present on an array so that multiple probes can simultaneously hybridize to a single biological sample. The probes can be spotted onto the array or synthesised in situ on the array. (See Lockhart et al., Nature Biotechnology, vol. 14, December 1996 "Expression monitoring by hybridisation to high density oligonucleotide arrays". A single array can contain more than 100, 500 or even 1,000 different probes in discrete locations.

The nucleic acid sequences, according to the invention may be produced using such recombinant or synthetic means, such as for example using PCR cloning mechanisms which generally involve making a pair of primers, which may be from approximately 10 to 50 nucleotides to a region of the gene which is desired to be cloned, bringing the primers into contact with mRNA, cDNA, or genomic DNA from a human cell, performing a polymerase chain reaction under conditions which brings about amplification of the desired region, isolating the amplified region or fragment and recovering the amplified DNA. Generally, such techniques are well known in the art, such as described in Sambrook et al. (Molecular Cloning: a Laboratory Manual, 1989).

The nucleic acids or oligonucleotides according to the invention may carry a revealing label. Suitable labels include radioisotopes such as $^{32}$P or $^{35}$S, enzyme labels or other protein labels such as biotin or fluorescent markers. Such labels may be added to the nucleic acids or oligonucleotides of the invention and may be detected using known techniques per se.

Advantageously, human allelic variants or polymorphisms of the DNA molecule according to the invention may be identified by, for example, probing cDNA or genomic libraries from a range of individuals, for example, from different populations. Furthermore, nucleic acids and probes according to the invention may be used to sequence genomic DNA from patients using techniques well known in the art, such as the Sanger Dideoxy chain termination method, which may, advantageously, ascertain any predisposition of a patient to certain disorders associated with a growth factor according to the invention.

The protein according to the invention includes all possible amino acid variants encoded by the nucleic acid molecule according to the invention including a polypeptide encoded by said molecule and having conservative amino acid changes. Conservative amino acid substitution refers to a replacement of one or more amino acids in a protein as identified in Table 1. Proteins or polypeptides according to the invention further include variants of such sequences, including naturally occurring allelic variants which are substantially homologous to said proteins or polypeptides. In this context, substantial homology is regarded as a sequence which has at least 70%, preferably 80 or 90% and preferably 95% amino acid homology with the proteins or polypeptides encoded by the nucleic acid molecules according to the invention. The protein according to the invention may be recombinant, synthetic or naturally occurring, but is preferably recombinant.

The nucleic acid or protein according to the invention may be used as a medicament or in the preparation of a medicament for treating cancer or other diseases or conditions associated with expression of VEGF-X protein.

Advantageously, the nucleic acid molecule or the protein according to the invention may be provided in a pharmaceutical composition together with a pharmacologically acceptable carrier, diluent or excipient therefor.

The present invention is further directed to inhibiting VEGF-X in vivo by the use of antisense technology. Antisense technology can be used to control gene expression through triple-helix formation of antisense DNA or RNA, both of which methods are based on binding of a polynucleotide to DNA or RNA. For example, the 5' coding portion or the mature DNA sequence, which encodes for the protein of the present invention, is used to design an antisense RNA oligonucleotide of from 10 to 50 base pairs in length. A DNA oligonucleotide is designed to be complementary to a region of the gene involved in transcription (triple-helix—see Lee et al. Nucl. Acids Res., 6: 3073 (1979); Cooney et al., Science, 241: 456 (1988); and Dervan et al., Science, 251: 1360 (1991), thereby preventing transcription and the production of VEGF-X. The antisense RNA oligonucleotide hebridises to the mRNA in vivo and blocks translation of an mRNA molecule into the VEGF-X protein (antisense— Okano, J. Neurochem., 56: 560 (1991); Oligodeoxynucleotides as Antisense Inhibitors of Gene Expression, CRC Press, Boca Raton, Fla. (1988)).

Alternatively, the oligonucleotide described above can be delivered to cells by procedures in the art such that the anti-sense RNA and DNA may be expressed in vivo to inhibit production of VEGF-X in the manner described above.

Antisense constructs to VEGF-X, therefore, may inhibit the angiogenic activity of VEGF-X and prevent the further growth of or even regress solid tumours, since angiogenesis and neovascularization are essential steps in solid tumour growth. These antisense constructs may also be used to treat rheumatoid arthritis, psoriasis and diabetic retinopathy which are all characterized by abnormal angiogenesis.

A further aspect of the invention provides a host cell or organism, transformed or transfected with an expression vector according to the invention. The host cell or organism may advantageously be used in a method of producing VEGF-X, which comprises recovering any expressed VEGF-X from the host or organism transformed or transfected with the expression vector.

According to a further aspect of the invention there is also provided a transgenic cell, tissue or organism comprising a transgene capable of expressing VEGF-X protein according to the invention. The term "transgene capable of expression" as used herein means a suitable nucleic acid sequence which leads to expression of VEGF-X or proteins having the same function and/or activity. The transgene, may include, for example, genomic nucleic acid isolated from human cells or synthetic nucleic acid, including DNA integrated into the genome or in an extrachromosomal state. Preferably, the transgene comprises the nucleic acid sequence encoding the proteins according to the invention as described herein, or a functional fragment of said nucleic acid. A functional fragment of said nucleic acid should be taken to mean a fragment of the gene comprising said nucleic acid coding for the proteins according to the invention or a functional equivalent, derivative or a non-functional derivative such as a dominant negative mutant, or bioprecursor of said proteins. For example, it would be readily apparent to persons skilled in the art that nucleotide substitutions or deletions may be used using routine techniques, which do not affect the protein sequence encoded by said nucleic acid, or which encode a functional protein according to the invention.

VEGF-X protein expressed by said transgenic cell, tissue or organism or a functional equivalent or bioprecursor of said protein also forms part of the present invention.

Antibodies to the protein or polypeptide of the present invention may, advantageously, be prepared by techniques which are known in the art. For example, polyclonal antibodies may be prepared by inoculating a host animal, such as a mouse or rabbit, with the polypeptide according to the invention or an epitope thereof and recovering immune serum. Monoclonal antibodies may be prepared according to known techniques such as described by Kohler R. and Milstein C., Nature (1975) 256, 495–497. Advantageously, such antibodies may be included in a kit for identifying VEGF-X in a sample, together with means for contacting the antibody with the sample.

Advantageously, the antibody according to the invention may also be used as a medicament or in the preparation of a medicament for treating tumours or other diseases associated with expression of VEGF-X.

The invention also further provides a pharmaceutical composition comprising said antibody together with a pharmaceutically acceptable carrier diluent or excipient therefor.

Proteins which interact with the polypeptide of the invention may be identified by investigating protein-interactions using the two-hybrid vector system first proposed by Chien et al., (1991) Proc. Natl. Acad. Sci. USA 88: 9578–9582.

This technique is based on functional reconstitution in vivo of a transcription factor which activates a reporter gene. More particularly the technique comprises providing an appropriate host cell with a DNA construct comprising a reporter gene under the control of a promoter regulated by a transcription factor having a DNA binding domain and an activating domain, expressing in the host cell a first hybrid DNA sequence encoding a first fusion of a fragment or all of a nucleic acid sequence according to the invention and either said DNA binding domain or said activating domain of the transcription factor, expressing in the host at least one second hybrid DNA sequence, such as a library or the like, encoding putative binding proteins to be investigated together with the DNA binding or activating domain of the transcription factor which is not incorporated in the first fusion; detecting any binding of the proteins to be investigated with a protein according to the invention by detecting for the presence of any reporter gene product in the host cell; optionally isolating second hybrid DNA sequences encoding the binding protein.

An example of such a technique utilises the GAL4 protein in yeast. GAL4 is a transcriptional activator of galactose metabolism in yeast and has a separate domain for binding to activators upstream of the galactose metabolising genes as well as a protein binding domain. Nucleotide vectors may be constructed, one of which comprises the nucleotide residues encoding the DNA binding domain of GAL4. These binding domain residues may be fused to a known protein encoding sequence, such as for example, the nucleic acids according to the invention. The other vector comprises the residues encoding the protein binding domain of GAL4. These residues are fused to residues encoding a test protein. Any interaction between polypeptides encoded by the nucleic acid according to the invention and the protein to be tested leads to transcriptional activation of a reporter molecule in a GAL-4 transcription deficient yeast cell into which the vectors have been transformed. Preferably, a reporter molecule such as β-galactosidase is activated upon restoration of transcription of the yeast galactose metabolism genes.

A further aspect of the present invention also provides a method of identifying VEGF-X in a sample, which method comprises contacting said sample with an antibody according to the invention and monitoring for any binding of any proteins to said antibody. A kit for identifying the presence of VEGF-X in a sample is also provided comprising an antibody according to the invention and means for contacting said antibody with said sample.

VEGF-X may be recovered and purified from recombinant cell cultures by methods known in the art, including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography.

The VEGF-X protein of the present invention may be a naturally purified product, or a product of chemical synthetic procedures, or produced by recombinant techniques from a prokaryotic or eukaryotic host (for example, by bacterial yeast, higher plant, insect and mammalian cells in culture). Depending upon the host employed in a recombinant production procedure, the polypeptides of the present invention may be glycosylated with mammalian or other eukaryotic carbohydrates or may be non-glycosylated.

VEGF-X is particularly advantageous as a wound healing agent, where, for example, it is necessary to re-vascularize damaged tissues, or where new capillary angiogenesis is important. Accordingly, VEGF-X may be used for treatment of various types of wounds such as for example, dermal ulcers, including pressure sores, venous ulcers, and diabetic ulcers. In addition, it can be used in the treatment of full-thickness burns and injuries where angiogenesis is desired to prepare the burn in injured sites for a skin graft and flap. In this case, VEGF-X or the nucleic acid encoding it may be applied directly to the wound. VEGF-X may be used in plastic surgery when reconstruction is required following a burn, other trauma, or even for cosmetic purposes.

An important application of VEGF-X is to induce the growth of damaged bone, periodontium or ligament tissue. For example, it may be used in periodontal disease where VEGF-X is applied to the roots of the diseased teeth, leading to the formation of new bore and cementum with collagen fibre ingrowths. It can be used for regenerating supporting tissues of teeth, including alveolar bone, cementum and periodontal ligament, that have been damaged by disease and trauma.

Since angiogenesis is important in keeping wounds clean and non-infected, VEGF-X may be used in association with surgery and following the repair of cuts. It should be particularly useful in the treatment of abdominal wounds where there is a high risk of infection.

VEGF-X can also be used for the promotion of endothelialization in vascular graft surgery. In the case of vascular grafts using either transplanted or synthetic material, VEGF-X may be applied to the surface of the graft or at the junction to promote the growth of the vascular endothelial cells. One derivation of this is that VEGF-X can be used to repair the damage of myocardial and other occasions where coronary bypass surgery is needed by stimulating the growth of the transplanted tissue. Related to this is the use of VEGFX to repair the cardiac vascular system after ischemia.

The protein of the present invention may also be employed in accordance with the present invention by expression of such protein in vivo, which is often referred to as "gene therapy".

Thus, for example, cells such as bone marrow cells may be engineered with a polynucleotide (DNA or RNA) encoding for the protein ex vivo as defined herein, the engineered cells are then provided to a patient to be treated with the polypeptide. Such methods are well-known in the art. For example, cells may be engineered by procedures known in the art by use of a retroviral particle containing RNA encoding for the protein of the present invention.

Similarly, cells may be engineered in vivo for expression of the protein in vivo, for example, by procedures known in the art.

A further aspect of the invention comprises a method of treating a disorder mediated by expression of a protein according to the invention, by administering to a patient an amount of an antisense molecule as described herein, in sufficient concentration to alleviate or reduce the symptoms of said disorder.

Compounds which inhibit or enhance angiogenesis may be identified by providing a host cell or organism according to the invention or a transgenic cell, tissue or organism according to the invention, contacting a test compound with said cell, tissue or organism and monitoring for the effect of said compound compared to a cell tissue or organism which has not been contacted with said compound. These compounds may themselves be used as a medicament or included in a pharmaceutical composition for treatment of disorders mediated by inappropriate vascularisation or angiogenic activity.

The present inventors have also, advantageously, identified in the sequence encoding the VEGF-X protein a CUB domain, which has heretofore not previously been identified in VEGF-type growth factors. The VEGF-X protein may therefore exert dual regulatory effects via interaction with the VEGF tyrosine kinase receptors or with neuropilin receptors mediated by the CUB domain. Thus, the sequence encoding said CUB domain may be included in an expression vector for subsequent transformation of a host cell, tissue or organism.

VEGF-X or fragments thereof may be able to modulate the effects of pro-angiogenic growth factors such as VEGF as indicated in the findings presented in the examples below that the N-terminal part of the VEGF-X protein, a CUB-like domain, is able to inhibit VEGF-stimulated proliferation of HUVECs. VEGF-X or fragments thereof may therefore be useful in therapy of conditions involving inappropriate angiogenesis. Inhibition of the angiogenic activity of VEGF has been linked with inhibition of tumour growth in several models eg Kim K. J. et al, Nature 362: 841–844, (1993). Additionally, agents able to inhibit angiogenesis would be expected to be useful in treating other angiogenesis-dependent diseases such a retinopathy, osteoarthritis and psoriasis (Folkman, J., Nature Medicine 1: 27–31, (1995).

As identified in more detail in the Examples described herein the present inventors have surprisingly identified that the CUB domain of VEGF-X is able to inhibit stimulation of proliferation of HUVECs induced by either VEGF or bFGF. The CUB domain may, therefore, be utilised as a therapuetic agent for inhibition of angiogenesis and for treatment of condition associated with inappropriate vascularisation or angiogenesis.

Therefore according to a further aspect of the invention there is provided a method of inhibiting angiogenic activity and inappropriate vascularisation including formation and proliferation of new blood vessels, growth and development of tissues, tissue regeneration and organ and tissue repair in a subject said method comprising administering to said subject an amount of a polypeptide having an amino acid sequence from position 40 to 150 of the sequence illustrated in FIG. 10 or a nucleic acid molecule encoding the CUB domain according to the invention in sufficient concentration to reduce or prevent said angiogenic activity.

Furthermore there is also provided a method of treating or preventing any of cancer, rheumatoid arthritis, psoriasis and diabetic retinopathy, said method comprising administering to said subject an amount of a polypeptide having an amino acid sequence from position 40 to 150 of the sequence illustrated in FIG. 10 or a nucleic acid molecule encoding the CUB domain according to the invention in sufficient concentration to treat or prevent said disorders.

The CUB domain may also be used to identify compounds that inhibit or enhance angiogenic activity such as inappropriate vascularisation, in a method comprising contacting a cell expressing a VEGF receptor and/or a neuropilin 1 or 2 type receptor with said compound in the presence of a VEGF-X protein according to the invention and monitoring for the effect of said compound or said cell when compared to a cell which has not been contacted with said compound. Such compounds may then be used as appropriate to prevent or inhibit angiogenic activity to treat the disorders or conditions described herein, or in a pharmaceutical composition. An antibody to said CUB domain may also be useful in identifying other proteins having said sequences.

| Deposited Plasmids | Date of Deposit | Accession No. |
|---|---|---|
| Plasmid VEGFX/pCR2.1 1TOPO FL | Mar. 1, 1999 | LMBP 3925 |
| Plasmid VEGFX/pRSETB BD amino acids G230-G345 | Mar. 1, 1999 | LMBP 3926 |
| Plasmid VEGFX/pcR.2.1 FL Clone 9 | Oct. 20, 1999 | LMBP 3977 |
| Plasmid VEGF-X CUB PET22b | Dec. 20, 1999 | LMBP 3991 |

The above plasmids were deposited at the Belgian Coordinated Collections of Microorganisms (BCCM) at Laboratorium Voor Moleculaire Biologie-Plasmidencollectie (LMBP) B-9000, Ghent, Belgium, in accordance with the provisions of the Budapest Treaty of 28 Apr. 1977.

The invention may be more clearly understood with reference to the accompanying example, which is purely exemplary, with reference to the accompanying drawings, wherein:

FIG. 1: is a DNA sequence (SEQ ID NO:98) identified in the Incyte LifeSeq™ database coding for a novel VEGF-X protein.

FIG. 2: is an illustration of amino acid sequence (SEQ ID NO:99) of the nucleic acid sequence of FIG. 1.

FIG. 3: is an illustration of PCT primer sequences (SEQ ID NOs:4–13) utilised to identify the VEGF-X protein according to the invention.

FIG. 4: is a diagrammatic illustration of the spatial relationships in the VEGF-X sequence of the clones identified using the PCR primer sequences of FIG. 3.

FIG. 5: is an illustration of the nucleotide sequences of the 5' RACE primers (SEQ ID NOs:14–17) used to identify the 5' end of the VEGF-X open reading frame.

FIG. 6: is an illustration of the sequence (SEQ ID NO:100 and SEQ ID NO:101) obtained from the RACE experiment.

FIG. 7: is an illustration of the nucleotide sequences (SEQ ID NO:102 AND SEQ ID NO:103) obtained from the search of LifeSeq™ database using the sequence in FIG. 6.

FIG. 8: is an illustration of the primers used to clone the entire coding sequence of VEGF-X.

FIG. 9: is an illustration of the entire coding sequence (SEQ ID NO:104) of VEGF-X.

FIG. 10: is an illustration of the predicted amino acid sequence (SEQ ID NO:2) of the nucleotide sequence of FIG. 9. SEQ ID NO:1 is amino acids 23–345 of SEQ ID NO:2.

FIG. 11: is an alignment of the sequence of FIG. 10 with the sequences of VEGF-A to D (SEQ ID NOs:105–109).

FIG. 12: is an illustration of variant sequences (SEQ ID NOs:110–112) of the VEGF-X protein according to the invention.

FIG. 13: is an illustration of the oligonucleotide primers used for *E. coli* expression of VEGF-X domains and for expression of the full length sequence of VEGF-X in a baculovirus/insect cell expression system.

FIG. 14: depicts nucleic acid sequences (SEQ ID NOS: 30–47) of 18 human EST clones obtained from a BLAST search of the LifeSeq™ database used to identify the full sequence encoding VEGF-X.

FIG. 15: depicts the nucleotide sequences (SEQ ID NOs: 48–97) of 50 human EST clones obtained from the LifeSeq™ database.

FIG. 16: is an illustration of nucleotide sequences utilised as primers to identify the nucleotide sequence encoding VEGF-X.

FIG. 17: is a nucleotide sequence (SEQ ID NO:113 and SEQ ID NO:114) coding for a partial VEGF-X protein according to the invention.

FIG. 18: is an illustration of a partial nucleotide sequence encoding (SEQ ID NO:115 and SEQ ID NO:116) VEGF-X protein according to the invention.

FIG. 19: is an illustration of a DNA (SEQ ID NO:117) and polypeptide sequence (SEQ ID NO:118) used for mammalian cell expression of VEGF-X. The predicted VEGF-X signal sequence is in lower case letters. The C-terminal V5 epitope and His6 sequences are underlined.

FIG. 20: is an illustration of a DNA (SEQ ID NO:119) and polypeptide sequence (SEQ ID NO:120) used for baculovirus/insect cell expression of VEGF-X. In the polypeptide sequence the signal sequence is shown in lower case. The N-terminal peptide tag added to the predicted mature VEGF-X sequence is underlined.

FIG. 21: is an illustration of a DNA (SEQ ID NO:121) and polypeptide sequence (SEQ ID NO:122) used for *E. coli* expression of VEGF-X. The polypeptide sequences at the N- and C- termini derived from the MBP fusion and His6 tag respectively are underlined.

FIG. 22: illustrates the disulphide-linked dimerisation of VEGF-X. Protein samples were analysed by SDS-PAGE. Prior to loading the gel, samples were heated to 95° C. for 5 minutes in sample buffer in the presence (+) or absence (−) of reducing agent. (A) samples from COS cell expression of a C-terminally V5/His6 peptide-tagged construct. The left hand panel is total conditioned medium, the right hand panel is material purified on Nickel agarose resin. Reduced monomer and putative disulphide-linked, non-reduced dimer are indicated by arrows. There appears to be proteolysis of the protein during purification. Gels were blotted onto nylon membranes and protein detected with an anti V5 monoclonal antibody. (B) Samples from *E. coli* expression of a maltose-binding protein/His6 dual fusion construct. M indicates the molecular weight markers (Benchmark, LifeTechnologies). The gel was stained with Coomassie Blue by standard procedures. The fusion protein has an apparent molecular weight of 80 kDa.

Figure 22B:
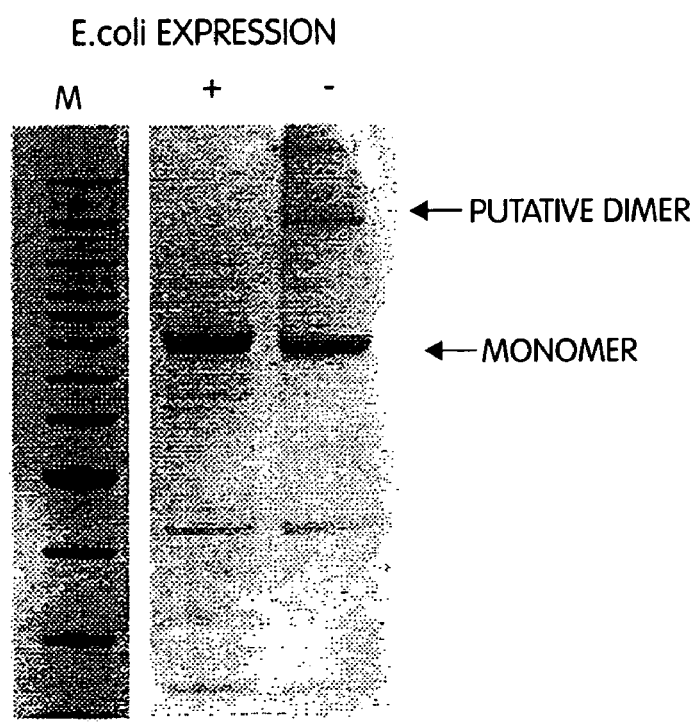
Figure 23:
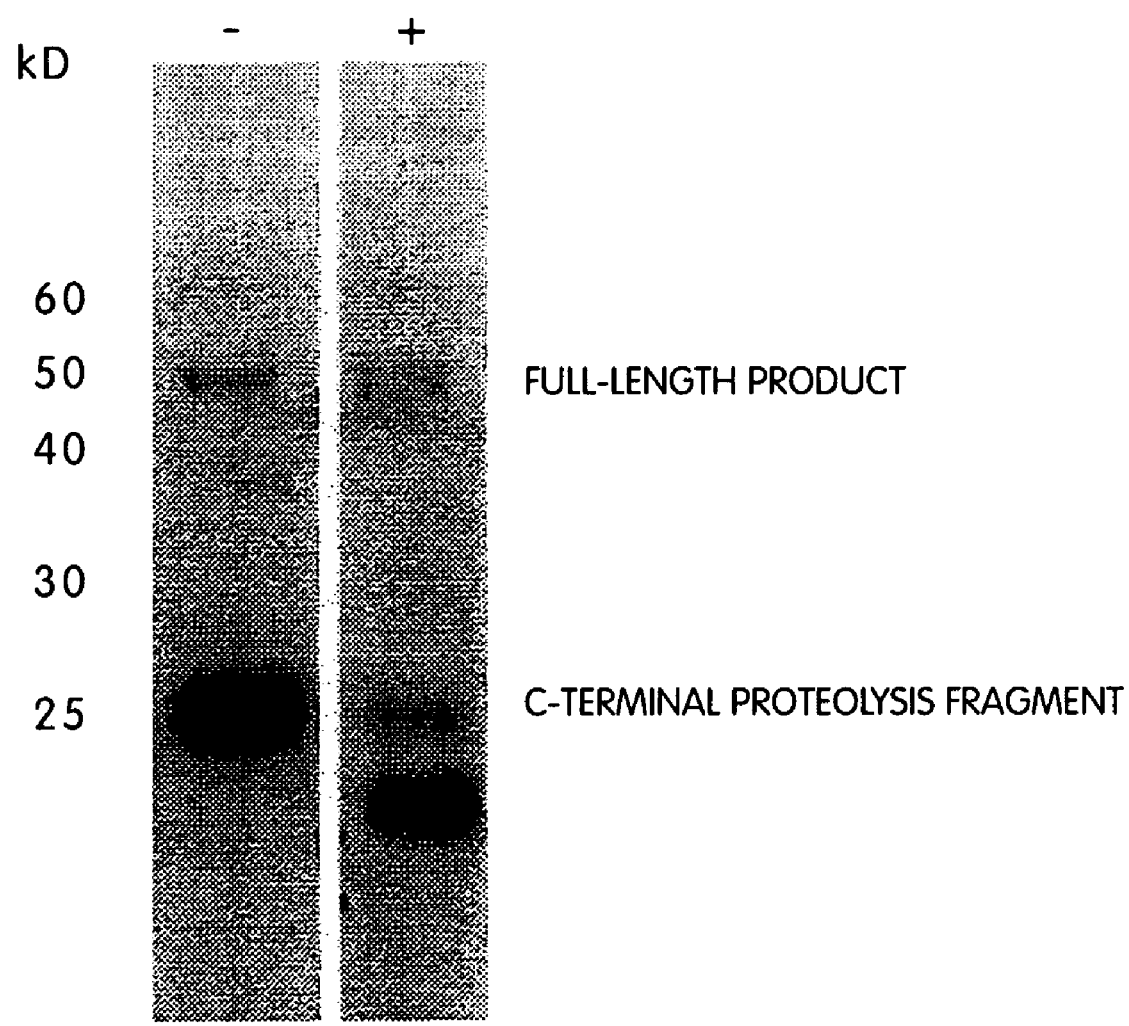

FIG. 23: illustrates the glycosylation of VEGF-X. VEGF-X was purified from the culture supernatant of COS cells transfected with the pcDNA6/V5-His construct. Supernatants were harvested 72 h post-transfection and purified on nickel resin. Samples were then treated with EndoH (+) or untreated (−) before SDS-PAGE and blotting, as described in the legend to FIG. 22.

FIG. 24: is an illustration of the DNA (SEQ ID NO:123) and polypeptide sequence (SEQ ID NO:124) used for *E. coli* expression of the VEGF-like domain of VEGF-X. Polypeptide sequences at the N-terminus of the protein derived from the vector are underlined.

Figure 25:
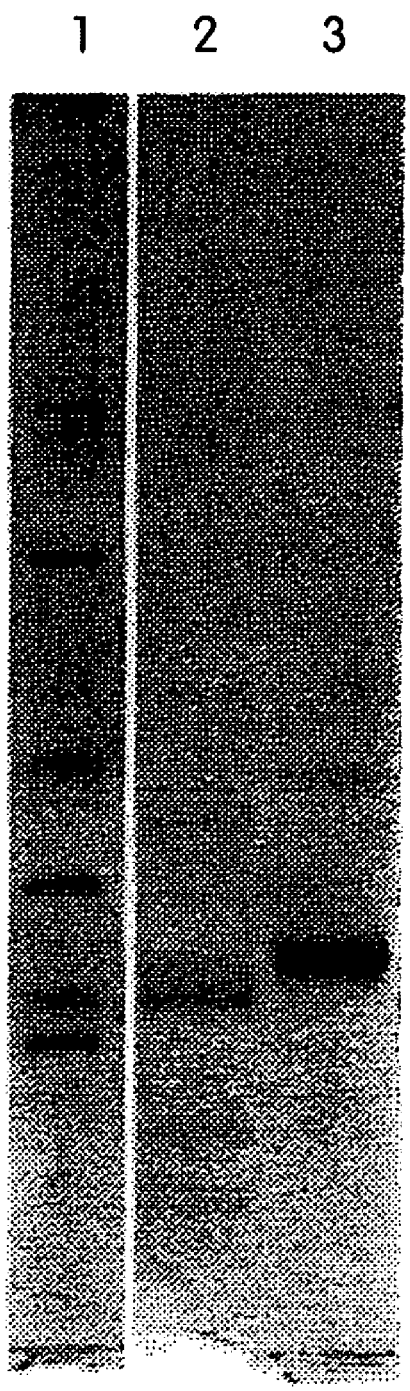

FIG. 25: shows expression of the VEGF-X VEGF domain in *E. coli*. Lane 1–10 μl broad range marker (New England Biolabs), lane 2–10 μl unreduced sample, lane 3–10 μl reduced sample. The reduced PDGF domain protein (lane 3) has an apparent molecular weight of approximately 19 kDa on SDS-PAGE.

FIG. 26: illustrates a DNA (SEQ ID NO:125) and polypeptide sequence (SEQ ID NO:126) used for *E. coli* expression of the CUB-like domain of VEGF-X. The polypeptide sequence at the N-terminus derived from the vector-encoded signal and the introduced His6 tag are underlined.

Figure 27:

FIG. 27: shows expression of the VEGF-X CUB domain in *E. coli*. The CUB domain protein was purified on Nickel chelate resin. The protein migrates at approximately 23 kDa on SDS-PAGE.

Figure 28A:
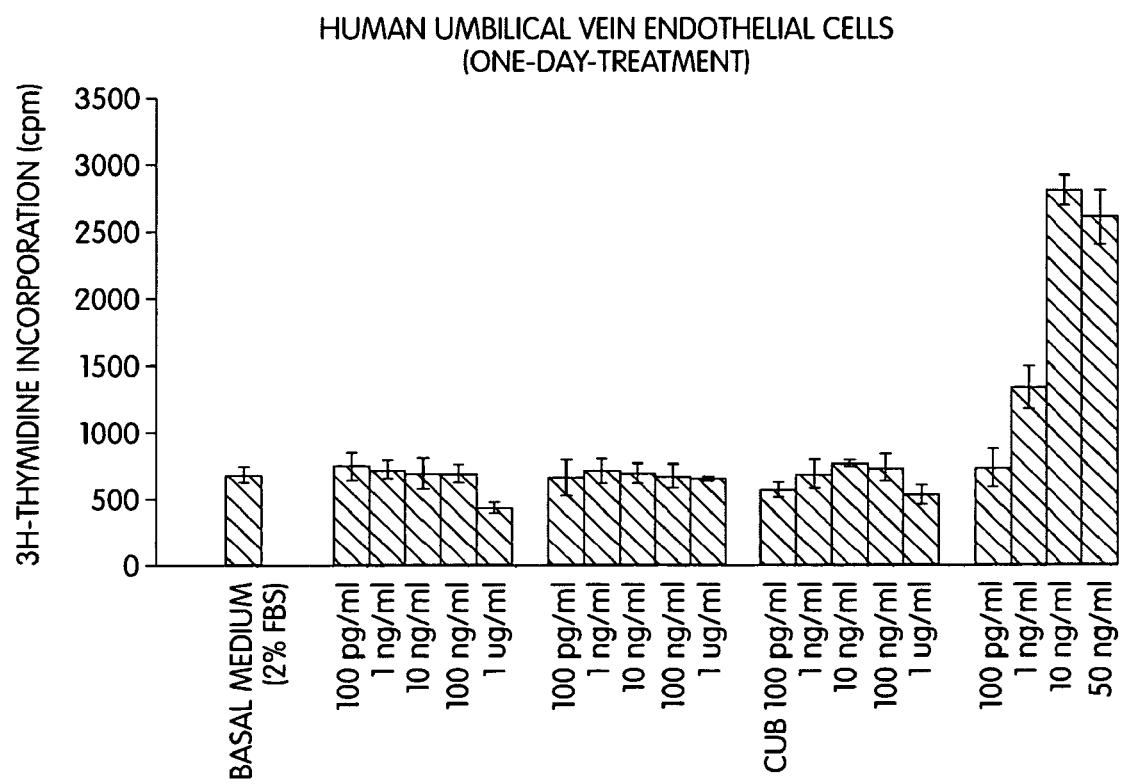
Figure 28B:
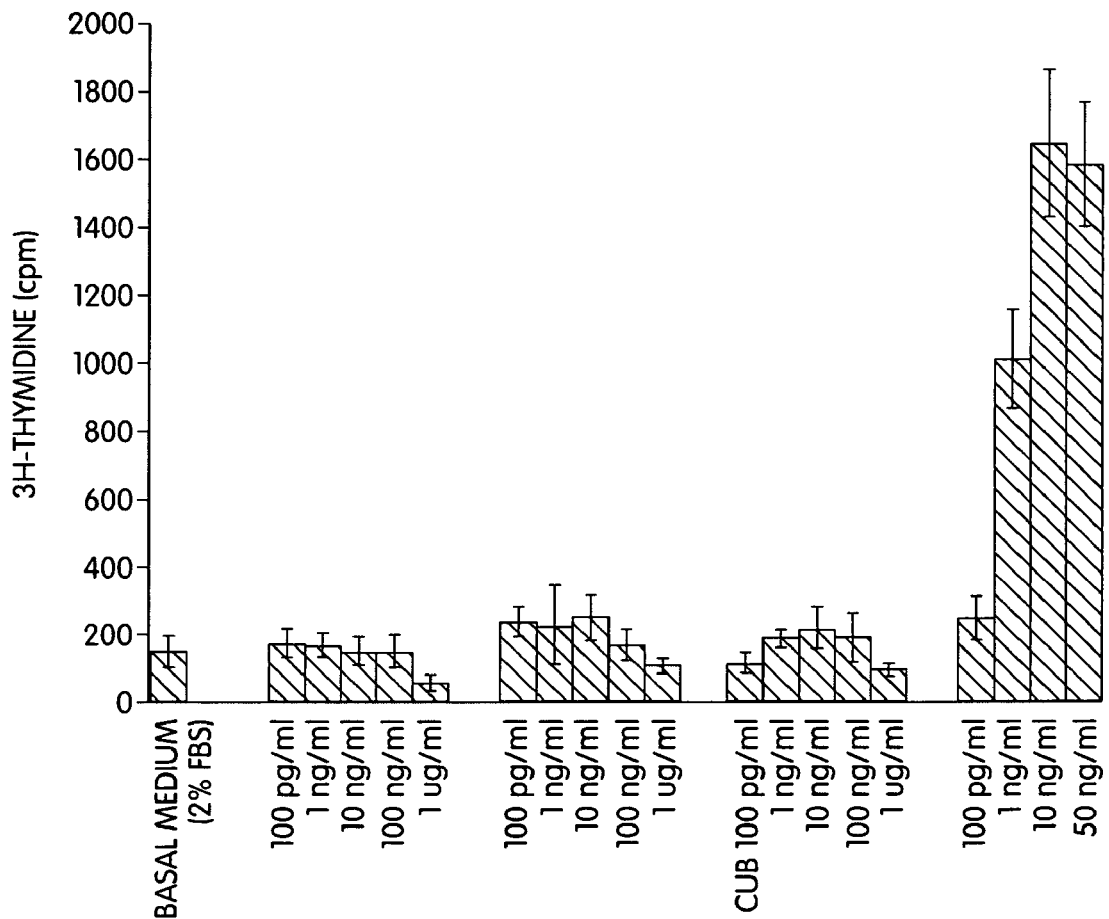
Figure 28C:
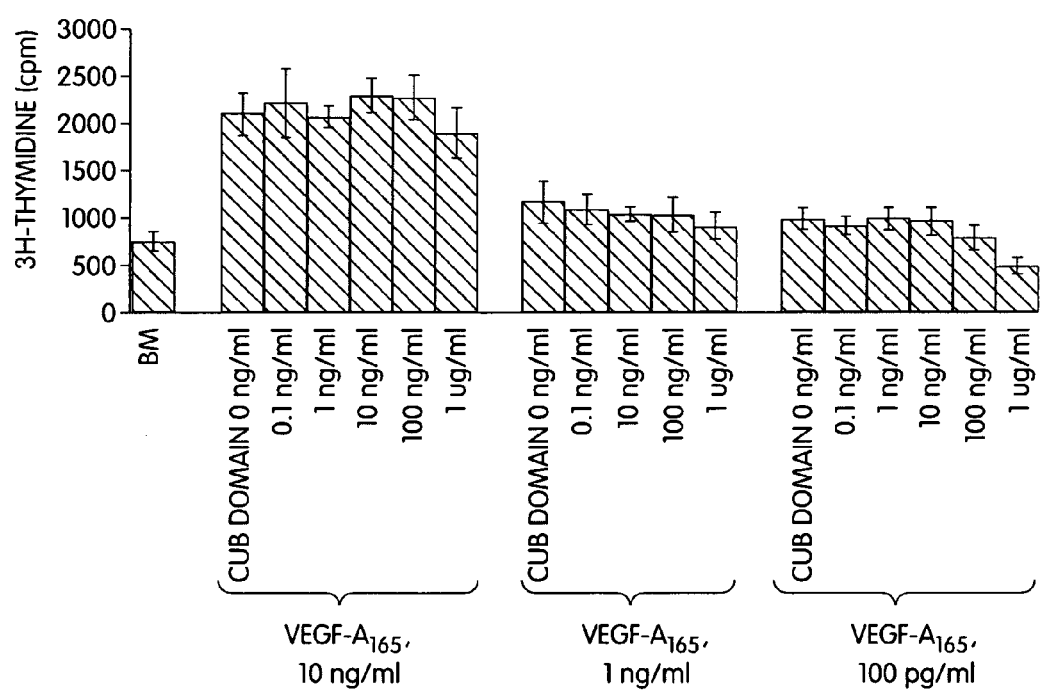

FIG. 28: illustrates the effect of truncated VEGF-X (CUB domain) on HUVEC proliferation. (A) Human Umbilical Vein Endothelial Cells (one-day-treatment). (B) Human Umbilical Vein Endothelial Cells (24-hour starving followed by one-day-treatment). (C) Effect of VEGF-$A_{165}$ and VEGF-X CUB domain on the proliferation of HUVEC (two-day-treatment).

FIG. 29: depicts the tissue distribution of VEGF-X mRNA analysed by Northern blotting and RT-PCR in (A) normal tissues and (B) tumour tissue and cell lines.

FIG. 30: depicts the partial intron/exon structure of the VEGF-X gene. (A) Genomic DNA sequences of 2 exons (SEO ID NO:127 and SEQ ID NO:128) determined by sequencing; exon sequence is in upper case, intron sequence is in lower case. (B) Shows the location of splice sites within the VEGF-X cDNA sequence (SEQ ID NO:129 and SEQ ID NO:130). The location of mRNA splicing events is indicated by vertical lines. The cryptic splice donor/acceptor site at nt. 998/999 (diagonal lines) gives rise to the splice variant forms of VEGF-X. No splice site information is given for the region shown in italics.

Figure 31:
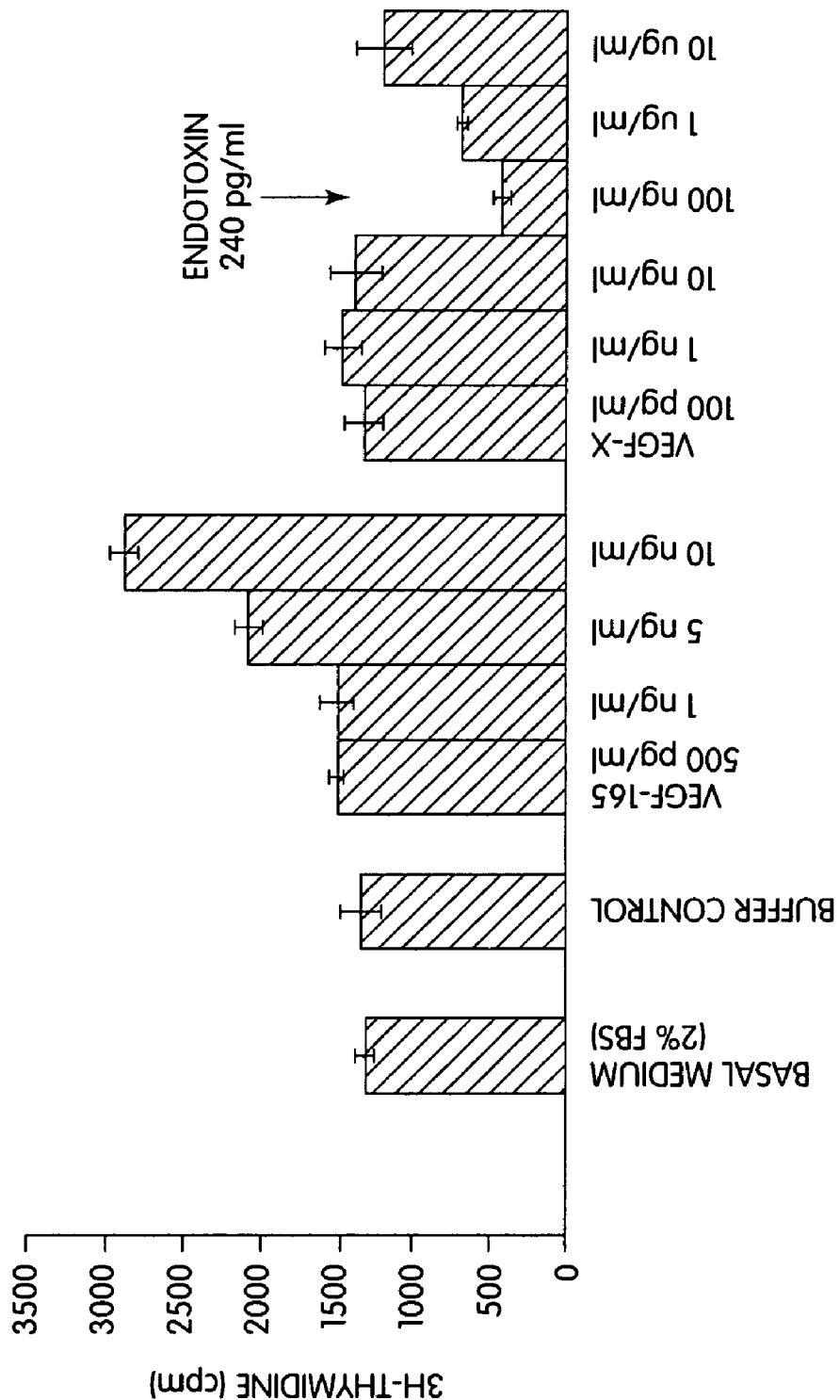

FIG. 31: is a graphic representation of the effect of FL-VEGF-X on HuVEC proliferation: (24 hour serum starvation followed by one day treatment).

Figure 32:
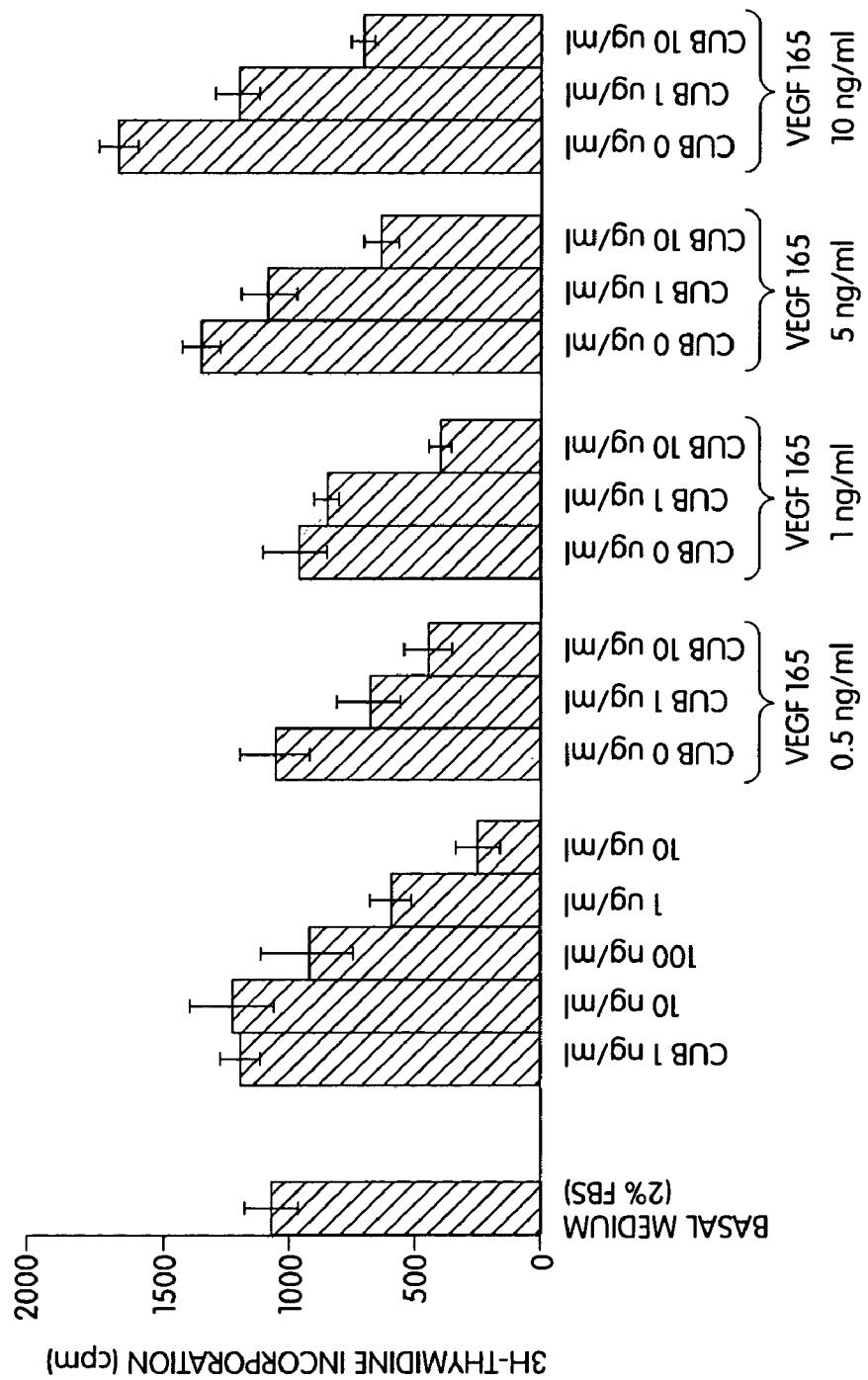

FIG. 32: is a graphic representation of the combined effect of truncated VEGF-X (CUB domain) and human recombinant VEGF$_{165}$ on HUVEC proliferation: (24 hour serum starvation followed by two day treatment).

Figure 33:
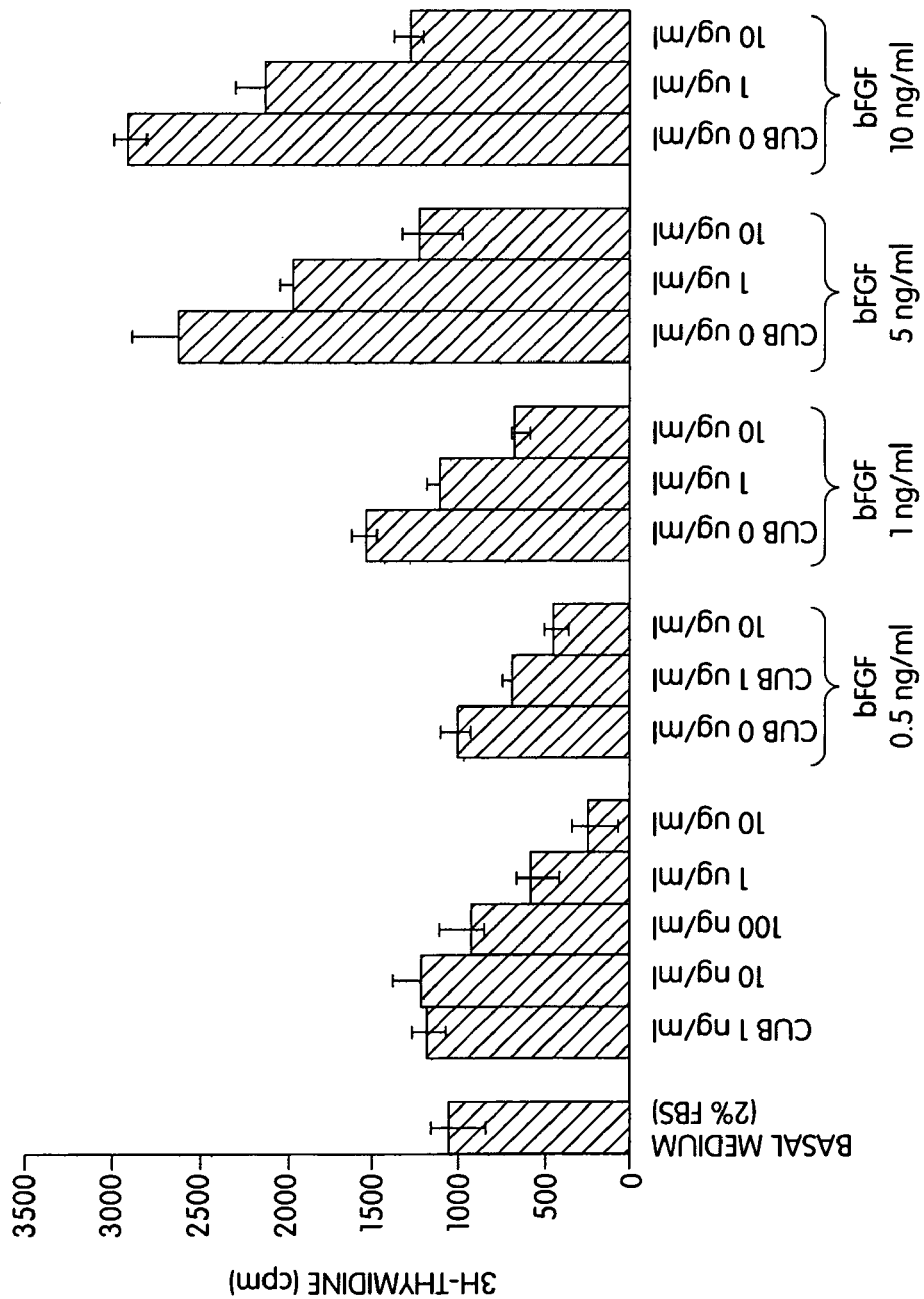

FIG. 33: is a graphic representation of the combined effect of the CUB domain and human recombinant bFGF on HuVEC proliferation: (24 hour serum starvation followed by two day treatment).

Figure 34:
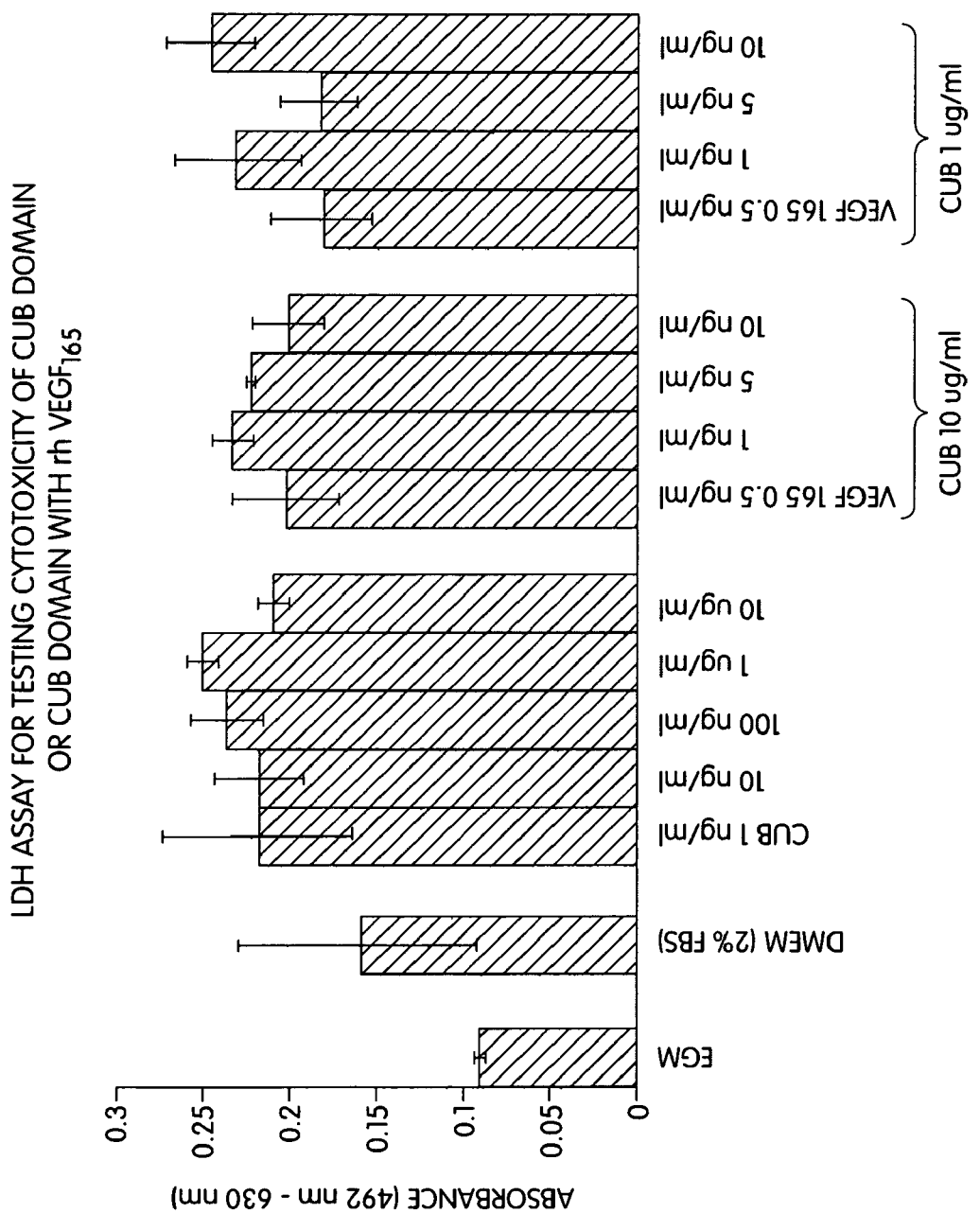

FIG. 34: is a graphic representation of the results of a LDH assay for testing cytotoxicity of the CUB domain or the CUB domain with rhVEGF$_{165}$.

Figure 35:
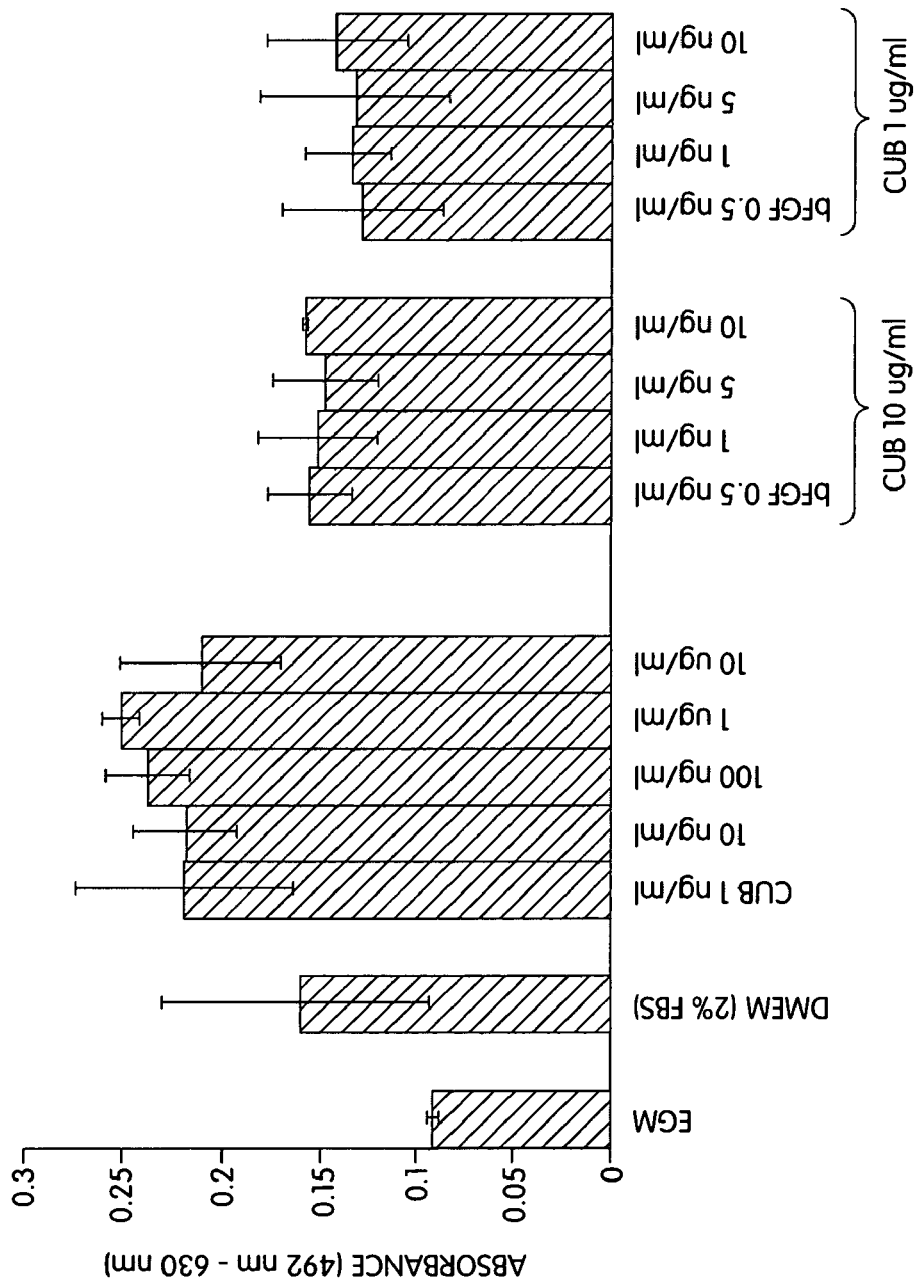

FIG. 35: is a graphic representation of the results obtained from a LDH assay for testing cytotoxicity of the CUB domain or CUB domain with rh-bFGF.

A BLAST (Basic Local Alignment Search Tool; Altschul et al., 1990 J. Mol. Biol. 215, 403–410) search was performed in the proprietary LifeSeq™ human EST database (Incyte Pharmaceuticals, Inc., Palo Alto, Calif., USA). BLAST produces alignments of both nucleotide and amino acid sequences to determine sequence similarity. Because of the local nature of the alignments, BLAST is especially useful in determining exact matches or in identifying homologues. While it is useful for matches which do not contain gaps, it is inappropriate for performing motif-style searching. The fundamental unit of BLAST algorithm output is the High-scoring Segment Pair (HSP).

Eighteen human EST clones (FIG. 14) with high similarity to the previously identified VEGF proteins were identified and a further fifty EST clones (FIG. 15) were identified using these sequences as query sequences, allowing us to deduce the putative sequence for the new VEGF-X protein. The sequences obtained were compared to known sequences to determine regions of homology and to identify the sequence as a novel VEGF-type protein. Using the DNA sequence information in the databases we were able to prepare suitable primers having the sequences of VEGF-X 1–10 illustrated in FIG. 3 for use in subsequent RACE experiments to obtain the complete DNA sequence for the VEGF-X gene.

Cloning

A profile was developed based on the VEGF-like domain in existing VEGF sequences (VEGF-A, B, C and D). This was used to search the public databases and the Incyte LifeSeq™ database. No significant novel matching sequences were found in the public databases. All of the matching sequences found in the LifeSeq™ database (~1000) were assembled to give a smaller number of sequences (~30), which included the known VEGFs and a potential novel VEGF (FIGS. 1 and 2). This sequence was named VEGF-X.

Oligonucleotides were designed to amplify the VEGF-X sequence from cDNA (FIG. 3). The ESTs found in LifeSeq™ were from a range of tissues, with a slight predominance of sequences from ovary, testis, placenta and lung (FIGS. 14 and 15). Accordingly the oligonucleotides were used to amplify cDNA derived from lung and placenta. First-round PCR products were found at ~200 bp larger than the expected sizes, while 3 major species appeared after a second round of PCR amplification, the smallest of which was of the expected size. These fragments were cloned and sequenced. The smallest fragment did indeed have the sequence originally identified from the LifeSeq database, while the others contained insertions (FIG. 4).

As the first round of amplification suggested that the major species found in cDNA from ovary and placenta was not that originally identified in the LifeSeq™ database, the focus of effort was switched to the presumed major species (it seemed likely that clones 57, 25–27 and 2.1 kb clones 1–3 in FIG. 4 represented the major mRNA species). Conceptual translation of the DNA sequences of these cloned PCR fragments indicated that the complete open reading frame was not present in the clones or in the sequence from LifeSeq™. While all clones contained the same sequence in the region of the translation termination codon, indicating that the end of the open reading frame had been identified, the 5' end of the open reading frame had not been cloned. 5' RACE experiments were therefore carried out in order to find the start of the reading frame. PCR primers designed for RACE experiments are shown in FIG. 5. RACE PCR products were sequenced directly. Sequence could be obtained from the 3' end of these RACE products but not from the 5' end; probably because the products were not cloned and were therefore heterogeneous at the 5' end. This new sequence was assembled with the existing cloned sequence to give the sequence shown in FIG. 6. Searching the LifeSeq™ database with this sequence identifies ESTs which extend the sequence a further 140 bp in the 5' direction and a further 160 bp in the 3' direction (FIG. 7). This longer contig was used to design oligonucleotide primers to amplify the entire coding sequence (these primer sequences are shown in FIG. 8). PCR was carried out using primers 5'-1 and vegfX10 (in order to clone a "full-length" cDNA), and with primers 5'-1 and vegfX6 (in order to clone the full coding region, see FIG. 3 for sequences of vegfX10 and vegfX6). A number of clones were obtained for the shorter fragment, of which clones 4 and 7 contain no PCR errors (sequence of clones 4 & 7 in FIG. 9). A single clone was obtained for the longer fragment (clone 9), but this sequence appears to contain 2 PCR errors.

The predicted polypeptide from these longer contigs is shown in FIG. 10. Amino acids 1–22 are predicted to encode a signal sequence (von Heijne, 1986, *Nucleic Acids Res.* 14, 4683–4690). FIG. 11 shows an alignment of the protein sequence with VEGFs A-D. The region homologous to the other VEGFs is located towards the C-terminus of the protein. As the VEGF homology domain is expected to belong to the TGF-beta superfamily of growth factors and to consist of a dimer containing both intra- and intermolecular disulphide bonds, initial alignments focussed on the cysteines. However, mapping of the sequence onto the known x-ray structure of the VEGF-A receptor-binding domain (Muller et al (1997) *Proc. Natl. Acad. Sci USA* 94, 7192–7197) suggests that the alignment in FIG. 11 is plausible, as the extra 4 cysteine residues within the VEGF-homology region of VEGF-X (compared to this region of VEGF-A) correspond to residues which are spatially close in VEGF-A, and may therefore be able to form disulphide bonds.

A search of the PFAM database of protein domains with the full-length polypeptide sequence from FIG. 10 identifies two domain consensus sequences within the polypeptide. The more C-terminal domain is a "VEGF" domain: (the known VEGFs all contain this domain and the structure of this region of VEGF-A is similar to that of PDGF). Additionally towards the N-terminus of the polypeptide there is a CUB domain (amino acids ~40–150). The CUB domain is a 100–110 amino acid extracellular domain found in a number of developmentally-regulated proteins. When the full-length protein is used to search the protein databases using the BLAST 2 algorithm, the scores for matches to CUB domain-containing proteins are more significant than those to the other VEGFs. Interestingly, the most significant matches are to the CUB domains of Neuropilins, and Neuropilin-1 was recently identified as a receptor of one of the VEGF-A isoforms VEGF-A$_{165}$ (Soker et al. (1998) *Cell* 92, 735–745).

Assuming that the variant sequences isolated by PCR (i.e. the smaller PCR fragments) use the same translation initiation site as the full-length sequence, they would result in production of the variant proteins shown in FIG. 12. It may be significant that both of these variant proteins retain the CUB domain and delete all or part of the VEGF-like domain. The production of these variant sequences can be explained by the use of a cryptic splice donor/acceptor site within the VEGF-X sequence (FIG. 30B, between nt. 998/999): one variant arises by splicing out of the region between nt. 729–998, the other by splicing out of the region between nt. 999–1187.

Expression

Full-Length Expression Constructs

Mammalian Cells

Clone 4 containing the full CDS of VEGF-X (see FIG. 9), was used to generate constructs for expression of full-length protein. The sequence was amplified by PCR and cloned into the vector pCDNA6/V5-His so as to add a C-terminal V5 epitope tag and His$_6$ tag. The DNA and polypeptide sequence in this vector is shown in FIG. 19. Transient expression in COS cells followed by western blotting and detection via an anti-V5 mAb demonstrates the secretion of a protein of ~50K into the medium in transfected cells only (FIG. 22A). This construct can also be used to generate VEGF-X expressing stable CHO cell lines.

Baculovirus/Insect-Cell Expression System

For expression in the baculovirus/insect cell system the DNA encoding the predicted mature VEGF-X polypeptide sequence was fused to a sequence encoding a signal derived from melittin, a secreted insect protein. An N-terminal 6His tag was also added to facilitate purification. The insert was then cloned into the baculovirus expression vector pFAST-BAC. The DNA and polypeptide sequence of this construct is shown in FIG. 20. Infection of *Trichoplusia ni* Hi5 cells with this recombinant baculovirus results in the secretion of a protein of approximately 45K into the medium (data not shown).

*E. coli*

The coding region of VEGF-X has been cloned in a variety of ways for expression as a secreted protein in *E. coli*. A particularly useful expression clone carries an N-terminal fusion to the *E. coli* maltose-binding protein (MBP-derived from the expression vector pMAL-p2, New England Biolabs) and a C-terminal fusion to a 6His tag. The DNA and polypeptide sequence of this vector is shown in FIG. 21. Sequential purification of cell fractions on Ni-NTA resin and amylose resin allows the isolation of the expressed protein (see FIG. 22B).

Expression of Fragments

VEGF

The VEGF domain of VEGF-X has been expressed in *E. coli*. Similar domains from VEGF-A (Christinger et al. (1996) *PROTEINS: Structure, Function and Genetics* 26, 353–357), and VEGF-D (Achen et al (1998) *Proc. Natl. Acad. Sci USA* 95, 548–553) have been shown to be capable of binding to the respective receptors. Expression of these domains was carried out using the bacterium *E. coli*. Additionally, the full-length protein was expressed using the baculovirus/insect cell expression system. The oligonucleotide primers which have been obtained for these experiments are shown in FIG. 13. The construct directed expression in the bacterial cytoplasm, and as expected the protein was produced in insoluble form in inclusion bodies (the DNA and polypeptide sequence used for PDGF domain expression is shown in FIG. 24). Inclusion bodies were washed, solubilized with urea and the protein purified under denaturing conditions, before refolding by dialysis to remove the urea. Soluble protein was obtained, but shows little evidence of the disulphide bond linked dimers seen with material derived from animal cells (FIG. 25, compare with FIGS. 22A & B). It is not clear therefore whether this protein is correctly folded.

CUB

The CUB domain has been expressed as a soluble secreted protein in *E. coli* (FIG. 26). The protein was purified by binding to Ni-NTA resin (FIG. 27) and assayed for activity on HUVECs in an in-vitro proliferation assay.

Properties of the VEGF-X Protein

The transient mammalian cell expression system described above has been used to generate full-length VEGF-X protein, as shown by antibody detection following Western blotting (see FIG. 22A).

Disulphide Bond Linked Dimers

The other members of the DGF family of growth factors, the PDGFs and VEGFs, all exist as dimers in which two monomers constituting the dimer are linked by interchain disulphide bonds. The x-ray structures of PDGF-BB (Oefner et al, 1992), and VEGF-A (Muller et al, 1997) are known and indicate that at least these two members of the family contain two interchain disulphide bonds. Practically this means that in SDS-PAGE analysis of these growth factors the presence of interchain disulphide bonds is shown by a large decrease in mobility in the absence of reducing agent (ie. the nonreduced dimer migrates more slowly through the gel than the reduced monomer). This effect was also expected for VEGF-X, and has been demonstrated for the material obtained from transient mammalian cell expression (FIG. 22A). In the case of the full length material produced in *E. coli* only some 10% of the total VEGF-X protein appears to be present as disulphide bond-linked dimers (FIG. 22B). However, these results provide evidence that the mammalian cell-derived protein is correctly folded, and that a portion of the *E. coli*-derived protein is too.

Glycosylation

There are 3 predicted potential N-linked glycosylation sites within the VEGF-X protein: at residues 25, 55 and 254 of the polypeptide sequence. The predicted molecular mass of the mature VEGF-X protein is 40 kDa, but SDS-PAGE and western blotting (detection via an introduced C-terminal epitope tag—see FIG. 19) of the full-length protein expressed in COS cells gives a band slightly larger than the expected size (45–50 kDa) as well as one at 25 kDa (FIG. 22A). This smaller band is presumed to be a C-terminal proteolysis fragment derived from the full-length molecule (controls from uninfected cells do not show this band), probably corresponding to a cleavage between the CUB and VEGF domains. EndoH treatment of the preparation gives a slight mobility change for the full-length protein (FIG. 23), but for the smaller VEGF domain fragment there is a clear change, indicating that the predicted glycosylation site within the VEGF domain at residue 254 is indeed glycosylated.

Activity of Proteins in Cell-based Assays

Protein samples were tested for activity in cell proliferation, cell migration and in-vitro angiogenesis assays. Active samples can also be tested in the in vivo matrigel mouse model of angiogenesis.

Full-length VEGF-X Protein

Conditioned medium derived from COS cells transiently expressing VEGF-X (see FIG. 22A) displayed no detectable activity in any of the assays. However, as VEGF-X protein could only be detected in this preparation by Western blotting, and not by Coomassie-staining of gels, it is clearly present at very low levels and this may be the reason for the observed lack of activity in the cell proliferation, migration or in vitro angiogenesis tests.

VEGF Domain

The VEGF domain protein described above has been tested in cell proliferation (on a range of cell types), cell migration and in vitro angiogenesis assays and has failed to show activity in any of these tests. As suggested above, this may be due to incorrect folding of this protein.

CUB Domain

The CUB domain protein at the highest dose tested (1 µg/ml) appears to inhibit proliferation of HUVECs in the absence of other stimulation (FIGS. 28A & B). This effect is also seen following stimulation with the lowest VEGF-A$_{165}$ dose tested (1 ng/ml—FIG. 28C).

The CUB domain of VEGF-X therefore appears to show antiproliferative activity on HUVECs, even in the presence of low VEGF-A$_{165}$ doses.

Tissue Distribution of mRNA

Figure 29A:
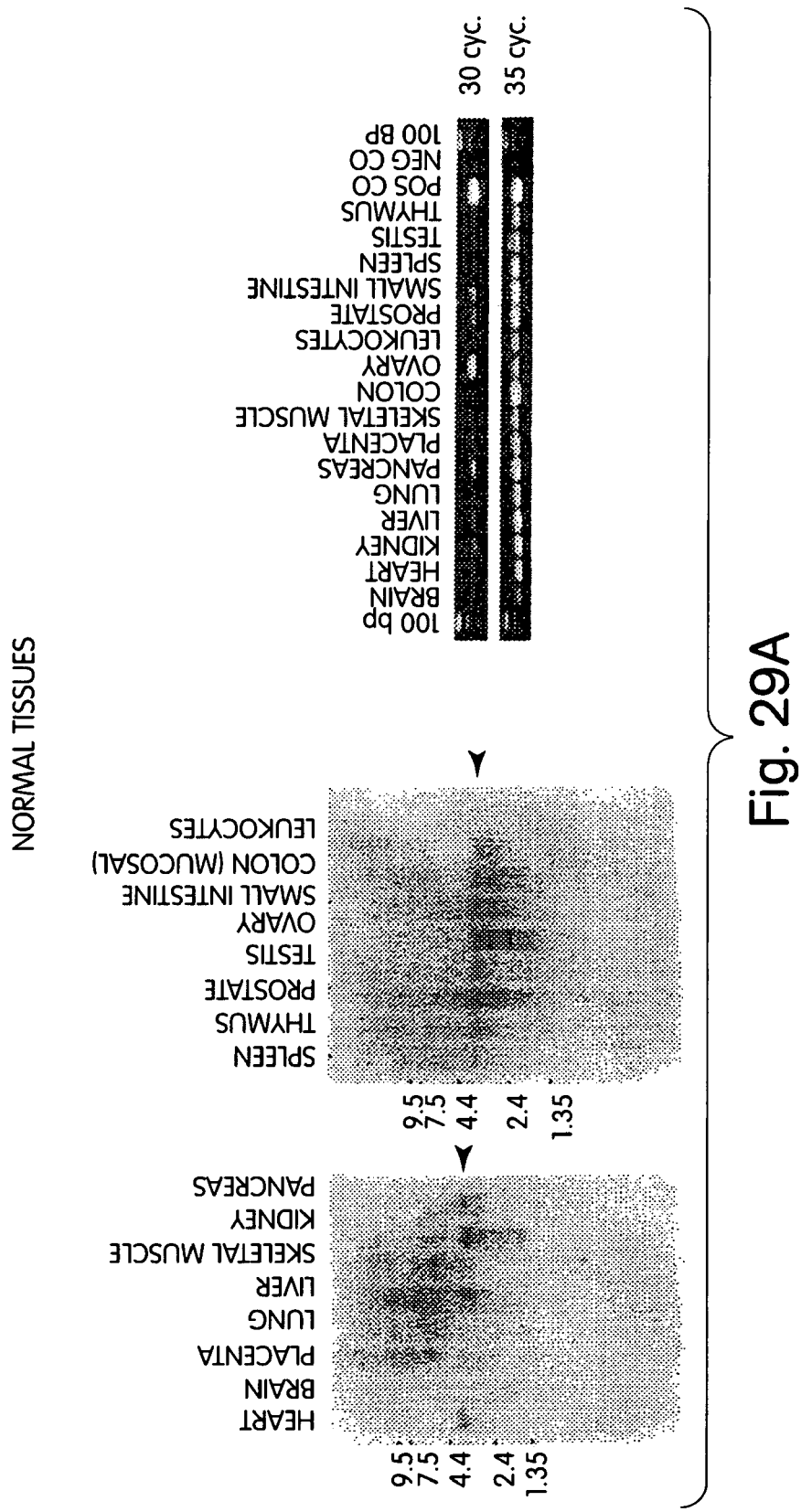
Figure 29B:
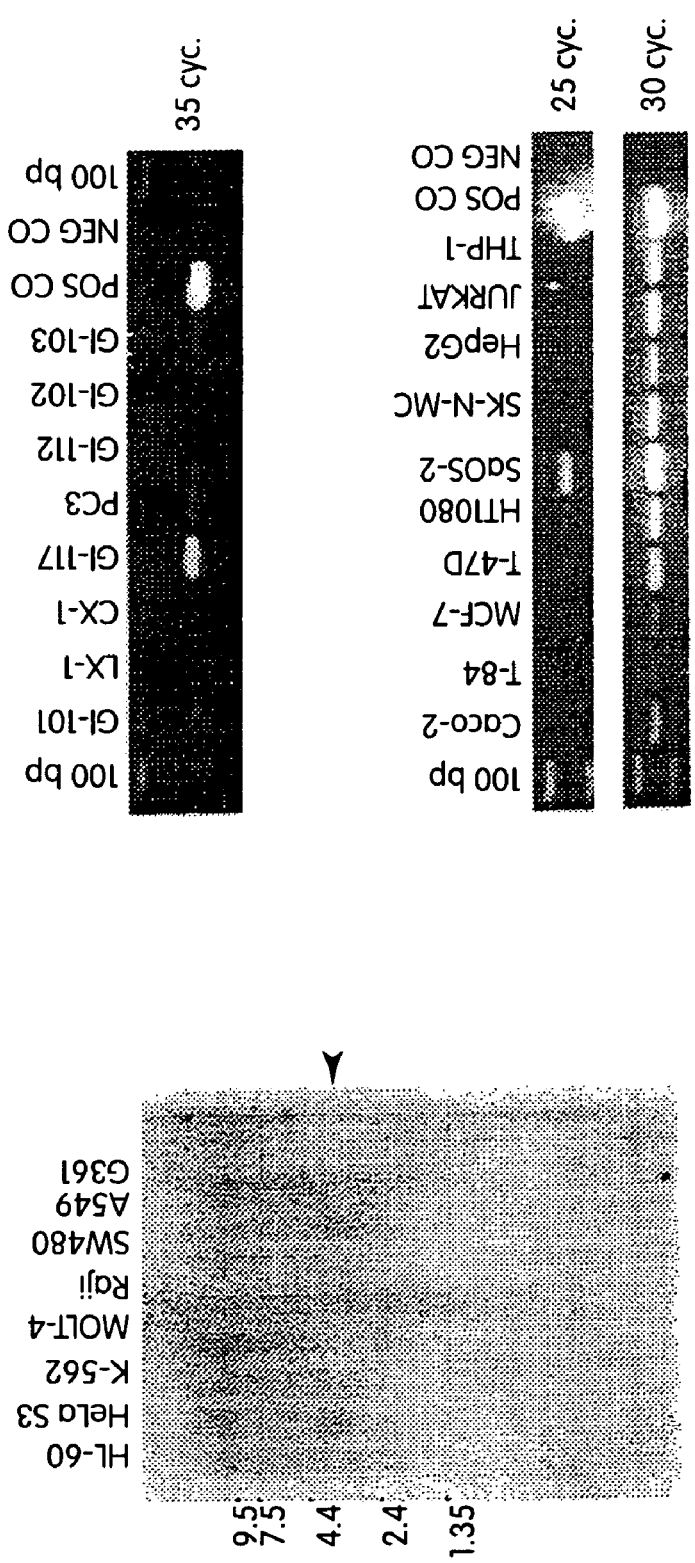

VEGF-A mRNA expression has been shown to be upregulated in a wide variety of human tumors (lung, breast, ovarian, colon, stomach, liver, pancreas, kidney, bladder and prostate—Takahashi et al, 1995). Tumor VEGF-A expression has been shown to correlate with tumor growth rate, microvascular density and tumor metastasis (Takahashi et al, 1995). It was thus of interest to examine the mRNA expression patterns of VEGF-X. Accordingly, Northern blot analysis of mRNA derived from different tissues has been carried out. The results indicate that although the VEGF-X mRNA is expressed at low levels, it is present in a wide range of tissues. PCR amplification of cDNA from a range of tissue sources supports this idea (FIG. 29A). The major mRNA species is approximately 30.1 kb in size. There is no significant upregulation seen in tumour cell lines or in tumour tissues tested (FIG. 29B), with the possible exception of the cell lines GI-117 (lung carcinoma) and SaOS-2 (osteosarcoma). The results of these initial tissue distribution studies do not, therefore, provide evidence for upregulation of VEGF-X in tumour growth, as is seen with VEGF-A.

Genomic Structure of the VEGF-X Gene

A genomic BAC clone covering the 3' part of the VEGF-X locus was isolated by hybridisation screening of nylon filters containing a human BAC library. Direct sequencing of this clone using oligonucleotide primers based on the VEGF-X cDNA sequence allowed the determination of several intron/exon boundaries (FIG. 30). Interestingly, the position of the mRNA splice site within the PDGF domain (nt 1187/1188 in FIG. 30B) is conserved with respect to those in the VEGF-A and VEGF-D genes (Tischer et al, 1991; Rocchigiani et al, 1998).

Materials & Methods

PCR, Cloning, DNA Sequence Determination and BAC Screening.

All primers were purchased from Eurogentec, Seraing, Belgium. Insert-specific sequencing primers (15- and 16-mers) were designed by visual inspection of the DNA sequences. DNA was prepared on Qiagen-tip-20 columns or on Qiaquick spin columns (Qiagen GmbH, Düsseldorf, Germany) and recovered from the spin columns in 30 μl Tris/EDTA-buffer (10 mM Tris HCl pH 7.5, 1 mM EDTA (sodium salt)). Sequencing reactions were performed using BigDye™ Terminator Cycle Sequencing Ready Reaction kits (Perkin Elmer, ABI Division, Foster City, Calif., USA) and were run on an Applied Biosystems 377 DNA sequencer (Perkin Elmer, ABI Division, Foster City, Calif., USA). Polymerase chain reactions were carried out according to standard procedures (Ausubel et al, 1997). The PCR fragments were cloned into vectors pCR2.1 (Invitrogen, Carlsbad, Calif. USA) or pCR-TOPO (Invitrogen, NL) according to the manufacturer's instructions. One of those vectors, plasmid VEGFX/pCR2.1 1TOPO FL was deposited on 1 Mar. 1999 under Accession No. LMBP 3925. After sequence determination, the inserts were cloned into the desired expression vectors (see FIGS. 19, 20, 21, 24 & 26).

A human genomic BAC library (Genome Systems, Inc., St Louis, Mich., USA) was screened by hybridisation to oligonucleotides derived from the VEGF-X cDNA sequence, according to the manufacturer's instructions. BAC DNA was prepared using a Qiagen plasmid midi kit (Qiagen GmbH, Düsseldorf, Germany according to the manufacturer's instructions with some modifications (after clearing of the lysate from chromosomal DNA, supernatants from individual preparations were pooled on a single column (tip 100), and after the 70% EtOH wash, the pellet was resuspended overnight at 4° C. in 100 μl TE). 20-mer sequencing primers were designed based on the known cDNA sequence, and sequencing carried out as above.

5' RACE

In order to extend the cDNA clone in a 5' direction RACE reactions were carried out. Since it was known that the mRNA is present in placenta and skeletal muscle, Marathon-Ready™ placenta and skeletal muscle cDNAs were purchased from Clontech (Palo Alto Calif. USA) and used according to the manufacturer's instructions. DNA fragments were excised from agarose gels, purified using QiaQuick PCR purification columns (Qiagen GmbH, Düsseldorf, Germany) and sequenced directly.

VEGF-X Protein Expression and Purification

DNA fragments encoding the desired protein sequences were amplified by PCR and cloned into appropriate expression vector systems.

For mammalian cell expression, the full coding sequence was cloned into the vector pcDNA6/V5-his (Invitrogen Leek, NL, see FIG. 19 for construct sequence), so as to add a C-terminal peptide tag to assist in detection and purification.

For insect cell expression the sequence of the predicted mature polypeptide was initially amplified to add an N-terminal 6His peptide and then cloned into the pMelBacB vector (Invitrogen, Leek, NL) to add an insect cell signal sequence. The entire insert was then PCR-cloned into the vector pFASTBAC-1 (LifeTechnologies, Gaithersburg, Mass., USA) for construction of a baculovirus according to the manufacturer's instructions.

For *E. coli* expression, the coding region was PCR amplified to add a C-terminal 6His tag and then cloned into the vector pMAL-p2 (New England Biolabs, Beverly, Mass., USA). The coding sequence of this construct is shown in FIG. 21). The protein was purified first on Ni-NTA resin (Qiagen GmbH, Düsseldorf, Germany) and then on amylose resin (New England Biolabs, Beverly, Mass., USA), according to the manufacturers' instructions.

DNA sequences encoding the CUB and VEGF domain fragments of VEGF-X were PCR amplified and cloned into pET22b and pET21a (Novagen, Madison, Wis., USA) respectively. The CUB domain protein was prepared either from the periplasm or medium of induced cultures by standard methods (Ausubel et al, 1997). The protein was initially purified by precipitation with 20% ammonium sulphate. After overnight dialysis vs 20 mM Tris Hcl pH7.5, 100 mM NaCl to remove ammonium sulphate, the protein was further purified on Ni-NTA resin as described above. The VEGF domain protein was expressed in insoluble form, and preparation of inclusion bodies was carried out using standard procedures (Ausubel et al 1997). Inclusion bodies were dissolved in 6M guanidine hydrochloride, 20 mM Tris Hcl pH8.0, 200 mM NaCl, 1 mM 2-mercaptoethanol, and purified on Ni-NTA resin (Qiagen GmbH, Düsseldorf, Germany) according to the manufacturer's instructions. The protein was refolded by dialysis against several changes of buffer containing decreasing concentrations of denaturant.

Analysis of protein glycosylation was carried out using EndoH (Roche Molecular Biochemicals, Brussels, BE) according to the manufacturer's instructions.

Cell Proliferation Assay

Human umbilical vein endothelial cells (HUVECs) (Clonetics, San Diego, Calif.) were trypsinized with 0.05% trypsin/0.53 mM EDTA (Gibco, Gaithersburg, Md.), resuspended in the EGM-2(Clonetics, San Diego, Calif.), counted, and distributed in a 96-well tissue culture plate at 5,000 cells/well. Following cell attachment and monolayer formation (16 hours), cells were stimulated with various concentrations of truncated VEGF-X (CUB domain or VEGF domain) or dilutions of culture supernatants of the full-length VEGF-X (COS 7 or HEK293) in DMEM (Gibco, Gaithersburg, Md.) containing 0.5% to 2% FBS (HyClone, Logan, Utah) as indicated. For human fetal dermal fibroblasts (American Type Culture Collection, Rockville, Md.), the growth medium was replaced by DMEM containing 0.1% BSA (Sigma, St. Louis, Mo.) with or without various concentrations of truncated VEGF-X proteins. For HCASMC (Clonetics, San Diego, Calif.), the medium was replaced by DMEM containing 0.5% FBS. The cells were treated for a further 24 hr–72 hr. For the measurement of proliferation, the culture media were replaced with 100 µl of DMEM containing 5% FBS and 3 µCi/ml of [3H]-thymidine (Amersham, Arlington Heights, Ill.). Following pulse labeling, cells were fixed with methanol/acetic acid (3:1, vol/vol) for 1 hour at room temperature. The cells were washed twice with 250 µl/well of 80% methanol. The cells were solubilized in 0.05% trypsin (100 µl/well) for 30 minutes then in 0.5% SDS (100 µl/well) for another 30 minutes. Aliquots of cell lysates (180 µl) were combined with 2 ml of scintillation cocktail (Fisher, Springfiled, N.J.) and the radioactivity of cell lysates was measured using a liquid scintillation counter (Wallac 1409). In each case, samples were performed in quadruplicate.

Chemotaxis Assay

The chemotactic response of HUVECs was assayed using a 48-well modified Boyden chamber (NeuroProbe, Cabin John, M. D.) and collagen-coated (0.1 mg/ml type I collagen, Collaboratic Biomedical, Bedford, Mass.) polycarbonate membrane filters with a pore diameter of 8 µm (NeuroProbe, Cabin John, M. D.). Cell suspensions (15,000/well) were loaded to the upper part of the chemotaxis chamber and stimulated for 4 hours with rhVEGF$_{165}$ (0.1–10 ng/ml) (Calbiochem, San Diego, Calif.) or various concentrations of truncated VEGF-X (PDGF domain). Cells remaining on the top of the membrane were removed. Migration was assessed by counting the number of cells that migrated to the lower side of the filter membrane. The membrane was fixed with 10% formaldehyde for 15 min, followed by staining with Gill's hemotoxylin III (Poly Scientific, Bay Shore, N.Y.). The assay was performed in triplicates and six independent high power fields per well were counted using a light microscope at 250 magnification. The results were expressed as the fold of unstimulated cells (EGM containing 0.1% BSA).

In Vitro Angiogenesis Assay

In vitro angiogenesis in fibrin gels was quantitated using spheroids of human umbilical vein endothelial cells (Korff et al., 1998). To generate endothelial cell spheroids of defined size and cell number, a specific number of cells (~800 cells per spheroid) was suspended in EGM-2 culture medium containing 20% methylcellulose (Sigma, St. Louis, Mo.), seeded into nonadherent round-bottom 96-well plates. All suspended cells in one well contributed to the formation of a single endothelial cell spheroid within 24 hours. A fibrin gel stock solution was prepared freshly prior to use by mixing 3 mg/ml fibrinogen (Calbiochem, San Diego, Calif.) in Medium 199 (Gibco, Gaithersburg, Md.). Assays were performed in 24-well culture plates. The 1 ml fibrinogen stock was mixed with 50 HUVEC spheroids and the corresponding test substance including rh-VEGF$_{165}$ or various concentration of VEGF-X. The spheriod-containing fibrinogen was rapidly transferred into 24-well plates. Fifteen microliters of thrombin (100 NIH U/ml stock, Sigma, St. Louis, Mo.) was added to the gel for the fibrin gel formation. The gel formation usually occurred within 30 seconds. After gel formation, 1 ml/well of Medium 199 supplemented with 20% FBS, 1 mg/ml ε-aminocaproic acid (Calbiochem, San Diego, Calif.) and antibiotics were added. The gel was incubated at 37° C. (5% $CO_2$, 95% air, 100% humidity). After 3 days, in vitro angiogenesis was quantitated by measuring the length of the three longest capillary sprouts that had grown out of each spheroid (100× magnification), analyzing at least 10 spheroids per experimental group and experiment.

Matrigel Mouse Assay

The matrigel mouse assay is carried out as described by Passanti et al (1992).

Analysis of VEGF-X Gene Expression by RT-PCR Analysis.

Oligonucleotide primers VEGF-E2 and VEGF-X14 (FIG. 16; FIG. 5) were used for the specific PCR amplification of a 350 bp fragment from VEGF-X. PCR amplifications were performed on human multiple tissue cDNA (MTC™) panels (Clontech human MTC panels I and II and human Tumor MTC panel) normalised to the mRNA expression levels of six different housekeeping genes. In addition, cDNA was made from different tumor cell cultures (Caco-2 colorectal adenocarcinoma; T-84 colorectal carcinoma; MCF-7 breast adenocarcinoma; T-47D breast ductal gland carcinoma; HT1080 bone fibrosarcoma; SaOS-2 osteosarcoma; SK-N-MC neuroblastoma; HepG2 hepatoblastoma; JURKAT T-cell leukemia and THP-1 myelomonocytic leukemia). For the preparation of tumor cell cDNA, cells were homogenised and total RNA prepared using the RNeasy Mini kit (Qiagen GmbH, Hilden, Germany) according to manufacturer's instructions. 1 μg of total RNA was reverse transcribed using oligo(dT)15 as a primer and 50 U of Expand™ Reverse Transcriptase (Boehringer Mannheim, Mannheim, Germany) according to the manufacturer's instructions. PCR reactions with VEGF-X-specific or glyceraldehyde-3-phosphate dehydrogenase (G3PDH)-specific primers were then performed on 1 μl of this cDNA. For all cDNAs, PCR reactions with VEGF-X specific primers were performed in a total volume of 50 μl, containing 5 μl (±1 ng) of cDNA, 1× Advantage KlenTaq PCR reaction buffer, 0.2 mM dNTP, 250 nM of primers VEGF-E2 and VEGF-X14 and 1 μl of Advantage KlenTaq polymerase mix. Samples were heated to 95° C. for 30 s and cycling was done for 30 s at 95° C. and 30 s at 68° C. for 25, 30 or 35 cycles. Control reactions using specific primers that amplify a 1 kb fragment of the housekeeping gene G3PDH were also performed according to the manufacturer's instructions.

Northern Blot Analysis of VEGF-X.

Northern blots containing 2 μg of poly(A)-rich RNA derived from different human tissues (Clontech Laboratories; MTN™ blot, MTN™ blot II and Cancer Cell Line MTN™ blot) were hybridized according to the manufacturers instructions with a α-[$^{32}$P]-dCTP random-priming labelled (Multiprime labelling kit, Roche Diagnostics) 293 bp specific VEGF-X fragment (PinAI-StuI fragment including 92 bp of the 3' end coding region and 201 bp of the 3' untranslated region of VEGF-X). The blots were hybridized overnight at 68° C. and final washes at high stringency were at 68° C. in 0.1×SSC/0.1% SDS. The membranes were autoradiographed for 1 to 3 days with intensifying screens.

Full Length VEGF-X

The effect of full length VEGF-X on proliferation of HuVEC cells was determined by the $^3$H-Thymidine incorporation assay. HuVEC cells were serum starved for 24 hours prior to treatment with the full length VEGF-X at the concentration range from 100 pg/ml-10 μg/ml. There was no effect of VEGF-X at 100 pg/ml-10 ng/ml on endothelial cell proliferation. At the higher concentrations of FL-VEGF-X (100 ng/ml and 1 μg/ml) there was a marked inhibition of endothelial cell proliferation. This is probably due to the very high endotoxin level in the samples. The VEGF-X sample was purified in order to decrease the endotoxin level and is currently tested in the cell proliferation assay.

The Summary from Testing the CUB Domain

The effect of CUB domain on inhibition of HuVEC prolieration either serum-(2%), rh-VEGF or bFGF-stimulated, was assessed by the $^3$H-Thymidine incorporation assay. Cells were serum starved followed by the treatment with the CUB domain and various growth factors. Results showed that the CUB domain inhibited endothelial cell proliferation, either serum-(2%), rh-VEGF or bFGF-stimulated in a dose dependent manner with maximal inhibition at 10 μg/ml. There was approximately a 2-fold inhibition of proliferation (at 10 μg/ml) of cells stimulated with VEGF and bFGF and nearly a 5-fold inhibition of cells stimulated with serum (2%). Results with the LDH assay showed that there was no cytotoxicity associated with the inhibition of cell proliferation by the CUB domain.

Therefore, the N-terminus of the polypeptide from FIG. 10 has been shown to possess a CUB domain. When database searches are carried out using the full-length coding sequence the best matches (i.e. for a BLAST search, those with the lowest probability score) are found with the CUB domain rather than with the VEGF-like domain. The best match from searching release 37 of the SWISSPROT database (February 1999) is to the CUB domain of a neuropilin from Xenopus laevis, and the matches to the CUB domains of human neuropilins 1 and 2 are also more significant than matches to the VEGFs.

This similarity is provocative, given the identification of neuropilin-1 and -2 as cellular receptors for the VEGF-A 165 (Stoker et al. 1998, reviewed in Neufeld et al. 1999). It is plausible therefore that VEGF-X could exert dual regulatory effects: via interaction with the tyrosine kinase VEGF-receptors mediated by the VEGF-like domain, as well as via interaction with VEGF isoforms or with the neurophilin receptors, mediated by the CUB domain.

To the best of our understanding the latter would be entirely novel, and searches on the most recent release of the Incyte database do not reveal any other proteins containing both CUB and VEGF-like domains. This arrangement of domains suggests possible positive or negative models of regulation:

Positive—the VEGF-like domain is able to interact productively with the tyrosine kinase VEGF receptors giving activation, and the CUB domain is able to interact productively with the neuropilin receptor giving activation.

Negative—the VEGF-like domain does not interact productively with the tyrosine kinase VEGF receptors, either preventing receptor dimerisation or blocking the VEGF binding sites. Further, the CUB domain does not interact productively with the neuropilin receptors, either preventing receptor activation or blocking the VEGF binding sites, or indeed by binding to VEGF isoforms and preventing their interaction with receptors.

TABLE 1

| ORIGINAL RESIDUE | EXEMPLARY SUBSTITUTIONS |
| --- | --- |
| ALA | SER, TER |
| ARG | LYS |
| ASN | HIS, SER |
| ASP | GLU, ASN |
| CYS | SER |
| GLN | ASN, HIS |
| GLU | ASP, GLU |
| GLY | ALA, SER |
| HIS | ASN, GLN |
| ILE | LEU, VAL, THR |
| LEU | ILE, VAL |
| LYS | ARG, GLN, GLU, THR |
| MET | LEU, ILE, VAL |
| PHE | LEU, TYR |
| SER | THR, ALA, ASN |
| THR | SER, ALA |
| TRP | ARG, SER |
| TYR | PHE |
| VAL | ILE, LEU ALA |
| PRO | ALA |

REFERENCES

1. Ausubel, F M, R Brent, R E Kingston, D D Moore, J G Seidman, J A Smith, K Struhl (Eds). (1997) Current Protocols in Molecular Biology, John Wiley and Sons.
2. von Heijne, G. (1986) Nucleic Acids Res. 14, 4683–4690.
3. Muller, Y A, B Li, H W Christinger, J A Wells, B C Cunningham and A M de Vos. (1997) Vascular endothelial growth factor: crystal structure and functional mapping of the kinase domain receptor binding site. Proc. Natl. Acad. Sci USA 94, 7192–7197.
4. Korff, T and Augustic, H. G. (1998) Integration of endothelial cells in multicellular spheroids prevents apoptosis and induced differentiation. The Journal of Cell Biology. 143, 1341–1352
5. Christinger, H W, Y A Muller, L T Berleau, B A Keyt, B C Cunningham, N Ferrara and A M de Vos. (1996) PROTEINS: Structure, Function and Genetics 26, 353–357.
6. Achen, M G, M Jeltsch, E Kukk, T Makinen, A Vitali, A F Wilks, K Alitalo and S A Stacker. (1998) Proc. Natl. Acad. Sci USA 95, 548–553.
7. Siemeister, G, B Schnurr, K Mohrs, C Schachtele, C Marme and G Martiny-Baron. (1996) Biochem. Biophys. Res. Commun. 222, 249–255.
8. Soker, S, S Takashima, H Q Miao, G Neufeld and M Klagsbrun (1998). Neuropilin-1 is expressed by endothelial and tumor cells as an isoform-specific receptor for vascular endothelial growth factor, Cell 92: 735–745.
9. Neufeld, G, T Cohen, S Gengrinovitch and Z Poltorak (1999). Vascular endothelial growth factor and its receptors, FASEB J. 13: 9–22.
10. Oefner, C., D'Arcy, A., Winkler, F. K., Eggimann, B. and Hosang, M. (1992). Crystal structure of human platelet-derived growth factor BB. EMBO J. 11, 3921–3926.
11. Passanti, A., Taylor, R. M., Pili, R., Guo, Y., Long, P. V., Haney, J. A., Pauly, R., Grant, D. S. and Martin, G. R. (1992) A simple, quantitative method for assessing angiogenesis and antiangiogenic agents using reconstituted basement membrane, heparin and fibroblast growth factor. *Laboratory Investigation,* 67, 519–528.

12. Rocchigiani, M., Lestingi, M., Luddi, A., Orlandini, M., Franco, B., Rossi, E., Ballabio, A., Zuffardi, O. and Oliviero, S. (1990). Human FIGF: cloning, gene structure, and mapping to chromosome Xp22.1 between the PIGA and the GRPR genes. *Genomics,* 47, 207–216.
13. Takahashi, Y., Kitadai, Y., Bucana, C. D., Cleary, K. R. and Ellis, L. M. (1995). Expression of vascular endothelial growth factor and its receptor, KDR, correlates with vascularity, metastasis and proliferation of human colon cancer. *Cancer Research,* 55: 3964–3968.
14. Tischer, E., Mitchell, R., Hartman, T., Silva, M., Gospodarowicz, D., Fiddes, J. C. and Abraham, J. A. (1991). The human gene for vascular endothelial growth factor: Multiple protein forms are encoded through alternative exon splicing. *J. Biol. Chem.* 266, 11947–11954.

SEQUENCE LISTING

Sequence ID No 1 corresponds to th amino acid sequence from position 23 to 345 of the amino acid sequence illustrated in FIG. 10.
Sequence ID No 2 is the amino acid sequence illustrated in FIG. 10.
Sequence ID No 3 corresponds to the sequence from position 257 to 1291 of the nucleotide sequence illustrated in FIG. 9.
Sequence ID No 4 corresponds to the polynucleotide sequence of VEGFX1 illustrated in FIG. 3.
Sequence ID No 5 corresponds to th polynucleotide sequence of VEGFX2 illustrated in FIG. 3.
Sequence ID No 6 corresponds to the polynucleotide sequence of VEGFX3 illustrated in FIG. 3.
Sequence ID No 7 corresponds to the polynucleotide sequence of VEGFX4 illustrated in FIG. 3.
Sequence ID No 8 corresponds to the polynucleotide sequence of VEGFX5 illustrated in FIG. 3.
Sequence ID No 9 corresponds to the polynucleotide sequence of VEGFX6 illustrated in FIG. 3.
Sequence ID No 10 corresponds to the polynucleotide sequence of VEGFX7 illustrated in FIG. 3.
Sequence ID No 11 corresponds to the polynucleotide sequence of VEGFX8 illustrated in FIG. 3.
Sequence ID No 12 corresponds to the polynucleotide sequence of VEGFX9 illustrated in FIG. 3.
Sequence ID No 13 corresponds to the polynucleotide sequence of VEGFX10 illustrated in in FIG. 3.
Sequence ID No 14 corresponds to the polynucleotide sequence of VEGFX11 illustrated in FIG. 5.
Sequence ID No 15 corresponds to the polynucleotide sequence of VEGFX12 illustrated in FIG. 5.
Sequence ID No 16 corresponds to the polynucleotide sequence of VEGFX13 illustrated in FIG. 5.
Sequence ID No 17 corresponds to the polynucleotide sequence of VEGFX14 illustrated in FIG. 5.
Sequence ID No 18 corresponds to the polynucleotide sequence 5'-1 in FIG. 8.
Sequence ID No 19 corresponds to the polynucleotide sequence 5'-2 in FIG. 8.
Sequence ID No 20 corresponds to the polynucleotide sequence of VEGFX6 illustrated in FIG. 13.
Sequence ID No 21 corresponds to the polynucleotide sequence of VEGFX7 illustrated in FIG. 13.
Sequence ID No 22 corresponds to the polynucleotide sequence of VEGFX8 illustrated in FIG. 13.
Sequence ID No 23 corresponds to the polynucleotide sequence of VEGFX9 illustrated in FIG. 13.
Sequence ID No 24 corresponds to the polynucleotide sequence of VEGBAC1 illustrated in FIG. 13.
Sequence ID No 25 corresponds to the polynucleotide sequence of VEGBAC2 illustrated in FIG. 13.
Sequence ID No 26 corresponds to the polypeptide having the amino acid sequence from amino acid position 40 to 150 of the sequence of FIG. 10.
Sequence ID No 27 corresponds to the polypeptide having the amino acid sequence illustrated in FIG. 26.
Sequence ID No 28 corresponds to the sequence from position 5 to 508 of the nucleotide sequence illustrated in FIG. 26.
Sequence ID NO: 29 corresponds to the sequence from position 214 to 345 of the amino acid sequence illustrated in FIG. 10.

The invention claimed is:

1. A pharmaceutical composition which inhibits proliferation of endothelial cells comprising the polypeptide of SEQ ID NO:26 together with a pharmaceutically acceptable carrier, diluent or excipient therefor.

2. The isolated polypeptide sequence of SEQ ID NO:26.

* * * * *